US010611754B2

(12) United States Patent
Min et al.

(10) Patent No.: US 10,611,754 B2
(45) Date of Patent: *Apr. 7, 2020

(54) HETEROCYCLIC COMPOUND AND PHARMACEUTICAL COMPOSITION COMPRISING SAME

(71) Applicant: BEYONDBIO INC., Daejeon (KR)

(72) Inventors: Changhee Min, Daejeon (KR);
Byungkyu Oh, Gyeryong (KR);
Yongeun Kim, Daejeon (KR);
Changmin Park, Daejeon (KR)

(73) Assignee: BEYONDBIO INC., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/241,177

(22) Filed: Jan. 7, 2019

(65) Prior Publication Data

US 2019/0135786 A1    May 9, 2019

Related U.S. Application Data

(63) Continuation of application No. 15/546,714, filed as application No. PCT/KR2016/001133 on Feb. 2, 2016, now Pat. No. 10,227,328.

(30) Foreign Application Priority Data

Feb. 4, 2015    (KR) ........................ 10-2015-0017339

(51) Int. Cl.

| C07D 401/14 | (2006.01) |
|---|---|
| C07D 239/24 | (2006.01) |
| C07D 401/04 | (2006.01) |
| A61P 25/28 | (2006.01) |
| A61P 35/00 | (2006.01) |
| A61P 25/14 | (2006.01) |
| A61P 25/16 | (2006.01) |
| A61K 31/444 | (2006.01) |
| A61K 31/495 | (2006.01) |
| A61K 31/506 | (2006.01) |
| C07D 403/14 | (2006.01) |
| A61K 31/5377 | (2006.01) |
| C07D 405/14 | (2006.01) |
| C07D 417/14 | (2006.01) |

(52) U.S. Cl.
CPC .......... *C07D 401/14* (2013.01); *A61K 31/444* (2013.01); *A61K 31/495* (2013.01); *A61K 31/506* (2013.01); *A61K 31/5377* (2013.01); *A61P 25/14* (2018.01); *A61P 25/16* (2018.01); *A61P 25/28* (2018.01); *A61P 35/00* (2018.01); *C07D 239/24* (2013.01); *C07D 401/04* (2013.01); *C07D 403/14* (2013.01); *C07D 405/14* (2013.01); *C07D 417/14* (2013.01)

(58) Field of Classification Search
CPC .. C07D 401/14; C07D 239/24; C07D 401/04; A61P 25/28; A61P 35/00; A61P 25/14; A61P 25/16; A61K 31/444; A61K 31/495; A61K 31/506

See application file for complete search history.

(56) References Cited

U.S. PATENT DOCUMENTS 7,173,021 B2    2/2007    Wang et al.

FOREIGN PATENT DOCUMENTS

| EP | 1 300 396 | 4/2003 |
|---|---|---|
| KR | 10-2005-0042478 A | 5/2005 |
| WO | 99/19305 | 4/1999 |
| WO | 01/93841 A2 | 12/2001 |
| WO | 02/096867 A2 | 12/2002 |
| WO | 03/047577 | 6/2003 |
| WO | 2004/016597 | 2/2004 |
| WO | 2010/018458 A2 | 2/2010 |

OTHER PUBLICATIONS

Yeon-Sun Seong et al., "Characterization of a Novel Cyclin-Dependent Kinase 1 Inhibitor, BMI-1026[1,2]", Cancer Research, Nov. 1, 2003, pp. 7384-7391, vol. 63, No. 21.
Shuhui Lim et al., "Cdks, cyclins and CKIs: roles beyond cell cycle regulation", Development, 2013, pp. 3079-3093, 140(15).
Todd M. Pitts et al., "Targeting nuclear kinases in cancer: Development of cell cycle kinase inhibitors", Pharmacology & Therapeutics, 2014, pp. 258-269, 142(2).
Jonathan C. Cruz et al., "Cdk5 deregulation in the pathogenesis of Alzheimer's disease", Trends in Molecular Medicine, Sep. 2004, pp. 452-458, vol. 10, No. 9.
International Search Report for PCT/KR2016/001133 dated Sep. 21, 2016 [PCT/ISA/210].
Written Opinion for PCT/KR2016/001133 dated Sep. 21, 2016 [PCT/ISA/237].
Korean Patent Office, Communication dated Sep. 22, 2017 by the Korean Patent Office in counterpart Application No. 9-5-2017-067052385.
European Patent Office, Communication dated Jun. 28, 2018 by the European Patent Office in counterpart Application No. 16 74 6826.
Kumar et al., Synthesis and neurite growth evaluation of new analogues of honokiol, a neolignan with potent neurotrophic activity, Bioorganic & Medicinal Chemistry Letters, 22, 2012, pp. 1439-1444.
Burlatsky et al., Detailed Equilibrium Principle in Reversible Bimolecular diffusion-Controlled Reactions, Chemical Physics Letters, vol. 66, No. 3, 1979, pp. 565-569.
Database Registry RN 6093-03-4, entered STN: Nov. 16, 1984.

*Primary Examiner* — Sahar Javanmard
(74) *Attorney, Agent, or Firm* — Sughrue Mion, PLLC

(57) ABSTRACT

The present invention relates to a novel heterocyclic compound inhibiting a cyclin-dependent kinase (CDK) and a pharmaceutical composition comprising the same as an effective ingredient. The heterocyclic compound according to the present invention or pharmaceutically acceptable salt thereof can be effectively used in treating or preventing cancers, degenerative brain diseases, etc.

9 Claims, 6 Drawing Sheets

【Fig. 1】
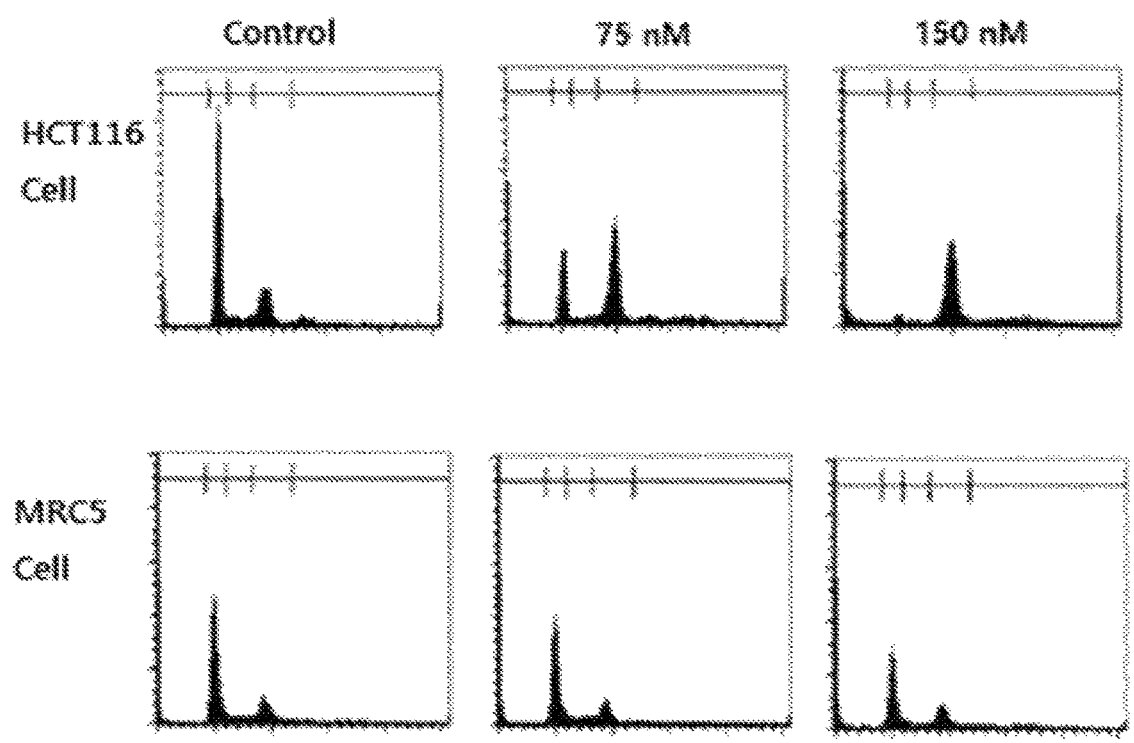

[Fig. 2]
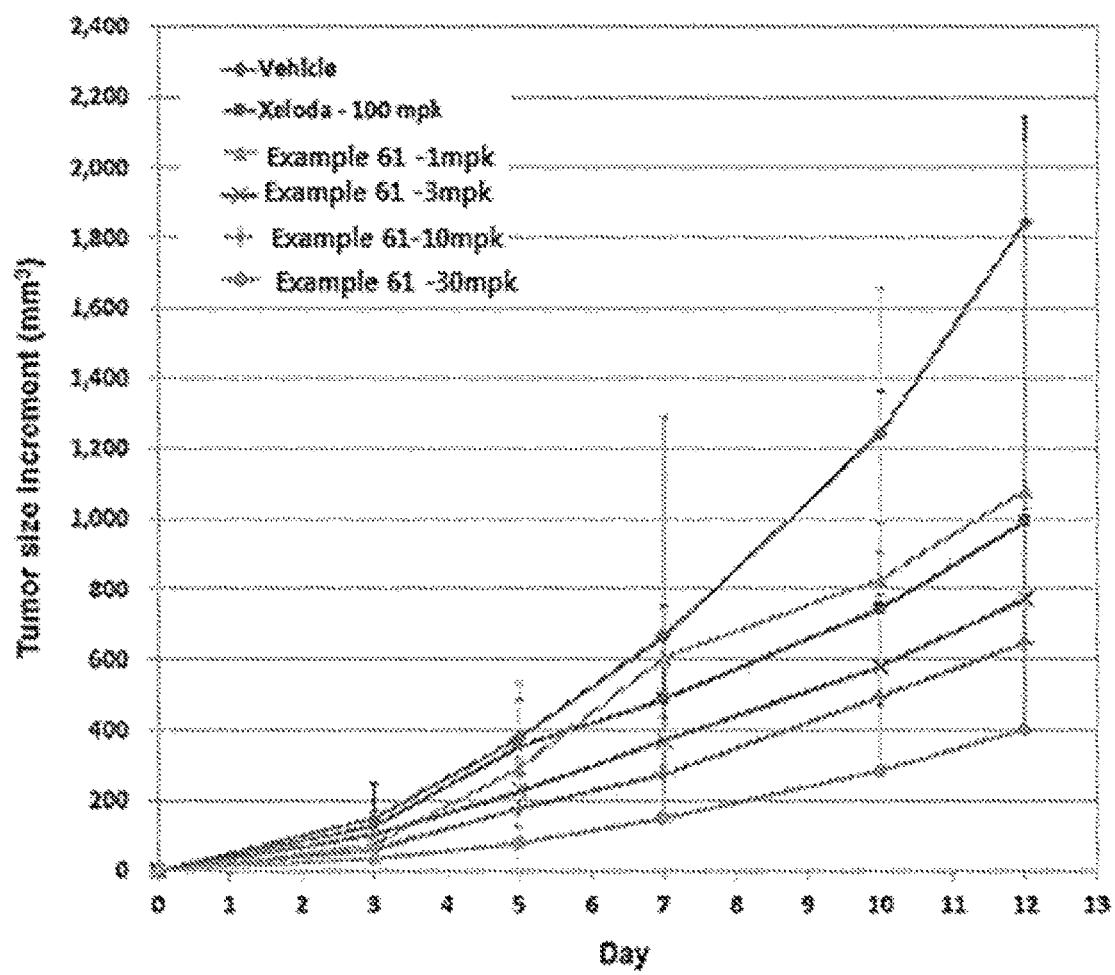

[Fig. 3]
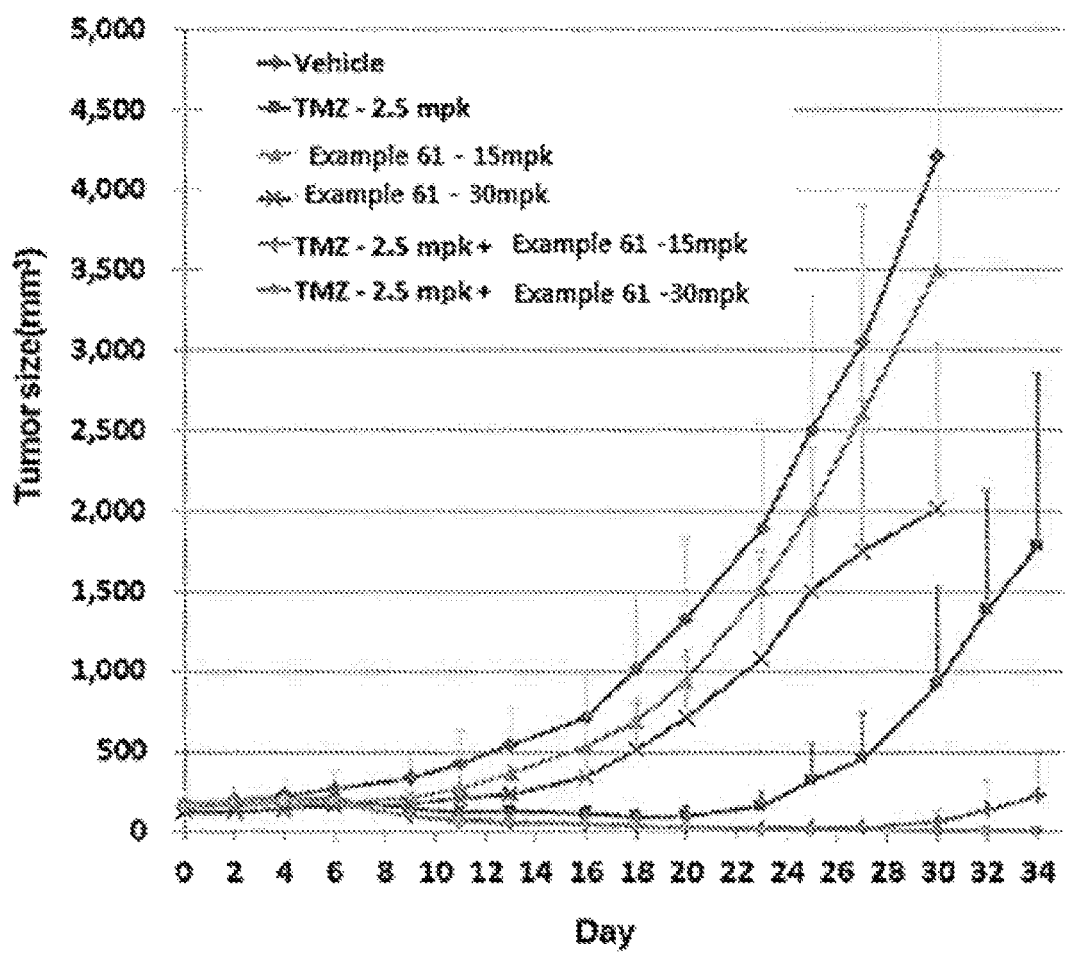

[Fig. 4]
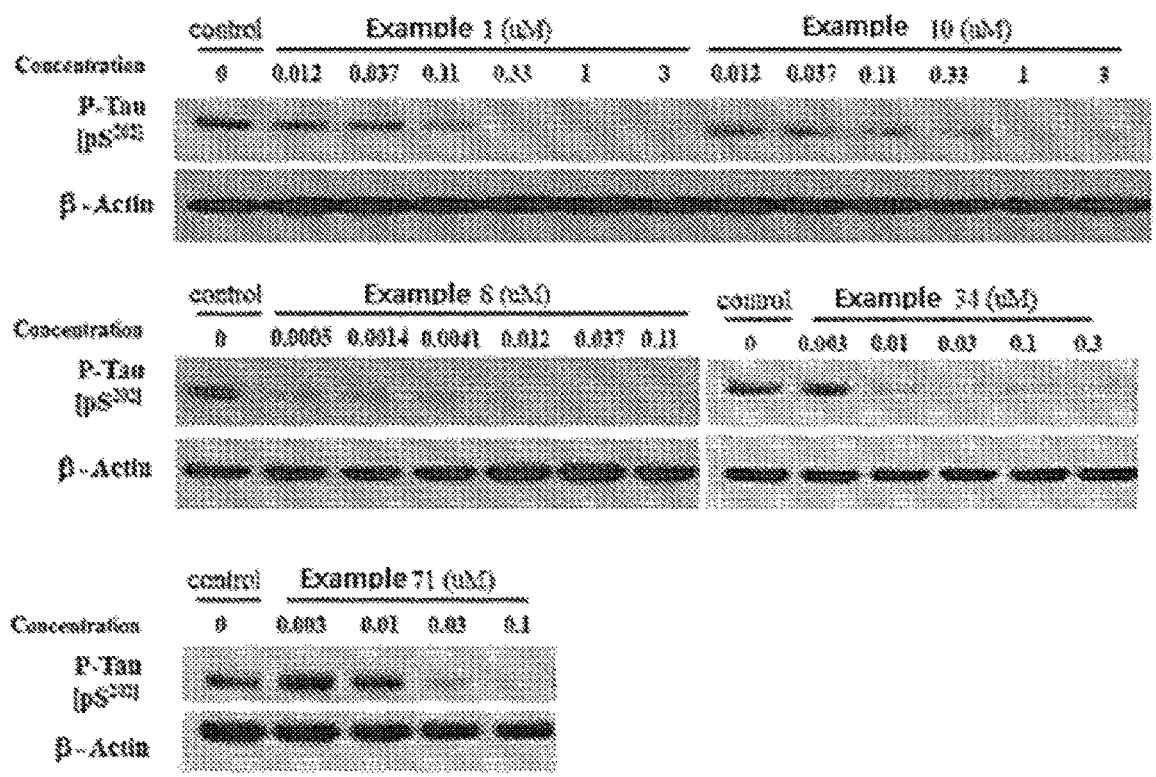

[Fig. 5]
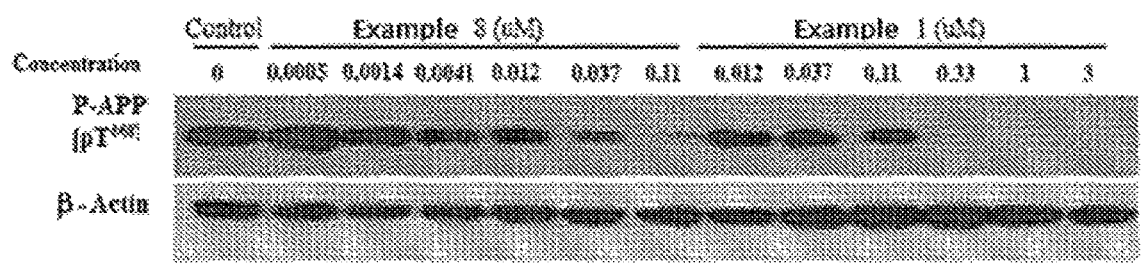
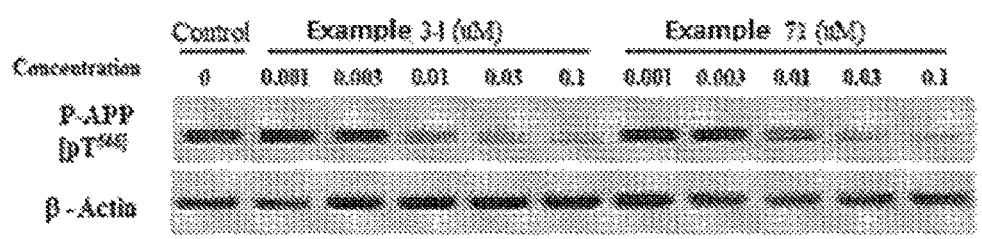

[Fig. 6]
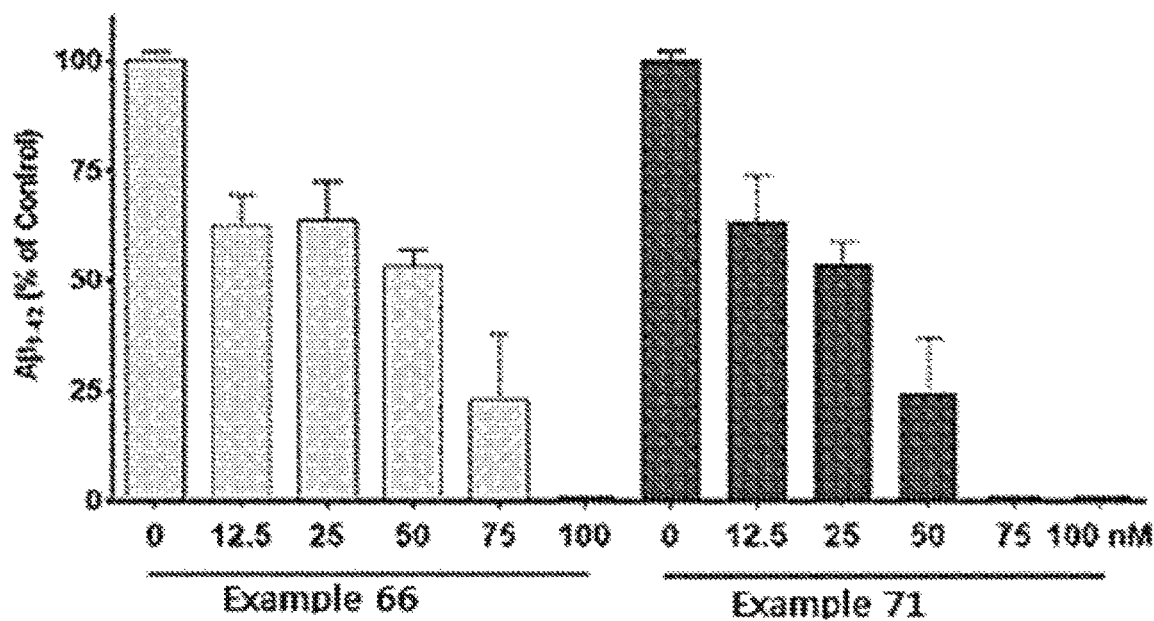

HETEROCYCLIC COMPOUND AND PHARMACEUTICAL COMPOSITION COMPRISING SAME

CROSS REFERENCE TO RELATED APPLICATIONS

This application is a Continuation of U.S. application Ser. No. 15/546,714 filed Jul. 27, 2017, which is a National Stage of International Application No. PCT/KR2016/001133 filed Feb. 2, 2016, claiming priority based on Korean Patent Application No. 10-2015-0017339 filed Feb. 4, 2015, the contents of all of which are incorporated herein by reference in their entirety.

TECHNICAL FIELD

The present invention relates to a novel heterocyclic compound inhibiting the activity of a cyclin-dependent kinase (CDK) and a pharmaceutical composition comprising the same as an effective ingredient.

BACKGROUND ART

A cyclin-dependent kinase (CDK) is a serine/threonine kinase and binds to a cyclin to form a complex which has kinase activity and substrate specificity. A CDK is known as a kinase regulating the cell cycle through an interaction with various cyclins. Further, a CDK is also involved in transcription regulation, epigenetic regulation, metabolism regulation, stem cell self-renewal, neuronal function, etc. (Lim S, et al., Development, 2013, 140(15): 3079-93).

There are 16 CDK isotypes and they play an important role in the cell cycle regulation or transcription regulation depending on the isotype. In particular, CDK1 and CDK2 among CDKs regulating the cell cycle play an important role in a mitosis. CDK2 induces DNA synthesis in S phase and the progression through the cell cycle. CDK1 is involved in the formation of many factors to drive M phase. Accordingly, abnormality of a CDK may cause various cancers. An anticancer agent targeted to CDK abnormality will be effective in treating blood cancers including acute lymphoblastic leukemia (ALL), chronic lymphoblastic leukemia (CLL), acute myeloid leukemia (AML), chronic myeloid leukemia (CML), multiple myeloma (MM), Hodgkin's lymphoma, and non-Hodgkin's lymphoma, and solid cancers including non-small cell lung cancer, small cell lung cancer, gastric cancer, pancreas cancer, glioma, colon cancer, breast cancer, head and neck squamous cell cancer, liver cancer, melanoma, uterine cancer, prostate cancer, ovarian cancer, thyroid cancer, biliary tract cancer, gallbladder cancer, bladder cancer, kidney cancer, esophageal cancer, etc. (Pitts T M, et al., Pharmacol Ther., 2014, 142(2): 58-69).

CDK5, which is not involved in the regulation of the cell cycle or a transcription, is mostly distributed in a brain, and is activated by binding to p25 which is stable in a cell, resulting in continuous activity and thus various degenerative brain diseases. A substance inhibiting CDK5 activity will be useful for treating Alzheimer's disease, Parkinson's disease, and Huntington's chorea. In particular, Alzheimer's disease is caused by the neurodegeneration which is the result of the formation of neurofibrillary tangles (NFT) and amyloid plaques, and CDK5 is important for their formation. CDK5 phosphorylates the serin or threonine residues at Thr181, Ser199, Ser202, Thr212, Ser214, Thr231, Ser235, Ser396, and Ser404 of tau protein and tau protein hyperphosphorylated by CDK5 forms a neurofibrillary tangle (NFT). Amyloid plaque is formed by accumulation of Aβ(amyloid beta protein) which is produced by degradation of Amyloid precursor protein (APP) by the aspartic proteases, β-secretase and γ-secretase, in a brain. In this regard, CDK5 phosphorylates Thr668 residue of APP so that APP can be degraded by β-secretase. Therefore, it is necessary to develop a compound which can inhibit CDK5 activity and thus prevent and treat degenerative brain diseases such as Alzheimer's disease caused by excessive action of CDK5 (Cruz J C, et al., Trends Mol Med., 2004, 10(9): 452-8).

DISCLOSURE

Technical Problem

The present inventors have extensively studied to develop a novel CDK inhibitor. As a result, they discovered that a heterocyclic compound of the following formula (I) shows an excellent CDK inhibitory effect in an in vitro experiment and an animal model experiment and thus can be used for the prevention and treatment of cancers, degenerative brain diseases, etc.

An object of the present invention is, therefore, to provide a compound of the following formula (I) having an excellent CDK inhibitory effect or pharmaceutically acceptable salt thereof.

Another object of the present invention is to provide a pharmaceutical composition comprising the compound of the above formula (I) or pharmaceutically acceptable salt thereof.

Technical Solution

One aspect of the present invention relates to a compound of the following formula (I) or pharmaceutically acceptable salt thereof.

wherein,
X, Y and Z are each independently carbon, nitrogen, oxygen or sulfur;
$R_1$ is aryl;
$R_2$ is hydrogen or $C_1$-$C_6$ alkyl; and
$R_3$ is aryl.

The term "$C_1$-$C_6$ alkyl" as used herein means a straight or branched hydrocarbon having 1 to 6 carbon atoms, which includes methyl, ethyl, n-propyl, i-propyl, n-butyl, i-butyl, n-pentyl, i-pentyl, n-hexyl, etc. but is not limited thereto.

The term "aryl" as used herein includes all of aromatic group, heteroaromatic group and partially reduced derivatives thereof. The aromatic group means a 5 to 15-membered simple or fused ring. The heteroaromatic group means an aromatic group containing at least one atom selected from oxygen, sulfur and nitrogen. Examples of the aryl include phenyl, naphthyl, pyridinyl, pyrimidinyl, pyridazinyl, pyrazinyl, triazinyl, furanyl, thiophenyl, pyrrolyl, indolyl, quinolinyl, imidazolinyl, oxazolyl, thiazolyl, triazolyl, tetrahydronaphthyl, etc., but are not limited thereto.

The term "$C_3$-$C_{10}$ cycloalkyl" as used herein means a simple or fused cyclic hydrocarbon having 3 to 10 carbon atoms, which includes cyclopropyl, cyclobutyl, cyclopentyl, cyclohexyl, etc. but is not limited thereto.

The term "$C_3$-$C_{10}$ heterocycloalkyl" as used herein means a simple or fused cyclic hydrocarbon having 3 to 10 carbon atoms wherein one or more cyclic carbon atoms are substituted with oxygen, sulfur or nitrogen, which includes tetrahydropyranyl, piperidinyl, morpholino, piperazinyl, etc, but are not limited thereto.

One or more hydrogens of the $C_1$-$C_6$ alkyl, $C_3$-$C_{10}$ cycloalkyl, $C_3$-$C_{10}$ heterocycloalkyl and aryl may be substituted with $C_1$-$C_6$ alkyl, $C_2$-$C_6$ alkenyl, $C_2$-$C_6$ alkynyl, $C_3$-$C_{10}$ cycloalkyl, $C_3$-$C_{10}$ heterocycloalkyl, $C_3$-$C_{10}$ heterocycloalkyloxy, $C_1$-$C_6$ haloalkyl, $C_1$-$C_6$ alkoxy, $C_1$-$C_6$ thioalkoxy, aryl, acyl, hydroxy, thio, halogen, amino, $C_1$-$C_6$ alkylamino, alkoxycarbonyl, carboxy, carbamoyl, cyano, nitro, etc.

In one embodiment of the present invention, the compound has formula (I)
wherein,
X, Y and Z are each independently carbon or nitrogen;
$R_1$ is 5- or 6-membered aromatic or heteroaromatic group substituted or unsubstituted with one or more substituents selected from the group consisting of $C_1$-$C_6$ alkyl, $C_3$-$C_{10}$ cycloalkyl, $C_3$-$C_{10}$ heterocycloalkyl, hydroxy, $C_1$-$C_6$ alkoxy, amino, $C_1$-$C_6$ alkylamino, halogen and nitro;
$R_2$ is hydrogen or $C_1$-$C_6$ alkyl; and
$R_3$ is 5- or 6-membered aromatic or heteroaromatic group substituted or unsubstituted with one or more substituents selected from the group consisting of $C_1$-$C_6$ alkyl, $C_3$-$C_{10}$ cycloalkyl, $C_3$-$C_{10}$ heterocycloalkyl, hydroxy, $C_1$-$C_6$ alkoxy, amino, $C_1$-$C_6$ alkylamino, halogen and nitro.

In one embodiment of the present invention, the compound has formula (I)
wherein,
X, Y and Z are each independently carbon or nitrogen;
$R_1$ is 5- or 6-membered aromatic or heteroaromatic group substituted or unsubstituted with one or more substituents selected from the group consisting of $C_1$-$C_6$ alkyl, $C_3$-$C_{10}$ cycloalkyl, $C_3$-$C_{10}$ heterocycloalkyl, hydroxy, $C_1$-$C_6$ alkoxy, amino, $C_1$-$C_6$ alkylamino, halogen and nitro;
$R_2$ is hydrogen or $C_1$-$C_6$ alkyl; and
$R_3$ is 5- or 6-membered heteroaromatic group substituted or unsubstituted with one or more substituents selected from the group consisting of $C_1$-$C_6$ alkyl, $C_3$-$C_{10}$ cycloalkyl, $C_3$-$C_{10}$ heterocycloalkyl, hydroxy, $C_1$-$C_6$ alkoxy, amino, $C_1$-$C_6$ alkylamino, halogen and nitro.

In one embodiment of the present invention, the compound has formula (I)
wherein,
X, Y and Z are each independently carbon or nitrogen;
$R_1$ is phenyl, pyridine, or pyrimidine substituted or unsubstituted with one or more substituents selected from the group consisting of $C_1$-$C_6$ alkyl, $C_3$-$C_{10}$ cycloalkyl, $C_3$-$C_{10}$ heterocycloalkyl, hydroxy, $C_1$-$C_6$ alkoxy, amino, $C_1$-$C_6$ alkylamino, halogen and nitro;
$R_2$ is hydrogen; and
$R_3$ is pyridine, pyrimidine or thiazol substituted or unsubstituted with one or more substituents selected from the group consisting of $C_1$-$C_6$ alkyl, $C_3$-$C_{10}$ cycloalkyl, $C_3$-$C_{10}$ heterocycloalkyl, hydroxy, $C_1$-$C_6$ alkoxy, amino, $C_1$-$C_6$ alkylamino, halogen and nitro.

In one embodiment of the present invention, the compound has formula (I)
wherein,
X, Y and Z are each independently carbon or nitrogen;
$R_1$ is phenyl, pyridine, or pyrimidine substituted or unsubstituted with one or more substituents selected from the group consisting of hydroxy, amino and halogen;
$R_2$ is hydrogen; and
$R_3$ is pyrimidine substituted or unsubstituted with one or more substituents selected from the group consisting of $C_1$-$C_6$ alkyl, $C_3$-$C_{10}$ heterocycloalkyl, amino, $C_1$-$C_6$ alkylamino and halogen.

In one embodiment of the present invention, the compound has formula (I)
wherein,
X is nitrogen; and
Y and Z are carbon.

In one embodiment of the present invention, the compound has formula (I)
wherein,
Y is nitrogen; and
X and Z are carbon.

In one embodiment of the present invention, the compound has formula (I)
wherein,
Z is nitrogen; and
X and Y are carbon.

In one embodiment of the present invention, the compound has formula (I)
wherein,
X and Y are nitrogen; and
Z is carbon.

In one embodiment of the present invention, the compound has formula (I)
wherein,
X and Z are nitrogen; and
Y is carbon.

The pharmaceutically acceptable salt of the present invention may include salts of nontoxic inorganic acid and organic acid such as hydrochloride, phosphate, sulfate, nitrate, stannate, methanesulfonate, p-toluensulfonate, acetate, trifluoroacetate, citrate, maleate, succinate, oxalate, benzoate, tartrate, fumarate, mandelate, propionate, lactate, glycolate, gluconate, galacturonate, glutamate, glutarate, glucuronate, aspartate, ascorbate, carbonate, vanillate, hydroiodate, malate, malonate, etc.

The representative compounds according to the present invention are selected from the following group.
2,6-bis(2-aminopyrimidin-4-yl)pyridin-3-ol;
3,5-bis(2-aminopyrimidin-4-yl)pyrazin-2-ol;
4,6-bis(2-aminopyrimidin-4-yl)pyridin-3-ol;
2'-amino-4-(2-aminopyrimidin-4-yl)-[2,4'-bipyridin]-5-ol;
2'-amino-2-(2-aminopyridin-4-yl)-[4,4'-bipyrimidin]-5-ol;
3,5-bis(2-aminopyrimidin-4-yl)pyridin-2-ol;
6'-amino-6-(2-aminopyrimidin-4-yl)-[2,2'-bipyridin]-3-ol;
2'-amino-6-(2-aminopyrimidin-4-yl)-3'-fluoro-[2,4'-bipyridin]-5-ol;
2-(2-aminopyrimidin-4-yl)-6-(4-hydroxyphenyl)pyridin-3-ol;
2'-amino-6-(2-aminopyrimidin-4-yl)-[2,4'-bipyridin]-5-ol;
6-(2-aminopyrimidin-4-yl)-[2,3'-bipyridin]-5-ol;
6-(2-aminopyrimidin-4-yl)-[2,4'-bipyridin]-5-ol;
2-(2-aminopyrimidin-4-yl)-6-(3-hydroxyphenyl)pyridin-3-ol;
6-(2-aminopyrimidin-4-yl)-3'-fluoro-[2,4'-bipyridin]-5-ol;
6-(4-amino-2-fluorophenyl)-2-(2-aminopyrimidin-4-yl)pyridin-3-ol;
6-(3-aminophenyl)-2-(2-aminopyrimidin-4-yl)pyridin-3-ol;

2-(2-aminopyrimidin-4-yl)-6-(2-fluoro-4-hydroxyphenyl)pyridin-3-ol;
6-(3-amino-2-fluorophenyl)-2-(2-aminopyrimidin-4-yl)pyridin-3-ol;
2-(2-aminopyrimidin-4-yl)-6-(3-fluoro-4-hydroxyphenyl)pyridin-3-ol;
2-(2-aminopyrimidin-4-yl)-6-(2,3-difluoro-4-hydroxyphenyl)pyridin-3-ol;
2'-amino-6-(2-aminopyrimidin-4-yl)-[2,4'-bipyridin]-3',5-diol;
6-(2-aminopyrimidin-4-yl)-2-(4-(methylamino)thiazol-2-yl)pyridin-3-ol;
6-(2-aminopyrimidin-4-yl)-6'-(methylamino)-[2,2'-bipyridin]-3-ol;
2'-amino-6-(2-amino-6-methylpyrimidin-4-yl)-3'-fluoro-[2,4'-bipyridin]-5-ol;
6-(2-amino-6-methylpyrimidin-4-yl)-[2,4'-bipyridin]-5-ol;
6-(2-amino-6-methylpyrimidin-4-yl)-3'-fluoro-[2,4'-bipyridin]-5-ol;
2-(2-amino-6-methylpyrimidin-4-yl)-6-(4-hydroxyphenyl)pyridin-3-ol;
2-(2-amino-6-methylpyrimidin-4-yl)-6-(2,3-difluoro-4-hydroxyphenyl)pyridin-3-ol;
2-(2-amino-6-methylpyrimidin-4-yl)-6-(2-fluoro-4-hydroxyphenyl)pyridin-3-ol;
2-(2-amino-6-methylpyrimidin-4-yl)-6-(3-aminophenyl)pyridin-3-ol;
2'-amino-6-(2-amino-6-isopropylpyrimidin-4-yl)-3'-fluoro-[2,4'-bipyridin]-5-ol;
2'-amino-6-(2-amino-6-(tetrahydro-2H-pyran-4-yl)pyrimidin-4-yl)-3'-fluoro-[2,4'-bipyridin]-5-ol;
2'-amino-6-(2-amino-6-(piperidin-4-yl)pyrimidin-4-yl)-3'-fluoro-[2,4'-bipyridin]-5-ol;
2'-amino-6-(2-amino-6-(1-methylpiperidin-4-yl)pyrimidin-4-yl)-3'-fluoro-[2,4'-bipyridin]-5-ol;
2'-amino-6-(2-amino-6-(1-ethylpiperidin-4-yl)pyrimidin-4-yl)-3'-fluoro-[2,4'-bipyridin]-5-ol;
2'-amino-6-(2-amino-6-(1-propylpiperidin-4-yl)pyrimidin-4-yl)-3'-fluoro-[2,4'-bipyridin]-5-ol;
2'-amino-6-(2-amino-6-(1-isopropylpiperidin-4-yl)pyrimidin-4-yl)-3'-fluoro-[2,4'-bipyridin]-5-ol;
2'-amino-6-(2-amino-6-(1-methylpiperidin-3-yl)pyrimidin-4-yl)-3'-fluoro-[2,4'-bipyridin]-5-ol;
2'-amino-6-(2-amino-6-(1-ethylpiperidin-3-yl)pyrimidin-4-yl)-3'-fluoro-[2,4'-bipyridin]-5-ol;
2'-amino-6-(2-amino-6-(1-propylpiperidin-3-yl)pyrimidin-4-yl)-3'-fluoro-[2,4'-bipyridin]-5-ol;
2'-amino-6-(2-amino-6-(1-isopropylpiperidin-3-yl)pyrimidin-4-yl)-3'-fluoro-[2,4'-bipyridin]-5-ol;
2'-amino-6-(2-amino-5-methyl-6-(1-methylpiperidin-4-yl)pyrimidin-4-yl)-3'-fluoro-[2,4'-bipyridin]-5-ol;
2'-amino-6-(2-amino-6-(1-ethylpiperidin-4-yl)-5-methylpyrimidin-4-yl)-3'-fluoro-[2,4'-bipyridin]-5-ol;
2'-amino-6-(2-amino-5-methyl-6-(1-propylpiperidin-4-yl)pyrimidin-4-yl)-3'-fluoro-[2,4'-bipyridin]-5-ol;
2'-amino-6-(2-amino-6-(1-isopropylpiperidin-4-yl)-5-methylpyrimidin-4-yl)-3'-fluoro-[2,4'-bipyridin]-5-ol;
2'-amino-6-(2-amino-5-methyl-6-(1-methylpiperidin-3-yl)pyrimidin-3-yl)-3'-fluoro-[2,4'-bipyridin]-5-ol;
2'-amino-6-(2-amino-5-methyl-6-(1-propylpiperidin-3-yl)pyrimidin-4-yl)-3'-fluoro-[2,4'-bipyridin]-5-ol;
2'-amino-6-(2-amino-6-(1-isopropylpiperidin-3-yl)-5-methylpyrimidin-4-yl)-3'-fluoro-[2,4'-bipyridin]-5-ol;
2'-amino-6-(2-amino-5-ethyl-6-(1-isopropylpiperidin-4-yl)pyrimidin-4-yl)-3'-fluoro-[2,4'-bipyridin]-5-ol;
2'-amino-6-(2-amino-6-(1-isopropylpiperidin-4-yl)-5-propylpyrimidin-4-yl)-3'-fluoro-[2,4'-bipyridin]-5-ol;

2'-amino-6-(2-amino-6-morpholinopyrimidin-4-yl)-3'-fluoro-[2,4'-bipyridin]-5-ol;
2'-amino-6-(2-amino-6-(dimethylamino)pyrimidin-4-yl)-3'-fluoro-[2,4'-bipyridin]-5-ol;
2'-amino-6-(2-amino-6-(4-methylpiperazin-1-yl)pyrimidin-4-yl)-3'-fluoro-[2,4'-bipyridin]-5-ol;
6-(2-amino-6-chloropyrimidin-4-yl)-[2,4'-bipyridin]-5-ol;
2'-amino-6-(2-amino-5-methylpyrimidin-4-yl)-3'-fluoro-[2,4'-bipyridin]-5-ol;
2'-amino-6-(2-amino-5-ethylpyrimidin-4-yl)-3'-fluoro-[2,4'-bipyridin]-5-ol;
2'-amino-6-(2-amino-5-propylpyrimidin-4-yl)-3'-fluoro-[2,4'-bipyridin]-5-ol;
2'-amino-6-(2-amino-5-isopropylpyrimidin-5-yl)-3'-fluoro-[2,4'-bipyridin]-5-ol;
2'-amino-3'-fluoro-6-(2-(methylamino)-6-(1-methylpiperidin-4-yl)pyrimidin-4-yl)-[2,4'-bipyridin]-5-ol;
2'-amino-6-(2-amino-5,6-dimethylpyrimidin-4-yl)-3'-fluoro-[2,4'-bipyridin]-5-ol;
2,6-bis(2-aminopyrimidin-4-yl)pyridin-3-ol 3hydrochloride;
2,6-bis(2-aminopyrimidin-4-yl)pyridin-3-ol oxalate;
2,6-bis(2-aminopyrimidin-4-yl)pyridin-3-ol malonate;
2,6-bis(2-aminopyrimidin-4-yl)pyridin-3-ol sulfate;
2'-amino-4-(2-aminopyrimidin-4-yl)-[2,4'-bipyridin]-5-ol oxalate;
2'-amino-6-(2-aminopyrimidin-4-yl)-3'-fluoro-[2,4'-bipyridin]-5-ol 3hydrochloride;
2'-amino-6-(2-aminopyrimidin-4-yl)-3'-fluoro-[2,4'-bipyridin]-5-ol acetate;
2'-amino-6-(2-aminopyrimidin-4-yl)-3'-fluoro-[2,4'-bipyridin]-5-ol oxalate;
2'-amino-6-(2-aminopyrimidin-4-yl)-3'-fluoro-[2,4'-bipyridin]-5-ol 2malonate;
2-(2-aminopyrimidin-4-yl)-6-(2-fluoro-4-hydroxyphenyl)pyridin-3-ol 2hydrochloride;
2'-amino-6-(2-amino-6-methylpyrimidin-4-yl)-3'-fluoro-[2,4'-bipyridin]-5-ol 3hydrochloride;
2'-amino-6-(2-amino-6-morpholinopyrimidin-4-yl)-3'-fluoro-[2,4'-bipyridin]-5-ol 4hydrochloride;
2'-amino-6-(2-amino-6-morpholinopyrimidin-4-yl)-3'-fluoro-[2,4'-bipyridin]-5-ol acetate;
2'-amino-6-(2-amino-6-(dimethylamino)pyrimidin-4-yl)-3'-fluoro-[2,4'-bipyridin]-5-ol 4hydrochloride;
2'-amino-6-(2-amino-6-(4-methylpiperazin-1-yl)pyrimidin-4-yl)-3'-fluoro-[2,4'-bipyridin]-5-ol 5hydrochloride;
2'-amino-6-(2-amino-6-(4-methylpiperazin-1-yl)pyrimidin-4-yl)-3'-fluoro-[2,4'-bipyridin]-5-ol acetate;
2'-amino-6-(2-amino-(6-(1-methylpiperidin-4-yl)pyrimidin-4-yl)-3'-fluoro-[2,4'-bipyridin]-5-ol 4hydrochloride;
2'-amino-6-(2-amino-6-(1-methylpiperidin-4-yl)pyrimidin-4-yl)-3'-fluoro-[2,4'-bipyridin]-5-ol 2acetate;
2'-amino-6-(2-amino-6-(1-methylpiperidin-4-yl)pyrimidin-4-yl)-3'-fluoro-[2,4'-bipyridin]-5-ol oxalate;
2'-amino-6-(2-amino-6-(1-methylpiperidin-4-yl)pyrimidin-4-yl)-3'-fluoro-[2,4'-bipyridin]-5-ol malonate;
2'-amino-6-(2-amino-6-isopropylpyrimidin-4-yl)-3'-fluoro-[2,4'-bipyridin]-5-ol 3hydrochloride;
2'-amino-6-(2-amino-6-isopropylpyrimidin-4-yl)-3'-fluoro-[2,4'-bipyridin]-5-ol 2acetate;
2'-amino-6-(2-amino-6-(piperidin-4-yl)pyrimidin-4-yl)-3'-fluoro-[2,4'-bipyridin]-5-ol 4hydrochloride;
2'-amino-6-(2-amino-6-(piperidin-4-yl)pyrimidin-4-yl)-3'-fluoro-[2,4'-bipyridin]-5-ol acetate;

2'-amino-6-(2-amino-6-(tetrahydro-2H-pyran-4-yl)pyrimidin-4-yl)-3'-fluoro-[2,4'-bipyridin]-5-ol 3hydrochloride;

2'-amino-6-(2-amino-6-(1-ethylpiperidin-4-yl)pyrimidin-4-yl)-3'-fluoro-[2,4'-bipyridin]-5-ol 4hydrochloride;

2'-amino-6-(2-amino-6-(1-propylpiperidin-4-yl)pyrimidin-4-yl)-3'-fluoro-[2,4'-bipyridin]-5-ol 4hydrochloride;

2'-amino-6-(2-amino-6-(1-isopropylpiperidin-4-yl)pyrimidin-4-yl)-3'-fluoro-[2,4'-bipyridin]-5-ol 4hydrochloride;

2'-amino-6-(2-amino-6-(1-methylpiperidin-3-yl)pyrimidin-4-yl)-3'-fluoro-[2,4'-bipyridin]-5-ol 4hydrochloride;

2'-amino-6-(2-amino-6-(1-ethylpiperidin-3-yl)pyrimidin-4-yl)-3'-fluoro-[2,4'-bipyridin]-5-ol 4hydrochloride;

2'-amino-6-(2-amino-6-(1-propylpiperidin-3-yl)pyrimidin-4-yl)-3'-fluoro-[2,4'-bipyridin]-5-ol 4hydrochloride;

2'-amino-6-(2-amino-6-(1-isopropylpiperidin-3-yl)pyrimidin-4-yl)-3'-fluoro[2,4'-bipyridin]-5-ol 4hydrochloride;

2'-amino-6-(2-amino-5-methyl-6-(1-methylpiperidin-4-yl)pyrimidin-4-yl)-3'-fluoro-[2,4'-bipyridin]-5-ol 4hydrochloride;

2'-amino-6-(2-amino-6-(1-ethylpiperidin-4-yl)-5-methylpyrimidin-4-yl)-3'-fluoro-[2,4'-bipyridin]-5-ol 4hydrochloride;

2'-amino-6-(2-amino-5-methyl-6-(1-propylpiperidin-4-yl)pyrimidin-4-yl)-3'-fluoro-[2,4'-bipyridin]-5-ol 4hydrochloride;

2'-amino-6-(2-amino-6-(1-isopropylpiperidin-4-yl)-5-methylpyrimidin-4-yl)-3'-fluoro-[2,4'-bipyridin]-5-ol 4hydrochloride;

2'-amino-6-(2-amino-5-methyl-6-(1-methylpiperidin-3-yl)pyrimidin-3-yl)-3'-fluoro-[2,4'-bipyridin]-5-ol 4hydrochloride;

2'-amino-6-(2-amino-5-methyl-6-(1-propylpiperidin-3-yl)pyrimidin-4-yl)-3'-fluoro-[2,4'-bipyridin]-5-ol 4hydrochloride;

2'-amino-6-(2-amino-6-(1-isopropylpiperidin-3-yl)-5-methylpyrimidin-4-yl)-3'-fluoro-[2,4'-bipyridin]-5-ol 4hydrochloride;

2'-amino-6-(2-amino-5-methylpyrimidin-4-yl)-3'-fluoro-[2,4'-bipyridin]-5-ol 3hydrochloride;

2'-amino-6-(2-amino-5,6-dimethylpyrimidin-4-yl)-3'-fluoro-[2,4'-bipyridin]-5-ol 3hydrochloride;

2'-amino-6-(2-amino-5-ethylpyrimidin-4-yl)-3'-fluoro-[2,4'-bipyridin]-5-ol 3hydrochloride;

2'-amino-6-(2-amino-5-propylpyrimidin-4-yl)-3'-fluoro-[2,4'-bipyridin]-5-ol 3hydrochloride;

2'-amino-6-(2-amino-5-isopropylpyrimidin-5-yl)-3'-fluoro-[2,4'-bipyridin]-5-ol 3hydrochloride;

2'-amino-6-(2-amino-5-ethyl-6-(1-isopropylpiperidin-4-yl)pyrimidin-4-yl)-3'-fluoro-[2,4'-bipyridin]-5-ol 4hydrochloride; and 2'-amino-6-(2-amino-6-(1-isopropylpiperidin-4-yl)-5-propylpyrimidin-4-yl)-3'-fluoro-[2,4'-bipyridin]-5-ol 4hydrochloride.

The processes for preparing the compounds according to the present invention are depicted in the following Reaction Schemes 1 to 10. However, those illustrated in the following Reaction Schemes represent only typical processes used in the present invention. The manipulation order, reagents, reaction conditions, etc. may be changed without limit.

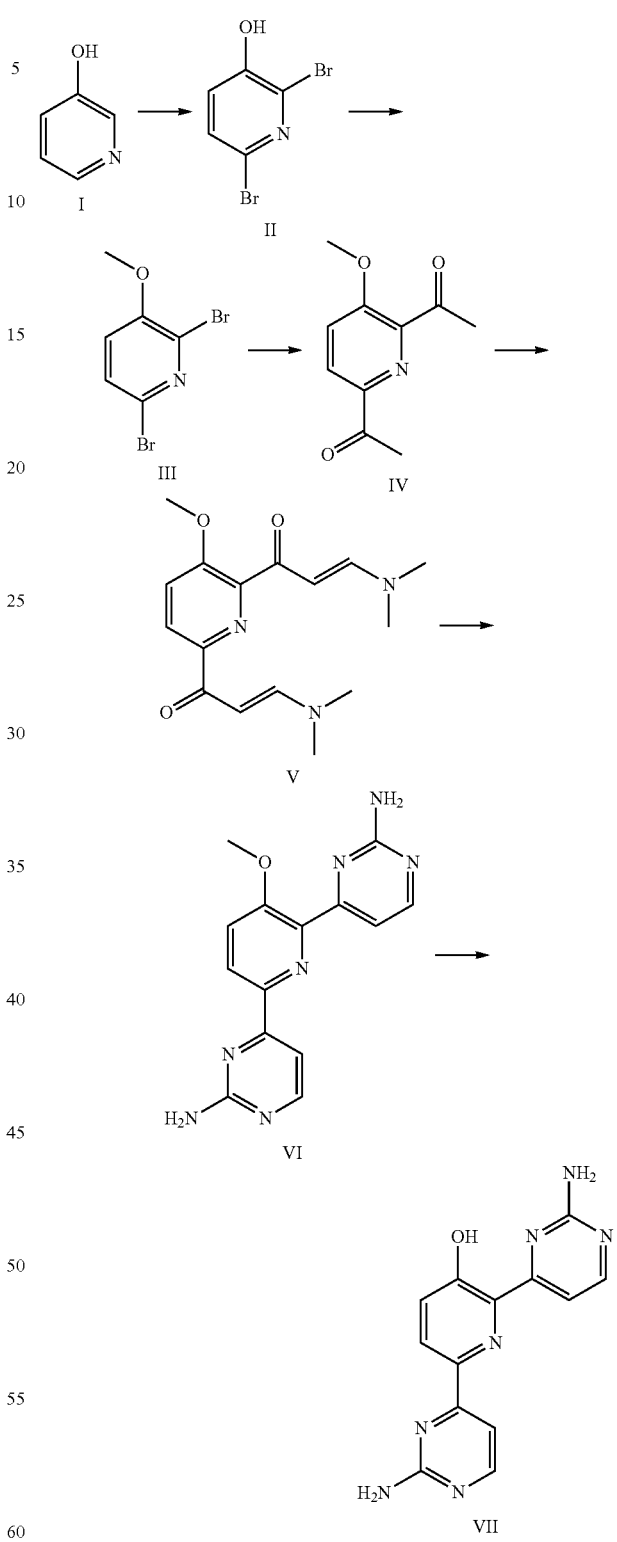

[Reaction Scheme 1]

Reaction Scheme 1 shows a process of six steps for preparing the compound (VII) using commercially available pyridine alcohol (I) as a starting material.

In step 1, 1 to 5 equivalents of bromine is added to an aqueous solution of 1 to 5 equivalents of inorganic bases such as KOH, NaOH, etc. and then the compound (I) is added to the mixture to react at 0° C. to room temperature to give the compound (II). 10 to 30% of the aqueous solution of inorganic bases is used.

In step 2, the compound (II) obtained in step 1 is reacted with 1 to 5 equivalents of iodomethane (CH₃I) in an organic solvent in the presence of a base such as potassium carbonate (K₂CO₃), sodium carbonate (Na₂CO₃), sodium hydrogen carbonate (NaHCO₃), etc. to give the compound (III). The organic solvent may be acetone, acetonitrile, dichloromethane, chloroform, tetrahydrofuran, N,N-dimethylformamide, etc. The base may be used in an amount of 1 to 3 equivalents relative to the compound (I) and the reaction of the base with the compound (I) may be conducted at room temperature to reflux temperature.

In step 3, the compound (III) obtained in step 2, palladium catalyst, and 1,3-bis(diphenylphosphino)propane (DPPP) are stirred with reflux in an organic solvent or an ionic liquid in the presence of butyl vinyl ether and triethylamine to give the compound (IV). The solvent may be ethylene glycol, or an ionic liquid such as 1-butyl-3-methylimidazolium tetrafluoroborate ([bmim][BF₄]), the palladium catalyst is 0.1 to 1 mol % of palladium (II) acetate (Pd(OAc)₂), and the ligand may be 0.1 to 1 mol % of 1,3-bis(diphenylphosphino) propane.

In step 4, the compound (IV) obtained in step 3 is stirred with reflux in the presence of 2 to 30 equivalents of N,N-Dimethylformamide dimethyl acetal (DMFDMA) to give the compound (V).

In step 5, the compound (V) obtained in step 4 is reacted with 1 to 3 equivalents of guanidine hydrochloride in an organic solvent in the presence of 4 to 12 equivalents of a base to give the compound (VI). The base may be sodium methoxide (NaOMe), sodium ethoxide (NaOEt), potassium hydroxide (KOH), etc. and the solvent may be methanol, ethanol, etc.

In step 6, the compound (VI) obtained in step 5 is reacted with 5 to 30 equivalents of pyridine hydrochloride to give the compound (VII). The reaction temperature is 150° C. to 200° C.

[Reaction Scheme 2]

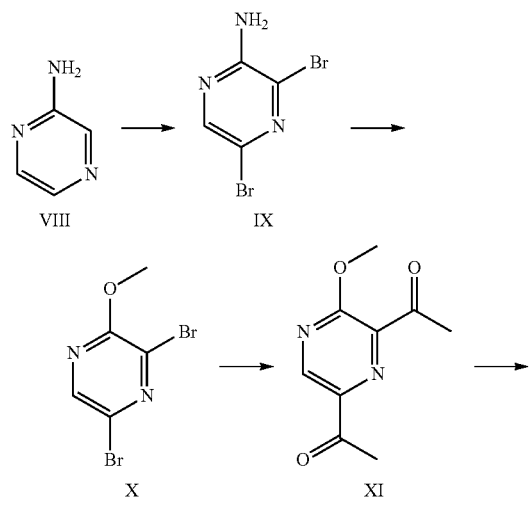

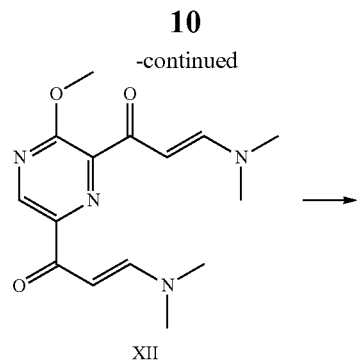

XII

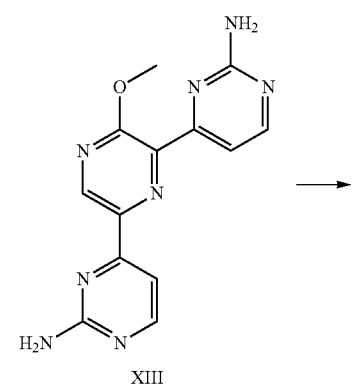

XIII

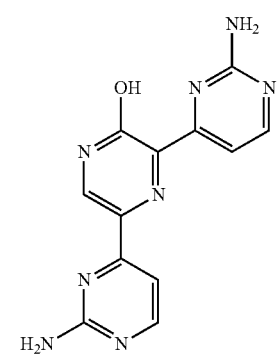

XIV

Reaction Scheme 2 shows a process of six steps for preparing the compound (XIV) using a commercially available aminopyrazine (VIII) as a starting material.

In step 1, aminopyrazine (VIII) is reacted with 2 to 4 equivalents of N-bromosuccinimide (NBS) at 0° C. to room temperature to give the compound (IX). A reaction solvent such as a mixture of water and dimethylsulfoxide (DMSO), acetonitrile, dichloromethane or chloroform may be used for the reaction.

In step 2, 1.5 to 5 equivalents of isoamylnitrite is used in methanol solvent to give the compound (X).

In step 3, the compound (XI) is prepared in accordance with the same procedure as the step 3 of Reaction Scheme 1. In step 4, the compound (XII) is prepared in accordance with the same procedure as the step 4 of Reaction Scheme 1. In step 5, the compound (XIII) is prepared in accordance with the same procedure as the step 5 of Reaction Scheme 1. In step 6, the compound (XIV) is prepared in accordance with the same procedure as the step 6 of Reaction Scheme 1.

[Reaction Scheme 3]

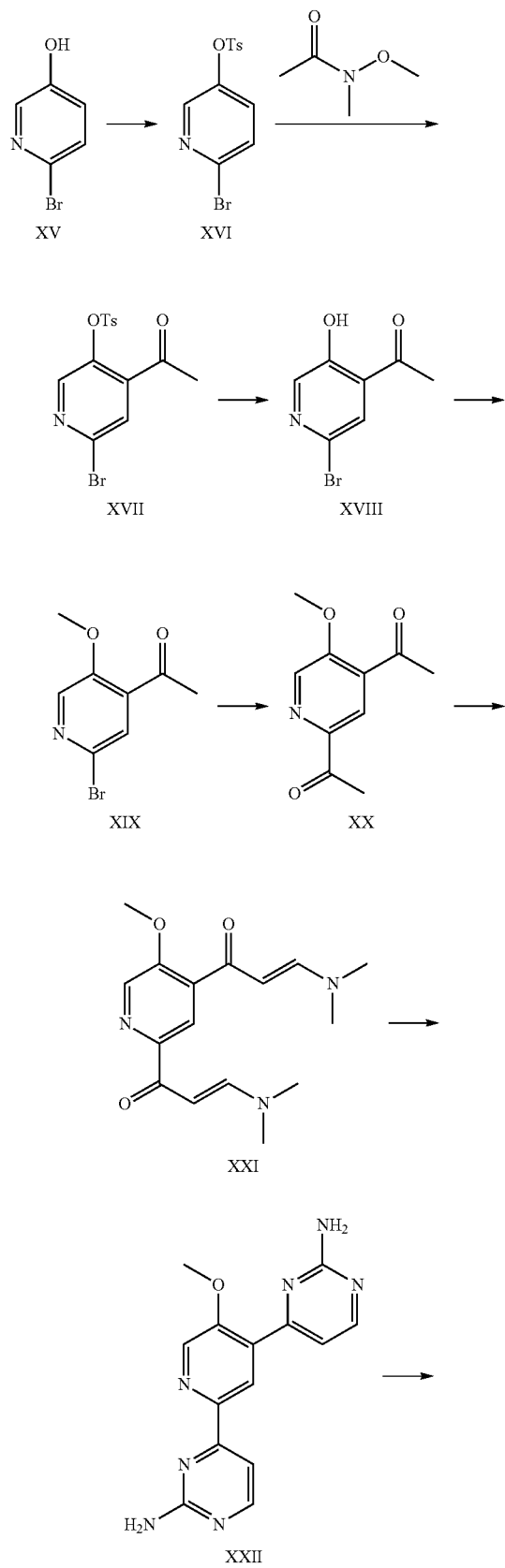

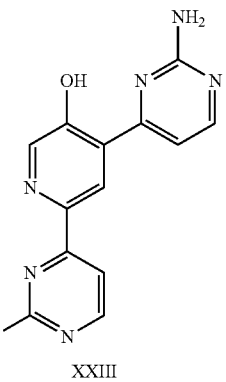

Reaction Scheme 3 shows a process of eight steps for preparing the compound (XXIII) using a commercially available 6-bromo-pyridin-3-ol (XV) as a starting material.

In step 1, 6-bromo-pyridin-3-ol (XV) is reacted with 4-toluenesulfonyl chloride (TsCl) in an organic solvent in the presence of 1 to 3 equivalents of a base such as triethylamine to give the compound (XVI). The organic solvent may be dichloromethane, chloroform, etc. and 4-toluenesulfonyl chloride is used in an amount of 1 to 2 equivalents.

In step 2, the compound (XVI) obtained in step 1 is dissolved in an organic solvent and then 1 to 4 equivalents of a base such as lithium diisopropylamide (LDA), n-butyl-lithium (n-BuLi), etc and 1.5 to 5 equivalents of N-methoxy-N-methyl acetamide are used to give the compound (XVII). The organic solvent may be tetrahydrofuran, diethylester, etc.

In step 3, the compound (XVII) obtained in step 2 is dissolved in an organic solvent, and then 1 to 4 equivalents of a base is used to give the compound (XVIII). The organic solvent is a mixture of tetrahydrofuran, methanol and water and the base may be lithium hydroxide (LiOH), sodium hydroxide (NaOH), potassium hydroxide (KOH), etc.

In step 4, the compound (XIX) is prepared in accordance with the same procedure as the step 2 of Reaction Scheme 1. In step 5, the compound (XX) is prepared in accordance with the same procedure as the step 3 of Reaction Scheme 1. In step 6, the compound (XXI) is prepared in accordance with the same procedure as the step 4 of Reaction Scheme 1. In step 7, the compound (XXII) is prepared in accordance with the same procedure as the step 5 of Reaction Scheme 1. In step 8, the compound (XXIII) is prepared in accordance with the same procedure as the step 6 of Reaction Scheme 1.

[Reaction Scheme 4]

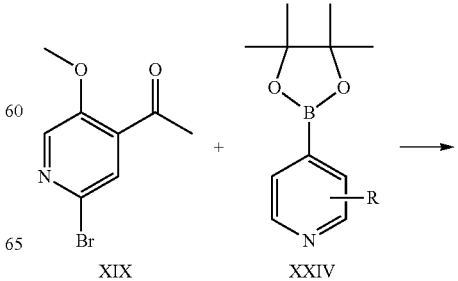

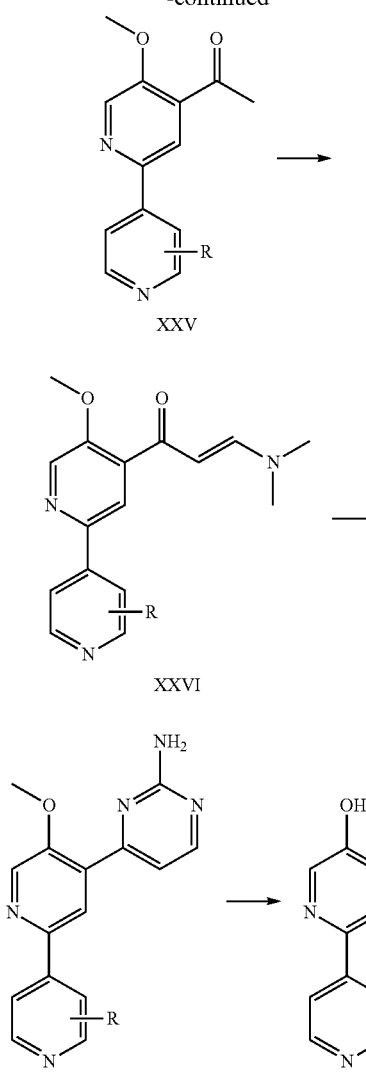

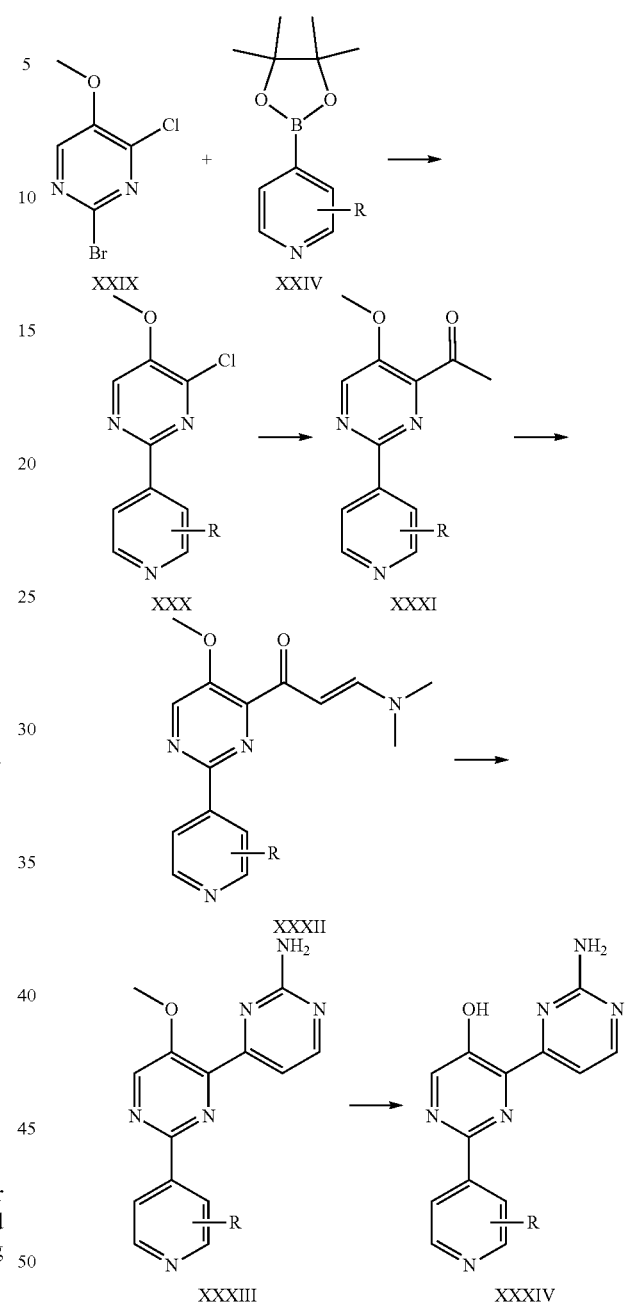

Reaction Scheme 4 shows a process of four steps for preparing the compound (XXVIII) using the compound (XIX) prepared in step 4 of Reaction Scheme 3 as a starting material.

In step 1, the compound (XXV) is prepared through Suzuki reaction using the compound (XIX) obtained in step 4 of Reaction Scheme 3, 0.5 to 3 equivalents of boronate compound (XXIV) which is commercially available or easily produced, and 1 to 5 mol % of a palladium catalyst. The palladium catalyst is tetrakis(triphenylphosphine)palladium(0) and the reaction solvent is a mixture of ethylene glycol dimethylester and water.

In step 2, the compound (XXVI) is prepared in accordance with the same procedure as the step 4 of Reaction Scheme 1. In step 3, the compound (XXVII) is prepared in accordance with the same procedure as the step 5 of Reaction Scheme 1. In step 4, the compound (XXVIII) is prepared in accordance with the same procedure as the step 6 of Reaction Scheme 1.

Reaction Scheme 5 shows a process of five steps for preparing the compound (XXXIV) using a commercially available 2,4-dichloro-5-methoxypyrimidine (XXIX) as a starting material.

In step 1, the compound (XXX) is prepared in accordance with the same procedure as the step 1 of Reaction Scheme 4. In step 2, the compound (XXXI) is prepared in accordance with the same procedure as the step 3 of Reaction Scheme 1. In step 3, the compound (XXXII) is prepared in accordance with the same procedure as the step 4 of Reaction Scheme 1. In step 4, the compound (XXXIII) is prepared in accordance with the same procedure as the step 5 of Reaction Scheme 1. In step 5, the compound (XXXIV) is prepared in accordance with the same procedure as the step 6 of Reaction Scheme 1.

[Reaction Scheme 6]

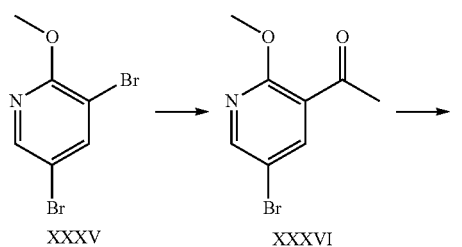

XXXV  XXXVI

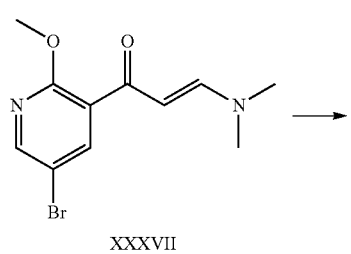

XXXVII

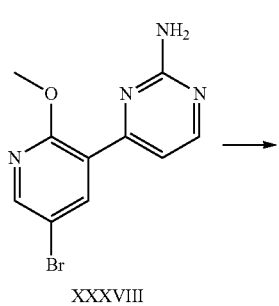

XXXVIII

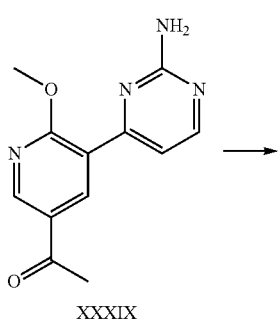

XXXIX

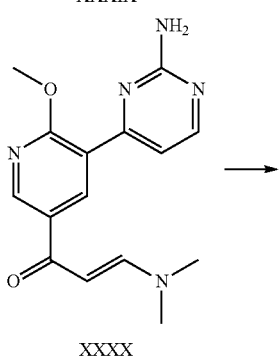

XXXX

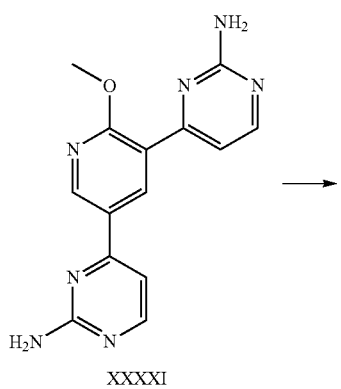

XXXXI

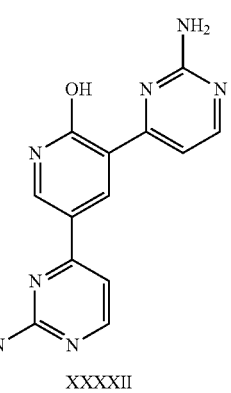

XXXXII

Reaction Scheme 6 shows a process of seven steps for preparing the compound (XXXXII) using a commercially available 3,5-bromo-2-methoxypyridine (XXXV) as a starting material.

In step 1, the compound (XXXVI) is prepared in accordance with the same procedure as the step 3 of Reaction Scheme 1. In step 2, the compound (XXXVII) is prepared in accordance with the same procedure as the step 4 of Reaction Scheme 1. In step 3, the compound (XXXVIII) is prepared in accordance with the same procedure as the step 5 of Reaction Scheme 1. In step 4, the compound (XXXIX) is prepared in accordance with the same procedure as the step 3 of Reaction Scheme 1. In step 5, the compound (XXXX) is prepared in accordance with the same procedure as the step 4 of Reaction Scheme 1. In step 6, the compound (XXXXI) is prepared in accordance with the same procedure as the step 5 of Reaction Scheme 1. In step 7, the compound (XXXXII) is prepared in accordance with the same procedure as the step 6 of Reaction Scheme 1.

[Reaction Scheme 7]

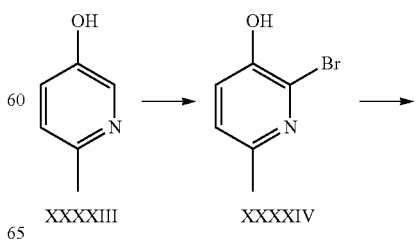

XXXXIII  XXXXIV

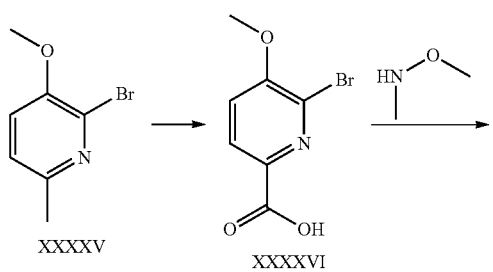
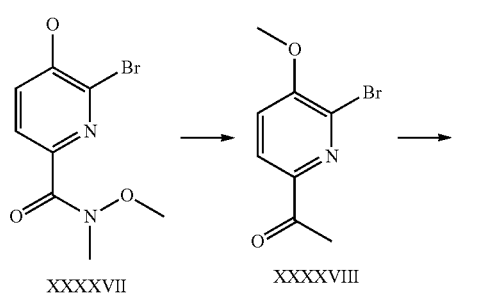
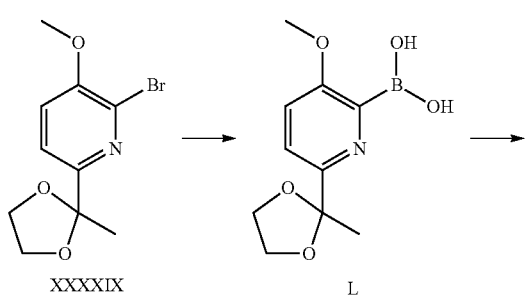
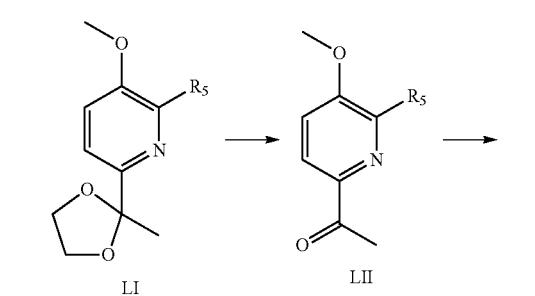
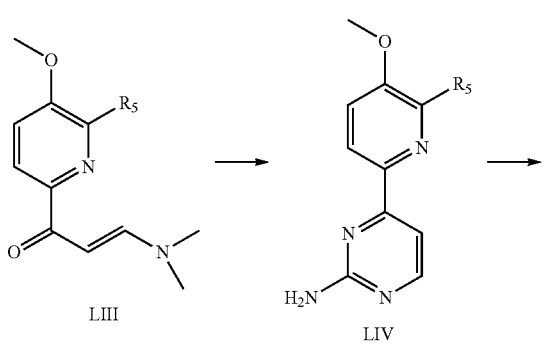

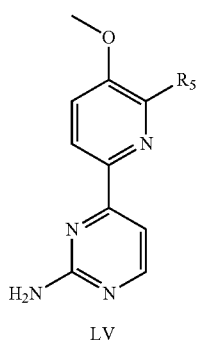

Reaction Scheme 7 shows a process of twelve steps for preparing the compound (LV) using a commercially available 5-hydroxy-2-methylpyridine (XXXXIII) as a starting material.

In step 1, 5-hydroxy-2-methylpyridine (XXXXIII) is reacted with 0.5 to 3 equivalents of bromine in pyridine solvent to give the compound (XXXXIV).

In step 2, the compound (XXXXV) is prepared in accordance with the same procedure as the step 2 of Reaction Scheme 1.

In step 3, the compound (XXXXV) obtained in step 2 is dissolved in water and then 2 to 5 equivalents of potassium permanganate ($KMnO_4$) is used to give the compound (XXXXVI).

In step 4, the compound (XXXXVI) obtained in step 3 is dissolved in an organic solvent and then it is subjected to 1-ethyl-3-(3-dimethylaminopropyl)carbodiimide (EDC) coupling reaction with N,O-dimethylhydroxyamine hydrochloride to give the compound (XXXXVII). The organic solvent may be dichloromethane, N,N-dimethylformamide, etc.

In step 5, the compound (XXXXVII) obtained in step 4 is dissolved in an organic solvent and then 1 to 3 equivalents of methylmagnesium bromide is used to give the compound (XXXXVIII). The organic solvent may be tetrahydrofuran, diethylester, etc.

In step 6, the compound (XXXXVIII) obtained in step 5 is dissolved in an organic solvent and then an acetyl group is converted to an acetal group using an excess amount of ethylene glycol and 0.1 to 0.5 equivalents of p-toluenesulfonic acid to give the compound (XXXXIX). The organic solvent may be benzene, toluene, etc.

In step 7, the compound (XXXXIX) obtained in step 6 is dissolved in an organic solvent and then 2 to 3 equivalents of triisopropyl borate is used to give boronic acid (L). The organic solvent may be diethylester, tetrahydrofuran, etc.

In step 8, the compound (LI) is prepared in accordance with the same procedure as the step 1 of Reaction Scheme 4.

In step 9, the compound (LI) obtained in step 8 is dissolved in a mixture of water and acetone and then it is reacted with 0.1 to 0.7 equivalents of pyridimium p-toluenesulfonate to remove the acetal group to give the compound (LII).

In step 10, the compound (LIII) is prepared in accordance with the same procedure as the step 4 of Reaction Scheme 1. In step 11, the compound (LIV) is prepared in accordance with the same procedure as the step 5 of Reaction Scheme 1. In step 12, the compound (LV) is prepared in accordance with the same procedure as the step 6 of Reaction Scheme 1.

[Reaction Scheme 8]

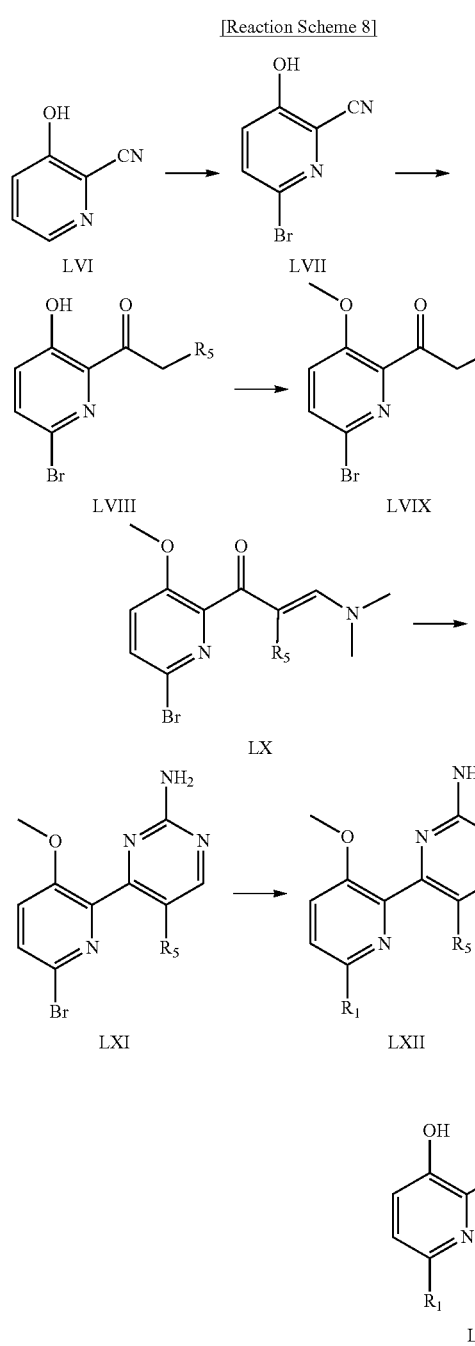

[Reaction Scheme 9]

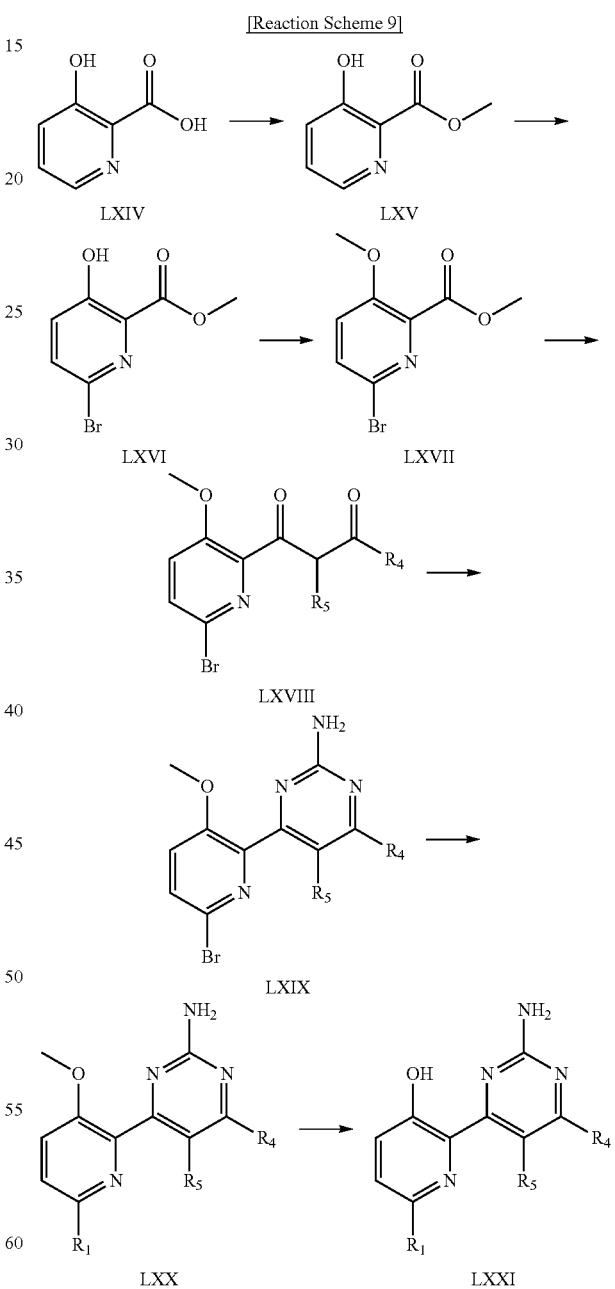

In step 3, the compound (LIX) is prepared in accordance with the same procedure as the step 2 of Reaction Scheme 1. In step 4, the compound (LX) is prepared in accordance with the same procedure as the step 4 of Reaction Scheme 1. In step 5, the compound (LXI) is prepared in accordance with the same procedure as the step 5 of Reaction Scheme 1. In step 6, the compound (LXII) is prepared in accordance with the same procedure as the step 1 of Reaction Scheme 4. In step 7, the compound (LXIII) is prepared in accordance with the same procedure as the step 6 of Reaction Scheme 1.

Reaction Scheme 8 shows a process of seven steps for preparing the compound (LXIII) using a commercially available 2-cyano-3-hydroxypyridine (LVI) as a starting material.

In step 1, 2-cyano-3-hydroxypyridine (LVI) is dissolved in distilled water and then 0.5 to 2 equivalents of N-Bromosuccinimide (NBS) is added to the resulting solution to give the compound (LVII) through a bromination reaction.

In step 2, the compound (LVII) obtained in step 1 is dissolved in an organic solvent and then 1 to 4 equivalents of alkylmagnesium bromide or alkylmagnesium chloride is used to introduce alkylcarbonyl group to give the compound (LVIII). The organic solvent may be tetrahydrofuran, diethylester, etc.

Reaction Scheme 9 shows a process of seven steps for preparing the compound (LXXI) using a commercially available 3-hydroxypicolinic acid (LXIV) as a starting material.

In step 1, 3-hydroxypicolinic acid (LXIV) is dissolved in methanol and then 0.5 mL/1 g to 2 mL/1 g of sulfuric acid is added to the resulting solution to give the compound (LXV) by esterification.

In step 2, the compound (LXVI) is prepared in accordance with the same procedure as the step 1 of Reaction Scheme 1. In step 3, the compound (LXVII) is prepared in accordance with the same procedure as the step 2 of Reaction Scheme 1.

In step 4, the compound (LXVII) obtained in step 3 is dissolved in an organic solvent, and then diketone is introduced using 1 to 3 equivalents of alkyl ketone to give the compound (LXVIII). The organic solvent may be tetrahydrofuran, diethylester, etc.

In step 5, the compound (LXVIII) obtained in step 4 is reacted with 1 to 3 equivalents of guanidine carbonate in an organic solvent in the presence of 0 to 4 equivalents of a base to give the compound (LXIX). The base may be potassium carbonate ($K_2CO_3$), sodium carbonate ($Na_2CO_3$), sodium methoxide (NaOMe), sodium ethoxide (NaOEt), potassium hydroxide (KOH), etc. and the solvent may be methanol, ethanol, etc.

In step 6, the compound (LXX) is prepared in accordance with the same procedure as the step 1 of Reaction Scheme 4. In step 7, the compound (LXXI) is prepared in accordance with the same procedure as the step 6 of Reaction Scheme 1.

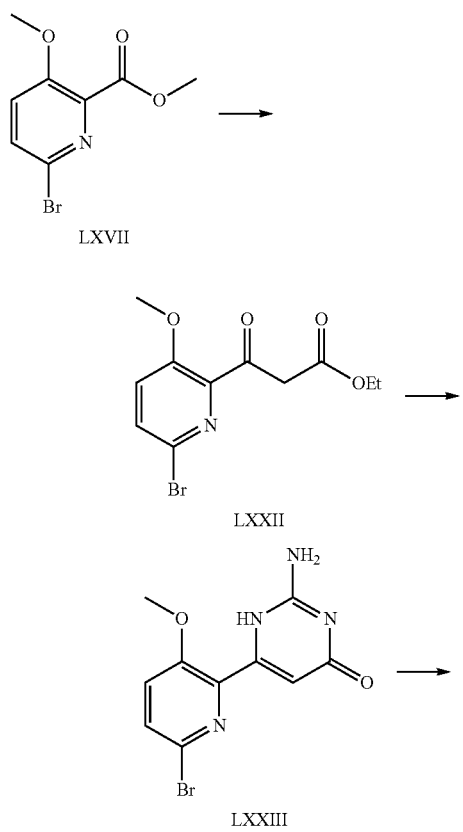

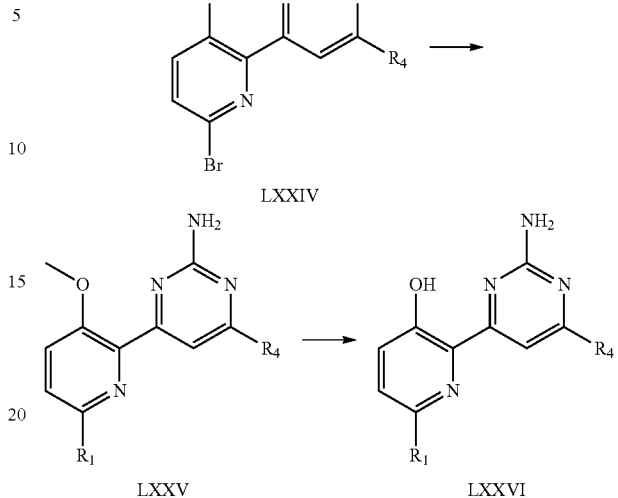

Reaction Scheme 10 shows a process of five steps for preparing the compound (LXXVI) using the compound (LXVII) obtained in step 3 of Reaction Scheme 9 as a starting material.

In step 1, the compound (LXVII) obtained in step 3 of Reaction Scheme 9 is dissolved in ethylacetate and then a base is used to give diketone. The base may be potassium t-butoxide (t-BuOK), lithium bis(trimethylsilyl)amide (LiHMDS), lithium diisopropylamine (LDA), etc.

In step 2, the compound (LXXII) obtained in step 1 is dissolved in an organic solvent, and then reacted with 1 to 4 equivalents of guanidine carbonate to give the compound (LXXIII) The solvent may be methanol, ethanol, isopropanol, etc.

In step 3, the compound (LXXIII) obtained in step 2 is dissolved in an organic solvent and then 1 to 4 equivalents of (benzotriazol-1-yloxy)tris(dimethylamino)phosphonium hexafluorophosphate (BOP) and 1 to 4 equivalents of 1,8-diazabicyclo[5,4,0]undec-7-ene (DBU) are added dropwise to the resulting solution and then an amine compound is added to the solution to give the compound (LXXIV). The solvent may be acetonitrile, tetrahydrofuran, etc.
and amine may be morpholine, piperidine, piperazine, etc.

In step 4, the compound (LXXV) is prepared in accordance with the same procedure as the step 1 of Reaction Scheme 4. In step 5, the compound (LXXVI) is prepared in accordance with the same procedure as the step 6 of Reaction Scheme 1.

The compounds according to the present invention prepared as described above may be prepared as a pharmaceutically acceptable salt in accordance with a conventional method in the art.

In one embodiment of the present invention, a useful pharmaceutically acceptable salt may be an acid addition salt formed by a free acid. An acid addition salt may be prepared by a conventional method in the art. For example, a compound is dissolved in an excess amount of aqueous solution of an acid at room temperature or with heat, and the resulting salt is precipitated with a water miscible organic solvent such as methanol, ethanol, acetone or acetonitrile. Or the mixture is evaporated to dry and recrystallized to give a salt.

One aspect of the present invention relates to a pharmaceutical composition for inhibiting a cyclin-dependent kinase (CDK) comprising the compound of the above formula (I) or pharmaceutically acceptable salt thereof together with a pharmaceutically acceptable carrier, in particular, a pharmaceutical composition for prevention or treatment of cancers or degenerative brain diseases.

In one embodiment of the present invention, the compound of the above formula (I) or pharmaceutically acceptable salt thereof induces anticancer effect through regulation of the cell cycle by inhibiting a CDK and therefore can be used for treating blood cancers including Acute lymphoblastic leukemia (ALL), Chronic lymphoblastic leukemia (CLL), Acute myeloid leukemia (AML), Chronic myeloid leukemia (CML), multiple myeloma (MM), Hodgkin's lymphoma, and non-Hodgkin's lymphoma, and solid cancers including non-small cell lung cancer, small cell lung cancer, gastric cancer, pancreas cancer, glioma, colon cancer, breast cancer, head and neck squamous cell cancer, liver cancer, melanoma, uterine cancer, prostate cancer, ovarian cancer, thyroid cancer, biliary tract cancer, gallbladder cancer, bladder cancer, kidney cancer, esophageal cancer, etc.

Further, the compound of the above formula (I) or pharmaceutically acceptable salt thereof can pass through blood brain barrier (BBB) and therefore can be used for treating glioma such as astrocytoma, anaplastic astrocytoma, and glioblastoma, brain tumor such as pituitary adenoma, medulloblastoma, and meningioma, or metastatic brain tumor metastasized from lung cancer, breast cancer, melanoma, etc.

In one embodiment of the present invention, the compound of the above formula (I) or pharmaceutically acceptable salt thereof inhibits a phosphorylation of tau protein and a generation of Aβ, which are causes of Alzheimer disease, by CDK5 inhibition. Therefore, the compound of the above formula (I) or pharmaceutically acceptable salt thereof can be used for treating Alzheimer's disease, Huntington's chorea, Parkinson's disease, etc.

The pharmaceutical composition according to the present invention can be administered orally, e.g., ingestion or inhalation; or parenterally, e.g., injection, deposition, implantation or suppositories. The injection can be, for example, intravenous, subcutaneous, intramuscular or intraperitoneal. Depending on the route of administration, the pharmaceutical composition of the present invention may be formulated as tablets, capsules, granules, fine subtilae, powders, sublingual tablets, suppositories, ointments, injection solutions, emulsions, suspensions, syrups, aerosols, etc. The above various forms of the pharmaceutical composition of the present invention can be prepared in a manner well known in the art using a pharmaceutically acceptable carrier (s) which are usually used for each form. Examples of the pharmaceutically acceptable carriers include excipient, binder, disintegrating agent, lubricant, preservative, antioxidant, isotonic agent, buffer, coating agent, sweetening agent, dissolvent, base, dispersing agent, wetting agent, suspending agent, stabilizer, colorant, etc.

The pharmaceutical composition according to the present invention contains 0.01 to 95 wt % of the compound of the above formula (I) or pharmaceutically acceptable salt thereof depending on the form thereof.

The specific dosage of the present pharmaceutical composition can be varied with species of mammals including a human-being, body weight, gender, severity of disease, judgment of doctor, etc. It is preferable that 0.01 to 50 mg of the active ingredient is administered per kg of body weight a day for oral use, while 0.01 to 10 mg of the active ingredient is administered per kg of body weight a day for parenteral use. The total daily dosage can be administered once or over several times depending on the severity of disease, judgment of doctor, etc.

In one embodiment of the present invention, the compound of the above formula (I) or pharmaceutically acceptable salt thereof may be administered in combination with one or more anticancer agents selected from the group consisting of capecitabine, 5-fluorouracil, thioguanine, chlorambucil, oxaliplatin, cisplatin, carboplatin, paclitaxel, docetaxel, irinotecan, doxorubicin, vinorelbin, gemcitabine, pemetrexed, etoposide, vincristine, citarabine, cyclophosphamide, iphosphamide, tamoxifen, anastrozole, retrozole, exemestane, fulvestrant, temozolomide, camustine, lomustine, epirubicine, eribulin, toremifene, goserelin, megestrol, vinblastine, bendamustine, thiotepa, bleomycin, topotecan, leucovorin, trifluridine, tipiracil, mitomycin C, aldesleukin, temsirolimus, everolimus, mitoxantrone, mecloretamine, methotrexate, trastuzumab, bevacizumab, cetuximab, aflibercept, pertuzumab, ramucirumab, panitumumab, nivolumab, necitumumab, pembrolizumab, obinutuzumab, ofatumumab, erlotinib, gefitinib, sorafenib, lapatinib, palbociclib, regorafenib, imatinib, sunitinib, axitinib, pazopanib, apatinib, ceritinib, crizotinib, osimertinib, bosutinib, dasatinib, nilotinib, ponatinib, hydroxyurea, and procarbazine, or one or more drugs for treating a degenerative brain disease selected from the group consisting of levodopa, bromocriptine, ropinirole, pramipexole, rotigotine, trihexyphenidyl, benztropine, procyclidine, entacapone, selegiline, rasagiline, amantadine, tetrabenazine, donepezil, rivastigmine, galantamine and memantine, in particular, temozolomide, to improve treatment. The specific dosage and administration time can be varied depending on a combined drug.

Advantageous Effects

The compound of the above formula (I) of the present invention or pharmaceutically acceptable salt thereof can be used in a pharmaceutical composition for preventing or treating cancers or degenerative brain diseases, etc., since it has an effect of inhibiting CDK activity.

BRIEF DESCRIPTION OF FIGURES

FIG. 1 shows changes in the cell cycle caused by the compound according to the present invention in a cancer cell and a normal cell.

FIG. 2 is a graph showing a tumor growth inhibitory effect of the compound according to the present invention in an animal model.

FIG. 3 is a graph showing a tumor growth inhibitory effect of the compound according to the present invention combined with a conventional anticancer drug in an animal model.

FIG. 4 shows an inhibitory effect of the compound according to the present invention on the phosphorylation of Tau protein.

FIG. 5 shows an inhibitory effect of the compound according to the present invention on the phosphorylation of APP protein.

FIG. 6 shows an inhibitory effect of the compound according to the present invention on the generation of Aβ.

BEST MODE

The present invention is further illustrated by the following examples, which are not to be construed to limit the scope of the invention.

Example 1: Preparation of 2,6-bis(2-aminopyrimidin-4-yl)pyridin-3-ol (VII)

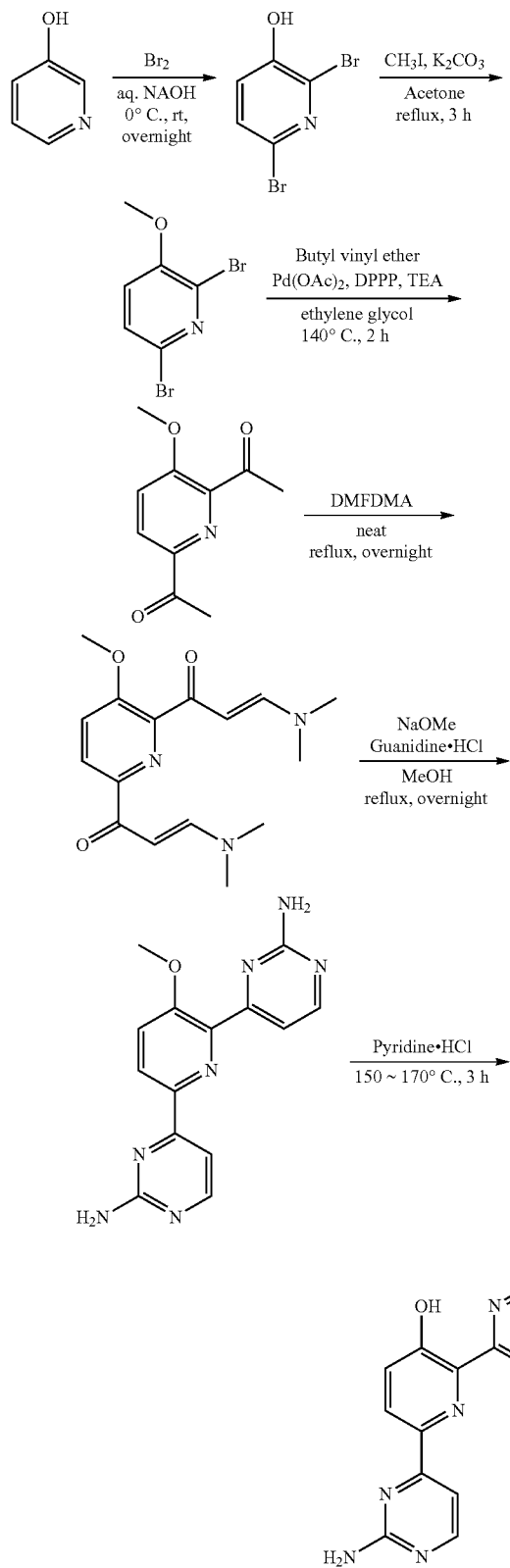

Example 1-1: Preparation of 2,6-dibromo-3-methoxypyridine (III)

Bromine (1.62 mL, 63.09 mmole) was slowly added dropwise to 25 mL of 20% sodium hydroxide (NaOH) aqueous solution at 0° C. and the mixture was stirred at 0° C. for 15 min. Then, 3-hydroxypyridine (I) (2.0 g, 21.03 mmole) dissolved in 20% sodium hydroxide (NaOH) aqueous solution was slowly added dropwise thereto at 0° C., and the mixture was stirred at 0° C. for 2 hours and then at room temperature for 12 hours. The mixture was filtered to remove floating matter and to the resulting solution was slowly added dropwise 2N hydrochloric acid (HCl) to adjust pH to 1-2. The resulting solid was filtered and dried to provide a white solid. The solid was dissolved in 60 ml of acetone and potassium carbonate ($K_2CO_3$) (2.64 g, 19.13 mmol) and methaneiodide ($CH_3I$) (893.03 uL, 14.34 mmole) were added dropwise thereto and the solution was stirred with reflux for 3 hrs. The resulting solution was evaporated under reduced pressure to concentrate, diluted with ethylacetate (EA), and washed with water. The washed organic solvent was dried over anhydrous magnesium sulfate ($MgSO_4$), filtered, and then evaporated under reduced pressure to concentrate. The resulting residue was isolated and purified by silica gel column chromatography (n-Hex/EA=5/1) to give the title compound (1.04 g, 19%).

$^1$H NMR (400 MHz, $CDCl_3$) δ 7.38 (d, J=8.4 Hz, 1H), 7.04 (d, J=8.0 Hz, 1H), 3.91 (s, 3H).

Example 1-2: Preparation of 1,1'-(3-methoxypyridin-2,6-diyl)diethanone (IV)

2,6-Dibromo-3-methoxypyridine (III) (450 mg, 1.69 mmole), palladium (II) acetate ($Pd(OAc)_2$) (15.14 mg, 67.44 umole), and 1,3-bis(diphenylphosphino)propane (DPPP) (55.63 mg, 134.87 umole) were dissolved in 3 mL of ethylene glycol. To the resulting reaction mixture butyl vinyl ether (1.09 mL, 8.43 mmole) and triethylamine (TEA) (704.94 uL, 50.6 mmole) were slowly added dropwise. The resulting mixture was stirred at 125° C. for 24 hrs and cooled to room temperature. 2N hydrochloric acid (HCl) was slowly added dropwise thereto to adjust pH to 1~2 and the mixture was stirred for 30 min and neutralized. The resulting solution was diluted with dichloromethane and washed with water. Then, the organic solvent was dried over anhydrous magnesium sulfate ($MgSO_4$), filtered, and evaporated under reduced pressure to concentrate. The resulting residue was isolated and purified by silica gel column chromatography (n-Hex/EA=3/1) to give the title compound (120 mg, 37%).

$^1$H NMR (400 MHz, $CDCl_3$) δ 8.20 (d, J=8.8 Hz, 1H), 7.42 (d, J=8.8 Hz, 1H), 3.98 (s, 3H), 2.73 (s, 3H), 2.71 (s, 3H).

Example 1-3: Preparation of 4,4'-(3-methoxypyridin-2,6-diyl)bis(pyrimidin-2-amine) (VI)

1,1'-(3-Methoxypyridin-2,6-diyl)diethanone (IV) (80 mg, 414.08 umole) was dissolved in N,N-dimethylformamide dimethyl acetal (DMFDMA) (831.6 uL, 6.21 mmole) and the resulting solution was stirred with reflux for 24 hrs. The resulting solution was cooled and evaporated and concentrated under reduced pressure to give a yellow solid. The solid was dissolved in methanol (MeOH) (1 mL), and 25% sodium methoxide (NaOMe) (757.4 uL, 3.31 mmole) and guanidine hydrochloride (118.67 mg, 1.24 mmole) were added dropwise thereto. And then, the resulting reaction mixture was stirred with reflux for 24 hrs and cooled. The resulting solution was diluted with ethylacetate (EA), washed with water, and the organic solvent was dried over anhydrous magnesium sulfate (MgSO₄), filtered, and evaporated and concentrated under reduced pressure to give the title compound (65 mg, 53%).

¹H NMR (400 MHz, DMSO-d₆) δ 8.37~8.32 (m, 3H), 7.75 (d, J=8.8 Hz, 1H), 7.36 (d, J=4.8 Hz, 1H), 6.84 (d, J=5.2 Hz, 1H), 6.73 (s, 2H), 6.69 (s, 2H), 3.87 (s, 3H).

Example 1-4: Preparation of 2,6-bis(2-aminopyrimidin-4-yl)pyridin-3-ol (VII)

4,4'-(3-Methoxypyridin-2,6-diyl)bis(pyrimidin-2-amine) (VI) (15 mg, 50.80 umole) was mixed with pyridine hydrochloride (Pyridine HCl) (58.70 mg, 507.96 umole) and the mixture was stirred at 170° C. for 4 hrs. The mixture was cooled to room temperature, neutralized with 2N sodium hydroxide (NaOH) solution, and diluted with ethylacetate (EA). The organic solvent was dried over anhydrous magnesium sulfate (MgSO₄), filtered, and evaporated and concentrated under reduced pressure to give the title compound (6.4 mg, 45%).

¹H NMR (400 MHz, DMSO-d₆) δ 8.52 (d, J=4.8 Hz, 1H), 8.37 (d, J=5.2 Hz, 1H), 8.32 (d, J=8.8 Hz, 1H), 7.69 (d, J=5.2 Hz 1H), 7.55 (d, J=4.8 Hz, 1H), 7.53 (d, J=8.4 Hz, 1H), 7.32 (s, 2H), 6.68 (s, 2H), 3.87 (s, 3H).

Example 2: Preparation of 3,5-bis(2-aminopyrimidin-4-yl)pyrazin-2-ol (XIV)

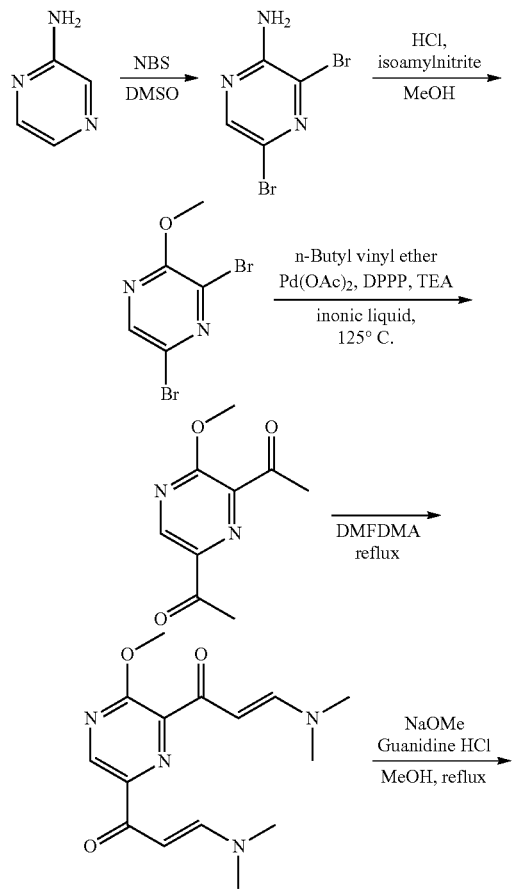

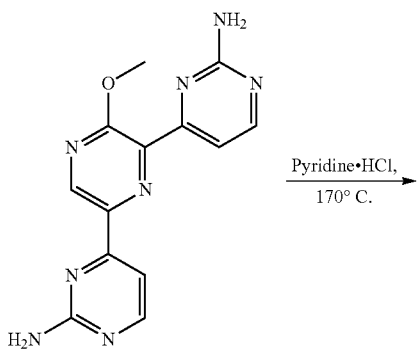

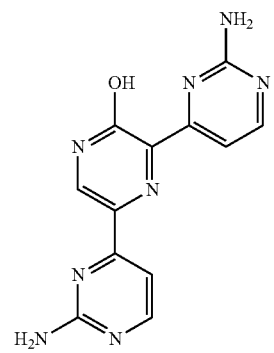

Example 2-1: Preparation of 3,5-dibromopyrazin-2-amine (IX)

Pyrazin-2-amine (VIII) (1.91 g, 20.08 mmol) was dissolved in dimethylsulfoxide (DMSO) (40 mL) and distilled water (1 mL). To the resulting solution was slowly added dropwise N-Bromosuccinimide (NBS) (8.20 g, 46.07 mmol) at 0° C. and the solution was stirred at room temperature for 16 hrs. Ice was added to the solution and the solution was stirred to give a yellow solid which was filtered to give the title compound (3.40 mg, 67%).

¹H NMR (400 MHz, CDCl₃) δ 8.04 (s, 1H), 5.05 (br, 2H).

Example 2-2: Preparation of 3,5-dibromo-2-methoxypyrazine (X)

3,5-Dibromopyrazin-2-amine (IX) (1.0 g, 4.0 mmole) was dissolved in methanol (MeOH) (10 mL), and 2.5M HCl/MeOH solution (0.32 mL, 0.80 mmol) and isoamylnitrite (1.5 mL, 12 mmol) were added dropwise to the resulting solution and the solution was stirred with reflux for 2 hrs. The reaction solution was evaporated and concentrated under reduced pressure, diluted with dichloromethane, and washed with water. The organic solvent was dried over anhydrous magnesium sulfate (MgSO₄), filtered, and evaporated under reduced pressure to concentrate. The resulting residue was isolated and purified by silica gel column chromatography (n-Hex/EA=5/1) to give the title compound (500 mg, 47%).

¹H NMR (400 MHz, CDCl₃) δ 8.14 (s, 1H), 4.04 (s, 3H).

Example 2-3: Preparation of 1,1'-(3-methoxypyrazin-2,6-diyl)diethanone (XI)

3,5-Dibromo-2-methoxypyrazine (X) (600 mg, 2.24 mmol), palladium(II) acetate (Pd(OAc)₂) (40.22 mg, 179.16 umole), and 1,3-bis(diphenylphosphino)propane (DPPP) (147.80 mg, 358.33 umole) were dissolved in 2.5 mL of 1-butyl-3-methylimidazolium tetrafluoroborate ([bmim][BF4]). To the resulting solution was slowly added dropwise butyl vinyl ether (2.32 mL, 17.92 mmole) and triethylamine (TEA) (1.0 mL, 7.17 mmole). The solution was stirred at 125° C. for 24 hrs and then cooled to room temperature. 2N hydrochloric acid (HCl) was slowly added dropwise to the solution to adjust pH to 1~2 and then the solution was stirred for 30 min and neutralized. The solution was diluted with dichloromethane and washed with water. The organic solvent was dried over anhydrous magnesium sulfate (MgSO₄), filtered, and evaporated under reduced pressure to concentrate. The resulting residue was isolated and purified by silica gel column chromatography (n-Hex/EA=3/1) to give the title compound (65 mg, 15%).

¹H NMR (400 MHz, CDCl₃) δ 8.98 (s, 1H), 4.15 (s, 3H), 2.73 (s, 3H), 2.70 (s, 3H).

Example 2-4: Preparation of 4,4'-(3-methoxypyrazin-2,6-diyl)bis(pyrimidin-2-amine) (XIII)

1,1'-(3-Methoxypyrazin-2,6-diyl)diethanone (XI) (65 mg, 334.72 umole) was dissolved in N,N-dimethylformamide dimethyl acetal (DMFDMA) (672.23 uL, 5.02 mmole) and the resulting solution was stirred with reflux for 24 hrs. The solution was cooled and evaporated under reduced pressure to concentrate. The resulting yellow solid was dissolved in methanol (MeOH) (1 mL), and 25% sodium methoxide (NaOMe) (612.29 uL, 2.68 mmole) and guanidine hydrochloride (95.93 mg, 1.0 mmole) were added dropwise to the solution. And then, the solution was stirred with reflux for 24 hrs and cooled. The solution was diluted with ethylacetate (EA) and washed with water, and the organic solvent was dried over anhydrous magnesium sulfate (MgSO₄), filtered, and evaporated and concentrated under reduced pressure to give the title compound (47 mg, 47%).

¹H NMR (400 MHz, DMSO-d₆) δ 8.75 (s, 1H), 8.17 (d, J=5.2 Hz, 1H), 8.12 (d, J=5.6 Hz, 1H), 7.40 (d, J=5.2 Hz, 1H), 7.15 (d, J=5.2 Hz, 1H), 6.39 (s, 2H), 6.32 (s, 2H), 3.17 (s, 3H).

Example 2-5: Preparation of 3,5-bis(2-aminopyrimidin-4-yl)pyrazin-2-ol (XIV)

4,4'-(3-Methoxypyrazin-2,6-diyl)bis(pyrimidin-2-amine) (XIII) (47 mg, 158.62 umole) was mixed with pyridine hydrochloride (Pyridine HCl) (11.3 mg, 40.03 umole) and the mixture was stirred at 170° C. for 4 hrs. The mixture was cooled to room temperature, neutralized with 2N sodium hydroxide (NaOH) solution, and diluted with ethylacetate (EA). The organic solvent was dried over anhydrous magnesium sulfate (MgSO₄), filtered, and evaporated and concentrated under reduced pressure to give the title compound (7.6 mg, 17%).

¹H NMR (400 MHz, CD₃OD) δ 8.92 (s, 1H), 8.29 (d, J=5.2 Hz, 1H), 8.18 (d, J=5.6 Hz, 1H), 7.62 (d, J=4.8 Hz, 1H), 7.53 (d, J=5.6 Hz, 1H), 6.39 (s, 2H), 6.32 (s, 2H), 3.17 (s, 3H).

Example 3: Preparation of 4,6-bis(2-aminopyrimidin-4-yl)pyridin-3-ol (XXIII)

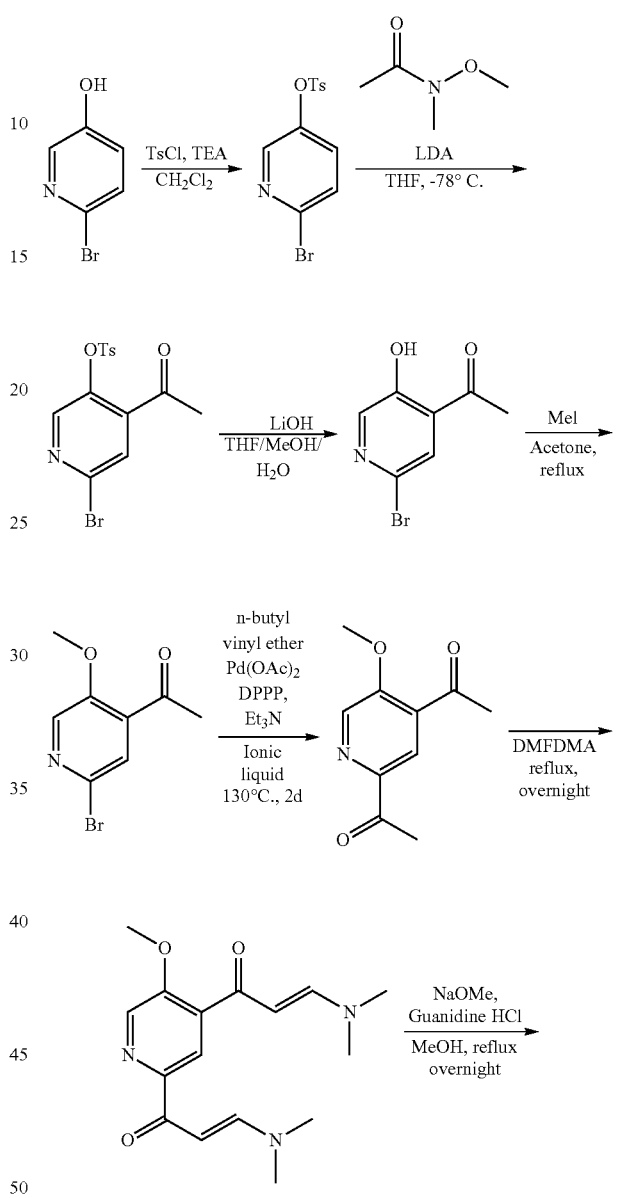

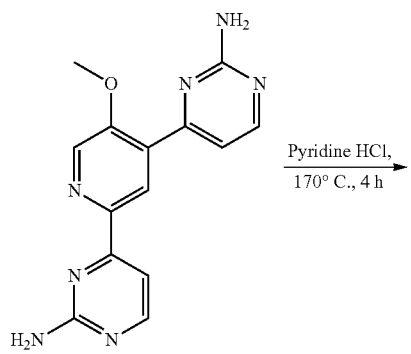

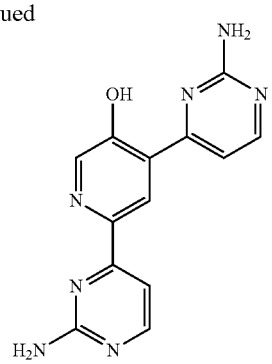

Example 3-1: Preparation of toluene-4-sulfonic acid 6-bromo-pyridin-3-yl ester (XVI)

6-Bromopyridin-3-ol (XV) (500 mg, 2.87 mmol) was dissolved in dichloromethane (3 mL). Then, triethylamine (TEA) (520 uL, 3.74 mmol) and 4-toluenesulfonyl chloride (TsCl) (657.41 mg, 3.45 mmol) were slowly added dropwise to the resulting solution at 0° C. and the solution was stirred at room temperature for 12 hrs. The solution was diluted with dichloromethane, washed with water and saturated sodium hydrogen carbonate (NaHCO$_3$). The organic solvent was dried over anhydrous magnesium sulfate (MgSO$_4$), filtered, and evaporated under reduced pressure to concentrate. The resulting residue was isolated and purified by silica gel column chromatography (n-Hex/EA=3/1) to give the title compound (980 mg, 100%).

$^1$H NMR (400 MHz, CDCl$_3$) δ 7.89 (d, J=3.2 Hz, 1H), 7.70 (d, J=8.0 Hz, 2H), 7.46 (d, J=8.8 Hz, 1H), 7.36-7.33 (m, 3H), 2.47 (s, 3H).

Example 3-2: Preparation of toluene-4-sulfonic acid 4-acetyl-6-bromo-pyridin-3-yl ester (XVII)

Toluene-4-sulfonic acid 6-bromo-pyridin-3-yl ester (XVI) (980 mg, 2.99 mmol) was dissolved in tetrahydrofuran (THF) (3 mL) and the resulting solution was cooled to −78° C. 2.0M lithium diisopropylamide (LDA) (2.24 mL, 4.48 mmol) dissolved in tetrahydrofuran was slowly added dropwise to the solution and the solution was stirred at −78° C. for 3 hrs. And then, N-methoxy-N-methyl acetamide (609.77 uL, 5.97 mmol) was slowly added dropwise to the solution and the solution was stirred for 2 hrs. Saturated sodium hydrogen carbonate (NaHCO$_3$) solution was added dropwise to the solution and the solution was diluted with ethylacetate (EA). Then, the organic solvent was dried over anhydrous magnesium sulfate (MgSO$_4$), filtered, and evaporated under reduced pressure to concentrate. The resulting residue was isolated and purified by silica gel column chromatography (n-Hex/EA=4/1) to give the title compound (570 mg, 52%).

$^1$H NMR (400 MHz, CDCl$_3$) δ 7.97 (s, 1H), 7.70 (d, J=8.0 Hz, 2H), 7.65 (s, 1H), 7.37 (d, J=8.0 Hz, 2H), 2.58 (s, 3H), 2.49 (s, 3H).

Example 3-3: Preparation of 1-(2-bromo-5-hydroxypyridin-4-yl)ethanone (XVIII)

Toluene-4-sulfonic acid 4-acetyl-6-bromo-pyridin-3-yl ester (XVII) (1.3 g, 3.51 mmol) was dissolved in a mixture of tetrahydrofuran (THF) (4 mL), methanol (MeOH) (4 mL) and water (H$_2$O) (2 mL). To the resulting solution was added dropwise lithium hydroxide (LiOH) (294.68 mg, 7.02 mmol) and the solution was stirred at room temperature for 12 hrs. The solution was evaporated under reduced pressure to concentrate, diluted with ethylacetate (EA). The organic solvent was dried over anhydrous magnesium sulfate (MgSO$_4$), filtered, and evaporated and concentrated under reduced pressure. The resulting residue was isolated and purified by silica gel column chromatography (n-Hex/EA=3/1) to give the title compound (620 mg, 82%).

$^1$H NMR (400 MHz, CDCl$_3$) δ 11.34 (s, 1H), 8.30 (s, 1H), 7.55 (s, 1H), 2.68 (s, 3H).

Example 3-4: Preparation of 1-(2-bromo-5-methoxypyridin-4-yl)ethanone (XIX)

1-(2-Bromo-5-hydroxypyridin-4-yl)ethanone (XVIII) (365 mg, 1.69 mmol) was dissolved in 6 mL of acetone, and then potassium carbonate (K$_2$CO$_3$) (373.63 mg, 2.70 mmol) and iodomethane (CH$_3$I) (126.22 uL, 2.03 mmole) were added dropwise thereto. The resulting solution was stirred with reflux for 3 hrs. The solution was evaporated under reduced pressure to concentrate, diluted with ethylacetate (EA) and washed with water. The washed organic solvent was dried over anhydrous magnesium sulfate (MgSO$_4$), filtered, and evaporated under reduced pressure to concentrate. The resulting residue was isolated and purified by silica gel column chromatography (n-Hex/EA=5/1) to give the title compound (381.0 mg, 98%).

$^1$H NMR (400 MHz, CDCl$_3$) δ 8.19 (s, 1H), 7.49 (s, 1H), 4.02 (s, 3H), 2.61 (s, 3H).

Example 3-5: Preparation of 1,1'-(5-methoxypyridin-2,4-diyl)diethanone (XX)

1-(2-Bromo-5-methoxypyridin-4-yl)ethanone (XIX) (260 mg, 1.13 mmol), palladium(II) acetate (Pd(OAc)$_2$) (10.15 mg, 45.20 umole), and 1,3-bis(diphenylphosphino)propane (DPPP) (37.29 mg, 90.41 umole) were dissolved in 1.0 mL of 1-butyl-3-methylimidazolium tetrafluoroborate ([bmim][BF4]), and butyl vinyl ether (731.23 uL, 5.65 mmole) and triethylamine (TEA) (252.03 uL, 1.81 mmole) were slowly added thereto. The resulting solution was stirred 125° C. for 24 hrs and then cooled to room temperature. 2N hydrochloric acid (HCl) was slowly added dropwise to the solution to adjust pH to 1~2 and the solution was stirred for 30 min and neutralized. The solution was diluted with dichloromethane and washed with water. The organic solvent was dried over anhydrous magnesium sulfate (MgSO$_4$), filtered, and evaporated under reduced pressure to concentrate. The resulting residue was isolated and purified by silica gel column chromatography (n-Hex/EA=3/1) to give the title compound (54 mg, 25%).

$^1$H NMR (400 MHz, CDCl$_3$) δ 8.47 (s, 1H), 8.23 (s, 1H), 4.11 (s, 3H), 2.69 (s, 3H), 2.62 (s, 3H).

Example 3-6: Preparation of 4,4'-(5-methoxypyridin-2,4-diyl)bis(pyrimidin-2-amine) (XXII)

1,1'-(5-Methoxypyridin-2,4-diyl)diethanone (XX) (54 mg, 279.50 umole) was dissolved in N,N-dimethylformamide dimethyl acetal (DMFDMA) (561.33 uL, 4.19 mmole) and the resulting solution was stirred with reflux for 24 hrs. The solution was cooled, and evaporated and concentrated under reduced pressure to provide a yellow solid. The solid was dissolved in methanol (MeOH) (1 mL), and 25% sodium methoxide (NaOMe) (511.28 uL, 2.24 mmole) and guanidine hydrochloride (80.10 mg, 838.51 umole) were added dropwise to the resulting solution. And then, the solution was stirred with reflux, cooled, diluted with ethylacetate (EA) and washed with water. The organic solvent was dried over anhydrous magnesium sulfate (MgSO$_4$), filtered, and evaporated and concentrated under reduced pressure to give the title compound (23 mg, 28%).

$^1$H NMR (400 MHz, DMSO-d$_6$) δ 8.56 (s, 1H), 8.52 (d, J=5.2 Hz, 1H), 8.46 (s, 1H), 8.36 (d, J=5.2 Hz, 1H), 7.37 (d, J=5.6 Hz, 1H), 7.30 (d, J=5.2 Hz, 1H), 6.72 (s, 2H), 6.66 (s, 2H), 4.03 (s, 3H).

Example 3-7: Preparation of 4,6-bis(2-aminopyrimidin-4-yl)pyridin-3-ol (XXIII)

4,4'-(5-Methoxypyridin-2,4-diyl)bis(pyrimidin-2-amine) (XXII) (23 mg, 778.87 umole) was mixed with pyridine hydrochloride (Pyridine HCl) (90 mg, 7.79 mmole) and the mixture was stirred at 170° C. for 4 hrs. The mixture was cooled to room temperature, neutralized with 2N sodium hydroxide (NaOH) solution, and diluted with ethylacetate (EA). The organic solvent was dried over anhydrous magnesium sulfate (MgSO$_4$), filtered, and evaporated and concentrated under reduced pressure to give the title compound (9.8 mg, 45%).

$^1$H NMR (400 MHz, DMSO-d$_6$) δ 8.71 (s, 1H), 8.53 (d, J=5.2 Hz, 1H), 8.42 (s, 1H), 8.34 (d, J=5.2 Hz, 1H), 7.39 (d, J=5.6 Hz, 1H), 7.33 (s, 2H), 7.30 (d, J=5.2 Hz, 1H), 6.66 (s, 2H).

Example 4: Preparation of 2'-amino-4-(2-aminopyrimidin-4-yl)-[2,4'-bipyridin]-5-(XXVIII)

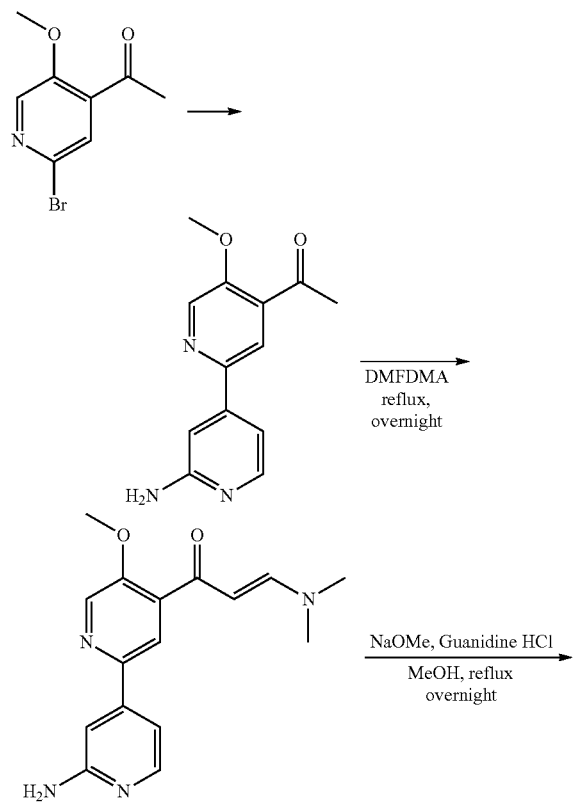

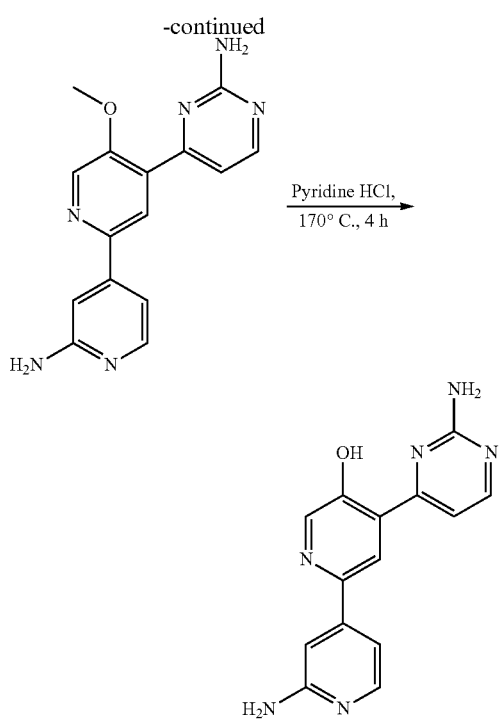

Example 4-1: Preparation of 1-(2'-amino-5-methoxy-[2,4']bipyridinyl-4-yl)-ethanone (XXV)

1-(2-Bromo-5-methoxypyridin-4-yl)ethanone (XIX) (1 g, 4.34 mmol) obtained in Example 3-4 and [4-(4,4,5,5-tetramethyl-[1,3,2]dioxaborolan-2-yl)-pyridin-2-yl]-carbamic acid-tert-butyl ester (1.16 g, 3.62 mmol) were dissolved in ethylene glycol dimethyl ester/distilled water (10 ml/2 ml) solution. To the resulting solution were added sodium carbonate (1.15 g, 10.86 mmol), and tetrakis(triphenylphosphine)palladium(0) (Pd(PPh$_3$)$_4$) (125.6 mg, 0.109 mmol) and the solution was stirred with reflux for 18 hrs. After completion of the reaction by addition of water, the solution was extracted with ethylacetate, washed with distilled water, and dried over magnesium sulfate (MgSO$_4$) to concentrate. The resulting residue was isolated and purified by silica gel column chromatography (hexane/ethylacetate=1/1) to give the brown title compound (317.2 mg, 30.0%).

$^1$H NMR (400 MHz, CDCl$_3$) δ 8.55 (s, 1H), 8.43 (s, 1H), 7.85 (d, J=8.0 Hz, 1H), 7.80 (dd, J=8.0, 7.6 Hz, 1H), 7.34 (d, J=7.6 Hz, 1H), 4.10 (s, 3H), 2.70 (s, 3H).

Example 4-2: Preparation of 4-(2-amino-pyrimidin-4-yl)-5-methoxy[2,4']bipyridinyl-2'-ylamine (XXVII)

1-(2'-Amino-5-methoxy-[2,4]bipyridinyl-4-yl)-ethanone (XXV) (317 mg, 1.303 mmol) was dissolved in N,N-dimethylformamide dimethyl acetal (DMFDMA) (1.7 ml, 13.03 mmol) and the resulting solution was stirred with reflux for 24 hrs. The reaction solution was cooled and evaporated and concentrated under reduced pressure to give a yellow solid. The solid was dissolved in methanol (MeOH) (1 mL), and to the resulting solution were added 25% sodium methoxide (NaOMe) (186 uL, 5.212 mmol) and guanidine hydrochloride (498.0 mg, 5.212 mmol). And then, the solution was stirred with reflux for 24 hrs and cooled.

The solution was diluted with ethylacetate (EA) and washed with water. The organic solvent was dried over anhydrous magnesium sulfate (MgSO$_4$), filtered, and then evaporated and concentrated under reduced pressure to give the title compound (111.2 mg, 29%).

$^1$H NMR (400 MHz, DMSO-d$_6$) δ 8.70 (s, 1H), 8.53 (d, J=5.4 Hz, 1H), 8.42 (s, 1H), 8.34 (d, J=5.4 Hz, 1H), 7.51 (s, 1H), 7.39 (d, J=5.6 Hz, 1H), 7.32 (s, 2H), 7.30 (d, J=5.2 Hz, 1H), 6.63 (s, 2H).

Example 4-3: Preparation of 2'-amino-4-(2-aminopyrimidin-4-yl)-[2,4'-bipyridin]-5-ol (XXVIII)

4-(2-Amino-pyrimidin-4-yl)-5-methoxy[2,4']bipyridinyl-2'-ylamine (XXVII) (30 mg, 0.102 mmol) was mixed with pyridine hydrochloride (Pyridine HCl) (100 mg, 1.019 mmol) and the mixture was stirred at 170° C. for 4 hrs. The mixture was cooled to room temperature, neutralized with 2N sodium hydroxide (NaOH) solution, and diluted with ethylacetate (EA). Then, the organic solvent was dried over anhydrous magnesium sulfate (MgSO$_4$), filtered, and then evaporated and concentrated under reduced pressure to give the title compound (12.8 mg, 45%).

$^1$H NMR (400 MHz, DMSO-d$_6$) δ 8.71 (s, 1H), 8.51 (d, J=5.2 Hz, 1H), 8.37 (s, 1H), 8.30 (d, J=5.2 Hz, 1H), 7.39 (d, J=5.6 Hz, 1H), 7.29 (s, 1H), 7.33 (s, 2H), 7.30 (d, J=5.2 Hz, 1H), 6.66 (s, 2H).

Example 5: Preparation of 2'-amino-2-(2-aminopyridin-4-yl)-[4,4'-bipyrimidin]-5-ol (XXXIV)

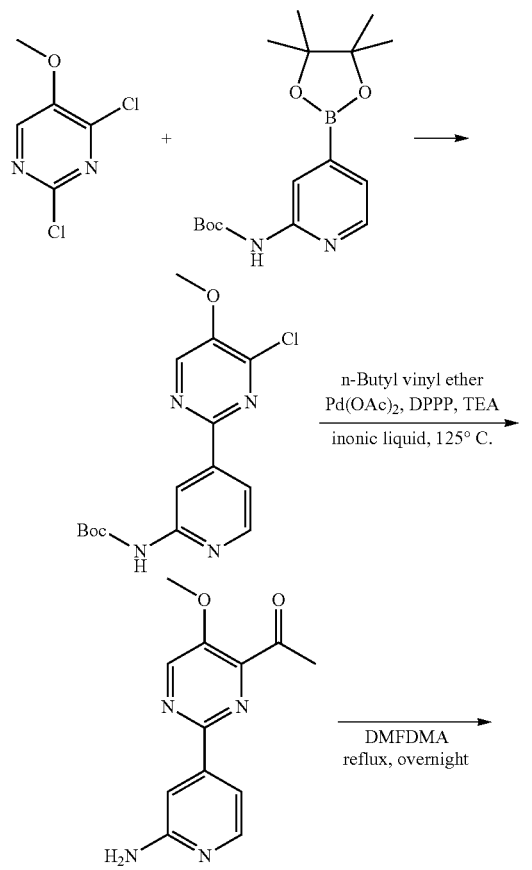

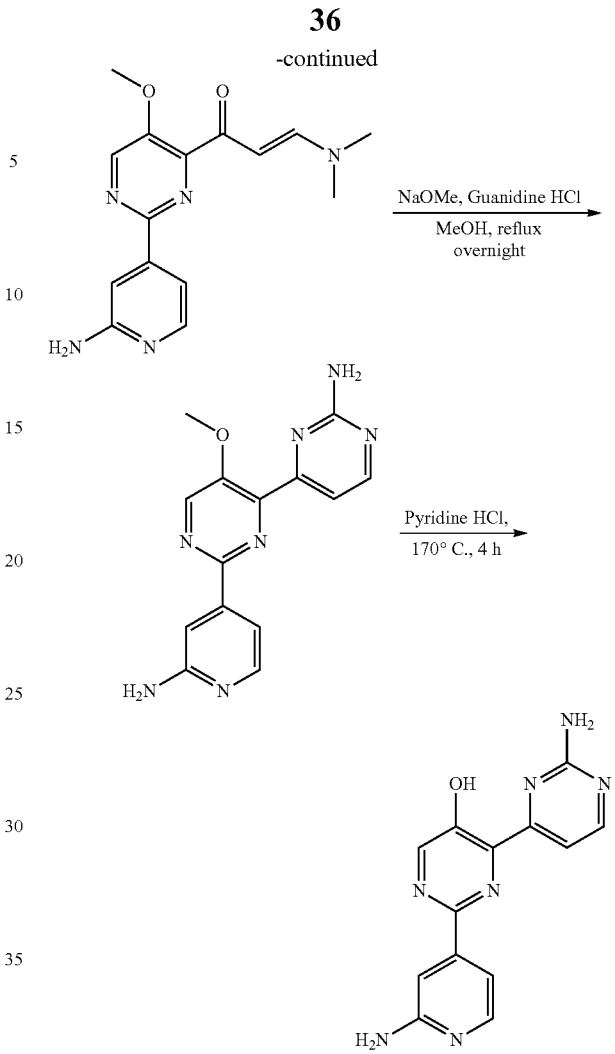

Example 5-1: Preparation of [4-(4-chloro-5-methoxy-pyrimidin-2-yl)-pyridin-2-yl]-carbamic acid-tert-butyl ester (XXX)

2,4-Dichloro-5-methoxypyrimidine (XXIX) (800 mg, 4.34 mmol) and [4-(4,4,5,5-tetramethyl-[1,3,2]dioxaborolan-2-yl)-pyridin-2-yl]-carbamic acid-tert-butyl ester (XXIV) (1.16 g, 3.62 mmol) were dissolved in ethylene glycol dimethyl ester/distilled water (10 ml/2 ml) solution. Sodium carbonate (1.15 g, 10.86 mmol) and tetrakis(triphenylphosphine)palladium(0) (Pd(PPh$_3$)$_4$) (125.6 mg, 0.109 mmol) were added to the resulting solution and then the solution was stirred with reflux for 18 hrs. After completion of the reaction by addition of water, the solution was extracted with ethylacetate, washed with distilled water, and dried over magnesium sulfate (MgSO$_4$) to concentrate. The resulting residue was isolated and purified by silica gel column chromatography (hexane/ethylacetate=1/1) to give the brown title compound (302.1 mg, 28.0%).

$^1$H NMR (400 MHz, CDCl$_3$) δ 8.43 (s, 1H), 8.01 (s, 1H), 7.89 (d, J=8.0 Hz, 1H), 7.30 (d, J=8.0 Hz, 1H), 3.99 (s, 3H), 1.48 (s, 9H).

Example 5-2: Preparation of 1-[2-(2-amino-pyridin-4-yl)-5-methoxy-pyrimidin-4-yl]-ethanone (XXXI)

[4-(4-chloro-5-methoxy-pyrimidin-2-yl)-pyridin-2-yl]-carbamic acid-tert-butyl ester (XXX) (200 mg, 1.13 mmol), palladium(II) acetate (Pd(OAc)₂) (10.15 mg, 45.20 umole), and 1,3-bis(diphenylphosphino)propane (DPPP) (37.29 mg, 90.41 umole) were dissolved in 1.0 mL of 1-butyl-3-methylimidazolium tetrafluoroborate ([bmim][BF4]). To the resulting solution were slowly added dropwise butyl vinyl ether (731.23 uL, 5.65 mmole) and triethylamine (TEA) (252.03 uL, 1.81 mmole). The resulting mixture was stirred at 125° C. for 24 hrs and then cooled to room temperature. 2N hydrochloric acid (HCl) was slowly added dropwise to the mixture to adjust pH to 1-2 and the mixture was stirred for 30 min and neutralized. The resulting solution was diluted with dichloromethane and washed with water. The organic solvent was dried over anhydrous magnesium sulfate (MgSO₄), filtered, and then evaporated under reduced pressure to concentrate. The resulting residue was isolated and purified by silica gel column chromatography (n-Hex/EA=3/1) to give the title compound (50 mg, 21%).

¹H NMR (400 MHz, CDCl₃) δ 8.42 (s, 1H), 8.03 (s, 1H), 7.89 (d, J=8.0 Hz, 1H), 7.29 (d, J=8.0 Hz, 1H), 3.99 (s, 3H), 1.72 (s, 3H)

Example 5-3: Preparation of 2'-(2-amino-pyridin-4-yl)-5'-methoxy-[4,4']bipyrimidinyl-2-ylamine (XXXIII)

1-[2-(2-Amino-pyridin-4-yl)-5-methoxy-pyrimidin-4-yl]-ethanone (XXXI) (200 mg, 1.404 mmol) was dissolved in N,N-dimethylformamide dimethyl acetal (DMFDMA) (1.7 ml, 14.03 mmol) and the resulting solution was stirred with reflux for 24 hrs. The solution was cooled and evaporated and concentrated under reduced pressure to give a yellow solid. The solid was dissolved in methanol (MeOH) (1 mL), and to the resulting solution were added dropwise 25% sodium methoxide (NaOMe) (186 uL, 6.212 mmol) and guanidine hydrochloride (498.0 mg, 6.212 mmol). And then, the solution was stirred with reflux for 24 hrs, cooled, diluted with ethylacetate (EA) and washed with water. Then, the organic solvent was dried over anhydrous magnesium sulfate (MgSO₄), filtered, and then evaporated and concentrated under reduced pressure to give the title compound (98.3 mg, 19%).

¹H NMR (600 MHz, DMSO-d₆) δ 9.90 (s, NH), 8.63 (s, 1H), 8.63 (d, J=5.4 Hz, 1H), 8.36 (d, J=4.8 Hz, 1H), 7.82 (s, 1H), 7.56 (d, J=5.4 Hz, 1H), 7.43 (d, J=4.8 Hz, 1H), 6.68 (s, NH2), 3.98 (s, 3H).

Example 5-4: Preparation of 2'-amino-2-(2-aminopyridin-4-yl)-[4,4'-bipyrimidin]-5-ol (XXXIV)

2'-(2-Amino-pyridin-4-yl)-5'-methoxy-[4,4']bipyrimidinyl-2-ylamine (XXXIII) (30 mg, 0.111 mmol) was mixed with pyridine hydrochloride (Pyridine HCl) (114 mg, 1.011 mmol) and the mixture was stirred at 170° C. for 4 hrs. The mixture was cooled to room temperature, neutralized with 2N sodium hydroxide (NaOH) solution, and diluted with ethylacetate (EA). The organic solvent was dried over anhydrous magnesium sulfate (MgSO₄), filtered, and evaporated and concentrated under reduced pressure to give the title compound (15.8 mg, 48%).

¹H NMR (600 MHz, CD₃OD) δ 14.88 (s, OH), 8.69 (s, 1H), 8.34 (s, 1H), 8.32 (d, J=4.8 Hz, 1H), 7.70 (dd, J=8.4, 7.8 Hz, 1H), 7.39 (d, J=4.8 Hz, 1H), 7.30 (d, J=7.8 Hz, 1H), 6.81 (s, NH2), 6.65 (s, NHJ2), 6.61 (d, J=8.4 Hz, 1H).

Example 6: Preparation of 3,5-bis(2-aminopyrimidin-4-yl)pyridin-2-ol (XXXXII)

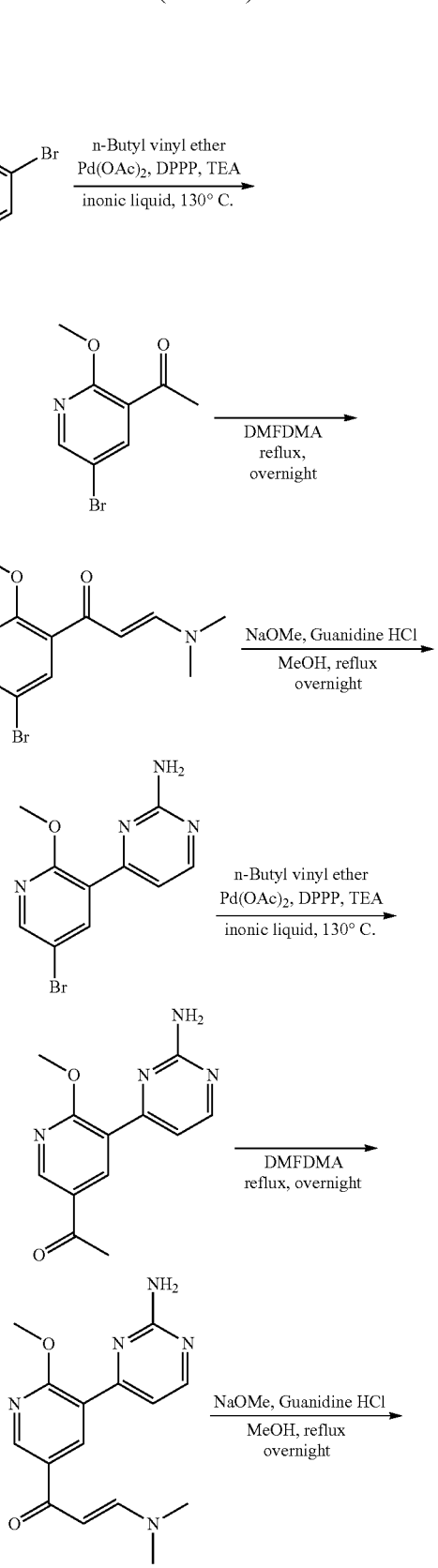

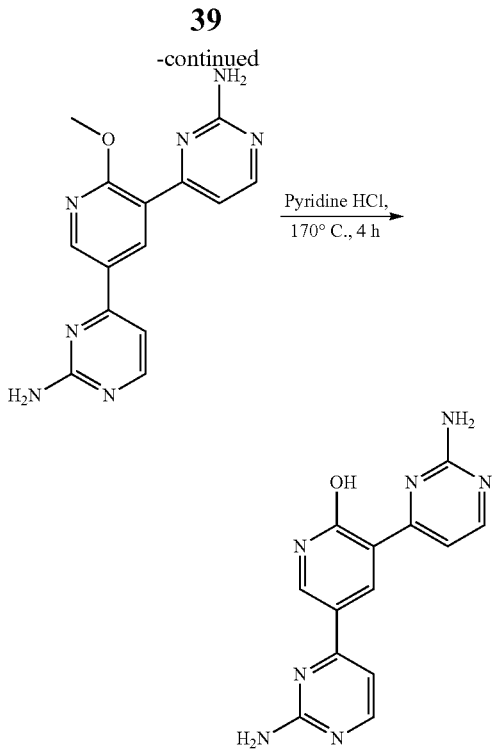

Example 6-1: Preparation of 1-(5-bromo-2-methoxy-pyridin-3-yl)-ethanone (XXXVI)

3,5-Bromo-2-methoxypyridine (XXXV) (100 mg, 1.13 mmol), palladium(II) acetate (Pd(OAc)$_2$) (5.03 mg, 25.04 umole), and 1,3-bis(diphenylphosphino)propane (DPPP) (14.4 mg, 45.3 umole) were dissolved in 1.0 mL of 1-butyl-3-methylimidazolium tetrafluoroborate ([bmim][BF4]), and butyl vinyl ether (345 uL, 2.56 mmole) and triethylamine (TEA) (125.03 uL, 0.192 mmole) were slowly added dropwise to the resulting solution. The resulting mixture was stirred at 130° C. for 24 hrs and cooled to room temperature. 2N hydrochloric acid (HCl) was slowly added dropwise to the mixture to adjust pH to 1-2 and the mixture was stirred for 30 min and neutralized. The resulting solution was diluted with dichloromethane, washed with water. The organic solvent was dried over anhydrous magnesium sulfate (MgSO$_4$), filtered, and evaporated under reduced pressure to concentrate. The resulting residue was isolated and purified by silica gel column chromatography (n-Hex/EA=3/1) to give the title compound (53 mg, 41%).

$^1$H NMR (400 MHz, CDCl$_3$) δ 7.85 (s, 1H), 7.06 (s, 1H), 3.89 (s, 3H), 2.48 (s, 3H).

Example 6-2: Preparation of 4-(5-bromo-2-methoxy-pyridin-3-yl)-pyrimidin-2-ylamine (XXXVIII)

1-(5-Bromo-2-methoxy-pyridin-3-yl)ethanone (XXXVI) (200 mg, 1.404 mmol) was dissolved in N,N-dimethylformamide dimethyl acetal (DMFDMA) (1.7 ml, 14.03 mmol), and the resulting solution was stirred with reflux for 24 hrs. The solution was cooled and evaporated and concentrated under reduced pressure to give a yellow solid. The solid was dissolved in methanol (MeOH) (1 mL) and 25% sodium methoxide (NaOMe) (186 uL, 6.212 mmole) and guanidin hydrochloride (498.0 mg, 6.212 mmole) were added dropwise to the resulting solution. And then, the solution was stirred with reflux for 24 hrs and cooled. The solution was diluted with ethylacetate (EA) and washed with water, and the organic solvent was dried over anhydrous magnesium sulfate (MgSO$_4$), filtered, and evaporated and concentrated under reduced pressure to give the title compound (20.3 mg, 55%).

$^1$H NMR (400 MHz, CDCl$_3$) δ 8.50 (s, 1H), 8.43 (s, 1H), 7.85 (d, J=8.0 Hz, 1H), 7.35 (d, J=7.6 Hz, 1H), 4.07 (s, 3H).

Example 6-3: Preparation of 1-[5-(2-amino-pyrimidin-4-yl)-6-methoxy-pyridin-3-yl]-ethanone (XXXIX)

4-(5-Bromo-2-methoxy-pyridin-3-yl)-pyrimidin-2-ylamine (XXXVIII) (200 mg, 2.22 mmol), palladium(II) acetate (Pd(OAc)$_2$) (10.1 mg, 50.22 umole), and 1,3-bis(diphenylphosphino)propane (DPPP) (28.33 mg, 90.5 umole) were dissolved in 1.0 mL of 1-butyl-3-methylimidazolium tetrafluoroborate ([bmim][BF4]). To the resulting solution were slowly added dropwise butyl vinyl ether (801 uL, 5.02 mmole) and triethylamine (TEA) (250.4 uL, 0.383 mmole). The resulting mixture was stirred at 125° C. for 24 hrs and then cooled to room temperature. 2N hydrochloric acid (HCl) was slowly added dropwise to the mixture to adjust pH to 1~2 and the mixture was stirred for 30 min and neutralized. The resulting solution was diluted with dichloromethane and washed with water. The organic solvent was dried over anhydrous magnesium sulfate (MgSO$_4$), filtered, and evaporated under reduced pressure to concentrate. The resulting residue was isolated and purified by silica gel column chromatography (n-Hex/EA=3/1) to give the title compound (101 mg, 70.2%).

$^1$H NMR (400 MHz, CDCl$_3$) δ 8.51 (s, 1H), 8.43 (s, 1H), 7.86 (d, J=8.0 Hz, 1H), 7.35 (d, J=7.6 Hz, 1H), 3.90 (s, 3H), 2.12 (s, 3H).

Example 6-4: Preparation of 4,4'-(2-methoxypyridin-3,5-diyl)bis(pyrimidin-2-amine) (XXXXI)

1-[5-(2-Amino-pyrimidin-4-yl)-6-methoxy-pyridin-3-yl]-ethanone (XXXIX) (100 mg, 0.712 mmol) was dissolved in N,N-dimethylformamide dimethyl acetal (DMFDMA) (0.8 ml, 7.03 mmol) and the resulting solution was stirred with reflux for 24 hrs. The solution was cooled and evaporated and concentrated under reduced pressure to give a yellow solid. The solid was dissolved in methanol (MeOH) (1 mL), and 25% sodium methoxide (NaOMe) (98 uL, 3.111 mmol) and guanidine hydrochloride (249.2 mg, 3.111 mmol) were added dropwise to the resulting solution. And then, the solution was stirred with reflux for 24 hrs and cooled. The solution was diluted with ethylacetate (EA) and washed with water, and the organic solvent was dried over anhydrous magnesium sulfate (MgSO$_4$), filtered, and evaporated and concentrated under reduced pressure to give the title compound (80 mg, 54%).

$^1$H NMR (400 MHz, DMSO-d$_6$) δ 8.35~8.30 (m, 3H), 7.75 (d, J=8.2 Hz, 1H), 7.36 (d, J=4.8 Hz, 1H), 6.84 (d, J=5.2 Hz, 1H), 6.73 (s, 2H), 6.69 (s, 2H), 4.07 (s, 3H).

Example 6-5: Preparation of 3,5-bis(2-aminopyrimidin-4-yl)pyridin-2-ol (XXXXII)

4,4'-(2-Methoxypyridin-3,5-diyl)bis(pyrimidin-2-amine) (XXXXI) (80 mg, 0.333 mmol) was mixed with pyridine hydrochloride (Pyridine HCl) (328 mg, 3.332 mmol) and the mixture was stirred at 170° C. for 4 hrs. The mixture was cooled to room temperature, neutralized with 2N sodium hydroxide (NaOH) solution, and diluted with ethylacetate (EA). The organic solvent was dried over anhydrous magnesium sulfate (MgSO$_4$), filtered, and evaporated and concentrated under reduced pressure to give the title compound (43.3 mg, 32%).

$^1$H NMR (400 MHz, DMSO-d$_6$) δ 8.60 (d, J=4.8 Hz, 1H), 8.33 (s, 1H), 8.32 (d, J=8.8 Hz, 1H), 7.69 (s, 1H), 7.55 (d, J=4.8 Hz, 1H), 7.50 (d, J=8.4 Hz, 1H), 7.30 (s, 2H), 6.66 (s, 2H), 3.88 (s, 3H).

Example 7: Preparation of 6'-amino-6-(2-aminopyrimidin-4-yl)-[2,2'-bipyridin]-3-ol (LV)

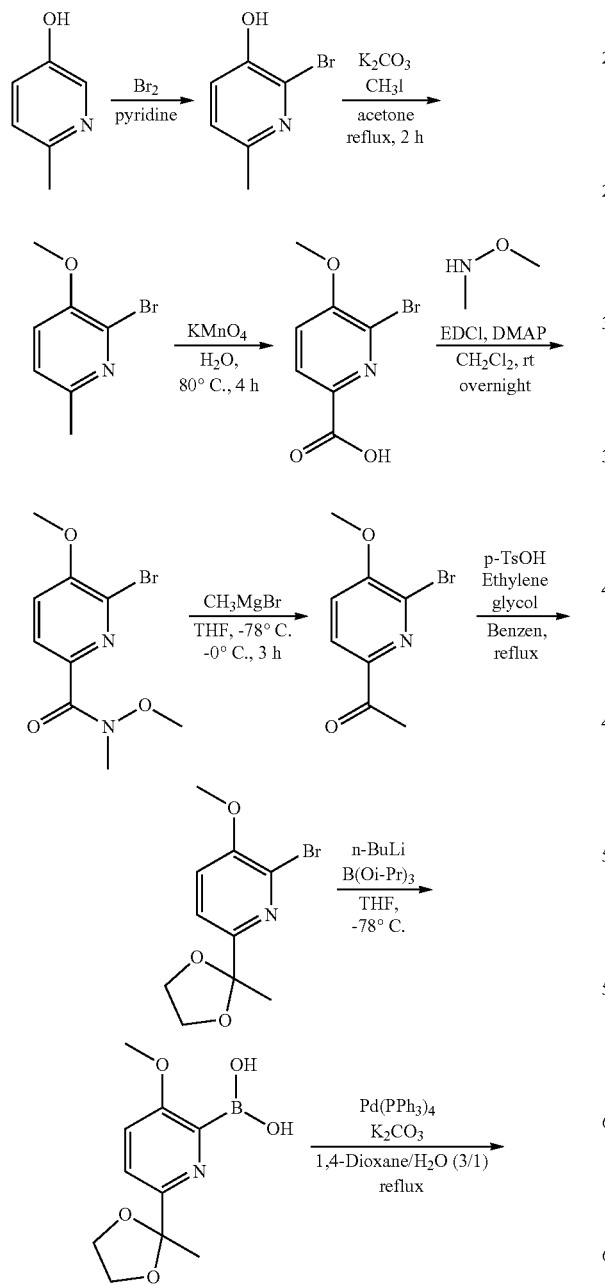
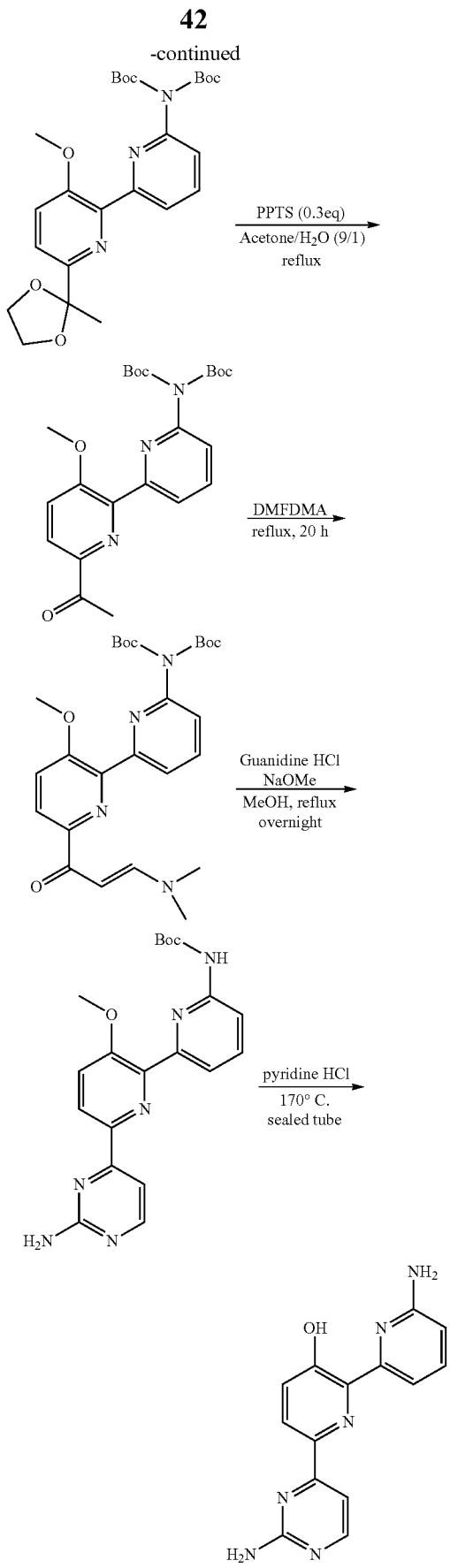

Example 7-1: Preparation of 2-bromo-6-methylpyridin-3-ol (XXXXIV)

5-Hydroxy-2-methylpyridine (XXXXIII) (1.0 g, 9.16 mmol) was dissolved in 30 ml of pyridine. To the resulting solution was slowly added bromine (879 mg, 5.50 mmol) at 0° C. and the solution was stirred at room temperature for 16 hrs. After pyridine was removed, the solution was extracted with 60 ml of ethylacetate (EA) and 60 ml of water. The organic layer was treated with magnesium sulfate ($MgSO_4$), filtered, and concentrated for a next reaction.

Example 7-2: Preparation of 2-bromo-3-methoxy-6-methylpyridine (XXXXV)

To 2-bromo-6-methylpyridin-3-ol (XXXXIV) were added 50 ml of acetone, potassium carbonate ($K_2CO_3$) (2.0 g, 14.66 mmol) and iodomethane (684 ul, 10.99 mmol), and the resulting mixture was stirred with reflux for 2 hrs. After TLC was conducted, the solvent was removed and the mixture was extracted with 60 ml of ethylacetate (EA) and 60 ml of water. The organic layer was treated with magnesium sulfate ($MgSO_4$) and filtered, and the solution was concentrated and purified through silica gel chromatography (normal hexane:ethylacetate=10:1, v/v) to give the title compound as pale yellow crystals (772 mg, 3.82 mmol, 42%).

$^1$H NMR (400 MHz, $CDCl_3$) δ 7.06 (s, 2H), 3.89 (s, 3H), 2.48 (s, 3H).

Example 7-3: Preparation of 6-bromo-5-methoxypicolinic acid (XXXXVI)

2-Bromo-3-methoxy-6-methylpyridine (XXXXV) 760 mg (3.76 mmol) was dissolved in 15 ml of water, and to the resulting solution was added potassium permanganate ($KMnO_4$) (1.49 g, 9.40 mmol) and the mixture was heated at 80° C. for 3 hrs. After TLC was conducted, pH was adjusted to 4 with 10% hydrochloric acid (HCl) and filtration was conducted with celite. The filtrate was extracted with 50 ml of ethylacetate (EA). The organic layer was treated with magnesium sulfate ($MgSO_4$) and filtered, and the solution was concentrated to give the title compound as a white solid (665 mg, 2.87 mmol, 75%) without purification.

$^1$H NMR (400 MHz, DMSO-$d_6$) δ 13.22 (s, OH), 8.05 (d, J=8.0 Hz, 1H), 7.60 (d, J=8.0 Hz, 1H), 4.02 (s, 3H).

Example 7-4: Preparation of 6-bromo-N,5-dimethoxy-N-methylpicolinamide (XXXXVII)

6-Bromo-5-methoxypicolinic acid (XXXXVI) (665 mg, 2.87 mmol) was dissolved in 10 ml of dichloromethane. N,O-dimethylhydroxyamine hydrochloride (336 mg, 3.44 mmol), 1-ethyl-3-(3-dimethylaminopropyl)carbodiimide (EDCI) (659 mg, 3.44 mmol), 4-dimethylaminopyridine (DMAP) (105 mg, 0.86 mmol), and triethylamine (TEA) (479 ul, 3.44 mmol) were added to the resulting solution and the solution was stirred at room temperature for 16 hrs. And then, the solution was extracted with 30 ml of dichloromethane and 30 ml of water. The organic layer was treated with magnesium sulfate ($MgSO_4$) and filtered, and the solution was concentrated and purified by silica gel column chromatography (normal hexane:ethylacetate=3:1, v/v) to give the title compound as colorless crystals (515 mg, 1.87 mmol, 65%).

$^1$H NMR (400 MHz, $CDCl_3$) δ 7.70 (d, J=8.4 Hz, 1H), 7.17 (d, J=8.4 Hz, 1H), 3.93 (s, 3H), 3.81 (s, 3H), 3.36 (s, 3H).

Example 7-5: Preparation of 1-(6-bromo-5-methoxypyridin-2-yl)ethanone (XXXXVIII)

6-Bromo-N,5-dimethoxy-N-methylpicolinamide (XXXXVII) (2.29 g, 8.32 mmol) was dissolved in 30 ml of tetrahydrofuran (THF) and the resulting solution was cooled to −78° C. To the solution was slowly added methylmagnesium bromide (1.4M) (7.73 ml, 10.82 mmol) and the solution was stirred at 0° C. for 1 hr. 60 ml of saturated ammonium chloride solution (Sat.$NH_4Cl$) was added to the solution and the solution was extracted with 60 ml of ethylacetate (EA). The organic layer was treated with magnesium sulfate ($MgSO_4$) and filtered, and the resulting solution was concentrated and purified by silica gel column chromatography (normal hexane:ethylacetate=3:1, v/v) to give the title compound as a white solid (1.88 g, 8.17 mmol, 98%).

$^1$H NMR (400 MHz, $CDCl_3$) δ 8.03 (d, J=8.4 Hz, 1H), 7.18 (d, J=8.4 Hz, 1H), 3.97 (s, 3H), 2.66 (s, 3H).

Example 7-6: Preparation of 2-bromo-3-methoxy-6-(2-methyl-1,3-dioxolan-2-yl)pyridine (XXXXIX)

1-(6-Bromo-5-methoxypyridin-2-yl)ethanone (XXXXVIII) (3.22 g, 14.00 mmol) was dissolved in 30 ml of benzene. To the resulting solution were added 3.9 ml of ethylene glycol and p-toluenesulfonic acid (p-TsOH) (799 mg, 4.20 mmol) and the solution was stirred with reflux for 40 hrs. After the reaction was completed, the solvent was concentrated under reduced pressure and extracted with 60 ml of water and 60 ml of ethylacetate. The organic layer was treated with magnesium sulfate ($MgSO_4$), and filtered, and the solution was concentrated and purified by silica gel column chromatography (normal hexane:ethylacetate=10:1, v/v) to give the title compound as a white solid (2.18 g, 7.95 mmol, 57%).

$^1$H NMR (400 MHz, $CDCl_3$) δ 7.46 (d, J=8.0 Hz, 1H), 7.10 (d, J=8.0 Hz, 1H), 4.06-4.10 (m, 2H), 3.92 (s, 3H), 3.86-3.92 (m, 2H), 1.72 (s, 3H).

Example 7-7: Preparation of (3-methoxy-6-(2-methyl-1,3-dioxolan-2-yl)pyridin-2-yl) boronic acid (L)

2-Bromo-3-methoxy-6-(2-methyl-1,3-dioxolan-2-yl)pyridine (XXXXIX) (300 mg, 1.09 mmol) obtained in step 6 was dissolved in 10 ml of tetrahydrofuran and the resulting solution was cooled to −78° C. To the solution was added n-butyllithium (n-BuLi) (820 ul, 1.31 mmol) and the solution was stirred at the same temperature for 90 min. Triisopropyl borate (0.302 ml, 2.18 mmol) was added to the solution and the solution was stirred at the same temperature for 5 min and then at room temperature for 90 min. After cooling to 0° C., 5% sodium hydroxide (NaOH) was added to the solution and the solution was stirred for 10 min and extracted with small amount of water. After removal of the organic layer, aqueous layer was neutralized with 2N hydrochloric acid (HCl) to pH 7 and used for next step.

Example 7-8: Preparation of tert-butyl-(3-methoxy-6-(2-methyl-1,3-dioxolan-2-yl)pyridin-2-yl)-[2,2'-pyridin]-6-yl)carbamate (LI)

To (3-methoxy-6-(2-methyl-1,3-dioxolan-2-yl)pyridin-2-yl)boronic acid (L) solution (1.09 mmol) were added 2-(6- chloro-2-pyridinyl)-1,3-bis(1,1-dimethylethyl)ester imidodicarbonic acid (358 mg, 1.09 mmol), tetrakis (triphenylphosphine)palladium(0) (Pd(PPh$_3$)$_4$) (63 mg, 0.05 mmol), and potassium carbonate (K$_2$CO$_3$) (1.0 g, 7.30 mmol). Then, the resulting mixture was refluxed with heat along with 1,4-dioxane for 3 hrs. After the reaction was completed, the solution was extracted 50 ml of water and 50 ml of ethylacetate. The organic layer was treated with magnesium sulfate (MgSO$_4$), and filtered, and the solution was concentrated and purified by silica gel column chromatography (normal hexane:ethylacetate=1:1, v/v) to give the title compound as a white solid (120 mg, 0.25 mmol, 23%).

$^1$H NMR (400 MHz, CDCl$_3$) δ 8.42 (s, 1H), 8.03 (s, 1H), 7.89 (d, J=8.0 Hz, 1H), 7.77 (dd, J=8.0, 8.0 Hz, 1H), 7.29 (d, J=8.0 Hz, 1H), 4.02-4.10 (m, 2H), 3.99 (s, 3H), 3.80-3.95 (m, 2H), 1.72 (s, 3H) 1.48 (s, 18H).

Example 7-9: Preparation of (6'-acetyl-3'methoxy-[2,2']bipyridinyl-6-yl)-imidocarbonic acid-1,3-bis(1,1-dimethylethyl)ester (LII)

Tert-butyl-(3-methoxy-6-(2-methyl-1,3-dioxolan-2-yl)pyridin-2-yl)-[2,2'-pyridine]-6-yl)carbamate (LI) (82 mg, 0.17 mmol) was dissolved in 3 ml of acetone and 330 ul of water. Pyridinium p-toluenesulfonate (PPTS) (13 mg, 0.05 mmol) was added to the resulting solution and the solution was refluxed with heat for 20 hrs. The solution was concentrated and purified by silica gel column chromatography (normal hexane:ethylacetate=3:1, v/v) to give the title compound as a white solid (55 mg, 0.12 mmol, 73%).

$^1$H NMR (400 MHz, CDCl$_3$) δ 8.56 (s, 1H), 8.44 (s, 1H), 7.85 (d, J=8.0 Hz, 1H), 7.79 (dd, J=8.0, 7.6 Hz, 1H), 7.35 (d, J=7.6 Hz, 1H), 4.08 (s, 3H), 2.70 (s, 3H), 1.50 (s, 18H).

Example 7-10: Preparation of [6'-(3-dimethyl-amino-acryloyl)-3'-methoxy-[2,2']bipyridinyl-6-yl-imidocarbonic acid-1,3-bis(1,1-dimethylethyl)ester (LIII)

(6'-Acetyl-3'methoxy-[2,2]bipyridinyl-6-yl)-imidodicarbonic acid-1,3-bis(1,1-dimethylethyl)ester (LII) (55 mg, 0.12 mmol) was added to 3 ml of N,N-dimethylformamide dimethyl acetal (DMFDMA) and the resulting mixture was stirred with reflux for 20 hrs. And then, the mixture was extracted with 30 ml of water and 30 ml of ethyl acetate. The organic layer was washed with brine two times. The organic layer was treated with magnesium sulfate (MgSO$_4$) and filtered, and the resulting solution was concentrated and purified by silica gel column chromatography (normal hexane:ethylacetate=1:1, v/v) to give the title compound as a solid (38 mg, 0.08 mmol, 67%).

$^1$H NMR (400 MHz, CD$_3$OD) δ 8.60 (s, 1H), 8.40 (s, 1H), 7.87 (d, J=12.0 Hz, 1H), 7.72-7.82 (m, 2H), 7.20-7.32 (m, 1H), 6.41 (d, J=12.0 Hz, 1H), 4.08 (s, 3H), 3.16 (brs, 3H), 2.99 (brs, 3H), 1.47 (s, 18H).

Example 7-11: Preparation of tert-butyl-(6'-(2-amino-pyrimidin-4-yl)-3'-methoxy-[2,2'-bipyridin]-6-yl)carbamate (LIV)

[6'-(3-dimethylamino-acryloyl)-3'-methoxy-[2,2']bipyridinyl-6-yl-imidodicarbonic acid-1,3-bis(1,1-dimethylethyl)ester (LIII) (38 mg, 0.08 mmol) was dissolved in 3 ml of methanol, and guanidine hydrochloride (7.6 mg, 0.08 mmol) and 25% sodium methoxide (NaOMe) (18 ul, 0.08 mmol) were added to the resulting solution and the solution was stirred with reflux for 20 hrs. After the reaction was completed, the solvent was concentrated under reduced pressure. Then, a small amount of water was added and the resulting solution was acidified with 4M hydrochloric acid (HCl) to pH 4. The resulting solid was filtered to give the title compound as a solid (22 mg, 0.06 mmol, 70%) without silica gel column chromatography.

$^1$H NMR (600 MHz, DMSO-d$_6$) δ 9.89 (s, NH), 8.64 (s, 1H), 8.63 (d, J=5.4 Hz, 1H), 8.36 (d, J=4.2 Hz, 1H), 7.84 (dd, J=5.4, 5.4 Hz, 1H), 7.82 (s, 1H), 7.56 (d, J=5.4 Hz, 1H), 7.44 (d, J=4.2 Hz, 1H), 6.66 (s, NH2), 4.04 (s, 3H).

Example 7-12: Preparation of 6'-amino-6-(2-aminopyrimidin-4-yl)-[2,2'-bipyridin]-3-ol (LV)

Tert-butyl-(6'-(2-amino-pyrimidin-4-yl)-3'-methoxy-[2,2'-bipyridin]-6-yl)carbamate (LIV) (22 mg, 0.06 mmol) was mixed with pyridine hydrochloride (Pyridine HCl) (104 mg, 0.90 mmol) in a sealed tube at 170° C. for 30 min. 2N sodium hydroxide (NaOH) was added to neutralize the resulting mixture to pH 7, and then the mixture was extracted with 30 ml of water and 30 ml of ethylacetate. The organic layer was treated with magnesium sulfate (MgSO$_4$), and filtered, and the resulting solution was concentrated to give the title compound as a yellow solid (6.7 mg, 0.02 mmol, 33%) without silica gel column chromatography.

$^1$H NMR (600 MHz, CD$_3$OD) δ 14.88 (s, OH), 8.69 (s, 1H), 8.34 (s, 1H), 8.32 (d, J=4.8 Hz, 1H), 7.70 (dd, J=8.4, 7.8 Hz, 1H), 7.39 (d, J=4.8 Hz, 1H), 7.30 (d, J=7.8 Hz, 1H), 6.81 (s, NH2), 6.65 (s, NHJ2), 6.61 (d, J=8.4 Hz, 1H).

Preparation Example 1: Preparation of 2-[3-fluoro-4-(4,4,5,5-tetramethyl-[1,3,2]dioxaborolan-2-yl)-2-pyridinyl]-imidodicarbonic acid-1,3-bis(1,1-dimethylethyl)ester

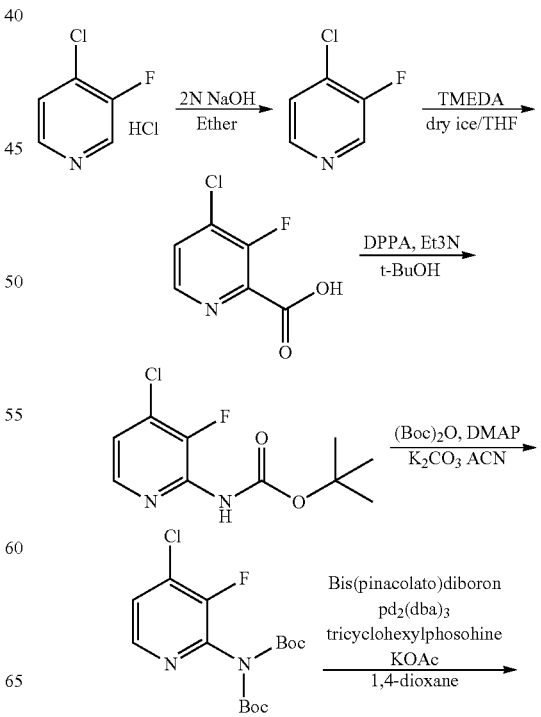

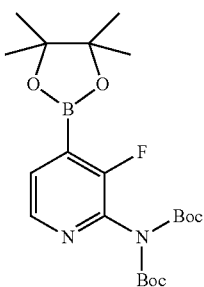

Preparation Example 1-1: Preparation of 4-chloro-3-fluoropyridine

4-Chloro-3-fluoropyridine hydrochloride (50 g, 0.298 mol) was dissolved in distilled water (200 ml) and 2N sodium hydroxide (NaOH) aqueous solution was added dropwise to basify the resulting solution (pH=14). And then, the solution was extracted with diethylether, dried over magnesium sulfate ($MgSO_4$), and concentrated under reduced pressure to use in a next reaction without isolation.

Preparation Example 1-2: Preparation of 4-chloro-3-fluoro-pyridin-2-carboxylic acid 2,2,6,6,-Tetramethylpiperidine (430 ml, 0.357 mol) was added dropwise to tetrahydrofuran (THF) (74 ml) at −78° C., and then 1.6M n-butyllithium hexane solution (220 ml, 0.357 mol) was added dropwise thereto and the resulting mixture was stirred for 30 min. To the mixture was slowly added dropwise 4-chloro-3-fluoropyridine diethylether solution obtained in Preparation Example 1-1 and the resulting solution was stirred at −78° C. for 1 hr. Carbon dioxide gas was passed through the solution at −78° C. for 1 hr, the solution was warmed to room temperature and then stirred for 1 hr. After completion of the reaction by addition of water, the organic layer was separated with diethylether and aqueous layer was acidified to pH 2 using 2N hydrochloric acid aqueous solution. And then, the solution was extracted with ethylacetate, washed with distilled water, and dried over magnesium sulfate ($MgSO_4$) to concentrate. The resulting residue was recrystallized with hexane/ethylacetate (1/1) to give the white title compound (13.06 g, 25.0%).

$^1$H NMR (400 MHz, DMSO) δ 8.47 (d, J=3.6 Hz, 1H), 7.95 (m, 1H).

Preparation Example 1-3: Preparation of (4-chloro-3-fluoro-pyridin-2-yl)-carbamic acid-tert-butyl ester 4-Chloro-3-fluoro-pyridin-2-carboxylic acid (13.06 g, 0.074 mol) was dissolved in tert-butanol (370 ml) and the temperature was lowered to 0° C. To the resulting solution was added dropwise triethylamine (15.56 ml, 0.112 mol). And then, the solution was stirred at room temperature for 40 min and the reaction temperature was lowered to 0° C. Diphenylphosphorylazide (DPPA) (24.09 ml, 0.112 mol) was added dropwise to the solution and the solution was stirred at room temperature for 1.5 hrs and then with reflux for 18 hrs. After completion of the reaction, the solution was extracted with ethylacetate, washed with distilled water, and then dried over magnesium sulfate ($MgSO_4$) to concentrate. The resulting residue was isolated and purified by silica gel column chromatography (hexane/ethylacetate=2/1) to give the brown title compound (5.51 g, 30.0%).

$^1$H NMR (600 MHz, $CDCl_3$) δ 9.76 (s, NH), 8.15 (d, J=6.0 Hz, 1H), 7.51 (m, 1H).

Preparation Example 1-4: Preparation of 2-(3-fluoro-4-chloropyridinyl)-imidocarbonic acid-1,3-bis (1,1-dimethylethyl)ester (4-Chloro-3-fluoro-pyridin-2-yl)-carbamic acid-tert-butyl ester (5.51 g 0.022 mol) was dissolved in acetonitrile (110 ml), and di-t-butyl dicarbonate (($Boc)_2O$) (7.31 g, 0.033 mol), potassium carbonate ($K_2CO_3$) (9.62 g, 0.67 mol), and 4-dimethylaminopyridine (820 mg, 0.007 mol) were added to the resulting solution. The solution was stirred at room temperature for 18 hrs. After completion of the reaction by addition of water, the solution was extracted with ethylacetate, washed with distilled water, and dried over magnesium sulfate ($MgSO_4$) to concentrate. The resulting residue was isolated and purified by silica gel column chromatography (hexane/ethylacetate=3/1) to give the brown title compound (7.36 g, 95.0%).

$^1$H NMR (600 MHz, $CDCl_3$) δ 8.22 (d, J=4.2 Hz, 1H), 7.51 (m, 1H), 1.43 (m, 18H).

Preparation Example 1-5: Preparation of 2-[3-fluoro-4-(4,4,5,5-tetramethyl-[1,3,2]dioxaborolan-2-yl)-2-pyridinyl]-imidodicarbonic acid-1,3-bis(1,1-dimethylethyl)ester 2-(3-Fluoro-4-chloropyridinyl)-imidocarbonic acid-1,3-bis(1,1-dimethylethyl)ester (7.36 g, 0.021 mol) was dissolved in 1,4-dioxane (20 ml), and bis(pinacolato)diboron (10.78 g, 0.042 mol), tris(dibenzylideneacetone)dipalladium (0) (970 mg, 1.0 mmol), tricyclohexylphosphine (450 mg, 1.607 mmol), and potassium acetate (8.33 g, 0.085 mol) were added to the resulting solution. The solution was stirred with reflux for 18 hrs. After completion of the reaction, the solid was removed through celite filter and the solvent was dried under reduced pressure. The resulting residue was isolated and purified by silica gel column chromatography (ethylacetate/methanol=10/1) to give the brown title compound (2.05 g, 22.0%).

$^1$H NMR (600 MHz, $CDCl_3$) δ 8.28 (d, J=7.2 Hz, 1H), 7.58 (m, 1H), 1.42 (s, 18H), 1.37 (s, 12H).

Preparation Example 2: Preparation of 4-(6-bromo-3-methoxy-pyridin-2-yl)-pyrimidin-2-ylamine (LXI)

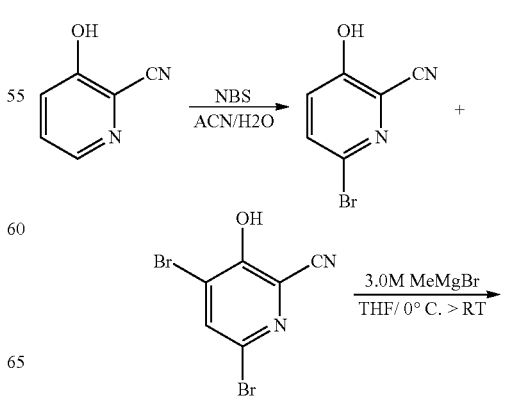

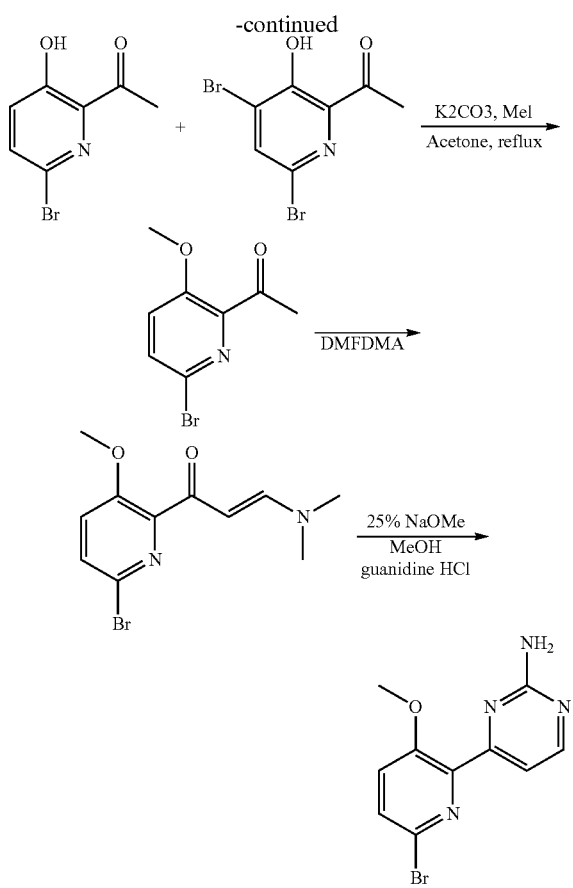

Preparation Example 2-1: Preparation of 6-bromo-3-hydroxy-pyridin-2-carbonitrile and 4,6-dibromo-3-hydroxy-pyridin-2-carbonitrile (LVII)

2-Cyano-3-hydroxypyridine (5 g, 0.042 mol) was dissolved in a mixture of acetonitrile (50 ml) and distilled water (10 ml) and the resulting solution was cooled to 0° C. N-bromosuccinimide (6 g, 0.050 mol) was slowly added to the solution and the solution was stirred at room temperature for 24 hrs. After completion of the reaction by addition of water, the solution was extracted with ethylacetate, washed with distilled water, and dried over magnesium sulfate (MgSO$_4$) to concentrate. The resulting residue was washed with small amount of ethylacetate and hexane to give the white title compound (8.28 g, 99.9%).

$^1$H NMR (400 MHz, CDCl$_3$) δ 11.03 (s, OH), 7.74 (d, J=6.0 Hz, 1H), 7.42 (d, J=6.0 Hz, 1H).

Preparation Example 2-2: Preparation of 1-(6-bromo-3-hydroxy-pyridin-2-yl)-ethanone and 1-(4,6-dibromo-3-hydroxy-pyridin-2-yl)-ethanone (LVIII)

6-Bromo-3-hydroxy-pyridin-2-carbonitrile and 4,6-dibromo-3-hydroxy-pyridin-2-carbonitrile (8.28 g, 0.042 mol) were dissolved in tetrahydrofuran (THF) (140 ml), and the resulting solution was cooled to 0° C. 3M methylmagnesium bromide tetrahydrofuran (THF) solution (40 ml) was added to the solution and the solution was stirred at room temperature for 3 hrs. After completion of the reaction by 5N hydrochloric acid aqueous solution (pH=2), aqueous layer was basified with saturated sodium bicarbonate aqueous solution. The solution was extracted with ethylacetate, washed with distilled water, and dried over magnesium sulfate (MgSO$_4$) to concentrate. The resulting residue was isolated and purified by silica gel column chromatography (hexane/ethylacetate/dichloromethane=10/2/3) to give the white title compound (3.15 g, 35.0%).

$^1$H NMR (400 MHz, CDCl$_3$) δ 11.79 (s, OH), 7.54 (m, 1H), 7.42 (d, J=6.0 Hz, 1H), 2.70 (s, 3H).

Preparation Example 2-3: Preparation of 1-(6-bromo-3-methoxy-pyridin-2-yl)-ethanone (LVIX)

1-(6-Bromo-3-hydroxy-pyridin-2-yl)-ethanone and 1-(4,6-dibromo-3-hydroxy-pyridin-2-yl)-ethanone (3.15 g, 0.012 mol) were dissolved in acetone (60 ml). Potassium carbonate (K$_2$CO$_3$) (6.04 g, 0.044 mol) and iodomethane (CH$_3$I) (1.81 ml, 0.026 mol) were added to the resulting solution and the solution was stirred with reflux for 18 hrs. After completion of the reaction by addition of water, the solution was extracted with ethylacetate, washed with distilled water, and dried over magnesium sulfate (MgSO$_4$) to concentrate. The resulting residue was isolated and purified by silica gel column chromatography (hexane/ethylacetate=1/1) to give the white title compound (3.18 g, 95.0%).

$^1$H NMR (400 MHz, CDCl$_3$) δ 7.77 (d, J=8.4 Hz, 1H), 7.64 (d, J=9.0 Hz, 1H), 3.30 (s, 3H).

Preparation Example 2-4: Preparation of 1-(6-bromo-3-methoxy-pyridin-2-yl)-3-dimethylamino-propenone (LX)

1-(6-Bromo-3-methoxy-pyridin-2-yl)-ethanone (3.18 g, 0.014 mol) was dissolved in N,N-dimethylformamide dimethyl acetal (DMFDMA) (18.53 ml) and the solution was stirred with reflux for 18 hrs. After completion of the reaction, N,N-dimethylformamide dimethyl acetal (DMFDMA) was removed by drying under reduced pressure, and the resulting solution was recrystallized with ethylacetate/hexane to give the brown title compound (3.55 g, 90%).

$^1$H NMR (400 MHz, CDCl$_3$) δ 7.8-7.5 (br, 1H), 7.42 (d, J=8.4 Hz, 1H), 7.16 (d, J=9.0 Hz, 1H), 5.61 (br, 1H), 3.85 (s, 3H).

Preparation Example 2-5: Preparation of 4-(6-bromo-3-methoxy-pyridin-2-yl)-pyrimidin-2-ylamine (LXI)

1-(6-Bromo-3-methoxy-pyridin-2-yl)-3-dimethylamino-propenone (3.55 g, 0.012 mol) was dissolved in methanol (60 ml). 25% Sodium methoxide (8.55 ml, 0.037 mol) and guanidine hydrochloride (1.79 g, 0.019 mol) were added to the resulting solution and the solution was stirred with reflux for 18 hrs. After completion of the reaction by addition of water, the solution was extracted with ethylacetate, washed with distilled water, and dried over magnesium sulfate (MgSO$_4$) to concentrate. The resulting residue was isolated and purified by silica gel column chromatography (hexane/ethylacetate=1/1) to give the brown title compound (2.98 g, 85.0%).

$^1$H NMR (400 MHz, DMSO) δ 8.31 (d, 1H), 7.66 (d, 1H), 7.84 (d, J=8.4 Hz, 1H), 7.16 (d, J=9.0 Hz, 1H), 5.61 (br, 1H), 3.85 (s, 3H).

Example 8: Preparation of 2'-amino-6'-(2-aminopyrimidin-4-yl)-3'-fluoro-[2,4'-bipyridin]-5-ol (LXIII)

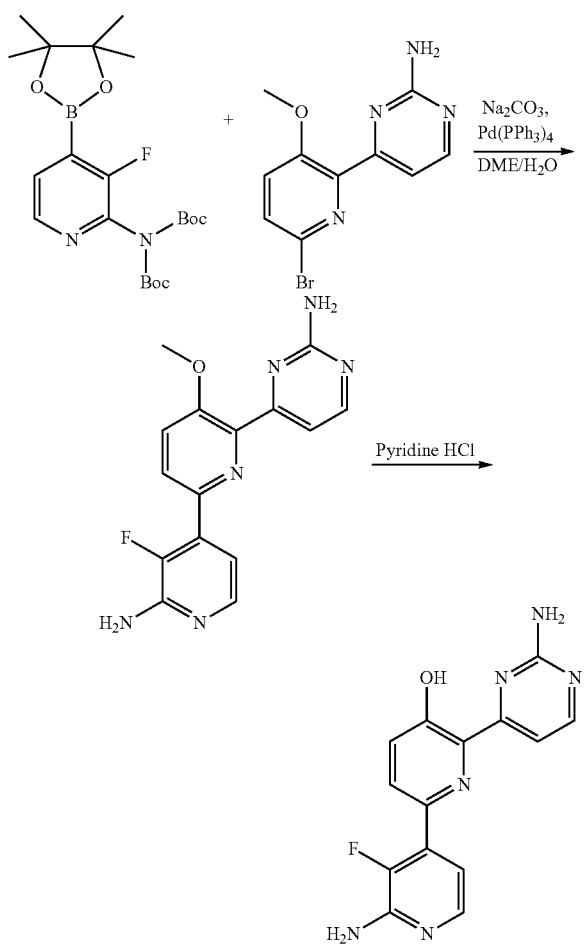

Example 8-1: Preparation of 6-(2-amino-pyrimidin-4-yl)-3'-fluoro-5-methoxy-[2,4']bipyridin-2'-ylamine (LXII)

4-(6-Bromo-3-methoxy-pyridin-2-yl)-pyrimidin-2-ylamine (830 mg, 2.95 mmol) obtained in Preparation Example 2 and 2-[3-fluoro-4-(4,4,5,5-tetramethyl-[1,3,2]dioxaborolan-2-yl)-2-pyridinyl]-imidodicarbonic acid-1,3-bis(1,1-dimethylethyl)ester (1.0 g, 2.281 mmol) obtained in Preparation Example 1 were dissolved in ethylene glycol dimethyl ester/distilled water (10 ml/2 ml) solution. Sodium carbonate (730 mg, 6.887 mmol) and tetrakis(triphenylphosphine)palladium(0) (Pd(PPh$_3$)$_4$) (80 mg, 0.069 mmol) were added to the resulting solution and the solution was stirred with reflux for 18 hrs. After completion of the reaction by addition of water, the solution was extracted with ethylacetate, washed with distilled water, and dried over magnesium sulfate (MgSO$_4$) to concentrate. The resulting residue was isolated and purified by silica gel column chromatography (hexane/ethylacetate=1/1) to give the brown title compound (210 mg, 30.0%).

$^1$H NMR (400 MHz, DMSO) δ 8.31 (d, J=3.2 Hz, 1H), 7.90 (dd, J=2.4 Hz, J=3.2 Hz, 1H), 7.71 (d, J=6.0 Hz, 1H), 6.98 (m, 1H), 6.82 (d, J=3.6 Hz, 1H), 3.87 (s, 3H).

Example 8-2: Preparation of 2'-amino-6'-(2-aminopyrimidin-4-yl)-3'-fluoro-[2,4'-bipyridin]-5-ol (LXIII)

6-(2-amino-pyrimidin-4-yl)-3'-fluoro-5-methoxy-[2,4']bipyridin-2'-ylamine (LXII) (210 mg, 0.672 mmol) was mixed with pyridine hydrochloride (Pyridine HCl) (790 mg, 6.720 mmol) and the mixture was stirred at 170° C. for 1 hr. The mixture was cooled to room temperature, neutralized with 2N sodium hydroxide (NaOH) solution, and diluted with ethylacetate (EA). Then, the organic solvent was dried over anhydrous magnesium sulfate (MgSO$_4$), filtered and evaporated under reduced pressure to concentrate to give the title compound (170 mg, 85%).

$^1$H NMR (400 MHz, DMSO) δ 8.50 (d, J=3.6 Hz, 1H), 7.90 (d, J=5.6 Hz, 1H), 7.83 (d, J=3.2 Hz, 1H), 7.59 (dd, J=3.2 Hz, J=3.6 Hz, 1H), 7.51 (d, J=5.6 Hz, 1H), 7.31 (br, 2H), 7.12 (m, 1H).

Example 9: Preparation of 2-(2-aminopyrimidin-4-yl)-6-(4-hydroxyphenyl)pyridin-3-ol

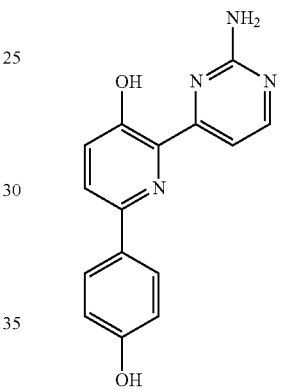

The title compound as a yellow solid (4.6 mg) was obtained according to the same procedure as Example 8, except for using 2-(4-methoxy-phenyl)-4,4,5,5-tetramethyl-[1,3,2]dioxaborolane instead of the compound obtained Preparation Example 1.

$^1$H NMR (600 MHz, DMSO) δ 13.54 (s, 1H), 9.62 (s, 1H), 8.47 (d, J=7.8 Hz, 1H), 7.93 (d, J=9.6 Hz, 1H), 7.86 (d, J=12.6 Hz, 1H), 7.64 (d, J=7.8 Hz, 1H), 7.37 (d, J=12.6 Hz, 1H), 7.22 (br, 2H), 6.84 (d, J=9.6 Hz, 1H).

Example 10: Preparation of 2'-amino-6-(2-aminopyrimidin-4-yl)-[2,4'-bipyridin]-5-ol

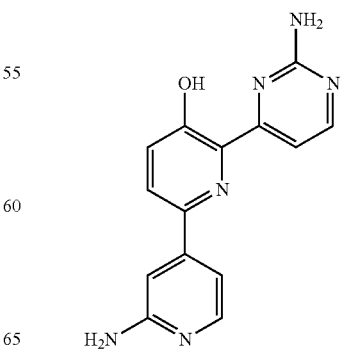

The title compound as a yellow solid (5.3 mg) was obtained according to the same procedure as Example 8, except for using 4-(4,4,5,5-tetramethyl-[1,3,2]dioxaborolane-2-yl)-pyridin-2-ylamine instead of the compound obtained in Preparation Example 1.

¹H NMR (600 MHz, DMSO) δ 13.56 (s, 1H), 9.66 (s, 1H), 8.49 (d, J=7.8 Hz, 1H), 7.94 (d, J=13.2 Hz, 1H), 7.88 (d, J=13.2 Hz, 1H), 7.66 (d, J=7.8 Hz, 1H), 7.39 (d, J=13.2 Hz, 1H), 7.25 (br, 2H), 6.85 (d, J=13.2 Hz, 1H).

Example 11: Preparation of 6-(2-aminopyrimidin-4-yl)-[2,3'-bipyridin]-5-ol

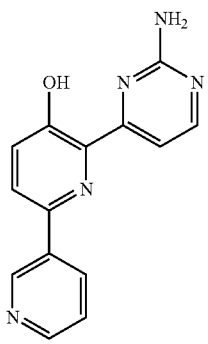 [SMILES: Nc1nccc(-c2nc(-c3cccnc3)ccc2O)n1]

The title compound as a yellow solid (8.8 mg) was obtained according to the same procedure as Example 8, except for using 3-(4,4,5,5-tetramethyl-[1,3,2]dioxaborolan-2-yl)-pyridine instead of the compound obtained in Preparation Example 1.

¹H NMR (600 MHz, DMSO) δ 13.81 (s, 1H), 9.29 (s, 1H), 8.58 (d, J=7.8 Hz, 1H), 8.48 (m, 2H). 8.11 (d, J=12.6 Hz, 1H), 7.70 (d, J=7.2 Hz, 1H), 7.50 (m, 2H), 7.29 (br, 2H).

Example 12: Preparation of 6-(2-aminopyrimidin-4-yl)-[2,4'-bipyridin]-5-ol

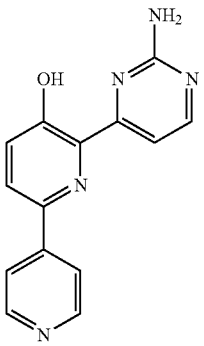 [SMILES: Nc1nccc(-c2nc(-c3ccncc3)ccc2O)n1]

The title compound as a yellow solid (7.3 mg) was obtained according to the same procedure as Example 8, except for using 4-(4,4,5,5-tetramethyl-[1,3,2]dioxaborolan-2-yl)-pyridine instead of the compound obtained in Preparation Example 1.

¹H NMR (600 MHz, DMSO) δ 13.99 (s, 1H), 8.69 (d, J=7.2 Hz, 1H), 8.52 (d, J=7.8 Hz, 1H). 8.20 (d, J=13.2 Hz, 1H), 8.15 (d, J=9.0 Hz, 1H), 7.71 (d, J=7.8 Hz, 1H), 7.53 (d, J=13.2 Hz, 1H), 7.36 (br, 2H).

Example 13: Preparation of 2-(2-aminopyrimidin-4-yl)-6-(3-hydroxyphenyl)pyridin-3-ol

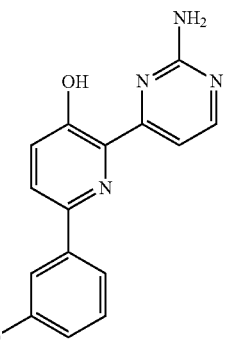

The title compound as a yellow solid (11.2 mg) was obtained according to the same procedure as Example 8, except for using 2-(3-methoxy-phenyl)-4,4,5,5-tetramethyl-[1,3,2]dioxaborolane instead of the compound obtained in Preparation Example 1.

¹H NMR (400 MHz, DMSO) δ 13.66 (s, 1H), 9.64 (s, 1H), 8.50 (d, J=5.2 Hz, 1H), 7.92 (d, J=8.8 Hz, 1H). 7.65 (d, J=4.8 Hz, 1H), 7.57 (s, 1H), 7.48 (d, J=7.6 Hz, 1H), 7.43 (d, J=8.8 Hz, 1H), 7.26 (m, 3H), 6.80 (d, J=8.0 Hz, 1H).

Example 14: Preparation of 6-(2-aminopyrimidin-4-yl)-3'-fluoro-[2,4'-bipyridin]-5-ol

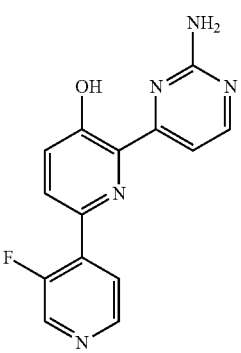 [SMILES: Nc1nccc(-c2nc(-c3ccncc3F)ccc2O)n1]

The title compound as a yellow solid (10.4 mg) was obtained according to the same procedure as Example 8, except for using 3-fluoro-4-(4,4,5,5-tetramethyl-[1,3,2]dioxaborolan-2-yl)-pyridine instead of the compound obtained in Preparation Example 1.

¹H NMR (400 MHz, CD₃OD) δ 8.55 (d, J=3.6 Hz, 1H), 8.49 (d, J=4.8 Hz, 1H). 8.45 (d, J=5.4 Hz, 1H), 8.21 (m, 1H), 8.02 (dd, J=8.4 Hz, J=9.6 Hz, 1H), 7.80 (d, J=5.4 Hz, 1H), 7.47 (d, J=9.0 Hz, 1H).

Example 15: Preparation of 6-(4-amino-2-fluoro-phenyl)-2-(2-aminopyrimidin-4-yl)pyridin-3-ol

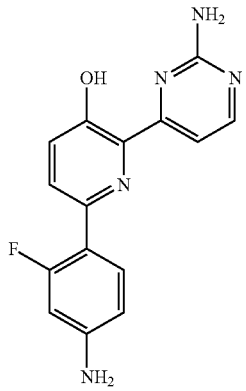 [SMILES: Nc1ccc(-c2ccc(O)c(-c3ccnc(N)n3)n2)c(F)c1]

The title compound as a yellow solid (7.9 mg) was obtained according to the same procedure as Example 8, except for using N-[3-fluoro-4-(4,4,5,5-tetramethyl-[1,3,2]dioxaborolan-2-yl)-phenyl]-2-phenyl-acetamide instead of the compound obtained in Preparation Example 1.

$^1$H NMR (400 MHz, DMSO) δ 13.49 (s, 1H), 8.44 (d, J=5.2 Hz, 1H), 7.73 (m, 1H), 7.63 (d, J=8.8 Hz, 1H). 7.56 (d, J=5.2 Hz, 1H), 7.34 (d, J=8.8 Hz, 1H), 7.18 (br, 2H), 6.47 (d, J=8.8 Hz, 1H), 6.35 (d, J=14.8 Hz, 1H), 5.62 (s, 2H).

Example 16: Preparation of 6-(3-aminophenyl)-2-(2-aminopyrimidin-4-yl)pyridin-3-ol

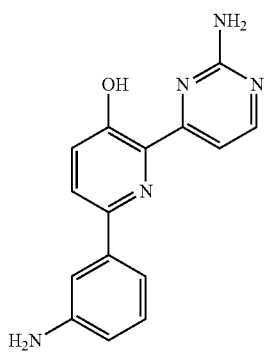

The title compound as a yellow solid (5.2 mg) was obtained according to the same procedure as Example 8, except for using 2-[5-(4,4,5,5-tetramethyl-[1,3,2]dioxaborolan-2-yl)phenyl]-1,3-bis(1,1-dimethylethyl)-ester-imidodicarbonic acid instead of the compound obtained in Preparation Example 1.

$^1$H NMR (400 MHz, DMSO) δ 13.62 (s, 1H), 8.50 (d, J=5.2 Hz, 1H), 7.84 (d, J=8.8 Hz, 1H), 7.67 (d, J=4.8 Hz, 1H), 7.48 (d, J=3.2 Hz, 1H). 7.35 (s, 1H), 7.25 (br, 2H), 7.19 (d, J=7.6 Hz, 1H), 7.11 (m, 1H), 6.59 (d, J=9.2 Hz, 1H), 6.35 (d, J=14.8 Hz, 1H), 5.16 (s, 2H).

Example 17: Preparation of 2-(2-aminopyrimidin-4-yl)-6-(2-fluoro-4-hydroxyphenyl)pyridin-3-ol

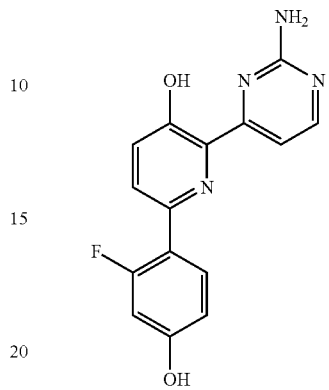

The title compound as a yellow solid (27 mg) was obtained according to the same procedure as Example 8, except for using 2-(2-fluoro-4-methoxy-phenyl)-4,4,5,5-tetramethyl-[1,3,2]dioxaborolane instead of the compound obtained in Preparation Example 1.

$^1$H NMR (600 MHz, DMSO) δ 13.63 (s, 1H), 10.11 (s, 1H), 8.48 (d, J=7.8 Hz, 1H), 7.89 (m, 1H), 7.72 (d, J=13.2 Hz, 1H), 7.59 (d, J=7.8 Hz, 1H), 7.42 (d, J=12.6 Hz, 1H). 7.24 (br, 2H), 6.76 (d, J=12.6 Hz, 1H), 6.65 (d, J=19.8 Hz, 1H).

Example 18: Preparation of 6-(3-amino-2-fluoro-phenyl)-2-(2-aminopyrimidin-4-yl)pyridin-3-ol

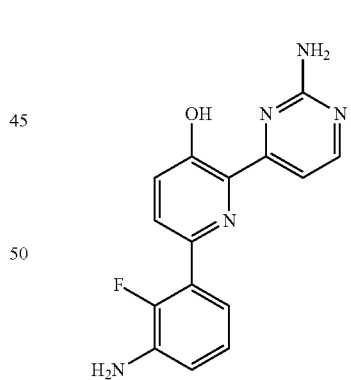

The title compound as a yellow solid (26 mg) was obtained according to the same procedure as Example 8, except for using 2-fluoro-3-[(4,4,5,5-tetramethyl-[1,3,2]dioxaborolan-2-yl)phenyl]-1,3-bis(1,1-dimethylethyl)-ester-imidodicarbonic acid instead of the compound obtained in Preparation Example 1.

$^1$H NMR (600 MHz, DMSO) δ 13.69 (s, 1H), 8.48 (d, J=7.8 Hz, 1H), 7.75 (d, J=13.2 Hz, 1H), 7.56 (d, J=7.8 Hz, 1H), 7.45 (d, J=13.2 Hz, 1H). 7.25 (br, 2H), 7.07 (m, 1H), 6.97 (m, 1H), 6.80 (m, 1H).

Example 19: Preparation of 2-(2-aminopyrimidin-4-yl)-6-(3-fluoro-4-hydroxyphenyl)pyridin-3-ol

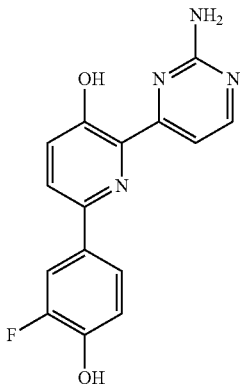 [SMILES: Nc1nccc(-c2nc(-c3ccc(O)c(F)c3)ccc2O)n1]

The title compound as a yellow solid (50.2 mg) was obtained according to the same procedure as Example 8, except for using 2-(3-fluoro-4-methoxy-phenyl)-4,4,5,5-tetramethyl-[1,3,2]dioxaborolane instead of the compound obtained in Preparation Example 1.

$^1$H NMR (400 MHz, DMSO) δ 13.64 (s, 1H), 10.16 (s, 1H), 8.49 (d, J=3.6 Hz, 1H), 7.94 (d, J=5.6 Hz, 1H), 7.90 (d, J=8.8 Hz, 1H), 7.77 (d, J=6.0 Hz, 1H). 7.41 (d, J=5.6 Hz, 1H), 7.25 (br, 2H), 7.07 (m, 1H).

Example 20: Preparation of 2-(2-aminopyrimidin-4-yl)-6-(2,3-difluoro-4-hydroxyphenyl)pyridin-3-ol

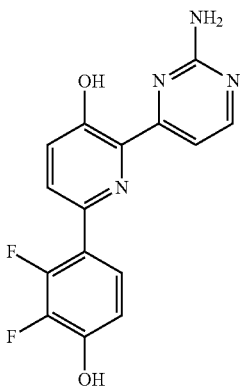 [SMILES: Nc1nccc(-c2nc(-c3ccc(O)c(F)c3F)ccc2O)n1]

The title compound as a yellow solid (12.6 mg) was obtained according to the same procedure as Example 8, except for using 2-(2,3-difluoro-4-methoxy-phenyl)-4,4,5,5-tetramethyl-[1,3,2]dioxaborolane instead of the compound obtained in Preparation Example 1.

$^1$H NMR (400 MHz, DMSO) δ 13.71 (s, 1H), 10.50 (br, 1H), 8.49 (d, J=3.6 Hz, 1H), 7.75 (d, J=8.8 Hz, 1H), 7.66 (m, 1H), 7.59 (d, J=5.2 Hz, 1H). 7.46 (d, J=8.4 Hz, 1H), 7.28 (br, 2H), 6.92 (m, 1H).

Example 21: Preparation of 2'-amino-6-(2-aminopyrimidin-4-yl)-[2,4'-bipyridin]-3',5-diol

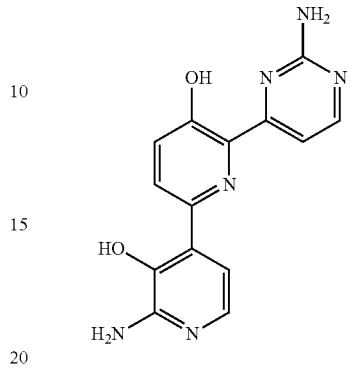

The title compound as a yellow solid (2.1 mg) was obtained according to the same procedure as Example 8, except for using 2-[3-hydroxy-4-(4,4,5,5-tetramethyl-[1,3,2]dioxaborolan-2-yl)-2-pyridinyl]-imidodicarbonic acid-1,3-bis(1,1-dimethylethyl)ester instead of the compound obtained in Preparation Example 1.

$^1$H NMR (400 MHz, DMSO-$d_6$) δ 8.61 (d, J=5.2 Hz, 1H), 8.28 (d, J=9.2 Hz, 1H), 7.68 (d, J=9.2 Hz, 1H), 7.51 (d, J=5.6 Hz, 1H), 7.46 (s, 2H), 7.15 (d, J=5.2 Hz, 1H), 7.13 (d, J=5.6 Hz, 1H), 5.96 (s, 2H).

Example 22: Preparation of 6-(2-aminopyrimidin-4-yl)-2-(4-(methylamino)thiazol-2-yl)pyridin-3-ol

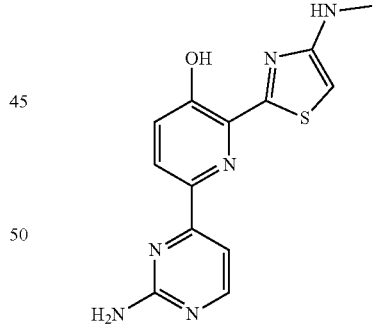

The title compound as a yellow solid (3.2 mg) was obtained according to the same procedure as Example 7, except for using (2-chloro-thiazol-4-yl)-methyl-amine instead of 2-(6-chloro-2-pyridinyl)-1,3-bis(1,1-dimethylethyl)ester imidodicarbonic acid in Example 7-8.

$^1$H NMR (400 MHz, DMSO-$d_6$) δ 9.04 (s, 1H), 8.73 (d, J=3.2 Hz, 1H), 8.38 (d, J=4.4 Hz, 1H), 7.43 (d, J=5.2 Hz, 1H), 7.04 (s, 1H), 6.71 (s, 2H), 6.66 (d, J=5.2 Hz, 1H), 3.70 (s, 3H).

Example 23: Preparation of 6-(2-aminopyrimidin-4-yl)-6'-(methylamino)-[2,2'-bipyridin]-3-ol

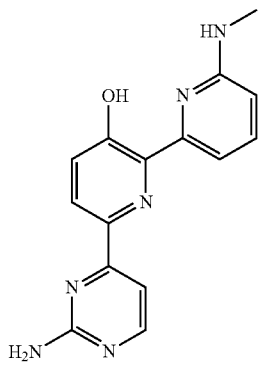 [SMILES: CNc1cccc(-c2nc(-c3ccnc(N)n3)ccc2O)n1]

The title compound as a yellow solid (8.4 mg) was obtained according to the same procedure as Example 7-12 using the by-product [6'-(2-amino-pyrimidin-4-yl)-3'methoxy-[2,2']bipyridinyl-6-yl]-methyl-amine obtained in Example 7-11.

$^1$H NMR (600 MHz, CD$_3$OD) δ 14.88 (s, OH), 8.69 (s, 1H), 8.34 (s, 1H), 8.32 (d, J=4.8 Hz, 1H), 7.70 (dd, J=8.4, 7.8 Hz, 1H), 7.39 (d, J=4.8 Hz, 1H), 7.30 (d, J=7.8 Hz, 1H), 6.81 (s, NH2), 6.65 (s, NH2), 6.61 (d, J=8.4 Hz, 1H), 3.48 (s, 1H).

Preparation Example 3: Preparation of 4-(6-bromo-3-methoxypyridin-2-yl)-6-methylpyrimidin-2-amine (LXIX)

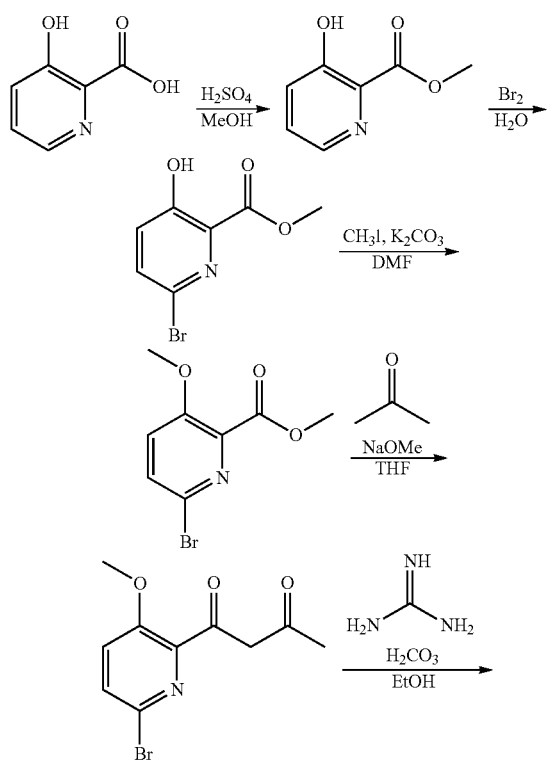

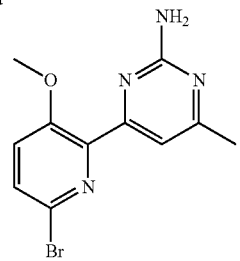

Preparation Example 3-1: Preparation of methyl 3-hydroxypicolinate (LXV)

3-Hydroxypicolinic acid (5.0 g, 35.94 mmol) was dissolved in methanol (120 mL). To the resulting solution was slowly added dropwise sulfuric acid (5.75 mL, 107.83 mmol) at 0° C. and the solution was refluxed with heat for 24 hrs, cooled to room temperature, and evaporated under reduced pressure. The resulting residue was diluted with dichloromethane and distilled water, neutralized with 6N sodium hydroxide, and extracted with dichloromethane. The organic solvent was dried over anhydrous magnesium sulfate (MgSO$_4$) to concentrate. The resulting residue was isolated and purified by silica gel column chromatography (hexane/ethylacetate=1/1) to give the white title compound (4.62 g, 83%).

$^1$H NMR (600 MHz, CDCl$_3$) δ 8.28 (dd, J=1.2, 2.4 Hz, 1H), 7.43 (dd, J=4.2, 4.2 Hz, 1H), 7.38, (dd, J=1.2, 7.2 Hz, 1H), 4.06 (s, 3H).

Preparation Example 3-2: Preparation of methyl 6-bromo-3-hydroxypicolinate (LXVI)

Methyl 3-hydroxypicolinate (4.62 g, 30.17 mmol) was dissolved in distilled water (200 mL). To the resulting solution was slowly added dropwise bromine water (1.7 mL, 33.18 mmol) and the solution was stirred at room temperature for 4 hrs. The solution was diluted with ethylacetate and washed with water. The washed organic solvent was dried over anhydrous magnesium sulfate (MgSO$_4$) to concentrate. The resulting residue was isolated and purified by silica gel column chromatography (hexane/ethylacetate=3/1) to give the white title compound (5.07 g, 72%).

$^1$H NMR (600 MHz, CDCl$_3$) δ 7.55 (d, J=9.0 Hz, 1H), 7.27 (d, J=9.0 Hz, 1H), 4.04 (s, 3H).

Preparation Example 3-3: Preparation of methyl 6-bromo-3-methoxypicolinate (LXVII)

Methyl 6-bromo-3-hydroxypicolinate (5.07 g, 21.85 mmol) was dissolved in acetone (75 mL). To the resulting solution were added dropwise potassium carbonate (K$_2$CO$_3$) (4.83 g, 34.96 mmol) and iodomethane (CH$_3$I) (1.77 mL, 28.41 mmol) and the solution was refluxed with heat for 3 hrs. The solution was evaporated under reduced pressure to concentrate, diluted with EtOAc, and washed with water. The washed organic solvent was dried over anhydrous magnesium sulfate (MgSO$_4$) to concentrate. The resulting residue was isolated and purified by silica gel column chromatography (hexane/ethylacetate=3/1) to give the white title compound (4.18 g, 78%).

$^1$H NMR (600 MHz, CDCl$_3$) δ 7.57 (d, J=9.0 Hz, 1H), 7.26 (d, J=9.0 Hz, 1H), 3.95 (s, 3H), 3.92 (s, 3H).

Preparation Example 3-4: Preparation of 1-(6-bromo-3-methoxypyridin-2-yl)butan-1,3-dione (LXVIII)

Methyl 6-bromo-3-methoxypicolinate (3.79 g, 15.40 mmole) was dissolved in tetrahydrofuran (THF). Acetone (1.52 g 26.18 mmole) and 30% sodium methoxide (30% NaOMe) (3.81 ml, 20.02 mmole) were added to the resulting solution and the solution was stirred at room temperature and evaporated under reduced pressure to concentrate. The resulting residue was diluted with distilled water, acidified with 2N hydrochloric acid (HCl) solution, and extracted with dichloromethane. The organic solvent was dried over anhydrous magnesium sulfate (MgSO$_4$), filtered and evaporated under reduced pressure to concentrate. The resulting residue was isolated and purified by silica gel column chromatography (hexane/ethylacetate=1/1) to give the title compound (2.51 g, 60%).

$^1$H NMR (400 MHz, CDCl$_3$) δ 7.52 (dd, J=6.8 Hz, 1.2 Hz, 1H), 7.25 (dd, J=6.8 Hz, 1.2 Hz, 1H), 6.43 (s, 1H), 3.92 (s, 3H), 2.18 (s, 3H).

Preparation Example 3-5: Preparation of 4-(6-bromo-3-methoxypyridin-2-yl)-6-methylpyrimidin-2-amine (LXIX)

1-(6-Bromo-3-methoxypyridin-2-yl)butan-1,3-dione (2.51 g, 9.22 mmole) and guanidine carbonate (1.83 g, 20.28 mmole) were dissolved in ethanol (EtOH). The resulting solution was stirred with reflux for 20 hrs, cooled to room temperature, and evaporated under reduced pressure to concentrate. The resulting residue was isolated and purified by silica gel column chromatography (ethylacetate/methanol=9/1) to give the title compound (680 mg, 25%).

$^1$H NMR (400 MHz, CDCl$_3$) δ 7.48 (d, J=9.2 Hz, 1H), 7.24 (d, J=9.2 Hz, 1H), 6.93 (s, 1H), 5.07 (s, 2H), 3.85 (s, 3H), 2.39 (s, 3H).

Example 24: Preparation of 2'-amino-6-(2-amino-6-methylpyrimidin-4-yl)-3'-fluoro-[2,4'-bipyridin]-5-ol (LXXI)

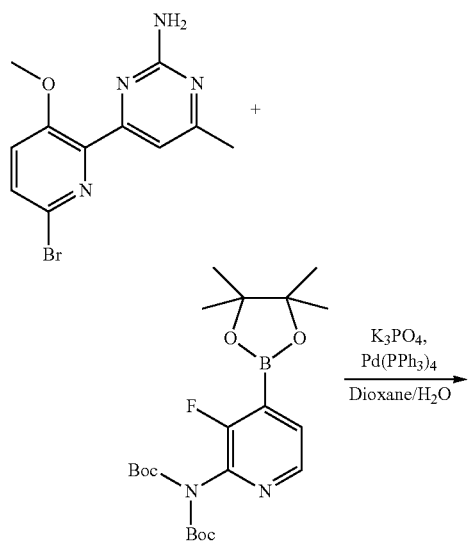

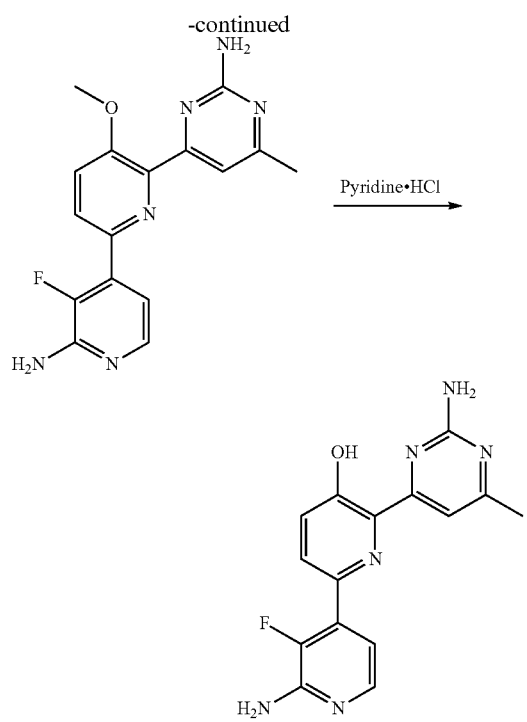

Example 24-1: Preparation of 6-(2-amino-6-methylpyrimidin-4-yl)-3'-fluoro-5-methoxy-[2,4'-bipyridin]-2'-amine (LXX)

4-(6-Bromo-3-methoxypyridin-2-yl)-6-methylpyrimidin-2-amine (2.34 g, 7.93 mmol) obtained in Preparation Example 3 and 2-[3-fluoro-4-(4,4,5,5-tetramethyl-[1,3,2]dioxaborolan-2-yl)-2-pyridinyl]-imidodicarbonic acid-1,3-bis(1,1-dimethylethyl)ester obtained in Preparation Example 1 (5.21 g, 11.89 mmol) were dissolved in dioxane/distilled water (6 ml/4 ml) solution. To the resulting solution were added potassium phosphate (5.48 g, 23.78 mmol) and tetrakis(triphenylphosphine)palladium(0) (Pd(PPh$_3$)$_4$) (458 mg, 0.4 mmol) and the reaction solution was stirred with reflux for 24 hrs, cooled to room temperature, and filtered with celite. The solvent was evaporated under reduced pressure to concentrate. The resulting residue was isolated and purified by silica gel column chromatography (dimethylchloride/methanol=9/1) to give the title compound (1.94 g, 75%).

$^1$H NMR (400 MHz, DMSO-d$_6$) δ 7.89 (d, J=9.0 Hz, 1H), 7.76 (d, J=5.4 Hz, 1H), 7.69 (d, J=9.0 Hz, 1H), 6.97 (t, 1H), 6.68 (s, 1H), 6.56 (s, 1H), 6.23 (s, 2H), 3.82 (s, 3H), 2.27 (s, 3H).

Example 24-2: Preparation of 2'-amino-6-(2-amino-6-methylpyrimidin-4-yl)-3'-fluoro-[2,4'-bipyridin]-5-ol (LXXI)

6-(2-Amino-6-methylpyrimidin-4-yl)-3'-fluoro-5-methoxy-[2,4'-bipyridin]-2'-amine (LXX) (1.94 g, 5.94 mmol) was mixed with pyridine hydrochloride (Pyridine HCl) (10 g) and the mixture was stirred at 170° C. for 1 hr. The mixture was cooled to room temperature, neutralized with 6N sodium hydroxide (NaOH) solution. The resulting solid was filtered and dried to give the title compound (1.67 g, 90%).

¹H NMR (400 MHz, DMSO-d₆) δ 14.13 (s, 1H), 7.86 (d, J=7.8 Hz, 1H), 7.81 (d, J=6.0 Hz, 1H), 7.47 (s, 1H), 7.46 (d, J=8.4 Hz, 1H), 7.18 (s, 2H), 7.12 (t, 1H), 6.25 (s, 1H), 2.36 (s, 3H).

Example 25: Preparation of 6-(2-amino-6-methyl-pyrimidin-4-yl)-[2,4'-bipyridin]-5-ol

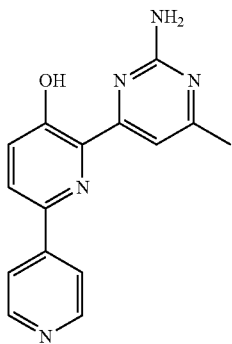 [SMILES: Cc1cc(-c2nc(-c3ccncc3)ccc2O)nc(N)n1]

The title compound as a yellow solid (15.2 mg) was obtained according to the same procedure as Example 24, except for using 4-(4,4,5,5-tetramethyl-1,3,2-dioxaborolan-2-yl)pyridine instead of the compound obtained in Preparation Example 1.

¹H NMR (400 MHz, DMSO-d₆) δ 13.77 (s, 1H), 9.61 (s, 1H), 7.93 (d, J=8.8 Hz, 2H), 7.84 (d, J=9.2 Hz, 1H), 7.54 (s, 1H), 7.35 (d, J=8.8 Hz, 1H), 7.12 (s, 2H), 6.84 (d, J=9.2 Hz, 1H), 2.36 (s, 3H).

Example 26: Preparation of 6-(2-amino-6-methyl-pyrimidin-4-yl)-3'-fluoro-[2,4'-bipyridin]-5-ol

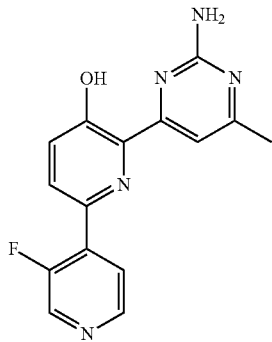 [SMILES: Cc1cc(-c2nc(-c3ccncc3F)ccc2O)nc(N)n1]

The title compound as a yellow solid (9.4 mg) was obtained according to the same procedure as Example 24, except for using 3-fluoro-4-(4,4,5,5-tetramethyl-1,3,2-dioxaborolan-2-yl)pyridine instead of the compound obtained in Preparation Example 1.

¹H NMR (400 MHz, DMSO-d₆) δ 14.14 (s, 1H), 7.85 (d, J=7.8 Hz, 1H), 7.81 (d, J=6.0 Hz, 1H), 7.47 (s, 1H), 7.46 (d, J=8.4 Hz, 1H), 7.12 (t, 1H), 6.25 (s, 1H), 2.36 (s, 3H).

Example 27: Preparation of 2-(2-amino-6-methyl-pyrimidin-4-yl)-6-(4-hydroxyphenyl)pyridin-3-ol

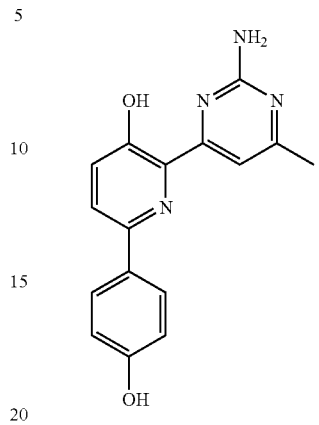

The title compound as a yellow solid (6.1 mg) was obtained according to the same procedure as Example 24, except for using 2-(4-methoxyphenyl)-4,4,5,5-tetramethyl-1,3,2-dioxaborolane instead of the compound obtained in Preparation Example 1.

¹H NMR (400 MHz, DMSO-d₆) δ 13.77 (s, 1H), 9.61 (s, 1H), 7.93 (d, J=8.8 Hz, 2H), 7.84 (d, J=9.2 Hz, 1H), 7.54 (s, 1H), 7.35 (d, J=8.8 Hz, 1H), 7.12 (s, 2H), 6.84 (d, J=9.2 Hz, 1H), 2.36 (s, 3H).

Example 28: Preparation of 2-(2-amino-6-methyl-pyrimidin-4-yl)-6-(2,3-difluoro-4-hydroxyphenyl)pyridin-3-ol

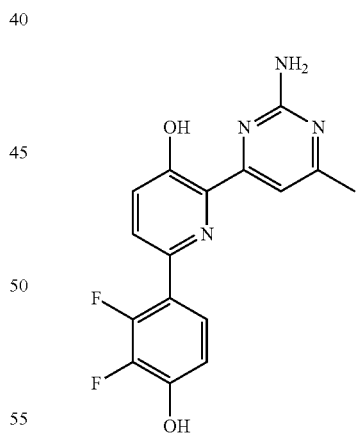

The title compound as a yellow solid (6.4 mg) was obtained according to the same procedure as Example 24, except for using 2-(2,3-difluoro-4-methoxyphenyl)-4,4,5,5-tetramethyl-1,3,2-dioxaborolane instead of the compound obtained in Preparation Example 1.

¹H NMR (400 MHz, CDCl₃) δ 13.2 (s, 1H), 7.60 (s, 1H), 7.27 (m, 5H), 5.07 (s, 2H), 2.46 (s, 3H).

Example 29: Preparation of 2-(2-amino-6-methyl-pyrimidin-4-yl)-6-(2-fluoro-4-hydroxyphenyl)pyridin-3-ol

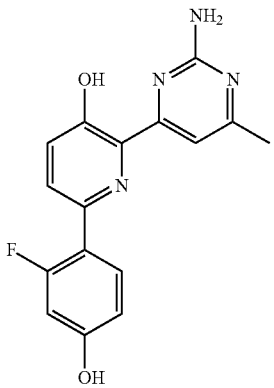 [SMILES: Cc1cc(-c2nc(-c3ccc(O)cc3F)ccc2O)nc(N)n1]

The title compound as a yellow solid (6.4 mg) was obtained according to the same procedure as Example 24, except for using 2-(2-fluoro-4-methoxyphenyl)-4,4,5,5-tetramethyl-1,3,2-dioxaborolane instead of the compound obtained in Preparation Example 1.

$^1$H NMR (600 MHz, DMSO-$d_6$) δ 7.89 (t, 1H), 7.69 (d, J=8.4 Hz, 1H), 7.49 (s, 1H), 7.39 (d, J=8.4 Hz, 1H), 7.13 (s, 2H), 6.76 (dd, J=8.4 Hz, 1.8 Hz, 1H), 6.65 (dd, J=8.4 Hz, 1.8 Hz, 1H), 2.36 (s, 3H).

Example 30: Preparation of 2-(2-amino-6-methyl-pyrimidin-4-yl)-6-(3-aminophenyl)pyridin-3-ol

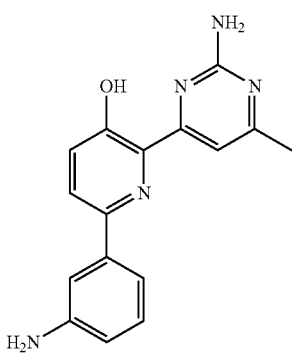 [SMILES: Cc1cc(-c2nc(-c3cccc(N)c3)ccc2O)nc(N)n1]

The title compound as a yellow solid (6.4 mg) was obtained according to the same procedure as Example 24, except for using 2-[5-(4,4,5,5-tetramethyl-[1,3,2]dioxaborolan-2-yl)phenyl]-1,3-bis(1,1-dimethylethyl)-ester-imidodicarbonic acid instead of the compound obtained in Preparation Example 1.

$^1$H NMR (600 MHz, DMSO-$d_6$) δ 13.83 (s, 1H), 7.80 (d, J=9.0 Hz, 1H), 7.55 (s, 1H), 7.38 (d, J=9.0 Hz, 1H), 7.33 (s, 1H), 7.18 (d, J=7.8 Hz, 1H), 7.11 (s, 2H), 7.09 (t, 1H), 6.58 (d, J=6.0 Hz, 1H) 15.084 (s, 2H), 2.38 (s, 3H).

Preparation Example 4: Preparation of 4-(6-bromo-3-methoxypyridin-2-yl)-6-isopropylpyrimidin-2-amine (LXIX)

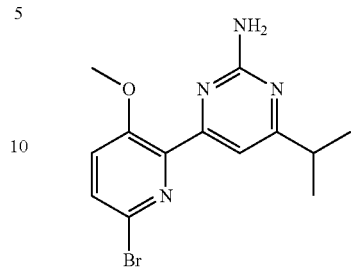

The title compound as a yellow solid (1.8 g) was obtained according to the same procedure as Preparation Example 3, except for using 3-methylbutan-2-one instead of acetone in Preparation Example 3-4.

$^1$H NMR (600 MHz, DMSO-$d_6$) δ 8.31 (s, 1H), 7.65 (d, J=13.8 Hz, 1H), 7.56 (d, J=12.6 Hz, 1H), 7.23 (br, 2H), 3.76 (s, 3H), 2.37 (m, 1H), 1.02 (d, J=10.8 Hz, 6H).

Example 31: Preparation of 2'-amino-6-(2-amino-6-isopropylpyrimidin-4-yl)-3'-fluoro-[2,4'-bipyridin]-5-ol

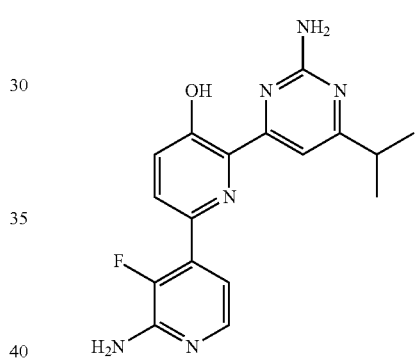

The title compound as a yellow solid (8.1 mg) was obtained according to the same procedure as Example 24, except for using 4-(6-bromo-3-methoxypyridin-2-yl)-6-isopropylpyrimidin-2-amine obtained in Preparation Example 4 instead of the compound obtained in Preparation Example 3.

$^1$H NMR (400 MHz, DMSO-$d_6$) δ 14.13 (s, 1H), 7.86 (d, J=7.8 Hz, 1H), 7.81 (d, J=6.0 Hz, 1H), 7.47 (s, 1H), 7.46 (d, J=8.4 Hz, 1H), 7.18 (s, 2H), 7.12 (t, 1H), 6.25 (s, 1H), 2.15 (m, 1H), 0.99 (d, J=8.4 Hz, 6H).

Preparation Example 5: Preparation of 4-(6-bromo-3-methoxypyridin-2-yl)-6-(tetrahydro-2H-pyran-4-yl)pyrimidin-2-amine (LXIX)

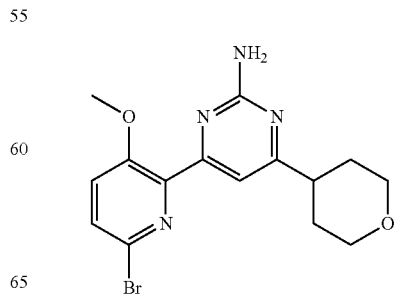

The title compound as a yellow solid (6.4 mg) was obtained according to the same procedure as Preparation Example 3, except for using 1-(tetrahydro-2H-pyran-4-yl)ethanone instead of acetone in Preparation Example 3-4.

$^1$H NMR (600 MHz, DMSO-$d_6$) δ 7.71 (d, J=9.0 Hz, 1H), 7.64 (d, J=8.4 Hz, 1H), 7.22 (br, 2H), 6.13 (s, 1H), 3.89 (s, 3H).

Example 32: Preparation of 2'-amino-6-(2-amino-6-(tetrahydro-2H-pyran-4-yl)pyrimidin-4-yl)-3'-fluoro-[2,4'-bipyridin]-5-ol

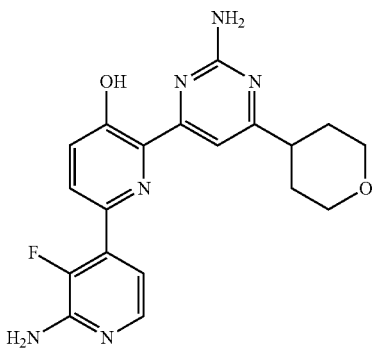 [SMILES: Nc1nc(-c2nc(-c3ccnc(N)c3F)ccc2O)cc(C2CCOCC2)n1]

The title compound as a yellow solid (8.4 mg) was obtained according to the same procedure as Example 24, except for using 4-(6-bromo-3-methoxypyridin-2-yl)-6-(tetrahydro-2H-pyran-4-yl)pyrimidin-2-amine obtained in Preparation Example 5 instead of the compound obtained in Preparation Example 3.

$^1$H NMR (600 MHz, DMSO-$d_6$) δ 7.82-7.80 (m, 2H), 7.41 (d, J=8.4 Hz, 1H), 7.14 (t, J=5.4 Hz, 1H), 7.03 (s, 1H), 6.82 (br, 2H), 6.25 (br, 2H), 3.70-3.68 (m, 4H), 3.64-3.63 (m, 4H).

Preparation Example 6: Preparation of 1-(1-methylpiperidin-4-yl)ethanone

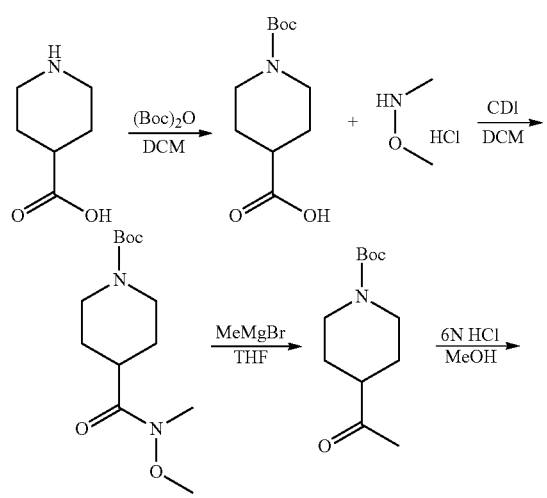

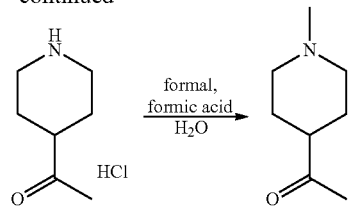

Preparation Example 6-1: Preparation of 1-(1-(tert-butoxycarbonyl)piperidine-4-carboxylic acid Isonipecotic acid (5.51 g, 0.022 mol) was dissolved in dichloromethane (110 ml). Di-t-butyl dicarbonate ((Boc)$_2$O) (7.31 g, 0.033 mol) and potassium carbonate (K$_2$CO$_3$) (9.62 g, 0.67 mol) were added to the resulting solution and the solution was stirred at room temperature for 18 hrs. After completion of the reaction by addition of water, the solution was extracted with ethylacetate, washed with distilled water, and dried over magnesium sulfate (MgSO$_4$) to concentrate. The resulting residue was isolated and purified by silica gel column chromatography (dichloromethane/methanol, 10/1) to give the white title compound (7.36 g, 95.0%).

$^1$H NMR (400 MHz, CD$_3$OD) δ 3.97 (m, 2H), 2.88 (br, 2H), 2.48 (m, 1H), 1.88 (m, 2H), 1.54 (m, 2H), 1.44 (s, 9H)

Preparation Example 6-2: Preparation of tert-butyl-4-(methoxy(methyl)carbamoyl)piperidine-1-carboxylate 1-(1-(tert-butoxycarbonyl)piperidine-4-carboxylic acid (6.51 g 0.022 mol) was dissolved in dichloromethane (50 ml). To the resulting solution were added 1,1'-carbonyldiimidazole (CDI) (6.31 g, 0.033 mol) and N,O-dimethylhydroxylamine hydrochloride (9.62 g, 0.67 mol) and the solution was stirred at room temperature for 18 hrs. After completion of the reaction by addition of water, the solution was extracted with dichloromethane, washed with distilled water, and dried over magnesium sulfate (MgSO$_4$) to concentrate. The resulting residue was isolated and purified by silica gel column chromatography (dichloromethane/methanol=10/1) to give the white title compound (5.36 g, 95.0%).

$^1$H NMR (400 MHz, CDCl$_3$) δ 4.14 (m, 2H), 3.71 (s, 3H), 3.13 (s, 3H), 2.79 (m, 5H), 1.42 (s, 9H).

Preparation Example 6-3: Preparation of tert-butyl 4-acetylpiperidine-1-carboxylate Tert-butyl-4-(methoxy(methyl)carbamoyl)piperidine-1-carboxylate (2.29 g, 8.32 mmol) was dissolved in 30 ml of tetrahydrofuran (THF) and the resulting solution was cooled to −78° C. To the solution was slowly added methylmagnesium bromide (3.0M) (7.73 ml, 10.82 mmol) and the solution was stirred at 0° C. for 1 hr. After completion of the reaction by 2N hydrochloric acid aqueous solution, 6N sodium hydroxide solution was added to adjust pH to 10 and then the solution was extracted with dichloromethane. The organic layer was treated with magnesium sulfate (MgSO$_4$) and filtered and the solution was concentrated. The resulting residue was isolated and purified by silica gel column chromatography (dichloromethane/methanol=10/1) to give the white title compound (6.36 g, 94.0%).

$^1$H NMR (400 MHz, CDCl$_3$) δ 3.90 (m, 2H), 2.98 (s, 2H), 2.51 (s, 1H), 2.15 (s, 3H), 1.67 (m, 4H), 1.49 (s, 9H).

Preparation Example 6-4: Preparation of 1-(piperidin-4-yl)ethanone hydrochloride Tert-butyl 4-acetylpiperidine-1-carboxylate (3.29 g, 8.32 mmol) was dissolved in 30 ml of methanol. To the resulting solution was slowly added 6N hydrochloric acid aqueous solution and the solution was stirred at room temperature for 18 hrs. After removal of the solvent, acetone was added and the resulting solid was filtered to give the white title compound (4.36 g, 95.0%).

$^1$H NMR (400 MHz, CDCl$_3$) δ 3.14 (m, 2H), 2.64 (m, 2H), 2.43 (s, 1H), 2.40 (s, 3H), 1.85 (m, 2H), 1.50 (m, 2H).

Preparation Example 6-5: Preparation of 1-(1-methylpiperidin-4-yl)ethanone 1-(Piperidin-4-yl)ethanone hydrochloride (4.5 g, 8.32 mmol) was added to 30 ml of formic acid and 30 ml of formaldehyde and the mixture was stirred with reflux for 18 hrs. The solvent was concentrated under reduced pressure and to the solution were added hydrochloric acid and acetone. The resulting solid was filtered to give the white title compound (6.36 g, 95.0%).

$^1$H NMR (400 MHz, CDCl$_3$) δ 2.80 (m, 2H), 2.21 (s, 3H), 2.16 (m, 1H), 2.09 (s, 3H), 1.94 (m, 2H), 1.80 (m, 2H), 1.63 (m, 2H).

Preparation Example 7: Preparation of 4-(6-bromo-3-methoxypyridin-2-yl)-6-(piperidin-4-yl)pyrimidin-2-amine (LXIX)

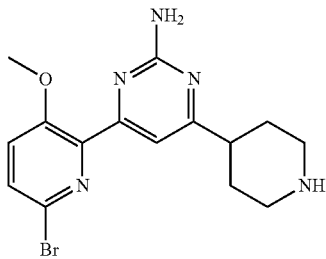 [SMILES: COc1ccc(Br)nc1-c1cc(C2CCNCC2)nc(N)n1]

The title compound as a yellow solid (21 mg) was obtained according to the same procedure as Preparation Example 3, except for using 1-(piperidin-4-yl)ethanone obtained in Preparation Example 6-4 instead of acetone in Preparation Example 3-4.

$^1$H NMR (600 MHz, DMSO-d$_6$) δ 7.70 (d, J=9.0 Hz, 1H), 7.64 (d, J=8.4 Hz, 1H), 7.22 (br, 2H), 6.13 (s, 2H), 3.89 (s, 3H), 3.14 (m, 2H), 2.64 (m, 2H), 2.43 (s, 1H), 1.85 (m, 2H), 1.50 (m, 2H).

Example 33: Preparation of 2'-amino-6-(2-amino-6-(piperidin-4-yl)pyrimidin-4-yl)-3'-fluoro-[2,4'-bipyridin]-5-ol

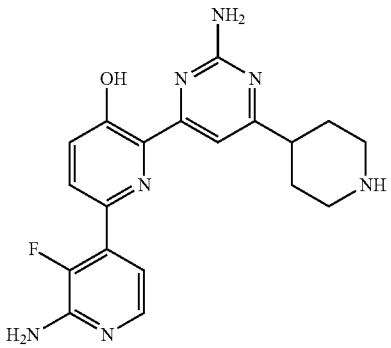 [SMILES: Nc1nc(-c2nc(-c3ccnc(N)c3F)ccc2O)cc(C2CCNCC2)n1]

The title compound as a yellow solid (6.8 mg) was obtained according to the same procedure as Example 24, except for using 4-(6-bromo-3-methoxypyridin-2-yl)-6-(piperidin-4-yl)pyrimidin-2-amine obtained in Preparation Example 7 instead of the compound obtained in Preparation Example 3.

$^1$H NMR (600 MHz, DMSO-d$_6$) δ 7.80 (m, 2H), 7.41 (d, J=8.4 Hz, 1H), 7.14 (t, J=5.4 Hz, 1H), 7.03 (s, 1H), 6.82 (br, 2H), 6.25 (br, 2H), 3.89 (s, 3H), 3.14 (m, 2H), 2.64 (m, 2H), 2.43 (s, 1H), 1.85 (m, 2H), 1.50 (m, 2H).

Preparation Example 8: Preparation of 4-(6-bromo-3-methoxypyridin-2-yl)-6-(1-methylpiperidin-4-yl)pyrimidin-2-amine (LXIX)

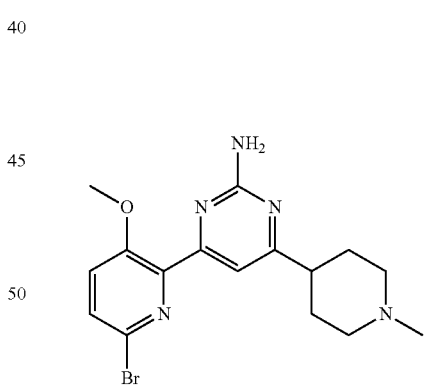

The title compound as a yellow solid (21.7 mg) was obtained according to the same procedure as Preparation Example 3, except for using 1-(1-methylpiperidin-4-yl)ethanone obtained in Preparation Example 6 instead of acetone in Preparation Example 3-4.

$^1$H NMR (600 MHz, DMSO-d$_6$) δ 7.71 (d, J=9.0 Hz, 1H), 7.64 (d, J=8.4 Hz, 1H), 7.22 (br, 2H), 6.13 (s, 2H), 3.88 (s, 3H), 3.14 (m, 2H), 2.64 (m, 2H), 2.49 (s, 3H), 2.43 (s, 1H), 1.85 (m, 2H), 1.49 (m, 2H).

Example 34: Preparation of 2'-amino-6-(2-amino-6-(1-methylpiperidin-4-yl)pyrimidin-4-yl)-3'-fluoro-[2,4'-bipyridin]-5-ol

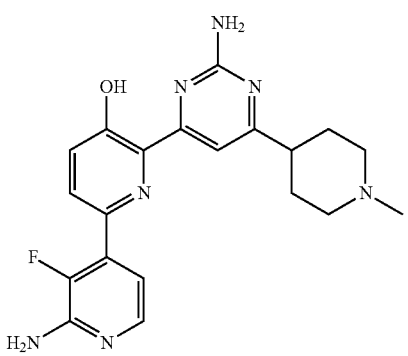 [SMILES: CN1CCC(c2cc(-c3nc(-c4ccnc(N)c4F)ccc3O)nc(N)n2)CC1]

The title compound as a yellow solid (11.5 mg) was obtained according to the same procedure as Example 24, except for using 4-(6-bromo-3-methoxypyridin-2-yl)-6-(1-methylpiperidin-4-yl)pyrimidin-2-amine obtained in Preparation Example 8 instead of the compound obtained in Preparation Example 3.

$^1$H NMR (600 MHz, DMSO-d$_6$) δ 7.74 (d, J=9.0 Hz, 1H), 7.64 (d, J=8.4 Hz, 1H), 7.22 (br, 2H), 6.13 (s, 2H), 3.89 (s, 3H), 3.14 (m, 2H), 2.64 (m, 2H), 2.49 (s, 3H), 2.43 (s, 1H), 1.85 (m, 2H), 1.50 (m, 2H).

Example 35: Preparation of 2'-amino-6-(2-amino-6-(1-ethylpiperidin-4-yl)pyrimidin-4-yl)-3'-fluoro-[2,4'-bipyridin]-5-ol

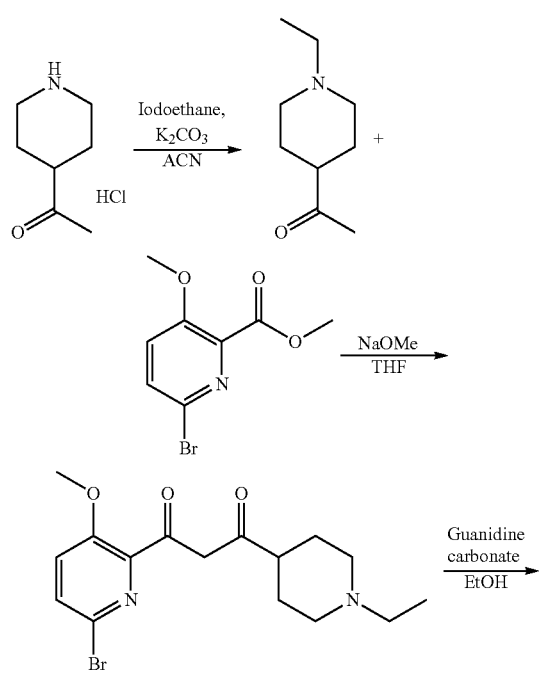

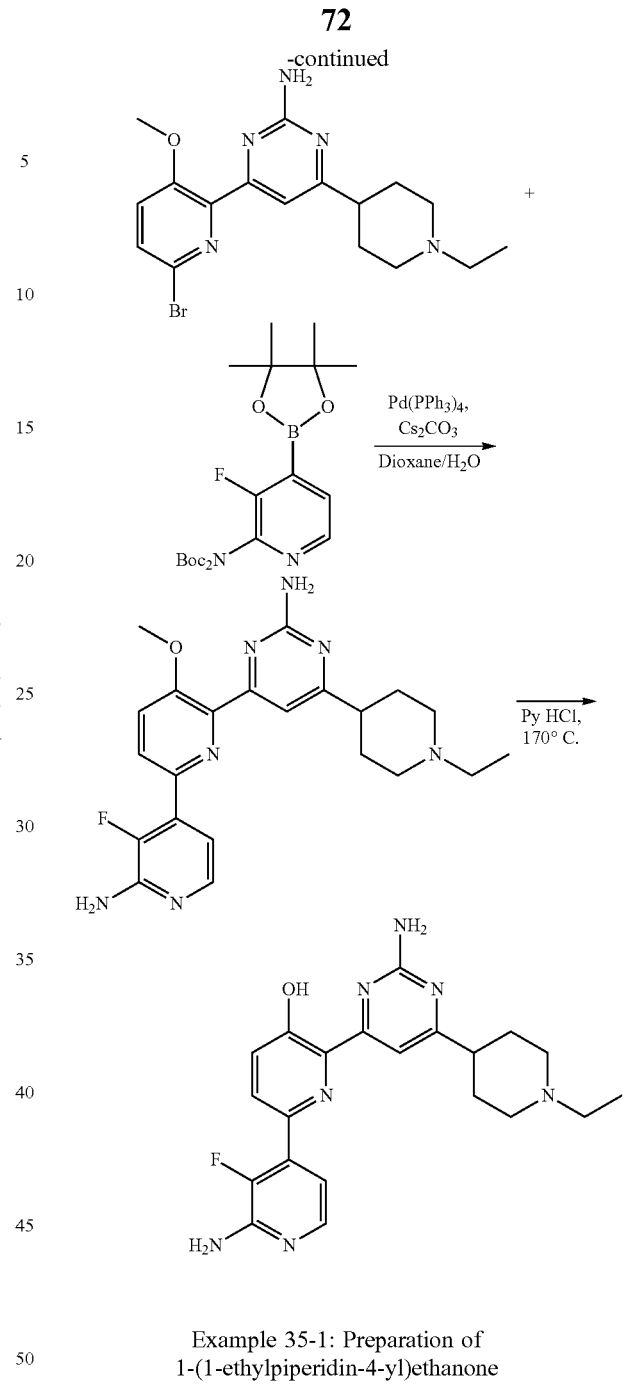

Example 35-1: Preparation of 1-(1-ethylpiperidin-4-yl)ethanone 1-(Piperidin-4-yl)ethanone hydrochloride (6.07 g 21.85 mmol) obtained in Preparation Example 6-4 was dissolved in acetonitrile (75 mL). Potassium carbonate (K$_2$CO$_3$) (5.83 g, 34.96 mmol) and iodoethane (CH$_3$CH$_2$I) (2.77 mL, 28.41 mmol) were added dropwise to the resulting solution and the solution was stirred for 18 hrs. The solution was evaporated under reduced pressure to concentrate, diluted with EtOAc, and washed with water. The washed organic solvent was dried over anhydrous magnesium sulfate (MgSO$_4$) to concentrate. The resulting residue was isolated and purified by silica gel column chromatography (dimethylchloride/methanol=10/1) to give the white title compound (5.18 g, 76%).

$^1$H NMR (400 MHz, CDCl$_3$) δ 2.81 (m, 2H), 2.24 (s, 3H), 2.16 (m, 1H), 2.09 (m, 2H), 1.94 (m, 2H), 1.80 (m, 2H), 1.60 (m, 2H), 1.48 (m, 3H).

Example 35-2: Preparation of 1-(6-bromo-3-methoxypyridin-2-yl)-3-(1-ethylpiperidin-4-yl)propan-1,3-dione Methyl 6-bromo-3-methoxypicolinate (4.79 g, 15.40 mmole) obtained in Preparation Example 3-3 was dissolved in tetrahydrofuran (THF). To the resulting solution were added 1-(1-ethylpiperidin-4-yl)ethanone (5.52 g 15.42 mmole) obtained in Example 35-1 and 30% sodium methoxide (30% NaOMe) (4.81 ml, 20.02 mmoles) and the solution was stirred at room temperature. The solution was evaporated under reduced pressure to concentrate. The resulting residue was diluted with distilled water, acidified with 2N hydrochloric acid (HCl) solution and extracted with dichloromethane. The organic solvent was dried over anhydrous magnesium sulfate (MgSO4), filtered, and evaporated under reduced pressure to concentrate. The resulting residue was isolated and purified by silica gel column chromatography (hexane/ethylacetate=1/1) to give the title compound (3.41 g, 61%).

$^1$H NMR (400 MHz, CDCl$_3$) δ 7.52 (d, J=6.8 Hz, 1H), 7.25 (d, J=6.8 Hz, 1H), 3.89 (s, 3H), 2.81 (m, 2H), 2.24 (s, 3H), 2.16 (m, 1H), 2.09 (m, 2H), 1.94 (m, 2H), 1.80 (m, 2H), 1.60 (m, 2H), 1.44 (m, 3H).

Example 35-3: Preparation of 4-(6-bromo-3-methoxypyridin-2-yl)-6-(1-ethylpiperidin-4-yl)pyrimidin-2-amine 1-(6-Bromo-3-methoxypyridin-2-yl)-3-(1-ethylpiperidin-4-yl)propan-1,3-dione (3.41 g, 9.22 mmole) and guanidine carbonate (2.75 g, 20.28 mmole) were dissolved in ethanol (EtOH) and the resulting solution was stirred with reflux for 20 hrs. The solution was cooled to room temperature and evaporated under reduced pressure to concentrate. The resulting residue was isolated and purified by silica gel column chromatography (ethylacetate/methanol=10/1) to give the title compound (752 mg, 28%).

$^1$H NMR (400 MHz, CDCl$_3$) δ 7.50 (d, J=6.8 Hz, 1H), 7.25 (d, J=6.8 Hz, 1H), 7.24 (s 1H), 6.84 (s 2H), 3.89 (s, 3H), 2.81 (m, 2H), 2.24 (s, 3H), 2.16 (m, 1H), 2.09 (m, 2H), 1.94 (m, 2H), 1.80 (m, 2H), 1.60 (m, 2H), 1.45 (m, 3H).

Example 35-4: Preparation of 6-(2-amino-6-(1-ethylpiperidin-4-yl)pyrimidin-4-yl)-3'-fluoro-5-methoxy-[2,4'-bipyridin]-2'-amine 4-(6-Bromo-3-methoxypyridin-2-yl)-6-(1-ethylpiperidin-4-yl)pyrimidin-2-amine (2.34 g, 7.93 mmol) and 2-[3-fluoro-4-(4,4,5,5-tetramethyl-[1,3,2]dioxaborolan-2-yl)-2-pyridinyl]-imidodicarbonic acid-1,3-bis(1,1-dimethylethyl) ester (5.21 g, 11.89 mmol) obtained in Preparation Example 1 were dissolved in dioxane/distilled water (6 ml/4 ml) solution. To the resulting solution were added cesium carbonate (Cs$_2$CO$_3$) (5.48 g, 23.78 mmol) and tetrakis(triphenylphosphine)palladium(0) (Pd(PPh$_3$)$_4$) (458 mg, 0.4 mmol) and the resulting reaction solution was stirred with reflux for 24 hrs. The solution was cooled to room temperature and filtered with celite. The solvent was evaporated under reduced pressure to concentrate. The resulting residue was isolated and purified by silica gel column chromatography (dimethylchloride/methanol=9/1) to give the title compound (1.94 g, 75%).

$^1$H NMR (600 MHz, DMSO-d$_6$) δ 7.74 (d, J=9.0 Hz, 1H), 7.64 (d, J=8.4 Hz, 1H), 7.22 (br, 2H), 6.13 (s, 2H), 3.89 (s, 3H), 3.14 (m, 2H), 2.64 (m, 2H), 2.49 (s, 3H), 2.43 (s, 1H), 1.85 (m, 2H), 1.50 (m, 3H).

Example 35-5: Preparation of 2'-amino-6-(2-amino-6-(1-ethylpiperidin-4-yl)pyrimidin-4-yl)-3'-fluoro-[2,4'-bipyridin]-5-ol 6-(2-Amino-6-(1-ethylpiperidin-4-yl)pyrimidin-4-yl)-3'-fluoro-5-methoxy-[2,4'-bipyridin]-2'-amine (3.88 g, 21.88 mmol) was mixed with pyridine hydrochloride (Pyridine HCl) (20 g) and the mixture was stirred at 170° C. for 1 hr. The mixture was cooled to room temperature and then neutralized with 6N sodium hydroxide (NaOH) solution. The resulting solid was filtered and dried to give the title compound (3.34 g, 89%).

$^1$H NMR (600 MHz, DMSO-d$_6$) δ 7.74 (d, J=9.0 Hz, 1H), 7.64 (d, J=8.4 Hz, 1H), 7.22 (br, 2H), 6.13 (s, 2H), 3.89 (s, 3H), 3.14 (m, 2H), 2.64 (m, 2H), 2.49 (s, 3H), 2.43 (s, 1H), 1.85 (m, 2H), 1.50 (m, 3H).

Example 36: Preparation of 2'-amino-6-(2-amino-6-(1-propylpiperidin-4-yl)pyrimidin-4-yl)-3'-fluoro-[2,4'-bipyridin]-5-ol

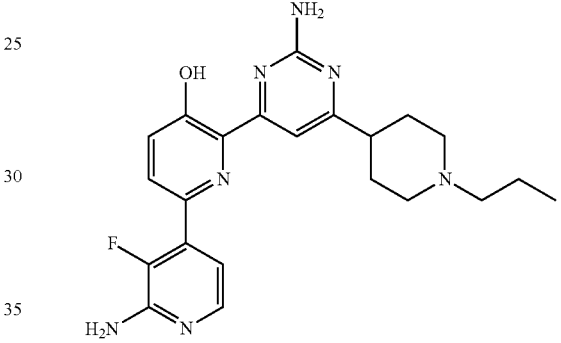

The title compound as a yellow solid (14.5 mg) was obtained according to the same procedure as Example 35, except for using 1-iodopropane(CH$_3$CH$_2$CH$_2$I) instead of iodoethane (CH$_3$CH$_2$I) in Example 35-1.

$^1$H NMR (600 MHz, DMSO-d$_6$) δ 7.75 (d, J=8.4 Hz, 1H), 7.64 (d, J=8.4 Hz, 1H), 7.22 (br, 2H), 6.13 (s, 2H), 3.89 (s, 3H), 3.14 (m, 2H), 2.64 (m, 2H), 2.51 (m, 2H), 2.49 (s, 3H), 2.43 (s, 1H), 1.85 (m, 2H), 1.50 (m, 3H).

Example 37: Preparation of 2'-amino-6-(2-amino-6-(1-isopropylpiperidin-4-yl)pyrimidin-4-yl)-3'-fluoro-[2,4'-bipyridin]-5-ol

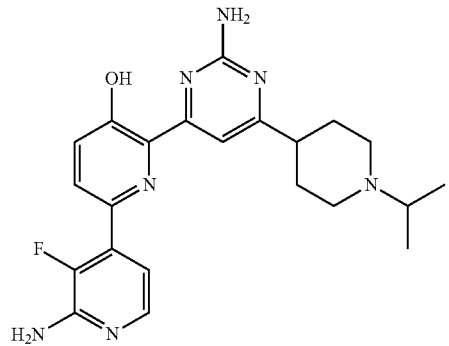 [SMILES: CC(C)N1CCC(c2cc(-c3nc(-c4ccnc(N)c4F)ccc3O)nc(N)n2)CC1]

The title compound as a yellow solid (27.5 mg) was obtained according to the same procedure as Example 35, except for using 2-iodopropane(CH₃CH(I)CH₃) instead of iodoethane (CH₃CH₂I) in Example 35-1.

¹H NMR (600 MHz, DMSO-d₆) δ 7.75 (d, J=9.0 Hz, 1H), 7.63 (d, J=8.4 Hz, 1H), 7.22 (br, 2H), 6.13 (s, 2H), 3.89 (s, 3H), 3.14 (m, 2H), 2.64 (m, 2H), 2.49 (s, 3H), 2.43 (s, 1H), 1.85 (m, 2H), 1.50 (m, 6H).

Preparation Example 9: Preparation of 4-(6-bromo-3-methoxypyridin-2-yl)-6-(1-methylpiperidin-3-yl)-pyrimidin-2-amine (LXIX)

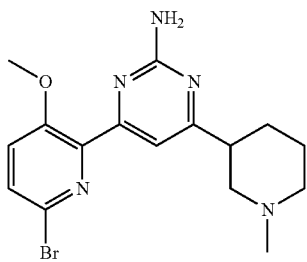 [SMILES: COc1ccc(Br)nc1-c1cc(C2CCCN(C)C2)nc(N)n1]

The title compound as a yellow solid (45.3 mg) was obtained according to the same procedure as Preparation Example 3, except for using 1-(1-methylpiperidin-3-yl)ethanone instead of acetone in Preparation Example 3-4.

¹H NMR (600 MHz, DMSO-d₆) δ 7.74 (d, J=9.0 Hz, 1H), 7.64 (d, J=8.4 Hz, 1H), 7.22 (br, 2H), 6.14 (s, 2H), 3.88 (s, 3H), 3.14 (m, 2H), 2.64 (m, 2H), 2.49 (s, 3H), 2.43 (s, 1H), 1.85 (m, 2H), 1.48 (m, 2H).

Example 38: Preparation of 2'-amino-6-(2-amino-6-(1-methylpiperidin-3-yl)pyrimidin-4-yl)-3'-fluoro-[2,4'-bipyridin]-5-ol

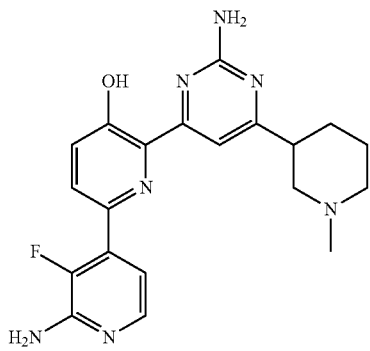 [SMILES: CN1CCCC(c2cc(-c3nc(-c4ccnc(N)c4F)ccc3O)nc(N)n2)C1]

The title compound as a yellow solid (12.8 mg) was obtained according to the same procedure as Example 24, except for using 4-(6-bromo-3-methoxypyridin-2-yl)-6-(1-methylpiperidin-3-yl)-pyrimidin-2-amine obtained in Preparation Example 9 instead of the compound obtained Preparation Example 3.

¹H NMR (600 MHz, DMSO-d₆) δ 7.74 (d, J=8.4 Hz, 1H), 7.64 (d, J=9.0 Hz, 1H), 7.22 (br, 2H), 6.13 (s, 2H), 3.14 (m, 2H), 2.64 (m, 2H), 2.49 (s, 3H), 2.43 (s, 1H), 1.85 (m, 2H), 1.50 (m, 2H).

Example 39: Preparation of 2'-amino-6-(2-amino-6-(1-ethylpiperidin-3-yl)pyrimidin-4-yl)-3'-fluoro-[2,4'-bipyridin]-5-ol

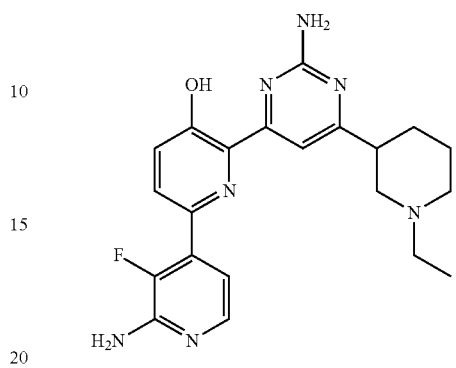

The title compound as a yellow solid (21.8 mg) was obtained according to the same procedure as Example 35, except for using 1-(piperidin-3-yl)ethanone instead of 1-(piperidin-4-yl)ethanone hydrochloride in Example 35-1.

¹H NMR (600 MHz, DMSO-d₆) δ 7.74 (d, J=8.4 Hz, 1H), 7.64 (d, J=9.0 Hz, 1H), 7.22 (br, 2H), 6.13 (s, 2H), 3.14 (m, 2H), 2.64 (m, 2H), 2.43 (s, 1H), 1.85 (m, 2H), 1.50 (m, 2H), 1.21 (m, 3H).

Example 40: Preparation of 2'-amino-6-(2-amino-6-(1-propylpiperidin-3-yl)pyrimidin-4-yl)-3'-fluoro-[2,4'-bipyridin]-5-ol

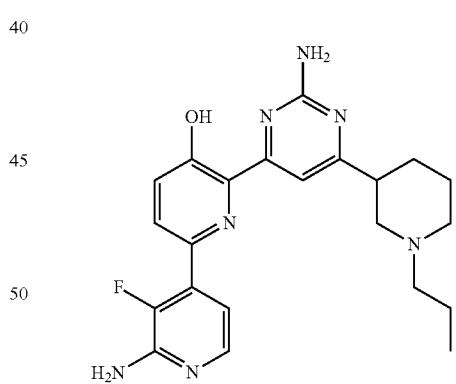

The title compound as a yellow solid (3.8 mg) was obtained according to the same procedure as Example 35, except for using 1-(piperidin-3-yl)ethanone and 1-iodopropane(CH₃CH₂CH₂I) instead of 1-(piperidin-4-yl)ethanone hydrochloride and iodoethane (CH₃CH₂I) in Example 35-1.

¹H NMR (600 MHz, DMSO-d₆) δ 7.75 (d, J=8.4 Hz, 1H), 7.64 (d, J=9.0 Hz, 1H), 7.22 (br, 2H), 6.13 (s, 2H), 3.14 (m, 2H), 2.64 (m, 2H), 2.43 (s, 1H), 1.85 (m, 2H), 1.50 (m, 2H), 1.20 (m, 3H).

Example 41: Preparation of 2'-amino-6-(2-amino-6-(1-isopropylpiperidin-3-yl)pyrimidin-4-yl)-3'-fluoro-[2,4'-bipyridin]-5-ol

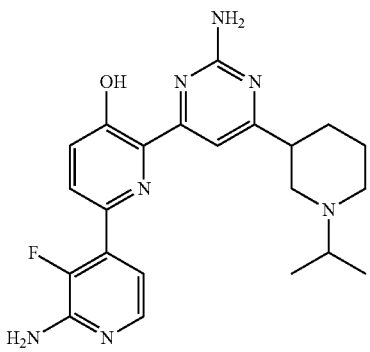 [SMILES: CC(C)N1CCCC(c2cc(-c3nc(-c4ccnc(N)c4F)ccc3O)nc(N)n2)C1]

The title compound as a yellow solid (32.5 mg) was obtained according to the same procedure as Example 35, except for using 1-(piperidin-3-yl)ethanone and 2-iodopropane(CH$_3$CH(I)CH$_3$) instead of 1-(piperidin-4-yl)ethanone hydrochloride and iodoethane (CH$_3$CH$_2$I) in Example 35-1.
$^1$H NMR (600 MHz, DMSO-d$_6$) δ 7.75 (d, J=9.0 Hz, 1H), 7.64 (d, J=9.0 Hz, 1H), 7.22 (m, 2H), 6.13 (s, 2H), 3.14 (m, 2H), 2.42 (s, 1H), 1.85 (m, 2H), 1.50 (m, 2H), 1.20 (m, 9H).

Preparation Example 10: Preparation of 1-(1-methylpiperidin-4-yl)propan-1-one

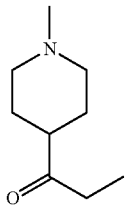

The title compound as a yellow solid (3.5 g) was obtained according to the same procedure as Preparation Example 6, except for using ethylmagnesium bromide instead of methylmagnesium bromide in Preparation Example 6-3.
$^1$H NMR (600 MHz, DMSO-d$_6$) δ 3.10 (m, 2H), 2.48 (m, 4H), 2.35 (s, 3H), 2.06 (m, 2H), 1.91 (m, 2H), 1.23 (t, 3H).

Preparation Example 11: Preparation of 4-(6-bromo-3-methoxypyridin-2-yl)-5-methyl-6-(1-methylpiperidin-4-yl)pyrimidin-2-amine (LXIX)

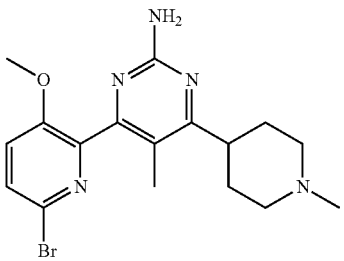 [SMILES: COc1ccc(Br)nc1-c1nc(N)nc(C2CCN(C)CC2)c1C]

The title compound as a yellow solid (26.2 mg) was obtained according to the same procedure as Preparation Example 3, except for using 1-(1-methylpiperidin-4-yl)pro-pan-1-one obtained in Preparation Example 10 instead of acetone in Preparation Example 3-4.
$^1$H NMR (400 MHz, DMSO-d$_6$) δ 7.84 (d, J=7.8 Hz, 1H), 7.81 (d, J=6.0 Hz, 1H), 7.47 (s, 1H), 7.18 (s, 2H), 3.84 (s, 3H), 3.10 (m, 2H), 2.48 (s, 3H), 2.56 (s, 3H), 2.35 (m, 3H), 2.06 (m, 2H), 1.91 (m, 2H).

Example 42: Preparation of 2'-amino-6-(2-amino-5-methyl-6-(1-methylpiperidin-4-yl)pyrimidin-4-yl)-3'-fluoro-[2,4'-bipyridin]-5-ol

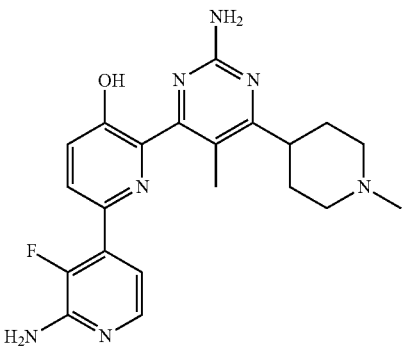 [SMILES: Cc1c(-c2nc(-c3ccnc(N)c3F)ccc2O)nc(N)nc1C1CCN(C)CC1]

The title compound as a yellow solid (11.3 mg) was obtained according to the same procedure as Example 24, except for using 4-(6-bromo-3-methoxypyridin-2-yl)-5-methyl-6-(1-methylpiperidin-4-yl)pyrimidin-2-amine obtained in Preparation Example 11 instead of the compound obtained in Preparation Example 3.
$^1$H NMR (400 MHz, DMSO-d$_6$) δ 14.13 (s, 1H), 7.86 (d, J=7.8 Hz, 1H), 7.81 (d, J=6.0 Hz, 1H), 7.47 (s, 1H), 7.46 (d, J=8.4 Hz, 1H), 7.18 (s, 2H), 7.12 (t, 1H), 6.25 (s, 1H), 3.10 (m, 2H), 2.48 (s, 3H), 2.36 (s, 3H), 2.35 (m, 3H), 2.06 (m, 2H), 1.91 (m, 2H).

Example 43: Preparation of 2'-amino-6-(2-amino-6-(1-ethylpiperidin-4-yl)-5-methylpyrimidin-4-yl)-3'-fluoro-[2,4'-bipyridin]-5-ol

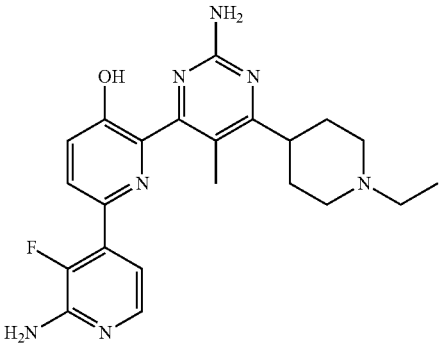 [SMILES: CCN1CCC(c2nc(N)nc(-c3nc(-c4ccnc(N)c4F)ccc3O)c2C)CC1]

The title compound as a yellow solid (42.1 mg) was obtained according to the same procedure as Example 35, except for using 1-(piperidin-4-yl)propan-1-one instead of 1-(piperidin-4-yl)ethanone hydrochloride in Example 35-1.
$^1$H NMR (400 MHz, DMSO-d$_6$) δ 14.12 (s, 1H), 7.85 (d, J=7.8 Hz, 1H), 7.80 (d, J=6.0 Hz, 1H), 7.47 (s, 1H), 7.45 (d, J=8.4 Hz, 1H), 7.18 (s, 2H), 7.12 (t, 1H), 6.25 (s, 2H), 3.10 (m, 2H), 3.03 (m, 2H), 2.36 (s, 3H), 2.35 (m, 3H), 2.06 (m, 2H), 1.91 (m, 2H), 2.48 (t, 3H).

Example 44: Preparation of 2'-amino-6-(2-amino-5-methyl-6-(1-propylpiperidin-4-yl)pyrimidin-4-yl)-3'-fluoro-[2,4'-bipyridin]-5-ol

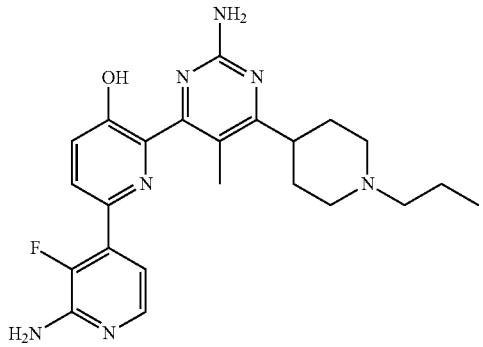 [SMILES: CCCN1CCC(c2nc(N)nc(-c3nc(-c4ccnc(N)c4F)ccc3O)c2C)CC1]

The title compound as a yellow solid (44.8 mg) was obtained according to the same procedure as Example 35, except for using 1-(piperidin-4-yl)propan-1-one and 1-iodopropane(CH$_3$CH$_3$CH$_3$I) instead of 1-(piperidin-4-yl)ethanone hydrochloride and iodoethane (CH$_3$CH$_2$I) in Example 35-1.

$^1$H NMR (400 MHz, DMSO-d$_6$) δ 14.12 (s, 1H), 7.85 (d, J=8.6 Hz, 1H), 7.80 (d, J=6.4 Hz, 1H), 7.47 (s, 1H), 7.45 (d, J=8.6 Hz, 1H), 7.18 (s, 2H), 7.12 (t, 1H), 6.25 (s, 2H), 3.82 (m, 2H), 3.10 (m, 2H), 3.03 (m, 2H), 2.36 (s, 3H), 2.35 (m, 3H), 2.06 (m, 2H), 1.91 (m, 2H), 1.45 (t, 3H).

Example 45: Preparation of 2'-amino-6-(2-amino-6-(1-isopropylpiperidin-4-yl)-5-methylpyrimidin-4-yl)-3'-fluoro-[2,4'-bipyridin]-5-ol

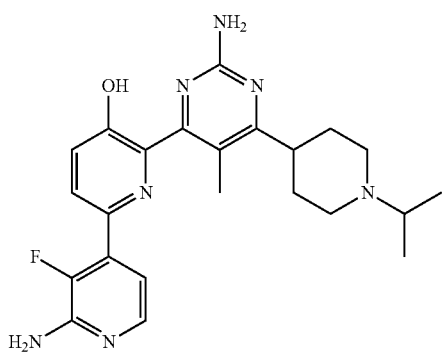 [SMILES: Cc1c(-c2nc(-c3ccnc(N)c3F)ccc2O)nc(N)nc1C1CCN(C(C)C)CC1]

The title compound as a yellow solid (54.1 mg) was obtained according to the same procedure as Example 35, except for using 1-(piperidin-4-yl)propan-1-one and 2-iodopropane(CH$_3$CH(I)CH$_3$) instead of 1-(piperidin-4-yl)ethanone hydrochloride and iodoethane (CH$_3$CH$_2$I) in Example 35-1.

$^1$H NMR (400 MHz, DMSO-d$_6$) δ 14.12 (s, 1H), 7.85 (d, J=8.6 Hz, 1H), 7.80 (d, J=6.4 Hz, 1H), 7.46 (s, 1H), 7.46 (d, J=8.0 Hz, 1H), 7.18 (s, 2H), 7.18 (t, 1H), 6.25 (s, 2H), 3.10 (m, 2H), 2.54 (m, 1H), 2.36 (s, 3H), 2.35 (m, 3H), 2.06 (m, 2H), 1.91 (m, 2H), 1.15 (d, 6H).

Preparation Example 12: Preparation of 1-(1-methylpiperidin-3-yl)propan-1-one

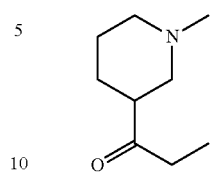

The title compound as a yellow solid (2.8 g) was obtained according to the same procedure as Preparation Example 6, except for using nipecotic acid and ethylmagnesium bromide instead of isonipecotic acid in Preparation Example 6-1 and methylmagnesium bromide in Preparation Example 6-3.

$^1$H NMR (600 MHz, DMSO-d$_6$) δ 3.11 (m, 2H), 3.24 (m, 2H), 2.48 (m, 3H), 2.35 (s, 3H), 2.06 (m, 2H), 1.91 (m, 2H), 1.23 (t, 3H).

Preparation Example 13: Preparation of 4-(6-bromo-3-methoxypyridin-2-yl)-5-methyl-6-(1-methylpiperidin-3-yl)pyrimidin-2-amine (LXIX)

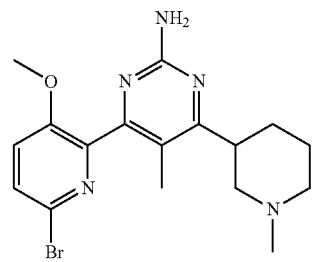 [SMILES: COc1ccc(Br)nc1-c1nc(N)nc(C2CCCN(C)C2)c1C]

The title compound as a yellow solid (1.42 g) was obtained according to the same procedure as Preparation Example 3, except for using 1-(1-methylpiperidin-3-yl)propan-1-one obtained in Preparation Example 12 instead of acetone in Preparation Example 3-4.

$^1$H NMR (400 MHz, DMSO-d$_6$) δ 7.44 (d, J=7.8 Hz, 1H), 7.41 (d, J=6.0 Hz, 1H), 7.18 (s, 2H), 3.83 (s, 3H), 3.12 (m, 2H), 2.48 (s, 3H), 2.56 (s, 3H), 2.35 (m, 3H), 2.06 (m, 2H), 1.28 (m, 2H).

Example 46: Preparation of 2'-amino-6-(2-amino-5-methyl-6-(1-methylpiperidin-3-yl)pyrimidin-3-yl)-3'-fluoro-[2,4'-bipyridin]-5-ol

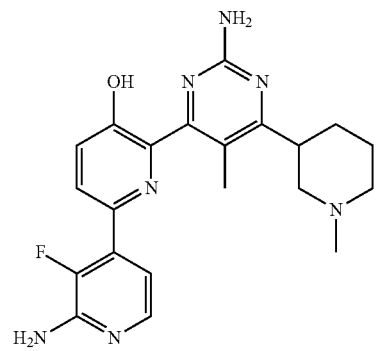 [SMILES: Cc1c(-c2nc(-c3ccnc(N)c3F)ccc2O)nc(N)nc1C1CCCN(C)C1]

The title compound as a yellow solid (33.8 mg) was obtained according to the same procedure as Example 24, except for using 4-(6-bromo-3-methoxypyridin-2-yl)-5-methyl-6-(1-methylpiperidin-3-yl)pyrimidin-2-amine obtained in Preparation Example 13 instead of the compound obtained in Preparation Example 3.

$^1$H NMR (400 MHz, DMSO-d$_6$) δ 14.13 (s, 1H), 7.86 (d, J=8.4 Hz, 1H), 7.81 (d, J=8.0 Hz, 1H), 7.47 (s, 1H), 7.46 (d, J=8.4 Hz, 1H), 7.18 (s, 2H), 7.12 (t, 1H), 6.25 (s, 1H), 3.24 (m, 2H), 3.10 (m, 2H), 2.53 (s, 3H), 2.48 (m, 3H), 2.35 (s, 3H), 2.06 (m, 2H), 1.91 (m, 2H).

Example 47: Preparation of 2'-amino-6-(2-amino-5-methyl-6-(1-propylpiperidin-3-yl)pyrimidin-4-yl)-3'-fluoro-[2,4'-bipyridin]-5-ol

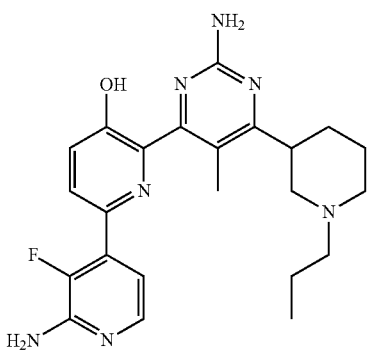 [SMILES: CCCN1CCCC(c2nc(N)nc(-c3nc(-c4ccnc(N)c4F)ccc3O)c2C)C1]

The title compound as a yellow solid (18.2 mg) was obtained according to the same procedure as Example 35, except for using 1-(piperidin-3-yl)propan-1-one and 1-iodopropane(CH$_3$CH$_3$CH$_3$I) instead of 1-(piperidin-4-yl)ethanone hydrochloride and iodoethane (CH$_3$CH$_2$I) in Example 35-1.

$^1$H NMR (400 MHz, DMSO-d$_6$) δ 14.13 (s, 1H), 7.85 (d, J=8.4 Hz, 1H), 7.81 (d, J=8.0 Hz, 1H), 7.47 (s, 1H), 7.45 (d, J=8.4 Hz, 1H), 7.18 (s, 2H), 7.13 (t, 1H), 6.25 (s, 1H), 3.23 (m, 2H), 2.35 (m, 2H), 3.10 (m, 2H), 2.48 (m, 3H), 2.35 (m, 2H), 2.06 (m, 2H), 1.91 (m, 2H), 1.23 (t, 3H).

Example 48: Preparation of 2'-amino-6-(2-amino-6-(1-isopropylpiperidin-3-yl)-5-methylpyrimidin-4-yl)-3'-fluoro-[2,4'-bipyridin]-5-ol

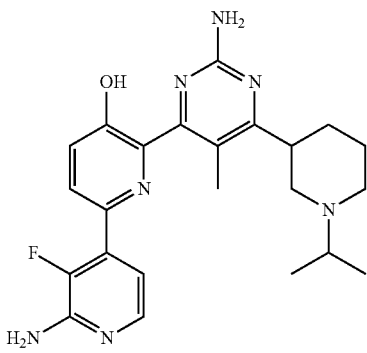

The title compound as a yellow solid (32 mg) was obtained according to the same procedure as Example 35, except for using 1-(piperidin-3-yl)propan-1-one and 2-iodopropane(CH$_3$CH(I)CH$_3$) instead of 1-(piperidin-4-yl)ethanone hydrochloride and iodoethane (CH$_3$CH$_2$I) in Example 35-1.

$^1$H NMR (400 MHz, DMSO-d$_6$) δ 14.11 (s, 1H), 7.85 (d, J=9.0 Hz, 1H), 7.81 (d, J=8.4 Hz, 1H), 7.47 (s, 1H), 7.45 (d, J=8.4 Hz, 1H), 7.18 (s, 2H), 7.13 (t, 1H), 6.25 (s, 1H), 3.14 (m, 2H), 2.54 (m, 1H), 2.36 (s, 3H), 2.35 (m, 3H), 2.06 (m, 2H), 1.91 (m, 2H), 1.15 (d, 6H).

Preparation Example 14: Preparation of 1-(1-isopropylpiperidin-4-yl)butan-1-one

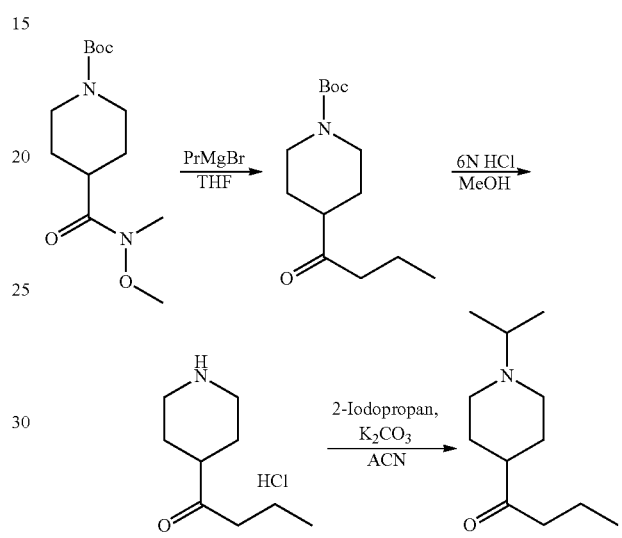

Preparation Example 14-1: Preparation of tert-butyl 4-butanoylpiperidine-1-carboxylate The title compound as a yellow solid (10.5 g) was obtained according to the same procedure as Preparation Example 6-3, except for using propylmagnesium bromide instead of methylmagnesium bromide in Preparation Example 6-3.

$^1$H NMR (400 MHz, CDCl$_3$) δ 3.76 (m, 2H), 2.98 (s, 2H), 2.84 (s, 2H), 2.51 (s, 1H), 2.24 (m, 2H), 2.15 (m, 2H), 1.67 (m, 3H), 1.49 (s, 9H).

Preparation Example 14-2: Preparation of 1-(piperidin-4-yl)butan-1-one hydrochloride The title compound as a yellow solid (5.07 g) was obtained according to the same procedure as Preparation Example 6-4, except for using tert-butyl 4-butanoylpiperidine-1-carboxylate instead of tert-butyl 4-acetylpiperidine-1-carboxylate in Preparation Example 6-4.

$^1$H NMR (400 MHz, CDCl$_3$) δ 3.86 (m, 2H), 2.78 (s, 2H), 2.84 (s, 2H), 2.51 (s, 1H), 2.24 (m, 4H), 1.45 (m, 3H).

Preparation Example 14-3: Preparation of 1-(1-isopropylpiperidin-4-yl)butan-1-one 1-(Piperidin-4-yl)butan-1-one hydrochloride (2.51 g, 10.9 mmol) obtained in Preparation Example 14-2 was dissolved in acetonitrile (35 mL). To the resulting solution were added dropwise potassium carbonate (K$_2$CO$_3$) (2.08 g, 18.9 mmol) and 2-iodopropane (CH$_3$CH(I)CH$_3$) (0.99 mL, 14.2 mmol)

and the solution was stirred for 18 hrs. The solution was evaporated under reduced pressure to concentrate, diluted with EtOAc, and washed with water. The washed organic solvent was dried over anhydrous magnesium sulfate (MgSO$_4$) to concentrate. The resulting residue was isolated and purified by silica gel column chromatography (dimethylchloride/methanol=10/1) to give the white title compound (2.09 g, 81%).

$^1$H NMR (400 MHz, CDCl$_3$) δ 3.88 (m, 2H), 3.79 (m, 2H), 2.84 (m, 2H), 2.51 (m, 3H), 2.31 (m, 1H), 2.24 (m, 4H), 1.45 (m, 3H), 1.24 (d, 6H)

Example 49: Preparation of 2'-amino-6-(2-amino-5-ethyl-6-(1-isopropylpiperidin-4-yl)pyrimidin-4-yl)-3'-fluoro-[2,4'-bipyridin]-5-ol

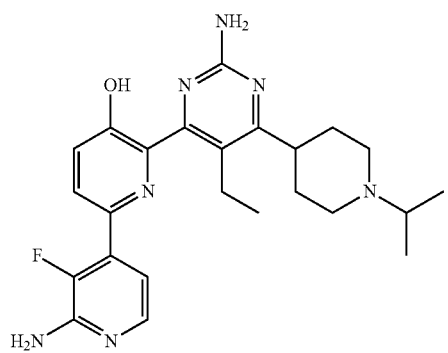 [SMILES: CCc1c(-c2nc(-c3ccnc(N)c3F)ccc2O)nc(N)nc1C1CCN(C(C)C)CC1]

The title compound as a yellow solid (21.5 mg) was obtained according to the same procedure as Example 35, except for using 1-(1-isopropylpiperidin-4-yl)butan-1-one obtained in Preparation Example 14 instead of 1-(1-ethylpiperidin-4-yl)ethanone in Example 35-2.

$^1$H NMR (400 MHz, MeOD-d$_4$) δ 10.0 (s, 1H), 8.01 (d, J=8.8 Hz, 1H), 7.85 (d, J=6.8 Hz, 1H), 7.66 (d, J=8.4 Hz, 1H), 7.26 (m, 1H), 3.08 (m, 2H), 2.93 (m, 3H), 2.74 (m, 1H), 2.24 (m, 2H), 2.00 (m, 2H), 1.62 (m, 2H), 1.25 (t, 3H), 1.04 (d, 6H).

Preparation Example 15: Preparation of 1-(1-isopropylpiperidin-4-yl)pentan-1-one

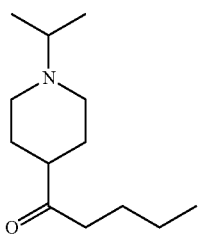

The title compound as a yellow solid (10.8 g) was obtained according to the same procedure as Preparation Example 14, except for using butylmagnesium chloride instead of propylmagnesium bromide in Preparation Example 14-1.

$^1$H NMR (400 MHz, MeOD-d$_4$) δ, 3.43 (m, 2H), 3.27 (m, 2H), 3.15 (m, 4H), 2.27 (m, 3H), 1.92 (m, 2H), 1.34 (m, 6H), 0.71 (m, 3H).

Example 50: Preparation of 2'-amino-6-(2-amino-6-(1-isopropylpiperidin-4-yl)-5-propylpyrimidin-4-yl)-3'-fluoro-[2,4'-bipyridin]-5-ol

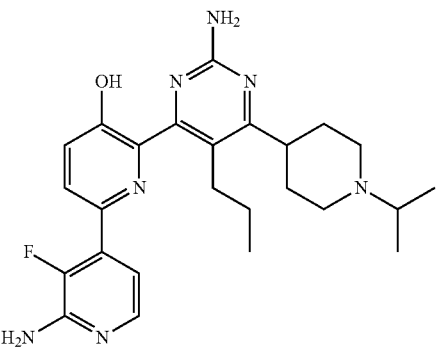 [SMILES: CCCc1c(-c2nc(-c3ccnc(N)c3F)ccc2O)nc(N)nc1C1CCN(C(C)C)CC1]

The title compound as a yellow solid (32.1 mg) was obtained according to the same procedure as Example 35, except for using 1-(1-isopropylpiperidin-4-yl)pentan-1-one obtained in Preparation Example 15 instead of 1-(1-ethylpiperidin-4-yl)ethanone in Example 35-2.

$^1$H NMR (400 MHz, MeOD-d$_4$) δ 10.1 (s, 1H), 8.01 (d, J=9.0 Hz, 1H), 7.84 (d, J=7.2 Hz, 1H), 7.64 (d, J=9.0 Hz, 1H), 7.26 (m, 1H), 3.08 (m, 2H), 2.93 (m, 3H), 2.74 (m, 1H), 2.52 (m, 1H), 2.24 (m, 2H), 2.00 (m, 2H), 1.63 (m, 2H), 1.23 (t, 3H), 1.02 (d, 6H).

Example 51: Preparation of 2'-amino-6-(2-amino-6-morpholinopyrimidin-4-yl)-3'-fluoro-[2,4'-bipyridin]-5-ol (LXXVI)

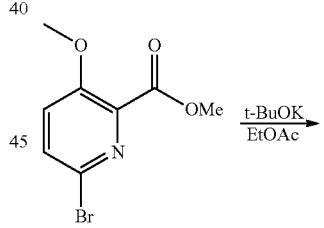

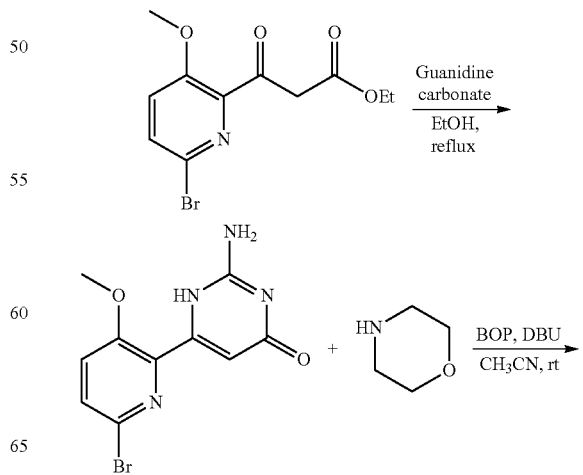

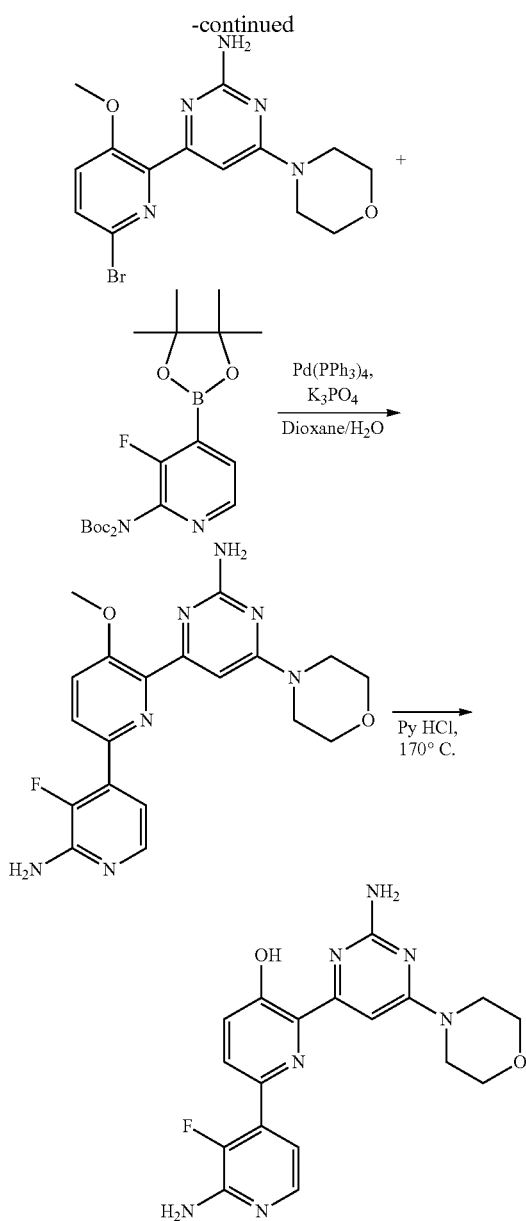

Example 51-1: Preparation of ethyl 3-(6-bromo-3-methoxypyridin-2-yl)-3-oxopropanoate (LXXII)

Methyl 6-bromo-3-methoxypicolinate (4.18 g, 16.99 mmol) obtained in Preparation Example 3-3 was dissolved in ethanol (85 mL). The resulting solution was cooled to 0° C. and potassium tert-butoxide (t-BuOK) was added dropwise thereto. The solution was stirred at room temperature for 2 hrs. Distilled water and acetic acid (5 mL) were added dropwise to the solution and the solution was stirred for 10 min. The solution was diluted with ethylacetate and washed with water. The washed organic solvent was dried over anhydrous magnesium sulfate (MgSO₄) to concentrate. The resulting residue was isolated and purified by silica gel column chromatography (hexane/ethylacetate=2/1) to give the white title compound (3.41 g, 66%).

¹H NMR (600 MHz, CDCl₃) δ 7.58 (d, J=8.4 Hz, 1H), 7.28 (d, J=8.4 Hz, 1H), 4.18 (q, J=7.2 Hz, 2H), 4.05 (s, 2H), 3.93 (s, 3H), 1.25 (t, J=7.2 Hz, 3H).

Example 51-2: Preparation of 2-amino-6-(6-bromo-3-methoxypyridin-2-yl)pyrimidin-4-(1H)-one (LXXIII)

Ethyl 3-(6-bromo-3-methoxypyridin-2-yl)-3-oxoproanoate (3.41 g, 11.29 mmol) was dissolved in ethanol (40 mL). To the resulting solution was added dropwise guanidine carbonate (2.64 g, 14.67 mmol) and the solution was refluxed with heat for 24 hrs. The mixture was cooled to room temperature and evaporated under reduced pressure to concentrate. The resulting residue was diluted with distilled water and neutralized with Conc. HCl to provide a solid. The solid was filtered to give the title compound (3.47 g, 100%).

¹H NMR (600 MHz, DMSO-d₆) δ 7.71 (d, J=9.0 Hz, 1H), 7.64 (d, J=8.4 Hz, 1H), 7.22 (br, 2H), 6.13 (s, 1H), 3.89 (s, 3H).

Example 51-3: Preparation of 4-(6-bromo-3-methoxypyridin-2-yl)-6-morpholinopyrimidin-2-amine (LXXIV)

2-Amino-6-(6-bromo-3-methoxypyridin-2-yl)pyrimidin-4-(1H)-one (100.0 mg, 336.58 umol) was dissolved in acetonitrile (3.36 mL). To the resulting solution were added dropwise (benzotriazol-1-yloxy)tris(dimethylamino)phosphonium hexafluorophosphate (BOP) (193.52 mg, 437.55 umol), 1,8-diazabicyclo[5,4,0]undec-7-ene (DBU) (75.5 uL, 504.86 umol) and the resulting mixture was stirred at room temperature for 10 min. Morpholine (44.43 uL, 504.86 umol) was added dropwise to the mixture and the mixture was stirred at room temperature for 24 hrs. The resulting solution was evaporated under reduced pressure to concentrate, diluted with ethylacetate, and washed with distilled water. The organic solvent was dried over anhydrous magnesium sulfate (MgSO₄), filtered, and evaporated under reduced pressure to concentrate. The resulting residue was isolated and purified by silica gel column chromatography (dichloromethane/methanol=15/1) to give the title compound (98 mg, 80%).

¹H NMR (600 MHz, MeOH-d₄) δ 7.77 (d, J=9.0 Hz, 1H), 7.71 (d, J=8.4 Hz, 1H), 7.36 (s, 1H), 4.09 (s, 3H), 3.88 (m, 4H), 3.79 (m, 4H).

Example 51-4: Preparation of 6-(2-amino-6-morpholinopyrimidin-4-yl)-3'-fluoro-5-methoxy-[2,4'-bipyridin]-2'-amine (LXXV)

4-(6-Bromo-3-methoxypyridin-2-yl)-6-morpholinopyrimidin-2-amine (157.91 mg, 431.21 umol) and 2-[3-fluoro-4-(4,4,5,5-tetramethyl-[1,3,2]dioxaborolan-2-yl)-2-pyridinyl]-imidodicarbonic acid-1,3-bis(1,1-dimethylethyl)ester (378 mg, 862.42 umol) obtained in Preparation Example 1 were dissolved in dioxane (4 mL). To the resulting solution were added dropwise potassium phosphate (K₃PO₄) (274.6 mg, 1.29 mmol) dissolved in distilled water (2 mL) and tetrakis(triphenylphosphine)palladium(0) (Pd(PPh₃)₄) (24.94 mg, 21.56 umol). The solution was refluxed with heat for 24 hrs, cooled and evaporated under reduced pressure to concentrate. The solution was diluted with dichloromethane and washed with water. The organic solvent was dried over anhydrous magnesium sulfate (MgSO₄), filtered, and evaporated under reduced pressure to concentrate. The resulting residue was isolated and purified by silica gel column chromatography (ethylacetate/hexane, 6/1) to give the title compound (47 mg, 27%).

$^1$H NMR (600 MHz, DMSO-$d_6$) δ 7.88 (d, J=7.8 Hz, 1H), 7.78 (d, J=4.8 Hz, 1H), 7.66 (d, J=8.4 Hz, 1H) 6.99 (t, J=6.0 Hz, 1H), 6.23 (m, 5H), 3.85 (s, 3H), 3.65 (m, 4H), 3.53 (m, 4H).

Example 51-5: Preparation of 2'-amino-6-(2-amino-6-morpholinopyrimidin-4-yl)-3'-fluoro-[2,4'-bipyridin]-5-ol (LXXVI)

6-(2-Amino-6-morpholinopyrimidin-4-yl)-3'-fluoro-5-methoxy-[2,4'-bipyridin]-2'-amine (120 mg, 301.95 umol) and pyridine hydrochloride (Pyridine HCl) (523.41 mg, 4.53 mmol) were stirred in a sealed tube at 170° C. for 30 min. The resulting mixture was cooled to room temperature, neutralized with 2N NaOH solution to provide a solid. The solid was filtered, washed with diethylether and dried to give the title compound (72 mg, 62%).

$^1$H NMR (600 MHz, DMSO-$d_6$) δ 7.82-7.80 (m, 2H), 7.41 (d, J=8.4 Hz, 1H), 7.14 (t, J=5.4 Hz, 1H), 7.03 (s, 1H), 6.82 (br, 2H), 6.25 (br, 2H), 3.70-3.68 (m, 4H), 3.64-3.63 (m, 4H).

Example 52: Preparation of 2'-amino-6-(2-amino-6-(dimethylamino)pyrimidin-4-yl)-3'-fluoro-[2,4'-bipyridin]-5-ol

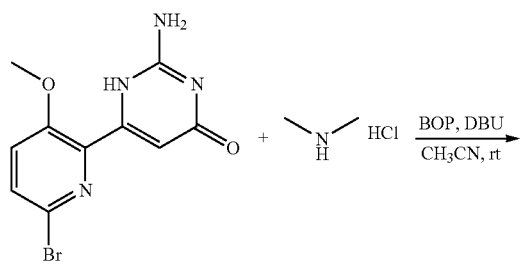

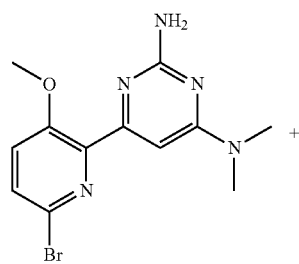

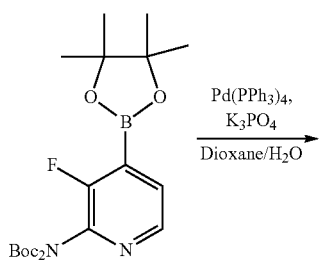

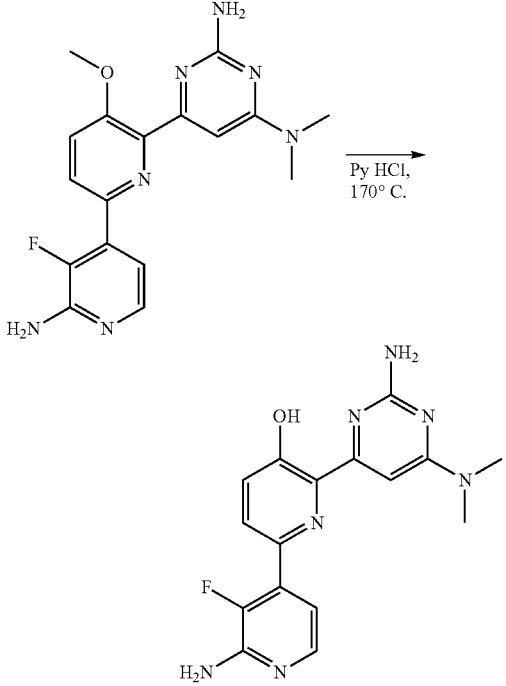

Example 52-1: Preparation of 6-(6-bromo-3-methoxypyridin-2-yl)-N4,N4-dimethylpyrimidin-2,4-diamine (LXXIV)

2-Amino-6-(6-bromo-3-methoxypyridin-2-yl)pyrimidin-4(1H)-one (400.0 mg, 1.35 mmol) obtained in Example 51-2 was dissolved in acetonitrile (136.5 mL). To the resulting solution were added dropwise (benzotriazole-1-yloxy)tris(dimethylamino)phosphonium hexafluorophosphate (BOP) (774.09 mg, 1.75 mmol) and 1,8-diazabicyclo[5,4,0]undec-7-ene (DBU) (604.1 uL, 4.04 mmol) and the solution was stirred at room temperature for 10 min. Dimethylamine hydrochloride (164.69 mg, 2.02 mmol) was added dropwise to the solution and the solution was stirred at room temperature for 24 hrs. The solution was evaporated under reduced pressure to concentrate, diluted with ethylacetate, and washed with distilled water. The organic solvent was dried over anhydrous magnesium sulfate (MgSO$_4$), filtered, and evaporated under reduced pressure to concentrate. The resulting residue was isolated and purified by silica gel column chromatography (dichloromethane/methanol=15/1) to give the title compound (436 mg, 99%).

$^1$H NMR (600 MHz, DMSO-$d_6$) δ 7.92 (d, J=9.0 Hz, 1H), 7.82 (d, J=9.0 Hz, 1H), 7.16 (s, 1H), 4.04 (s, 3H), 3.31 (s, 6H).

Example 52-2: Preparation of 6-(2'-amino-3'-fluoro-5-methoxy-[2,4'-bipyridin]-6-yl-N4,N4-dimethylpyrimidin-2,4-diamine (LXXV)

6-(6-Bromo-3-methoxypyridin-2-yl)-N4,N4-dimethylpyrimidin-2,4-diamine (214.49 mg, 661.65 umol) and 2-[3-fluoro-4-(4,4,5,5-tetramethyl-[1,3,2]dioxaborolan-2-yl)-2-pyridinyl]-imidodicarbonic acid-1,3-bis(1,1-dimethylethyl) ester (580 mg, 1.32 mmol) obtained in Preparation Example 1 were dissolved in dioxane (6 mL). To the resulting solution were added dropwise potassium phosphate (K$_3$PO$_4$) (421.34 mg, 1.98 mmol) dissolved in distilled water (3 mL) and tetrakis(triphenylphosphine)palladium(0) (Pd(PPh₃)₄) (38.26 mg, 33.08 umol). The solution was refluxed with heat for 24 hrs, cooled, and evaporated under reduced pressure to concentrate. The solution was diluted with distilled water and dichloromethane and then the resulting solid was filtered, washed with diethylether, and dried to give the title compound (96 mg, 41%).

$^1$H NMR (600 MHz, DMSO-$d_6$) δ 7.93 (d, J=8.4 Hz, 1H), 7.80 (d, J=5.4 Hz, 1H), 7.74 (d, J=8.4 Hz, 1H), 7.03 (t, J=4.8 Hz, 1H), 6.59 (s, 2H), 6.41 (s, 1H), 6.28 (s, 2H), 3.90 (s, 3H), 3.08 (s, 6H).

Example 52-3: Preparation of 2'-amino-6-(2-amino-6-(dimethylamino)pyrimidin-4-yl)-3'-fluoro-[2,4'-bipyridin]-5-ol (LXXVI)

6-(2'-Amino-3'-fluoro-5-methoxy-[2,4'-bipyridin]-6-yl)-N4,N4-dimethylpyrimidin-2,4-diamine (96 mg, 270.13 umol) and pyridine hydrochloride (Pyridine HCl) (936.5 mg, 8.10 mmol) were stirred in a sealed tube at 170° C. for 2 hrs. The resulting mixture was cooled to room temperature and neutralized with 2N NaOH solution to provide a solid. The solid was filtered, washed with diethylether, and dried to give the title compound (22 mg, 24%).

$^1$H NMR (600 MHz, DMSO-$d_6$) δ 7.82 (d, J=5.4 Hz, 1H), 7.80 (d, J=7.2 Hz, 1H), 7.39 (d, J=8.4 Hz, 1H), 7.12 (t, J=5.4 Hz, 1H), 6.94 (s, 1H), 6.72 (br, 2H), 6.25 (br, 2H), 3.11 (s, 6H).

Example 53: Preparation of 2'-amino-6-(2-amino-6-(4-methylpiperazin-1-yl)pyrimidin-4-yl)-3'-fluoro-[2,4'-bipyridin]-5-ol

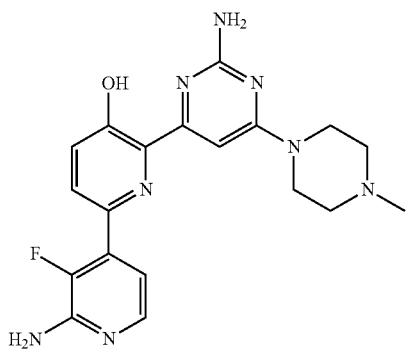

The title compound as a yellow solid (28 mg) was obtained according to the same procedure as Example 52, except for using 4-methylpiperazine instead of dimethylamine hydrochloride in Example 52-1.

$^1$H NMR (600 MHz, DMSO-$d_6$) δ 7.84-7.82 (m, 2H), 7.44 (d, J=9.0 Hz, 1H), 7.19 (t, J=4.8 Hz, 1H), 7.10 (s, 1H), 6.94 (br, 2H), 6.30 (br, 2H), 3.47 (m, 4H), 3.06 (m, 4H), 2.79 (s, 3H).

Example 54: Preparation of 6-(2-amino-6-chloropyrimidin-4-yl)-[2,4'-bipyridin]-5-ol

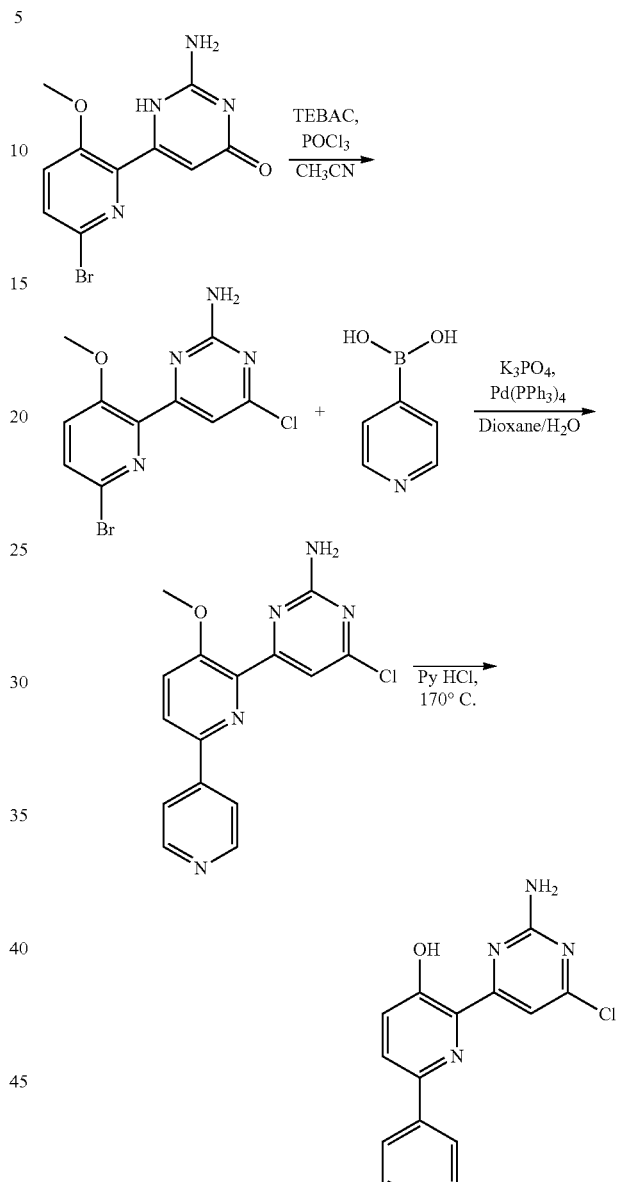

Example 54-1: Preparation of 4-(6-bromo-3-methoxypyridin-2-yl)-6-chloropyrimidin-2-amine 2-Amino-6-(6-bromo-3-methoxypyridin-2-yl)pyrimidin-4(1H)-one (100 mg, 336.58 mol) obtained in Example 51-2 was dissolved in acetonitrile (2 mL). To the resulting solution were added dropwise benzyltriethylammonium chloride (TEBAC) (153.33 mg, 673.15 umol), triethylamine (93.82 uL, 673.15 umol) and phosphoryl chloride (POCl₃) (313.72 uL, 3.37 mmol) and the solution was refluxed with heat for 4 hrs and cooled to room temperature. The solution was evaporated under reduced pressure to concentrate and neutralized with 6N sodium hydroxide. After extraction of the solution with dichloromethane, the organic solvent was dried over anhydrous magnesium sulfate (MgSO₄), filtered, and evaporated under reduced pressure to concentrate. The resulting solid was washed with diethylether to give the title compound (26 mg, 24%).

$^1$H NMR (600 MHz, DMSO-$d_6$) δ 7.72 (d, J=9.0 Hz, 1H), 7.64 (d, J=9.0 Hz, 1H), 7.28 (br, 2H), 6.93 (s, 1H).

Example 54-2: Preparation of 4-chloro-6-(5-methoxy-[2,4'-bipyridin]-6-yl)pyrimidin-2-amine 4-(6-Bromo-3-methoxypyridin-2-yl)-6-chloropyrimidin-2-amine (26 mg, 82.39 umol) and pyridin-4-ylboronic acid (12.15 mg, 98.87 umol) were dissolved in dioxane (300 uL). To the resulting solution were added dropwise potassium phosphate ($K_3PO_4$) (52.47 mg, 247.18 umol) dissolved in distilled water (100 uL) and tetrakis(triphenylphosphine)palladium(0) (Pd(PPh$_3$)$_4$) (4.76 mg, 4.12 umol). The solution was refluxed with heat for 24 hrs, cooled, evaporated under reduced pressure to concentrate, and diluted with distilled water and dichloromethane. The resulting solid was filtered, washed with diethylether, and dried to give the title compound (7.6 mg, 29%).

$^1$H NMR (600 MHz, MeOD-$d_4$) δ 8.60 (m, 2H), 8.16 (d, J=9.0 Hz, 1H), 8.10 (m, 2H), 7.74 (d, J=9.6 Hz, 1H), 7.15 (s, 1H), 3.98 (s, 3H).

Example 54-3: Preparation of 6-(2-amino-6-chloro-pyrimidin-4-yl)-[2,4'-bipyridin]-5-ol 4-Chloro-6-(5-methoxy-[2,4'-bipyridin]-6-yl)pyrimidin-2-amine (20 mg, 63.74 umol) and pyridine hydrochloride (Pyridine HCl) (73.66 mg, 637.45 mmol) were stirred in a sealed tube at 170° C. for 3 hrs. The mixture was cooled to room temperature and neutralized with 2N NaOH solution. The resulting solid was filtered, washed with diethylether, and dried to give the title compound (6 mg, 31%).

$^1$H NMR (600 MHz, DMSO-$d_6$) δ 8.64 (m, 2H), 8.16 (d, J=5.4 Hz, 2H), 8.05 (d, J=9.0 Hz, 1H), 7.41 (d, J=8.4 Hz, 1H), 6.97 (s, 1H).

Preparation Example 16: Preparation of 4-(6-bromo-3-methoxypyridin-2-yl)-5-methylpyrimidin-2-amine (LXIX)

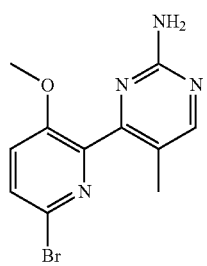 [SMILES: COc1ccc(Br)nc1-c1nc(N)ncc1C]

The title compound as a yellow solid (4.1 g) was obtained according to the same procedure as Preparation Example 2, except for using 3M ethylmagnesium bromide diethylether solution instead of 3M methylmagnesium bromide tetrahydrofuran (THF) solution in Preparation Example 2-2.

$^1$H NMR (600 MHz, MeOH-$d_4$) δ 7.77 (d, J=9.0 Hz, 1H), 7.71 (d, J=8.4 Hz, 1H), 7.36 (s, 1H), 3.87 (s, 3H), 2.45 (s, 3H).

Example 55: Preparation of 2'-amino-6-(2-amino-5-methylpyrimidin-4-yl)-3'-fluoro-[2,4'-bipyridin]-5-ol

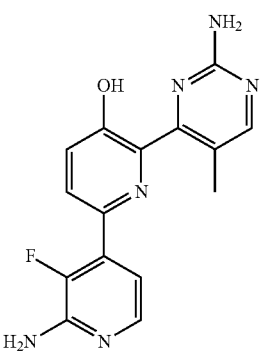 [SMILES: Cc1cnc(N)nc1-c1nc(-c2ccnc(N)c2F)ccc1O]

The title compound as a yellow solid (8.4 mg) was obtained according to the same procedure as Example 24, except for using 4-(6-bromo-3-methoxypyridin-2-yl)-5-methylpyrimidin-2-amine obtained in Preparation Example 16 instead of the compound obtained in Preparation Example 3.

$^1$H NMR (600 MHz, CD$_3$OD) δ 8.32 (s, 1H), 8.01 (d, J=9.0 Hz, 1H), 7.78 (d, J=9.0 Hz, 1H), 7.49 (d, J=9.0 Hz, 1H), 7.41 (t, 1H), 2.64 (s, 3H).

Preparation Example 17: Preparation of 4-(6-bromo-3-methoxypyridin-2-yl)-5-ethylpyrimidin-2-amine (LXIX)

The title compound as a yellow solid (451 mg) was obtained according to the same procedure as Preparation Example 2, except for using 3M propylmagnesium bromide diethylether solution instead of 3M methylmagnesium bromide tetrahydrofuran (THF) solution in Preparation Example 2-2.

$^1$H NMR (600 MHz, MeOH-$d_4$) δ 7.76 (d, J=8.4 Hz, 1H), 7.71 (d, J=8.4 Hz, 1H), 7.36 (s, 1H), 3.87 (s, 3H), 2.89 (m, 2H), 0.73 (t, 3H).

Example 56: Preparation of 2'-amino-6-(2-amino-5-ethylpyrimidin-4-yl)-3'-fluoro-[2,4'-bipyridin]-5-ol

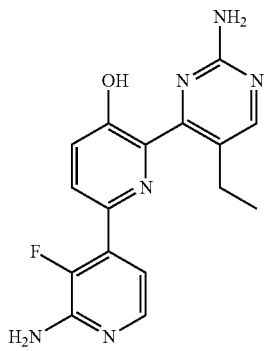 [SMILES: CCc1cnc(N)nc1-c1nc(-c2ccnc(N)c2F)ccc1O]

The title compound as a yellow solid (18.9 mg) was obtained according to the same procedure as Example 24, except for using 4-(6-bromo-3-methoxypyridin-2-yl)-5-ethylpyrimidin-2-amine obtained in Preparation Example 17 instead of the compound obtained in Preparation Example 3.

$^1$H NMR (600 MHz, DMSO-d$_6$) δ 8.32 (s, 1H), 7.85 (d, J=9.0 Hz, 1H), 7.79 (d, J=9.0 Hz, 1H), 7.78 (s, 2H), 6.78 (m, 1H), 6.25 (s, 2H), 2.85 (m, 2H), 1.04 (t, 3H).

Example 57: Preparation of 2'-amino-6-(2-amino-5-propylpyrimidin-4-yl)-3'-fluoro-[2,4'-bipyridin]-5-ol

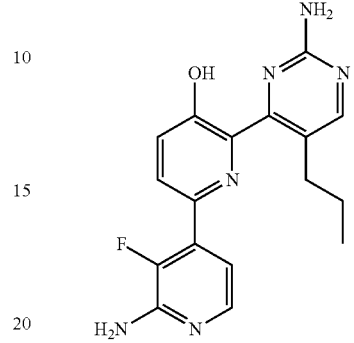

The title compound as a yellow solid (6.4 mg) was obtained according to the same procedure as Example 24, except for using 4-(6-bromo-3-methoxypyridin-2-yl)-5-propylpyrimidin-2-amine obtained in Preparation Example 18 instead of the compound obtained in Preparation Example 3.

$^1$H NMR (600 MHz, DMSO-d$_6$) δ 13.93 (s, 1H), 8.27 (s, 1H), 7.51 (d, J=9.0 Hz, 1H), 7.42 (d, J=9.0 Hz, 1H), 6.98 (s, 2H), 6.78 (m, 1H), 6.25 (s, 2H), 2.85 (m, 2H), 1.44 (m, 2H), 1.04 (t, 3H).

Preparation Example 18: Preparation of 4-(6-bromo-3-methoxypyridin-2-yl)-5-propylpyrimidin-2-amine (LXIX)

The title compound as a yellow solid (28 mg) was obtained according to the same procedure as Preparation Example 2, except for using 3M butylmagnesium chloride diethylether solution instead of 3M methylmagnesium bromide tetrahydrofuran (THF) solution in Preparation Example 2-2.

$^1$H NMR (600 MHz, DMSO-d$_6$) δ 8.27 (s, 1H), 7.51 (d, J=9.0 Hz, 1H), 7.42 (d, J=9.0 Hz, 1H), 3.85 (s, 3H), 2.85 (m, 2H), 1.44 (m, 2H), 1.04 (t, 3H)

Preparation Example 19: Preparation of 4-(6-bromo-3-methoxypyridin-2-yl)-5-isopropylpyrimidin-2-amine (LXIX)

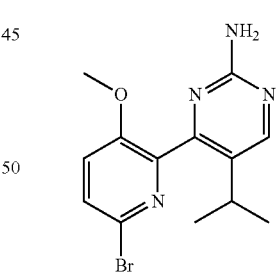

The title compound as a yellow solid (120 mg) was obtained according to the same procedure as Preparation Example 2, except for using 3M isobutylmagnesium chloride diethylether solution instead of 3M methylmagnesium bromide tetrahydrofuran (THF) solution in Preparation Example 2-2.

$^1$H NMR (600 MHz, DMSO-d$_6$) δ 8.11 (s, 1H), 7.54 (d, J=9.0 Hz, 1H), 7.42 (d, J=9.0 Hz, 1H), 3.27 (m, 2H), 1.04 (d, 6H)

Example 58: Preparation of 2'-amino-6-(2-amino-5-isopropylpyrimidin-5-yl)-3'-fluoro-[2,4'-bipyridin]-5-ol

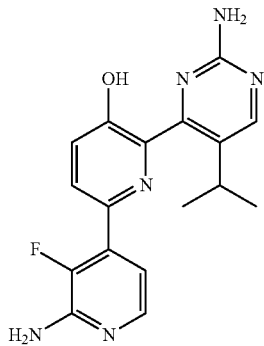 [SMILES: CC(C)c1cnc(N)nc1-c1nc(-c2ccnc(N)c2F)ccc1O]

The title compound as a yellow solid (21.8 mg) was obtained according to the same procedure as Example 24, except for using 4-(6-bromo-3-methoxypyridin-2-yl)-5-isopropylpyrimidin-2-amine obtained in Preparation Example 19 instead of the compound obtained in Preparation Example 3.

$^1$H NMR (600 MHz, DMSO-d$_6$) δ 13.12 (s, 1H), 8.23 (s, 1H), 7.51 (d, J=9.0 Hz, 1H), 7.40 (d, J=9.0 Hz, 1H), 6.98 (s, 2H), 6.78 (m, 1H), 6.25 (s, 2H), 3.26 (m, 2H), 1.11 (d, 6H).

Preparation Example 20: Preparation of 4-(6-bromo-3-methoxypyridin-2-yl)-N-methyl-6-(1-methylpiperidin-4-yl)pyrimidin-2-amine (LXIX)

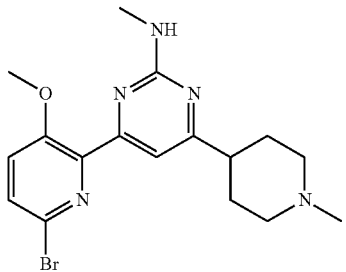 [SMILES: CNc1nc(-c2nc(Br)ccc2OC)cc(C2CCN(C)CC2)n1]

The title compound as a yellow solid (331 mg) was obtained according to the same procedure as Preparation Example 3, except for using 1-(1-methylpiperidin-4-yl)ethanone obtained in Preparation Example 6 instead of acetone in Preparation Example 3-4 and using 1-methylguanidine instead of guanidine in Preparation Example 3-5.

$^1$H NMR (400 MHz, DMSO-d$_6$) δ 7.56 (d, J=7.8 Hz, 1H), 7.41 (d, J=6.0 Hz, 1H), 7.38 (s, 2H), 7.32 (t, 1H), 3.48 (s, 3H), 3.10 (m, 2H), 2.48 (s, 3H), 2.42 (s, 3H), 2.35 (m, 3H), 2.14 (m, 2H), 1.28 (m, 2H).

Example 59: Preparation of 2'-amino-3'-fluoro-6-(2-(methylamino)-6-(1-methylpiperidin-4-yl)pyrimidin-4-yl)-[2,4'-bipyridin]-5-ol

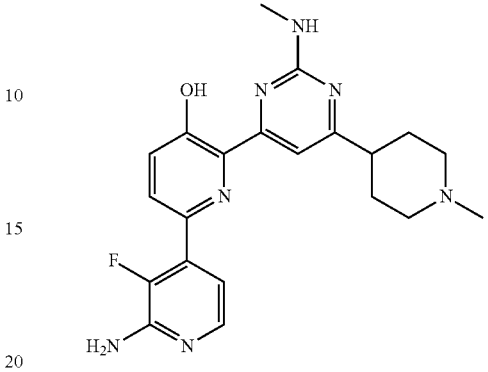

The title compound as a yellow solid (29.9 mg) was obtained according to the same procedure as Example 24, except for using 4-(6-bromo-3-methoxypyridin-2-yl)-N-methyl-6-(1-methylpiperidin-4-yl)pyrimidin-2-amine obtained in Preparation Example 20 instead of the compound obtained in Preparation Example 3.

$^1$H NMR (400 MHz, DMSO-d$_6$) δ 14.13 (s, 1H), 7.86 (d, J=7.8 Hz, 1H), 7.81 (d, J=6.0 Hz, 1H), 7.47 (s, 1H), 7.46 (d, J=8.4 Hz, 1H), 7.18 (s, 2H), 7.12 (t, 1H), 6.25 (s, 1H), 3.10 (m, 2H), 2.48 (s, 3H), 2.36 (s, 3H), 2.35 (m, 3H), 2.06 (m, 2H), 1.91 (m, 2H).

Preparation Example 21: Preparation of 4-(6-bromo-3-methoxypyridin-2-yl)-5,6-dimethylpyrimidin-2-amine

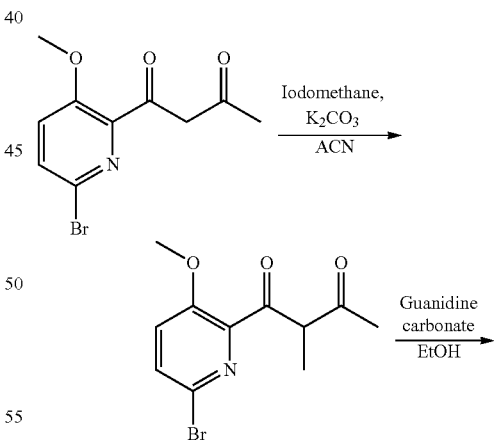

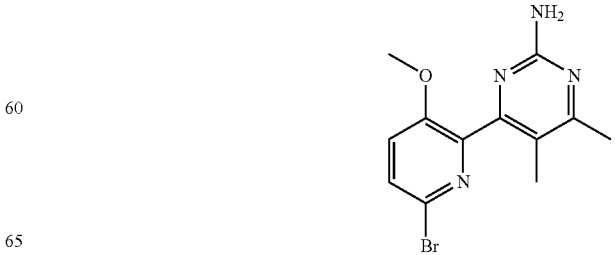

Preparation Example 21-1: Preparation of 1-(6-bromo-3-methoxypyridin-2-yl)-2-methylbutan-1,3-dione 1-(6-bromo-3-methoxypyridin-2-yl)butan-1,3-dione (15.41 g, 45.21 mmol) obtained in Preparation Example 3-4 was dissolved in acetonitrile (100 mL). To the resulting solution were added dropwise potassium carbonate ($K_2CO_3$) (16.88 g, 135.63 mmol) and iodomethane ($CH_3I$) (4.56 mL, 90.42 mmol) and the solution was stirred for 18 hrs. The solution was evaporated under reduced pressure to concentrate, diluted with EtOAc, and washed with water. The washed organic solvent was dried over anhydrous magnesium sulfate ($MgSO_4$) to concentrate. The resulting residue was isolated and purified by silica gel column chromatography (hexane/ethylacetate=3/1) to give the white title compound (15.18 g, 67%).

$^1$H NMR (600 MHz, $CDCl_3$) δ 7.57 (d, J=9.0 Hz, 1H), 7.26 (d, J=9.0 Hz, 1H), 3.95 (s, 3H), 2.85 (s, 3H), 2.45 (s, 3H).

Preparation Example 21-2: Preparation of 4-(6-bromo-3-methoxypyridin-2-yl)-5,6-dimethylpyrimidin-2-amine The title compound as a yellow solid (3.12 g) was obtained according to the same procedure as Preparation Example 3-5, except for using 1-(6-bromo-3-methoxypyridin-2-yl)-2-methylbutan-1,3-dione obtained in Preparation Example 21-1 instead of the compound obtained in Preparation Example 3-4.

$^1$H NMR (600 MHz, DMSO-$d_6$) δ 7.80 (d, J=9.0 Hz, 1H), 7.38 (d, J=9.0 Hz, 1H), 3.95 (s, 3H), 2.85 (s, 3H), 2.45 (s, 3H).

Example 60: Preparation of 2'-amino-6-(2-amino-5,6-dimethylpyrimidin-4-yl)-3'-fluoro-[2,4'-bipyridin]-5-ol

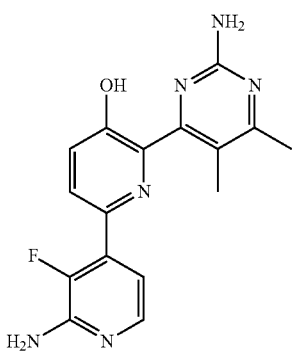 [SMILES: Cc1nc(N)nc(-c2nc(-c3ccnc(N)c3F)ccc2O)c1C]

The title compound as a yellow solid (34.8 mg) was obtained according to the same procedure as Example 24, except for using 4-(6-bromo-3-methoxypyridin-2-yl)-5,6-dimethylpyrimidin-2-amine obtained in Preparation Example 21 instead of the compound obtained in Preparation Example 3.

$^1$H NMR (600 MHz, DMSO-$d_6$) δ 7.94 (d, J=9.0 Hz, 1H), 7.90 (d, J=8.4 Hz, 1H), 7.54 (m, 1H), 7.11 (m, 1H), 6.96 (s, 2H), 6.79 (s, 2H), 2.44 (s, 3H), 2.22 (s, 3H).

Example 61: Preparation of 2,6-bis(2-aminopyrimidin-4-yl)pyridin-3-ol 3hydrochloride

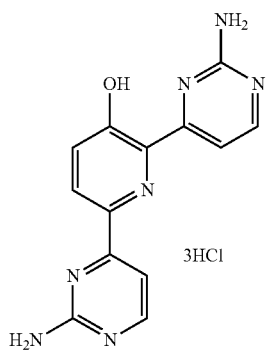 [SMILES: Nc1nccc(-c2ccc(O)c(-c3ccnc(N)n3)n2)n1]

The title compound as a yellow solid (4.6 mg) was obtained by reacting the compound obtained in Example 1 with hydrochloric acid.

$^1$H NMR (400 MHz, DMSO-$d_6$) δ 8.56 (d, J=4.8 Hz, 1H), 8.49 (d, J=5.2 Hz, 1H), 8.39 (d, J=8.8 Hz, 1H), 7.86 (d, J=5.2 Hz 1H), 7.79 (d, J=4.8 Hz, 1H), 7.63 (d, J=8.4 Hz, 1H), 3.97 (br, 7H).

Example 62: Preparation of 2,6-bis(2-aminopyrimidin-4-yl)pyridin-3-ol oxalate

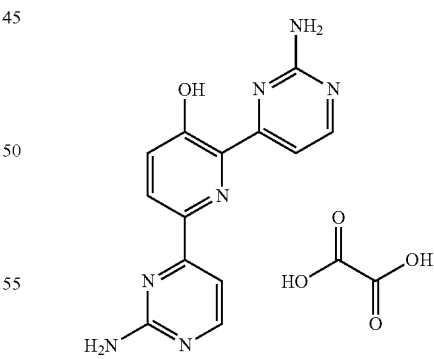

The title compound as a yellow solid (3.2 mg) was obtained by reacting the compound obtained in Example 1 with oxalic acid.

$^1$H NMR (400 MHz, DMSO-$d_6$) δ 8.57 (d, J=4.8 Hz, 1H), 8.47 (d, J=5.2 Hz, 1H), 8.39 (d, J=8.8 Hz, 1H), 7.86 (d, J=5.2 Hz 1H), 7.79 (d, J=4.8 Hz, 1H), 7.63 (d, J=8.4 Hz, 1H).

Example 63: Preparation of 2,6-bis(2-aminopyrimidin-4-yl)pyridin-3-ol malonate

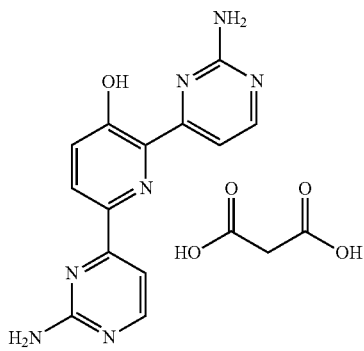

The title compound as a yellow solid (4.9 mg) was obtained by reacting the compound obtained in Example 1 with malonic acid.

$^1$H NMR (400 MHz, DMSO-$d_6$) δ 8.57 (d, J=4.8 Hz, 1H), 8.47 (d, J=5.2 Hz, 1H), 8.39 (d, J=8.8 Hz, 1H), 7.86 (d, J=5.2 Hz 1H), 7.79 (d, J=4.8 Hz, 1H), 7.63 (d, J=8.4 Hz, 1H), 3.17 (s, 2H).

Example 64: Preparation of 2,6-bis(2-aminopyrimidin-4-yl)pyridin-3-ol sulfate

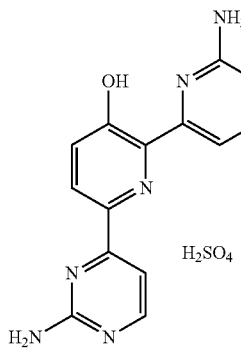

The title compound as a yellow solid (3.2 mg) was obtained by reacting the compound obtained in Example 1 with sulfuric acid.

$^1$H NMR (400 MHz, DMSO-$d_6$) δ 8.57 (d, J=4.8 Hz, 1H), 8.47 (d, J=5.2 Hz, 1H), 8.39 (d, J=8.8 Hz, 1H), 7.86 (d, J=5.2 Hz 1H), 7.79 (d, J=4.8 Hz, 1H), 7.63 (d, J=8.4 Hz, 1H).

Example 65: Preparation of 2'-amino-4-(2-aminopyrimidin-4-yl)-[2,4'-bipyridin]-5-ol oxalate

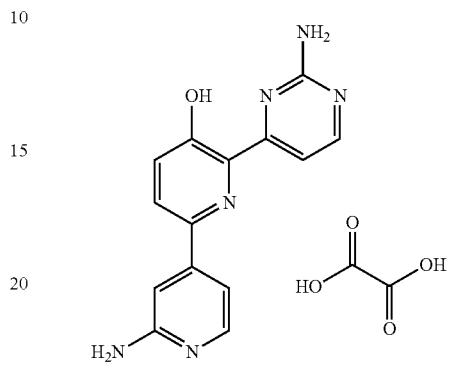

The title compound as a yellow solid (1.9 mg) was obtained by reacting the compound obtained in Example 10 with oxalic acid.

$^1$H NMR (600 MHz, DMSO) δ 13.55 (s, 1H), 9.66 (s, 1H), 8.48 (d, J=7.8 Hz, 1H), 7.94 (d, J=13.2 Hz, 1H), 7.89 (d, J=13.2 Hz, 1H), 7.65 (d, J=7.8 Hz, 1H), 7.39 (d, J=13.2 Hz, 1H), 7.25 (br, 2H), 6.85 (d, J=13.2 Hz, 1H).

Example 66: Preparation of 2'-amino-6'-(2-aminopyrimidin-4-yl)-3'-fluoro-[2,4'-bipyridin]-5-ol 3hydrochloride

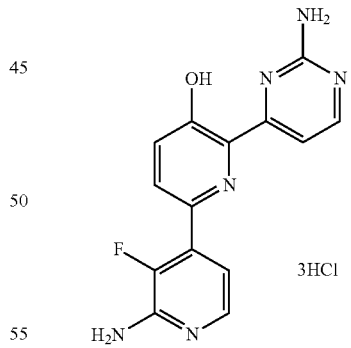

The title compound as a yellow solid (58 mg) was obtained by reacting the compound obtained in Example 8 with hydrochloric acid.

$^1$H NMR (600 MHz, DMSO) δ 14.10 (s, 1H), 8.55 (d, J=7.8 Hz, 1H), 8.03 (d, J=12.6 Hz, 1H), 7.88 (d, J=9.6 Hz, 1H), 7.61 (m, 2H), 7.46 (m, 3H).

Example 67: Preparation of 2'-amino-6-(2-aminopyrimidin-4-yl)-3'-fluoro-[2,4'-bipyridin]-5-ol acetate

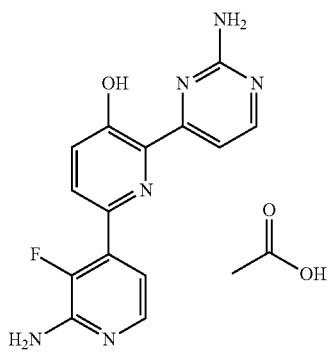

The title compound as a yellow solid (12.5 mg) was obtained by reacting the compound obtained in Example 8 with acetic acid.

$^1$H NMR (600 MHz, DMSO) δ 14.11 (s, 1H), 8.53 (d, J=7.8 Hz, 1H), 8.01 (d, J=12.6 Hz, 1H), 7.88 (d, J=9.6 Hz, 1H), 7.60 (m, 2H), 7.45 (m, 3H), 2.12 (s, 3H).

Example 68: Preparation of 2'-amino-6-(2-aminopyrimidin-4-yl)-3'-fluoro-[2,4'-bipyridin]-5-ol oxalate

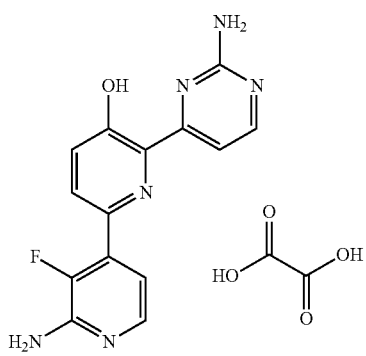 [SMILES: Nc1nccc(-c2nc(-c3ccnc(N)c3F)ccc2O)n1 ; O=C(O)C(=O)O]

The title compound as a yellow solid (12.4 mg) was obtained by reacting the compound obtained in Example 8 with oxalic acid.

$^1$H NMR (600 MHz, DMSO) δ 14.10 (s, 1H), 8.53 (d, J=7.8 Hz, 1H), 8.01 (d, J=12.6 Hz, 1H), 7.88 (d, J=9.6 Hz, 1H), 7.59 (m, 2H), 7.45 (m, 3H).

Example 69: Preparation of 2'-amino-6-(2-aminopyrimidin-4-yl)-3'-fluoro-[2,4'-bipyridin]-5-ol 2malonate

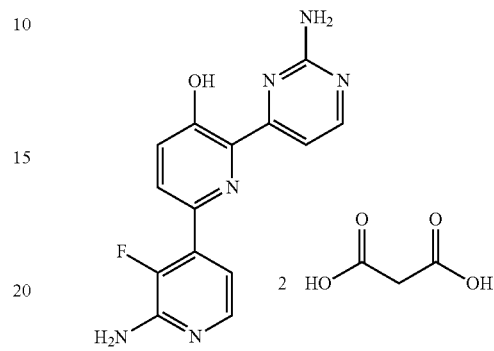

The title compound as a yellow solid (9.1 mg) was obtained by reacting the compound obtained in Example 8 with malonic acid.

$^1$H NMR (600 MHz, DMSO) δ 14.11 (s, 1H), 8.53 (d, J=7.8 Hz, 1H), 8.01 (d, J=12.6 Hz, 1H), 7.88 (d, J=9.6 Hz, 1H), 7.60 (m, 2H), 7.45 (m, 3H), 3.12 (s, 3H).

Example 70: Preparation of 2-(2-aminopyrimidin-4-yl)-6-(2-fluoro-4-hydroxyphenyl)pyridin-3-ol 2hydrochloride

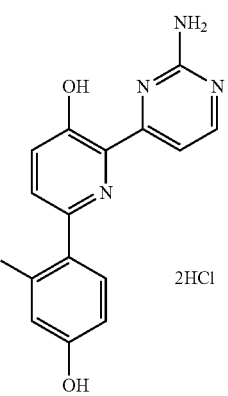

The title compound as a yellow solid (10.1 mg) was obtained by reacting the compound obtained in Example 17 with hydrochloric acid.

$^1$H NMR (600 MHz, DMSO) δ 10.18 (s, 1H), 8.05 (s, 1H), 7.89 (m, 1H), 7.77 (m, 1H), 7.68 (m, 1H), 7.46 (m, 1H), 6.77 (d, J=7.8 Hz, 1H), 6.67 (d, J=13.2 Hz, 1H).

Example 71: Preparation of 2'-amino-6-(2-amino-6-methylpyrimidin-4-yl)-3'-fluoro-[2,4'-bipyridin]-5-ol 3hydrochloride

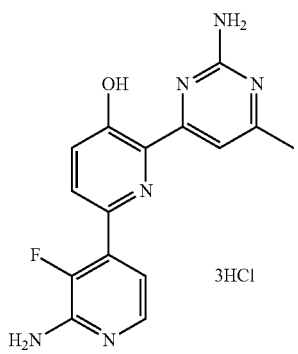 [SMILES: Cc1cc(-c2nc(-c3ccnc(N)c3F)ccc2O)nc(N)n1]

The title compound as a yellow solid (10.1 mg) was obtained by reacting the compound obtained in Example 24 with hydrochloric acid.

$^1$H NMR (400 MHz, DMSO-d$_6$) δ 7.84 (d, J=9.0 Hz, 1H), 7.82 (d, J=5.4 Hz, 1H), 7.48 (m, 2H), 7.20 (br, 2H), 7.13 (t, 1H), 6.28 (br, 2H), 2.38 (s, 3H).

Example 72: Preparation of 2'-amino-6-(2-amino-6-morpholinopyrimidin-4-yl)-3'-fluoro-[2,4'-bipyridin]-5-ol 4hydrochloride

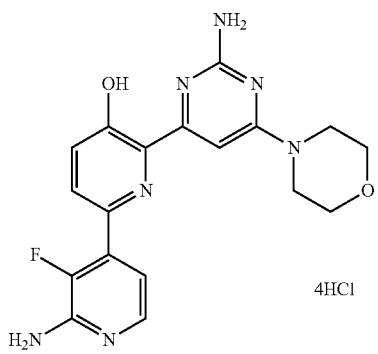 [SMILES: Nc1nc(-c2nc(-c3ccnc(N)c3F)ccc2O)cc(N2CCOCC2)n1]

The title compound as a yellow solid (203 mg) was obtained by reacting the compound obtained in Example 51 with hydrochloric acid.

$^1$H NMR (600 MHz, MeOD-d$_4$) δ 8.17 (dd, J=1.8, 8.4 Hz, 1H), 7.82 (d, J=7.2 Hz, 1H), 7.77 (t, J=7.2 Hz, 1H), 7.70 (d, J=9.0 Hz, 1H), 7.65 (s, 1H), 4.06 (m, 2H), 3.82-3.76 (m, 6H).

Example 73: Preparation of 2'-amino-6-(2-amino-6-morpholinopyrimidin-4-yl)-3'-fluoro-[2,4'-bipyridin]-5-ol acetate

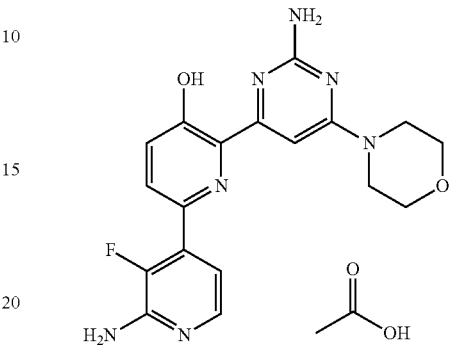

The title compound as a yellow solid (203 mg) was obtained by reacting the compound obtained in Example 51 with acetic acid.

$^1$H NMR (600 MHz, MeOD-d$_4$) δ 7.84 (dd, J=2.4, 8.4 Hz, 1H), 7.78 (d, J=5.4 Hz, 1H), 7.34 (d, J=8.4 Hz, 1H), 7.26 (t, J=5.4 Hz, 1H), 7.23 (s, 1H), 3.78-3.72 (m, 8H), 1.99 (s, 3H).

Example 74: Preparation of 2'-amino-6-(2-amino-6-(dimethylamino)pyrimidin-4-yl)-3'-fluoro-[2,4'-bipyridin]-5-ol 4hydrochloride

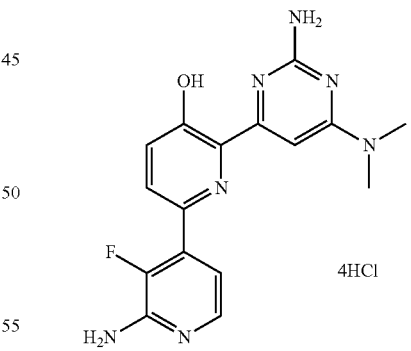

The title compound as a yellow solid (242 mg) was obtained by reacting the compound obtained in Example 52 with hydrochloric acid.

$^1$H NMR (600 MHz, DMSO-d$_6$) δ 8.04 (d, J=5.4 Hz, 1H), 7.95 (d, J=7.2 Hz, 1H), 7.40 (d, J=8.4 Hz, 1H), 7.12 (t, J=5.4 Hz, 1H), 6.94 (s, 1H), 6.72 (br, 2H), 6.25 (br, 2H), 3.41 (s, 6H).

Example 75: Preparation of 2'-amino-6-(2-amino-6-(4-methylpiperazin-1-yl)pyrimidin-4-yl)-3'-fluoro-[2,4'-bipyridin]-5-ol 5hydrochloride

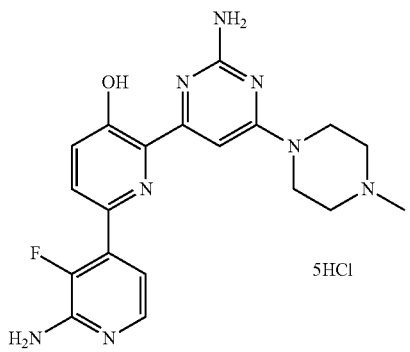 [SMILES: CN1CCN(c2cc(-c3nc(-c4ccnc(N)c4F)ccc3O)nc(N)n2)CC1]

The title compound as a yellow solid (48 mg) was obtained by reacting the compound obtained in Example 53 with hydrochloric acid.
$^1$H NMR (600 MHz, DMSO-$d_6$) δ 8.04 (d, J=7.8 Hz, 1H), 7.87 (d, J=6.0 Hz, 1H), 7.73 (m, 1H), 7.63 (m, 1H), 7.34 (s, 1H), 3.72 (m, 4H), 3.56 (m, 2H), 3.13 (m, 2H), 2.81 (s, 3H).

Example 76: Preparation of 2'-amino-6-(2-amino-6-(4-methylpiperazin-1-yl)pyrimidin-4-yl)-3'-fluoro-[2,4'-bipyridin]-5-ol acetate

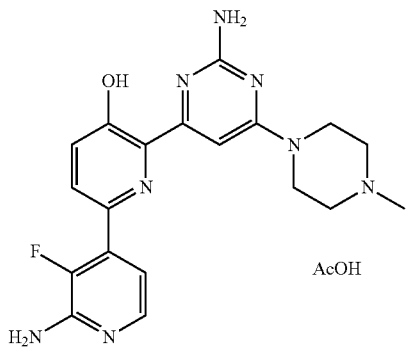 [SMILES: "AcOH" ; CN1CCN(c2cc(-c3nc(-c4ccnc(N)c4F)ccc3O)nc(N)n2)CC1]

The title compound as a yellow solid (32 mg) was obtained by reacting the compound obtained in Example 53 with acetic acid.
$^1$H NMR (600 MHz, MeOD-$d_4$) δ 7.94 (d, J=8.4 Hz, 1H), 7.85 (d, J=5.4 Hz, 1H), 7.58 (m, 1H), 7.37 (m, 1H), 7.22 (s, 1H), 3.53-3.37 (m, 6H), 3.18 (m, 2H), 2.81 (s, 3H).

Example 77: Preparation of 2'-amino-6-(2-amino-(6-(1-methylpiperidin-4-yl)pyrimidin-4-yl)-3'-fluoro-[2,4'-bipyridin]-5-ol 4hydrochloride

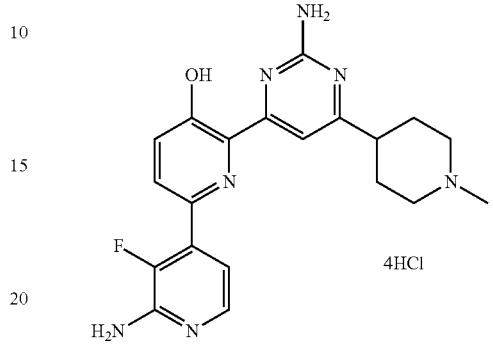

The title compound as a yellow solid (32 mg) was obtained by reacting the compound obtained in Example 34 with hydrochloric acid.
$^1$H NMR (600 MHz, DMSO-$d_6$) δ 8.04 (d, J=8.4 Hz, 1H), 7.64 (d, J=8.4 Hz, 1H), 7.22 (br, 2H), 6.13 (s, 2H), 3.89 (s, 3H), 3.14 (m, 2H), 2.64 (m, 2H), 2.81 (s, 3H), 2.43 (s, 1H), 1.84 (m, 2H), 1.40 (m, 2H).

Example 78: Preparation of 2'-amino-6-(2-amino-6-(1-methylpiperidin-4-yl)pyrimidin-4-yl)-3'-fluoro-[2,4'-bipyridin]-5-ol 2acetate

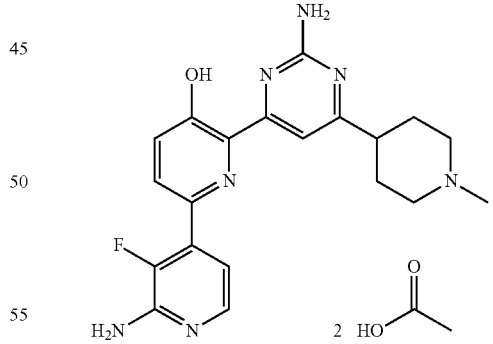

The title compound as a yellow solid (31 mg) was obtained by reacting the compound obtained in Example 34 with acetic acid.
$^1$H NMR (600 MHz, DMSO-$d_6$) δ 8.05 (d, J=9.4 Hz, 1H), 7.64 (d, J=9.0 Hz, 1H), 7.22 (br, 2H), 6.22 (s, 2H), 3.89 (s, 3H), 3.14 (m, 2H), 2.64 (m, 2H), 2.49 (s, 3H), 2.43 (s, 1H), 1.98 (s, 2H), 1.85 (m, 2H), 1.49 (m, 2H).

Example 79: Preparation of 2'-amino-6-(2-amino-6-(1-methylpiperidin-4-yl)pyrimidin-4-yl)-3'-fluoro-[2,4'-bipyridin]-5-ol oxalate

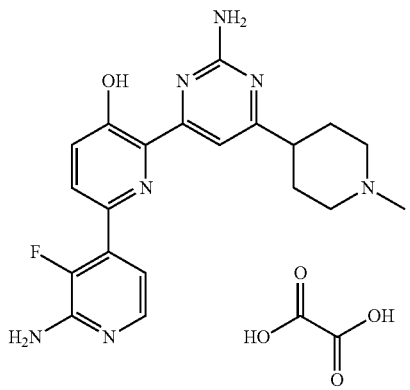 [SMILES: CN1CCC(c2cc(-c3nc(-c4ccnc(N)c4F)ccc3O)nc(N)n2)CC1 ; O=C(O)C(=O)O]

The title compound as a yellow solid (21 mg) was obtained by reacting the compound obtained in Example 34 with oxalic acid.

$^1$H NMR (600 MHz, DMSO-d$_6$) δ 8.05 (d, J=9.0 Hz, 1H), 7.64 (d, J=8.4 Hz, 1H), 7.22 (br, 2H), 6.13 (s, 2H), 3.89 (s, 3H), 3.14 (m, 2H), 2.64 (m, 2H), 2.49 (s, 3H), 2.43 (s, 1H), 1.85 (m, 2H), 1.50 (m, 2H).

Example 80: Preparation of 2'-amino-6-(2-amino-6-(1-methylpiperidin-4-yl)pyrimidin-4-yl)-3'-fluoro-[2,4'-bipyridin]-5-ol malonate

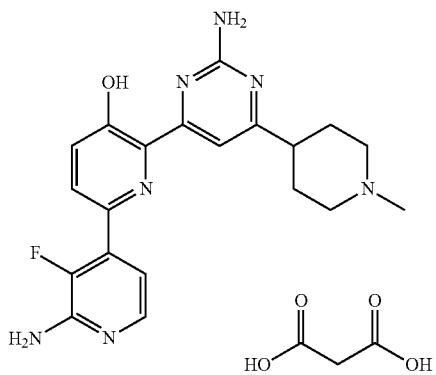 [SMILES: CN1CCC(c2cc(-c3nc(-c4ccnc(N)c4F)ccc3O)nc(N)n2)CC1 ; O=C(O)CC(=O)O]

The title compound as a yellow solid (19 mg) was obtained by reacting the compound obtained in Example 34 with malonic acid.

$^1$H NMR (600 MHz, DMSO-d$_6$) δ 8.05 (d, J=9.0 Hz, 1H), 7.64 (d, J=8.4 Hz, 1H), 7.22 (br, 2H), 6.13 (s, 2H), 4.02 (s, 2H), 3.89 (s, 3H), 3.14 (m, 2H), 2.64 (m, 2H), 2.49 (s, 3H), 2.43 (s, 1H), 1.85 (m, 2H), 1.53 (m, 2H).

Example 81: Preparation of 2'-amino-6-(2-amino-6-isopropylpyrimidin-4-yl)-3'-fluoro-[2,4'-bipyridin]-5-ol 3hydrochloride

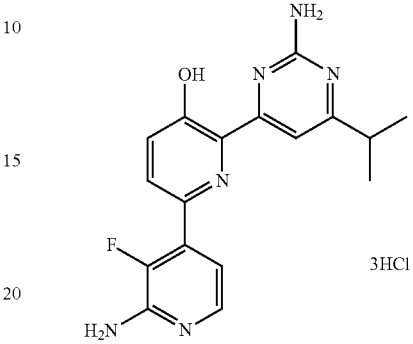

The title compound as a yellow solid (45 mg) was obtained by reacting the compound obtained in Example 31 with hydrochloric acid.

$^1$H NMR (400 MHz, DMSO-d$_6$) δ 14.13 (s, 1H), 8.02 (d, J=7.8 Hz, 1H), 7.92 (d, J=6.0 Hz, 1H), 7.56 (s, 1H), 7.48 (d, J=8.4 Hz, 1H), 7.18 (s, 2H), 7.12 (t, 1H), 6.25 (s, 1H), 2.15 (m, 1H), 0.97 (d, J=8.4 Hz, 6H).

Example 82: Preparation of 2'-amino-6-(2-amino-6-isopropylpyrimidin-4-yl)-3'-fluoro-[2,4'-bipyridin]-5-ol 2acetate

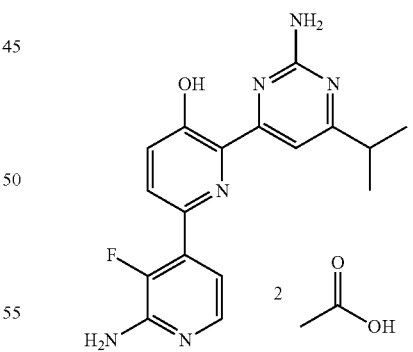

The title compound as a yellow solid (28.3 mg) was obtained by reacting the compound obtained in Example 31 with acetic acid.

$^1$H NMR (400 MHz, DMSO-d$_6$) δ 14.13 (s, 1H), 8.21 (d, J=8.6 Hz, 1H), 7.99 (d, J=6.0 Hz, 1H), 7.54 (s, 1H), 7.52 (d, J=8.4 Hz, 1H), 7.48 (s, 2H), 7.32 (t, 1H), 6.25 (s, 1H), 2.15 (m, 1H), 1.28 (d, J=8.0 Hz, 6H).

Example 83: Preparation of 2'-amino-6-(2-amino-6-(piperidin-4-yl)pyrimidin-4-yl)-3'-fluoro-[2,4'-bipyridin]-5-ol 4hydrochloride

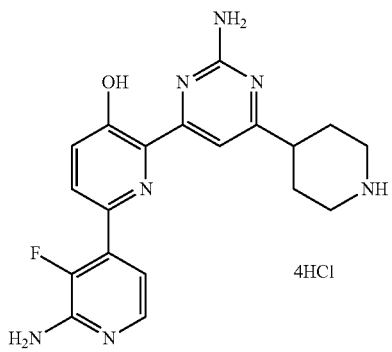 [SMILES: Nc1nc(-c2nc(-c3ccnc(N)c3F)ccc2O)cc(C2CCNCC2)n1]

The title compound as a yellow solid (12.5 mg) was obtained by reacting the compound obtained in Example 33 with hydrochloric acid.

$^1$H NMR (600 MHz, DMSO-d$_6$) δ 7.80 (m, 2H), 8.00 (d, J=9.0 Hz, 1H), 7.54 (t, J=5.4 Hz, 1H), 7.32 (s, 1H), 6.99 (br, 2H), 6.25 (br, 2H), 3.89 (s, 3H), 3.14 (m, 2H), 2.64 (m, 2H), 2.43 (s, 1H), 1.85 (m, 2H), 1.51 (m, 2H).

Example 84: Preparation of 2'-amino-6-(2-amino-6-(piperidin-4-yl)pyrimidin-4-yl)-3'-fluoro-[2,4'-bipyridin]-5-ol acetate

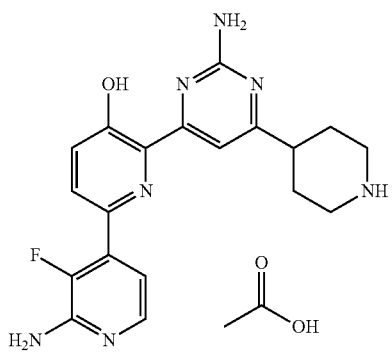

The title compound as a yellow solid (9.8 mg) was obtained by reacting the compound obtained in Example 33 with acetic acid.

$^1$H NMR (600 MHz, DMSO-d$_6$) δ 8.02 (m, 2H), 7.59 (d, J=8.4 Hz, 1H), 7.52 (t, J=5.4 Hz, 1H), 7.18 (s, 1H), 6.82 (br, 2H), 6.25 (br, 2H), 3.89 (s, 3H), 3.14 (m, 2H), 2.64 (m, 2H), 2.43 (s, 1H), 1.85 (m, 2H), 1.22 (m, 2H).

Example 85: Preparation of 2'-amino-6-(2-amino-6-(tetrahydro-2H-pyran-4-yl)pyrimidin-4-yl)-3'-fluoro-[2,4'-bipyridin]-5-ol 3hydrochloride

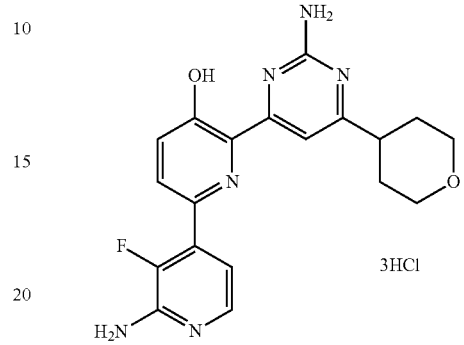

The title compound as a yellow solid (8.2 mg) was obtained by reacting the compound obtained in Example 32 with hydrochloric acid.

$^1$H NMR (600 MHz, DMSO-d$_6$) δ 8.02 (m, 2H), 7.55 (d, J=8.4 Hz, 1H), 7.44 (t, J=5.4 Hz, 1H), 7.03 (s, 1H), 6.82 (s, 2H), 6.33 (sr, 2H), 3.70 (m, 4H), 3.65 (m, 4H).

Example 86: Preparation of 2'-amino-6-(2-amino-6-(1-ethylpiperidin-4-yl)pyrimidin-4-yl)-3'-fluoro-[2,4'-bipyridin]-5-ol 4hydrochloride

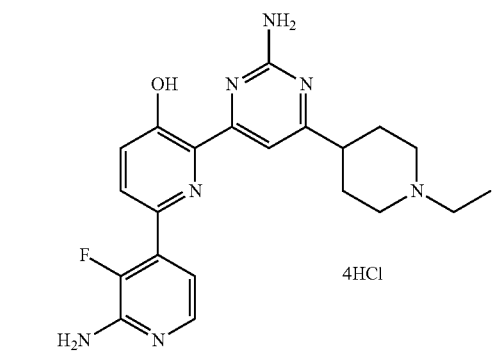 [SMILES: CCN1CCC(c2cc(-c3nc(-c4ccnc(N)c4F)ccc3O)nc(N)n2)CC1]

The title compound as a yellow solid (18.6 mg) was obtained by reacting the compound obtained in Example 35 with hydrochloric acid.

$^1$H NMR (600 MHz, DMSO-d$_6$) δ 8.02 (d, J=8.4 Hz, 1H), 7.84 (d, J=8.4 Hz, 1H), 7.81 (br, 2H), 222 (s, 2H), 3.14 (m, 2H), 2.64 (m, 2H), 2.49 (m, 3H), 2.43 (m, 1H), 1.85 (m, 2H), 1.54 (m, 3H).

Example 87: Preparation of 2'-amino-6-(2-amino-6-(1-propylpiperidin-4-yl)pyrimidin-4-yl)-3'-fluoro-[2,4'-bipyridin]-5-ol 4hydrochloride

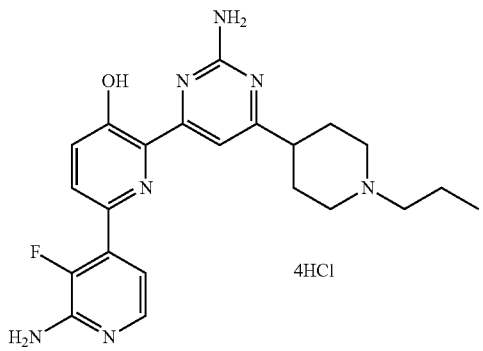 [SMILES: CCCN1CCC(c2cc(-c3nc(-c4ccnc(N)c4F)ccc3O)nc(N)n2)CC1]

The title compound as a yellow solid (11.8 mg) was obtained by reacting the compound obtained in Example 36 with hydrochloric acid.
$^1$H NMR (600 MHz, DMSO-d$_6$) δ 8.01 (d, J=8.4 Hz, 1H), 7.65 (d, J=8.4 Hz, 1H), 7.51 (br, 2H), 7.13 (s, 2H), 3.14 (m, 2H), 2.64 (m, 2H), 2.51 (m, 2H), 2.49 (s, 3H), 2.43 (m, 1H), 1.85 (m, 2H), 1.23 (m, 3H).

Example 88: Preparation of 2'-amino-6-(2-amino-6-(1-isopropylpiperidin-4-yl)pyrimidin-4-yl)-3'-fluoro-[2,4'-bipyridin]-5-ol 4hydrochloride

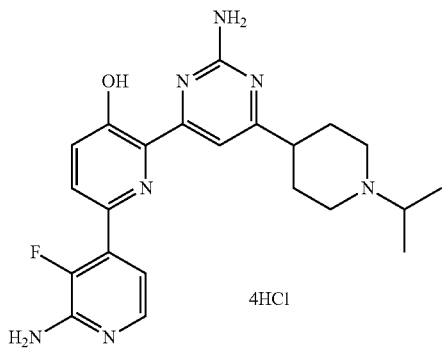 [SMILES: CC(C)N1CCC(c2cc(-c3nc(-c4ccnc(N)c4F)ccc3O)nc(N)n2)CC1]

The title compound as a yellow solid (11.4 mg) was obtained by reacting the compound obtained in Example 37 with hydrochloric acid.
$^1$H NMR (600 MHz, DMSO-d$_6$) δ 8.01 (d, J=8.4 Hz, 1H), 7.63 (d, J=8.4 Hz, 1H), 7.54 (br, 2H), 7.13 (s, 2H), 3.14 (m, 2H), 2.64 (m, 2H), 2.49 (s, 3H), 2.43 (m, 1H), 1.85 (m, 2H), 1.50 (m, 6H).

Example 89: Preparation of 2'-amino-6-(2-amino-6-(1-methylpiperidin-3-yl)pyrimidin-4-yl)-3'-fluoro-[2,4'-bipyridin]-5-ol 4hydrochloride

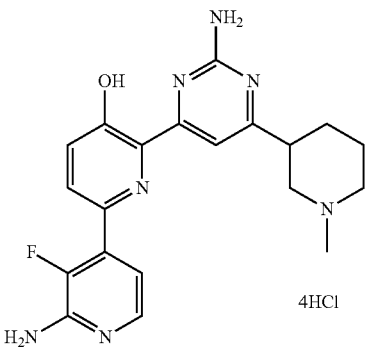 [SMILES: CN1CCCC(c2cc(-c3nc(-c4ccnc(N)c4F)ccc3O)nc(N)n2)C1]

The title compound as a yellow solid (9.8 mg) was obtained by reacting the compound obtained in Example 38 with hydrochloric acid.
$^1$H NMR (600 MHz, DMSO-d$_6$) δ 8.04 (d, J=8.4 Hz, 1H), 7.64 (d, J=9.0 Hz, 1H), 7.55 (br, 2H), 7.13 (br, 2H), 3.14 (m, 2H), 2.64 (m, 2H), 2.49 (s, 3H), 2.43 (s, 1H), 1.85 (m, 2H), 1.50 (m, 2H).

Example 90: Preparation of 2'-amino-6-(2-amino-6-(1-ethylpiperidin-3-yl)pyrimidin-4-yl)-3'-fluoro-[2,4'-bipyridin]-5-ol 4hydrochloride

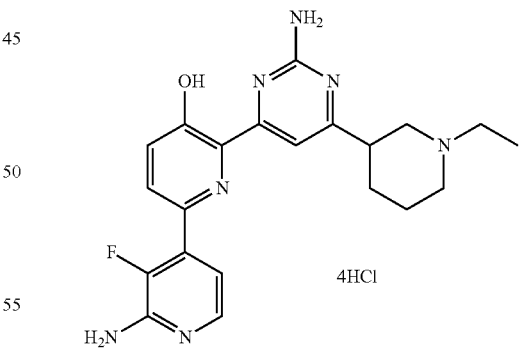

The title compound as a yellow solid (9.2 mg) was obtained by reacting the compound obtained in Example 39 with hydrochloric acid.
$^1$H NMR (600 MHz, DMSO-d$_6$) δ 8.02 (d, J=9.0 Hz, 1H), 7.64 (d, J=9.0 Hz, 1H), 7.32 (br, 2H), 7.13 (s, 2H), 3.14 (m, 2H), 2.64 (m, 2H), 2.43 (m, 1H), 1.85 (m, 2H), 1.50 (m, 2H), 1.21 (t, 3H).

Example 91: Preparation of 2'-amino-6-(2-amino-6-(1-propylpiperidin-3-yl)pyrimidin-4-yl)-3'-fluoro-[2,4'-bipyridin]-5-ol 4hydrochloride

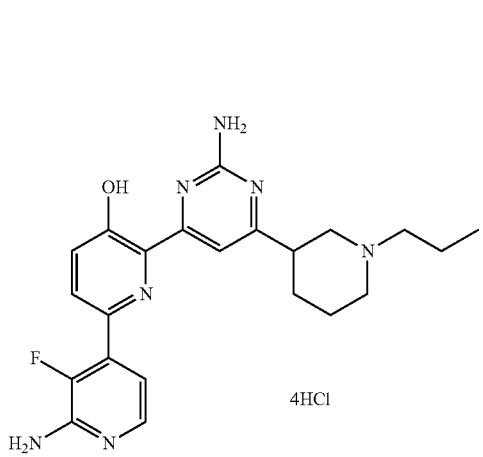 [SMILES: CCCN1CCCC(c2cc(-c3nc(-c4ccnc(N)c4F)ccc3O)nc(N)n2)C1]

The title compound as a yellow solid (18.6 mg) was obtained by reacting the compound obtained in Example 40 with hydrochloric acid.
$^1$H NMR (600 MHz, DMSO-d$_6$) δ 8.03 (d, J=9.04 Hz, 1H), 7.64 (d, J=9.0 Hz, 1H), 7.52 (br, 2H), 7.13 (s, 2H), 3.14 (m, 2H), 2.64 (m, 2H), 2.43 (m, 1H), 1.85 (m, 4H), 1.50 (m, 4H), 1.20 (t, 3H).

Example 92: Preparation of 2'-amino-6-(2-amino-6-(1-isopropylpiperidin-3-yl)pyrimidin-4-yl)-3'-fluoro [2,4'-bipyridin]-5-ol 4hydrochloride

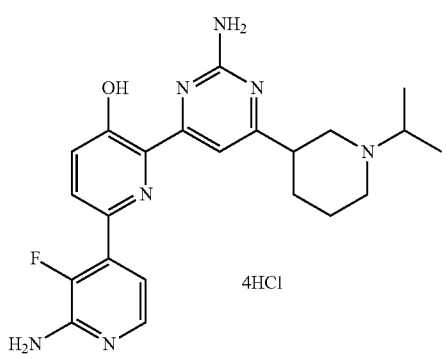 [SMILES: CC(C)N1CCCC(c2cc(-c3nc(-c4ccnc(N)c4F)ccc3O)nc(N)n2)C1]

The title compound as a yellow solid (25.1 mg) was obtained by reacting the compound obtained in Example 41 with hydrochloric acid.
$^1$H NMR (600 MHz, DMSO-d$_6$) δ 8.03 (d, J=9.0 Hz, 1H), 7.64 (d, J=9.0 Hz, 1H), 7.62 (m, 2H), 7.13 (s, 2H), 3.14 (m, 2H), 2.42 (s, 1H), 1.85 (m, 4H), 1.50 (m, 4H), 1.20 (m, 9H).

Example 93: Preparation of 2'-amino-6-(2-amino-5-methyl-6-(1-methylpiperidin-4-yl)pyrimidin-4-yl)-3'-fluoro-[2,4'-bipyridin]-5-ol 4hydrochloride

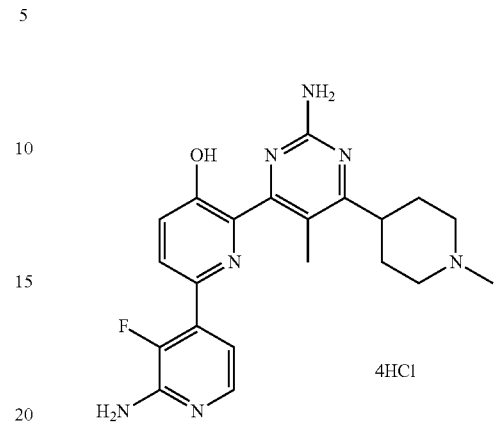

The title compound as a yellow solid (28.9 mg) was obtained by reacting the compound obtained in Example 42 with hydrochloric acid.
$^1$H NMR (400 MHz, DMSO-d$_6$) δ 14.00 (s, 1H), 8.04 (d, J=7.8 Hz, 1H), 7.85 (d, J=6.4 Hz, 1H), 7.67 (s, 1H), 754 (d, J=8.4 Hz, 1H), 7.33 (s, 2H), 7.30 (t, 1H), 6.25 (s, 1H), 3.10 (m, 2H), 2.48 (s, 3H), 2.36 (s, 3H), 2.35 (m, 3H), 2.06 (m, 2H), 1.84 (m, 2H).

Example 94: Preparation of 2'-amino-6-(2-amino-6-(1-ethylpiperidin-4-yl)-5-methylpyrimidin-4-yl)-3'-fluoro-[2,4'-bipyridin]-5-ol 4hydrochloride

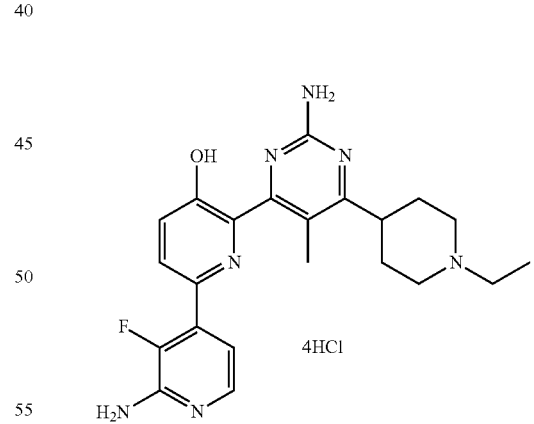

The title compound as a yellow solid (42.1 mg) was obtained by reacting the compound obtained in Example 43 with hydrochloric acid.
$^1$H NMR (400 MHz, DMSO-d$_6$) δ 8.02 (d, J=7.8 Hz, 1H), 7.80 (d, J=6.0 Hz, 1H), 7.77 (s, 1H), 7.45 (d, J=8.4 Hz, 1H), 7.32 (s, 2H), 7.12 (t, 1H), 6.25 (s, 2H), 3.10 (m, 2H), 3.03 (m, 2H), 2.36 (s, 3H), 2.35 (m, 3H), 2.06 (m, 2H), 1.91 (m, 2H), 1.24 (t, 3H).

Example 95: Preparation of 2'-amino-6-(2-amino-5-methyl-6-(1-propylpiperidin-4-yl)pyrimidin-4-yl)-3'-fluoro-[2,4'-bipyridin]-5-ol 4hydrochloride

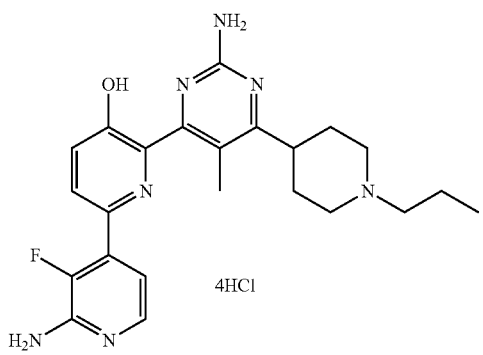 [SMILES: CCCN1CCC(c2nc(N)nc(-c3nc(-c4ccnc(N)c4F)ccc3O)c2C)CC1]

The title compound as a yellow solid (45.9 mg) was obtained by reacting the compound obtained in Example 44 with hydrochloric acid.

$^1$H NMR (400 MHz, DMSO-$d_6$) δ 8.02 (d, J=6.4 Hz, 1H), 7.80 (d, J=6.4 Hz, 1H), 7.67 (s, 1H), 7.44 (d, J=8.6 Hz, 1H), 7.35 (s, 2H), 7.12 (t, 1H), 6.65 (s, 2H), 3.82 (m, 2H), 3.10 (m, 2H), 3.03 (m, 2H), 2.36 (s, 3H), 2.35 (m, 3H), 2.06 (m, 2H), 1.91 (m, 2H), 1.45 (t, 3H).

Example 96: Preparation of 2'-amino-6-(2-amino-6-(1-isopropylpiperidin-4-yl)-5-methylpyrimidin-4-yl)-3'-fluoro-[2,4'-bipyridin]-5-ol 4hydrochloride

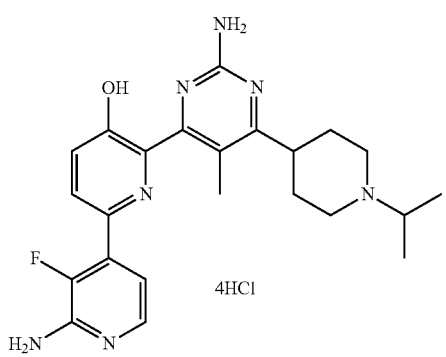 [SMILES: Cc1c(-c2nc(-c3ccnc(N)c3F)ccc2O)nc(N)nc1C1CCN(C(C)C)CC1]

The title compound as a yellow solid (84.3 mg) was obtained by reacting the compound obtained in Example 45 with hydrochloric acid.

$^1$H NMR (400 MHz, DMSO-$d_6$) 8.04 (d, J=6.4 Hz, 1H), 7.54 (d, J=6.4 Hz, 1H), 7.52 (s, 1H), 7.46 (d, J=8.0 Hz, 1H), 7.38 (s, 2H), 7.18 (t, 1H), 6.35 (s, 2H), 3.10 (m, 2H), 2.54 (m, 1H), 2.36 (s, 3H), 2.35 (m, 3H), 2.06 (m, 2H), 1.91 (m, 2H), 1.15 (d, 6H).

Example 97: Preparation of 2'-amino-6-(2-amino-5-methyl-6-(1-methylpiperidin-3-yl)pyrimidin-3-yl)-3'-fluoro-[2,4'-bipyridin]-5-ol 4hydrochloride

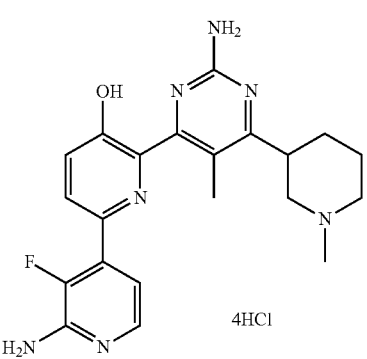 [SMILES: Cc1c(-c2nc(-c3ccnc(N)c3F)ccc2O)nc(N)nc1C1CCCN(C)C1]

The title compound as a yellow solid (28.1 mg) was obtained by reacting the compound obtained in Example 46 with hydrochloric acid.

$^1$H NMR (400 MHz, DMSO-$d_6$) δ 8.03 (d, J=8.0 Hz, 1H), 7.81 (d, J=8.0 Hz, 1H), 7.56 (s, 1H), 7.51 (d, J=8.4 Hz, 1H), 7.18 (s, 2H), 7.13 (t, 1H), 7.01 (s, 1H), 3.24 (m, 2H), 3.10 (m, 2H), 2.53 (s, 3H), 2.48 (m, 3H), 2.35 (s, 3H), 2.06 (m, 2H), 1.23 (m, 2H).

Example 98: Preparation of 2'-amino-6-(2-amino-5-methyl-6-(1-propylpiperidin-3-yl)pyrimidin-4-yl)-3'-fluoro-[2,4'-bipyridin]-5-ol 4hydrochloride

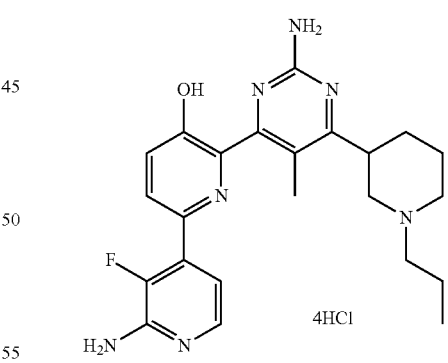

The title compound as a yellow solid (33.6 mg) was obtained by reacting the compound obtained in Example 47 with hydrochloric acid.

$^1$H NMR (400 MHz, DMSO-$d_6$) δ 8.03 (d, J=8.4 Hz, 1H), 7.80 (d, J=8.4 Hz, 1H), 7.47 (s, 1H), 7.45 (d, J=8.4 Hz, 1H), 7.18 (s, 2H), 7.13 (t, 1H), 7.01 (s, 1H), 3.23 (m, 2H), 2.35 (m, 2H), 3.10 (m, 2H), 2.48 (m, 3H), 2.35 (m, 2H), 2.06 (m, 2H), 1.91 (m, 2H), 1.23 (t, 3H).

Example 99: Preparation of 2'-amino-6-(2-amino-6-(1-isopropylpiperidin-3-yl)-5-methylpyrimidin-4-yl)-3'-fluoro-[2,4'-bipyridin]-5-ol 4hydrochloride

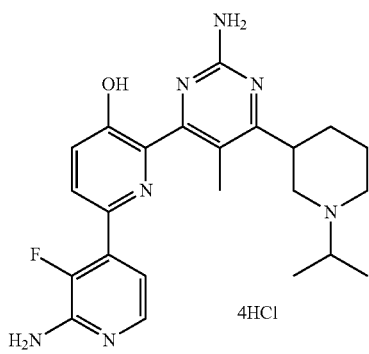 [SMILES: Cc1c(-c2nc(-c3ccnc(N)c3F)ccc2O)nc(N)nc1C1CCCN(C(C)C)C1]

The title compound as a yellow solid (21.4 mg) was obtained by reacting the compound obtained in Example 48 with hydrochloric acid.

$^1$H NMR (400 MHz, DMSO-d$_6$) δ 8.02 (d, J=9.0 Hz, 1H), 7.54 (d, J=9.0 Hz, 1H), 7.50 (s, 1H), 7.48 (d, J=8.4 Hz, 1H), 7.28 (s, 2H), 7.23 (t, 1H), 7.02 (s, 1H), 3.14 (m, 2H), 2.54 (m, 1H), 2.36 (s, 3H), 2.35 (m, 3H), 2.06 (m, 2H), 1.91 (m, 2H), 1.08 (d, 6H).

Example 100: Preparation of 2'-amino-6-(2-amino-5-methylpyrimidin-4-yl)-3'-fluoro-[2,4'-bipyridin]-5-ol 3hydrochloride

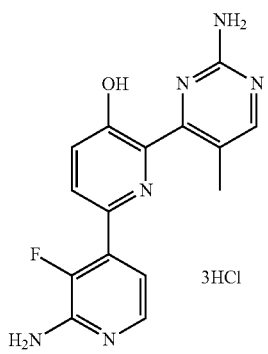 [SMILES: Cc1cnc(N)nc1-c1nc(-c2ccnc(N)c2F)ccc1O]

The title compound as a yellow solid (22.2 mg) was obtained by reacting the compound obtained in Example 55 with hydrochloric acid.

$^1$H NMR (600 MHz, DMSO-d$_6$) δ 8.02 (s, 1H), 8.01 (d, J=9.0 Hz, 1H), 7.78 (d, J=9.0 Hz, 1H), 7.49 (d, J=9.0 Hz, 1H), 7.41 (t, 1H), 2.45 (s, 3H).

Example 101: Preparation of 2'-amino-6-(2-amino-5,6-dimethylpyrimidin-4-yl)-3'-fluoro-[2,4'-bipyridin]-5-ol 3hydrochloride

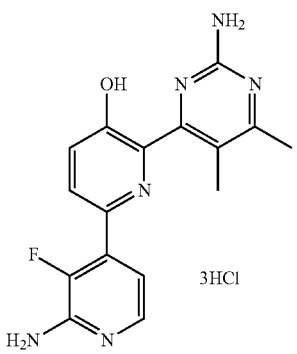 [SMILES: Cc1nc(N)nc(-c2nc(-c3ccnc(N)c3F)ccc2O)c1C]

The title compound as a yellow solid (18.7 mg) was obtained by reacting the compound obtained in Example 60 with hydrochloric acid.

$^1$H NMR (600 MHz, DMSO-d$_6$) δ 8.03 (d, J=9.0 Hz, 1H), 7.90 (d, J=8.4 Hz, 1H), 7.57 (m, 1H), 7.54 (m, 1H), 7.23 (s, 2H), 7.01 (s, 2H), 2.49 (s, 3H), 2.25 (s, 3H).

Example 102: Preparation of 2'-amino-6-(2-amino-5-ethylpyrimidin-4-yl)-3'-fluoro-[2,4'-bipyridin]-5-ol 3hydrochloride

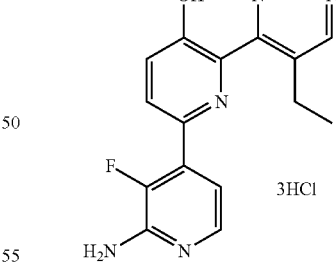

The title compound as a yellow solid (13.0 mg) was obtained by reacting the compound obtained in Example 56 with hydrochloric acid.

$^1$H NMR (600 MHz, DMSO-d$_6$) δ 10.0 (s, 1H), 8.01 (d, J=8.8 Hz, 1H), 7.84 (d, J=6.8 Hz, 1H), 7.61 (d, J=8.4 Hz, 1H), 7.24 (m, 1H), 3.43 (m, 2H), 3.14 (m, 2H), 2.21 (m, 1H), 1.94 (m, 2H), 0.92 (m, 3H).

Example 103: Preparation of 2'-amino-6-(2-amino-5-propylpyrimidin-4-yl)-3'-fluoro-[2,4'-bipyridin]-5-ol 3hydrochloride

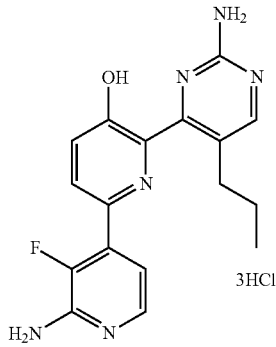 [SMILES: CCCc1cnc(N)nc1-c1nc(-c2ccnc(N)c2F)ccc1O]

The title compound as a yellow solid (28.4 mg) was obtained by reacting the compound obtained in Example 57 with hydrochloric acid.

$^1$H NMR (600 MHz, DMSO-d$_6$) δ 10.0 (s, 1H), 8.01 (d, J=8.8 Hz, 1H), 7.84 (d, J=6.8 Hz, 1H), 7.65 (d, J=8.4 Hz, 1H), 7.26 (m, 1H), 3.44 (m, 2H), 3.14 (m, 2H), 2.21 (m, 3H), 1.94 (m, 2H), 0.92 (m, 3H).

Example 104: Preparation of 2'-amino-6-(2-amino-5-isopropylpyrimidin-5-yl)-3'-fluoro-[2,4'-bipyridin]-5-ol 3hydrochloride

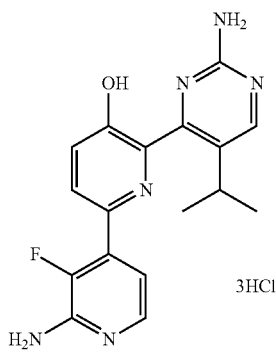 [SMILES: CC(C)c1cnc(N)nc1-c1nc(-c2ccnc(N)c2F)ccc1O]

The title compound as a yellow solid (22.2 mg) was obtained by reacting the compound obtained in Example 58 with hydrochloric acid.

$^1$H NMR (600 MHz, DMSO-d$_6$) δ 8.62 (s, 1H), 8.04 (d, J=9.2 Hz, 1H), 8.87 (d, J=6.0 Hz, 1H), 7.69 (d, J=8.4 Hz, 1H), 7.27 (m, 1H), 2.92 (m, 1H), 1.14 (d, J=6.4 Hz, 6H).

Example 105: Preparation of 2'-amino-6-(2-amino-5-ethyl-6-(1-isopropylpyrimidin-4-yl)pyrimidin-4-yl)-3'-fluoro-[2,4'-bipyridin]-5-ol 4hydrochloride

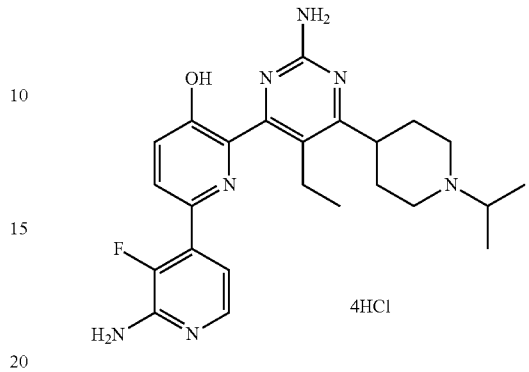

The title compound as a yellow solid (65.3 mg) was obtained by reacting the compound obtained in Example 49 with hydrochloric acid.

$^1$H NMR (600 MHz, DMSO-d$_6$) δ 9.98 (s, 1H), 8.01 (d, J=8.8 Hz, 1H), 7.85 (d, J=6.8 Hz, 1H), 7.67 (d, J=8.4 Hz, 1H), 7.26 (m, 1H), 3.43 (m, 2H), 3.27 (m, 2H), 3.15 (m, 4H), 2.27 (m, 3H), 1.92 (m, 2H), 1.34 (d, J=6.4 Hz, 6H), 0.71 (m, 3H).

Example 106: Preparation of 2'-amino-6-(2-amino-6-(1-isopropylpiperidin-4-yl)-5-propylpyrimidin-4-yl)-3'-fluoro-[2,4'-bipyridin]-5-ol 4hydrochloride

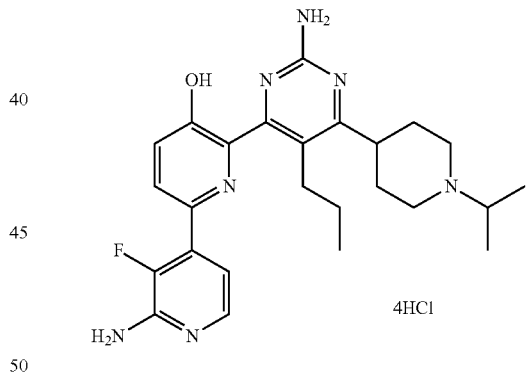

The title compound as a yellow solid (18.8 mg) was obtained by reacting the compound obtained in Example 50 with hydrochloric acid.

$^1$H NMR (600 MHz, DMSO-d$_6$) δ 10.0 (s, 1H), 8.01 (d, J=8.8 Hz, 1H), 7.85 (d, J=6.8 Hz, 1H), 7.66 (d, J=8.4 Hz, 1H), 7.26 (m, 1H), 3.44 (m, 2H), 3.28 (m, 2H), 3.14 (m, 4H), 2.21 (m, 3H), 1.93 (m, 2H), 1.34 (d, J=6.4 Hz, 6H), 0.95 (m, 3H).

Experimental Example 1: Analysis for Inhibition of CDK Enzyme Activity

The following experiment was conducted to confirm whether the compounds according to the present invention inhibit the activities of CDK1, CDK2, CDK4, CDK5, and CDK6 which are isotypes of a CDK.

Test compounds were prepared by dissolving the compounds obtained in the above Examples in dimethylsulfoxide (DMSO) at a concentration of 10 mM. The test compounds were diluted to 200 nM, 50 nM, 1.5 nM, 3.13 nM, 0.78 nM, and 0.2 nM and used in an enzyme reaction.

CDK enzyme reaction was conducted in a buffer containing 50 mM Tris-HCl (pH 7.5), 10 mM $MgCl_2$, 1 mM EGTA, 1 mM EDTA, and 2 mM DTT. CDK1/cyclinB, CDK2/cylcinE, CDK5/p25, and CDK6/cyclinD3 enzymes commercially available from Merck Millipore were used for CDK1, CDK2, CDK5, and CDK6 enzymes, respectively, and CDK4/cyclinD1 enzyme commercially available from Signalchem (US) was used for CDK4. For CDK1, a reaction proceeded by adding 10 nM CDK1/cyclinB and 0.125 mg/ml histone H1 (Merck Millipore) substrate to the buffer and then adding 10 uM ATP thereto. For CDK2, a reaction was proceeded by adding 10 nM CDK2/cyclinE and 0.125 mg/ml histone H1 substrate to the buffer and then adding 10 uM ATP thereto. For CDK5, a reaction was proceeded by adding 10 nM CDK5/p25 and 0.125 mg/ml histone H1 substrate to the buffer and then adding 10 uM ATP thereto. For CDK4, a reaction was proceeded by adding 20 nM CDK4/cyclinD1 and 0.125 mg/ml Rb protein (Merck Millipore) to the buffer and then adding 10 uM ATP thereto. For CDK6, a reaction was proceeded by adding 50 nM CDK6/cyclinD3 and 0.125 mg/ml histone H1 substrate to the buffer and then adding 10 uM ATP thereto. Each enzyme reaction was incubated at 30° C. for 60 min. Then, the amount of ADP produced was measured using Victor X4 instrument (Perkin Elmer) after generating luminescence using ADP-Glo kinase assay kit (Promega, US). An inhibition effect on each enzyme was represented as a percentage of the luminescence value in the presence of the test compounds relative to the luminescence value without the test compounds. $IC_{50}$ (nM) is the concentration of the compound to inhibit 50% of the enzyme activity. The results are shown in Table 1 below.

TABLE 1

| | $IC_{50}$ (nM) | | | | |
|---|---|---|---|---|---|
| | CDK1/cyclinB | CDK2/cyclinE | CDK4/cyclinD | CDK5/p25 | CDK6/cyclinD |
| Example 1 | 1.5 | 1.5 | 854.5 | 2.4 | >200 |
| Example 8 | 2.1 | 2.1 | 107.8 | 0.22 | 47 |
| Example 9 | 11.6 | 6.4 | 287.1 | 2.3 | 44.8 |
| Example 10 | 3.6 | 2.6 | 202.6 | 1.2 | >200 |
| Example 12 | 12.6 | 6.6 | >200 | 5.9 | 50.7 |
| Example 17 | 30.8 | 9.4 | >200 | 3.3 | 65.3 |
| Example 18 | 26.8 | 10.7 | >200 | 6.1 | 180.5 |
| Example 19 | 19.6 | 14.6 | >200 | 6.4 | 128.8 |
| Example 21 | 6.1 | 4.5 | 402.8 | 1.5 | 73.6 |
| Example 24 | 0.6 | 0.9 | 341.5 | 0.7 | 33.8 |
| Example 31 | 2.3 | 0.59 | 35.9 | 3.13 | 61.5 |
| Example 33 | 17.1 | 3.7 | 39.3 | 9.89 | 239.8 |
| Example 34 | 2.1 | 2.2 | 31.5 | 2.2 | 176.3 |
| Example 51 | 1.0 | 4.5 | 81.3 | 2.8 | 35.8 |
| Example 52 | 0.7 | 14.6 | 63.7 | 1.9 | 59.6 |
| Example 53 | 4.0 | 10.8 | >200 | 2.8 | 86.8 |
| Example 61 | 0.4 | 0.5 | | 0.9 | |
| Example 66 | 0.6 | 1.0 | | 0.3 | |
| Example 71 | 0.2 | 0.3 | 124.9 | 0.3 | 29.8 |
| Example 104 | 1.3 | 1.6 | 15.2 | 0.8 | 54.1 |

From Table 1 above, it is shown that the compounds according to the present invention effectively inhibit the activity of a CDK enzyme. Further, it is also shown that the inhibition activity of the compounds according to the present invention is more selective for CDK1, CDK2, and CDK5.

Experimental Example 2: Analysis for Inhibition of Cancer Cell Proliferation

The following experiment was conducted to confirm whether the compounds according to the present invention inhibit a cancer cell proliferation and thus exhibit anticancer effect.

A test was conducted to confirm whether the compounds obtained in the above Examples can inhibit proliferation of human colon carcinoma cell line HCT116, glioblastoma cell lines U-87MG and T98G, neuroblastoma cell lines SH-SY5Y and SK-N-SH, and lung cancer cell lines A549 and NCI-H23.

HCT116, U-87MG, SH-SY5Y, SK-N-SH and A549 cells were cultured in DMEM medium containing 10% FBS. T98G cells were cultured in MEM medium containing 10% FBS and NCI-H23 cells were cultured in RPMI1664 medium containing 10% FBS. In order to analyze an inhibition of proliferation, HCT116 cells were dispensed in 2000 cells/well into 96 well plate, and SH-SY5Y, SK-N-SH, U-87MG, T98G, A549, and NCI-H23 cells were dispensed in 3000 cells/well into 96 well plate. And then, the cells were cultured at 5% $CO_2$ and 37° C. for 16 hrs to allow the cells to attach to the wells. The compounds of the above Examples were added to each well at a concentration of 0.004, 0.013, 0.04, 0.12, 0.37, 1.1, 3.3, and 10 uM, and the culture volume was adjusted to 100 ul. A control group was treated with dimethylsulfoxide (DMSO) at the same concentration, 0.08%, as used to treat the test compounds. Afterwards, cells were cultured at 5% $CO_2$ and 37° C. for 72 hrs. And then, 10 ul of the solution of MTT (3-(4,5-dimethylthiazol-2-yl)-2,5-diphenyltetrazolium bromide) dissolved in PBS at 5 mg/ml was added to each well to identify viable cells and the cells were cultured for further 2 hrs. The culture solution was removed, 100 ul of DMSO was added to dissolve the formed formazan and then an absorbance was measured at 535 nm. Based on the absorbance of the control cells not treated with the compounds, the amounts of the viable cells according to the concentration of the compounds were calculated. $GI_{50}$ (growth inhibition 50) value which is the concentration of the compound to inhibit cancer cell proliferation by 50% was calculated using Graphpad Prism 5.0 program. The results are shown in Table 2 below.

TABLE 2

| | $GI_{50}$ (uM) | | | | | | |
|---|---|---|---|---|---|---|---|
| | HCT116 | SH-SY5Y | SK-N-SH | U-87 MG | T98G | A549 | NCI-H23 |
| Example 1 | 0.15 | 0.15 | 0.28 | 0.85 | | | |
| Example 3 | 1.15 | 0.88 | 1.43 | 2.64 | | | |
| Example 5 | 3.59 | | | | | | |
| Example 6 | 2.30 | | | | | | |
| Example 7 | 0.67 | | | | | | |
| Example 8 | 0.01 | 0.01 | 0.01 | 0.06 | 0.19 | | |
| Example 9 | 0.20 | 0.09 | 0.20 | 0.63 | | | |
| Example 10 | 0.26 | 0.11 | 0.24 | 0.38 | | | |
| Example 11 | 6.08 | | | | | | |
| Example 12 | 0.23 | 0.24 | 0.42 | 0.79 | 1.83 | | |
| Example 13 | 6.97 | 0.68 | 7.22 | 4.60 | | | |
| Example 14 | 0.59 | 0.54 | 1.04 | 3.41 | | | |
| Example 16 | 1.33 | 0.57 | 2.91 | 3.60 | | | |
| Example 17 | 0.61 | 0.29 | 0.84 | 1.70 | | | |
| Example 18 | 0.34 | 0.20 | 0.78 | 5.86 | | | |
| Example 19 | 0.46 | 0.12 | 0.21 | 0.44 | 2.61 | | |
| Example 20 | 0.52 | 0.19 | 0.39 | 1.18 | 4.31 | | |
| Example 21 | 0.14 | 0.11 | 0.31 | 0.89 | | | |

TABLE 2-continued

| | GI$_{50}$ (uM) | | | | | | |
|---|---|---|---|---|---|---|---|
| | HCT116 | SH-SY5Y | SK-N-SH | U-87 MG | T98G | A549 | NCI-H23 |
| Example 24 | 0.02 | | | | | | |
| Example 25 | 0.29 | | | | | | |
| Example 26 | 1.18 | | | | | | |
| Example 27 | 0.29 | | | | | | |
| Example 29 | 1.26 | | | | | | |
| Example 30 | 0.72 | | | | | | |
| Example 31 | 0.03 | | | | | 0.18 | 0.10 |
| Example 32 | 0.03 | | | 0.10 | 0.11 | 0.08 | 0.19 |
| Example 33 | 0.05 | | | 0.15 | 0.26 | 0.19 | 1.71 |
| Example 34 | 0.02 | | | 0.03 | 0.15 | 0.04 | 0.07 |
| Example 35 | 0.01 | | | 0.03 | 0.21 | 0.02 | 0.06 |
| Example 36 | 0.01 | | | 0.01 | 0.02 | 0.02 | 0.05 |
| Example 37 | 0.01 | | | 0.01 | 0.03 | 0.02 | 0.06 |
| Example 38 | 0.002 | | | 0.004 | 0.02 | 0.005 | 0.02 |
| Example 39 | 0.17 | | | 0.39 | 0.69 | 0.40 | 1.79 |
| Example 40 | 0.01 | | | 0.02 | 0.05 | 0.01 | 0.03 |
| Example 41 | 0.02 | | | 0.04 | 0.11 | 0.04 | 0.07 |
| Example 42 | 0.18 | | | 0.27 | 0.40 | 0.38 | 0.89 |
| Example 43 | 0.23 | | | 0.28 | 0.46 | 0.46 | 0.96 |
| Example 44 | 0.06 | | | 0.09 | 0.13 | 0.14 | 0.33 |
| Example 45 | 0.09 | | | 0.10 | 0.16 | 0.15 | 0.40 |
| Example 46 | 0.14 | | | 0.15 | 0.25 | 0.21 | 0.41 |
| Example 47 | 0.81 | | | 1.09 | 1.41 | 1.44 | 2.23 |
| Example 48 | 2.91 | | | 3.82 | | | |
| Example 49 | 0.02 | | | 0.03 | 0.05 | 0.05 | 0.07 |
| Example 50 | 0.04 | | | 0.07 | 0.13 | 0.15 | 0.16 |
| Example 51 | 0.003 | | | 0.01 | 0.01 | 0.01 | 0.01 |
| Example 52 | 0.01 | | | | | 0.02 | 0.03 |
| Example 53 | 0.01 | | | 0.03 | | 0.02 | 0.04 |
| Example 55 | 0.05 | | | 0.11 | 0.13 | 0.16 | 0.18 |
| Example 56 | 0.03 | | | 0.06 | 0.13 | 0.08 | 0.09 |
| Example 57 | 0.02 | | | 0.02 | 0.06 | 0.04 | 0.04 |
| Example 58 | 0.03 | | | 0.06 | 0.04 | 0.07 | 0.06 |
| Example 59 | 0.04 | | | 0.07 | 0.11 | 0.07 | 0.13 |
| Example 60 | 0.05 | | | 0.22 | 0.26 | 0.12 | 0.22 |
| Example 61 | 0.09 | | | | | 0.21 | 0.43 |
| Example 62 | 0.19 | | | | | | |
| Example 63 | 0.19 | | | | | | |
| Example 64 | 0.19 | | | | | | |
| Example 65 | 0.39 | | | | | | |
| Example 66 | 0.01 | | | 0.02 | 0.03 | 0.03 | 0.03 |
| Example 67 | 0.01 | 0.01 | 0.02 | 0.09 | | | |
| Example 68 | 0.01 | 0.01 | 0.03 | 0.1 | | | |
| Example 69 | 0.08 | 0.004 | 0.02 | 0.09 | | | |
| Example 70 | 0.53 | 0.16 | 0.58 | 1.65 | | | |
| Example 71 | 0.01 | | | 0.01 | 0.06 | 0.02 | 0.04 |
| Example 77 | 0.003 | | | 0.01 | 0.03 | 0.01 | 0.03 |
| Example 78 | 0.04 | | | | | | |
| Example 79 | 0.04 | | | | | | |
| Example 80 | 0.14 | | | | | | |
| Example 81 | 0.02 | | | | | 0.14 | 0.07 |
| Example 82 | 0.02 | | | | | 0.17 | 0.09 |
| Example 83 | 0.03 | | | 0.09 | 0.15 | 0.12 | 1.18 |
| Example 84 | 0.06 | | | 0.18 | 0.29 | 0.22 | 2.03 |
| Example 85 | 0.02 | | | 0.07 | 0.09 | 0.06 | 0.14 |
| Example 86 | 0.01 | | | 0.03 | 0.19 | 0.02 | 0.05 |
| Example 87 | 0.003 | | | 0.01 | 0.02 | 0.01 | 0.04 |
| Example 88 | 0.04 | | | 0.01 | 0.02 | 0.02 | 0.04 |
| Example 89 | 0.00 | | | 0.00 | 0.02 | 0.01 | 0.02 |
| Example 90 | 0.04 | | | 0.10 | 0.19 | 0.11 | 0.39 |
| Example 91 | 0.02 | | | 0.03 | 0.07 | 0.03 | 0.05 |
| Example 92 | 0.02 | | | 0.03 | 0.09 | 0.03 | 0.05 |
| Example 93 | 0.07 | | | 0.11 | 0.10 | 0.10 | 0.23 |
| Example 94 | 0.15 | | | 0.32 | 0.48 | 0.23 | 0.52 |
| Example 95 | 0.06 | | | 0.10 | 0.16 | 0.08 | 0.15 |
| Example 96 | 0.06 | | | 0.08 | 0.19 | 0.13 | 0.21 |
| Example 97 | 0.11 | | | 0.12 | 0.16 | 0.16 | 0.29 |
| Example 98 | 0.89 | | | 0.97 | 1.75 | 1.30 | 2.06 |
| Example 99 | 2.03 | | | 2.57 | 3.79 | | |
| Example 100 | 0.03 | | | 0.06 | 0.05 | 0.07 | 0.07 |
| Example 101 | 0.06 | | | 0.23 | 0.29 | 0.12 | 0.23 |
| Example 102 | 0.01 | | | 0.03 | 0.02 | 0.04 | 0.03 |
| Example 103 | 0.01 | | | 0.01 | 0.01 | 0.01 | 0.02 |
| Example 104 | 0.03 | | | 0.07 | 0.05 | 0.08 | 0.08 |
| Example 105 | 0.03 | | | 0.04 | 0.06 | 0.06 | 0.09 |
| Example 106 | 0.06 | | | 0.09 | 0.14 | 0.82 | 0.17 |

As shown in Table 2 above, the compounds according to the present invention can effectively inhibit cancer cell proliferation. Since the compounds effectively inhibit neuroblastoma and glioblastoma as well as colon cancer cells and lung cancer cells, the compounds may be effectively used to treat brain tumor.

Experimental Example 3: Analysis for the Cell Cycle Change

The following experiment was conducted to confirm whether the compounds according to the present invention arrest the cell cycle of a cancer cell in G2/M phase.

A human colon carcinoma cell line HCT116 and a human normal lung cell line MRC5 were cultured in DMEM medium containing 10% FBS. Each cultured cells were harvested, placed in 6 well plate at 1×10$^6$ cells/well, and cultured at 5% $CO_2$ and 37° C. for 16 hrs. The compounds of the above Examples at 75 nM and 150 nM in DMEM containing 5% FBS were added to the cells in each well, and after 24 hrs a change in the cell cycle was analyzed using a flow cytometry. Media of treatment groups and a control group were removed, trypsin was added to isolate cells from the plates and the cells were centrifuged at 1000 g for 3 min. The isolated cells were washed with a cold phosphate buffer (PBS) two times. Afterwards, 1 ml of 70% ethanol was added to the cells and the cells were maintained at 4° C. for 30 min or more to fix the cells. The fixed cells were centrifuged at 1000 g for 3 min to remove ethanol, and washed with phosphate buffer (PBS) two times to remove ethanol completely. The washed cells were suspended in 250 ul of PBS, 6.25 ul of 10 mg/ml RNaseA was added to the suspension and reacted for 15 min at room temperature to degrade all RNA. 12.5 ul of 1 mg/ml propidium iodide (PI, sigma) was added to stain intracellular DNA. The cell cycles of 10,000 stained cells were measured using FACS calibur (Becton-Dickinson, USA) and cell numbers present in G1, S and G2/M phases were calculated as percentage using a cell cycle analysis program. Tables 3 and 4 show the results of cell cycle analysis for the compound obtained in Example 1 in cancer cells and normal cells, respectively.

TABLE 3

| | Sub-G1 | G1 | S | G2/M | Polyploidy |
|---|---|---|---|---|---|
| Control | 1.5 | 54.0 | 8.0 | 26.8 | 10.1 |
| Example 1 - 75 nM | 4.9 | 22.3 | 5.3 | 51.5 | 16.3 |
| Example 1 - 150 nM | 5.8 | 4.3 | 2.6 | 54.4 | 23.3 |

TABLE 4

| | Sub-G1 | G1 | S | G2/M | Polyploidy |
|---|---|---|---|---|---|
| Control | 5.5 | 60.4 | 8.0 | 20.4 | 6.0 |
| Example 1 - 75 nM | 8.8 | 50.7 | 9.1 | 22.8 | 8.8 |
| Example 1 - 150 nM | 12.8 | 44.0 | 6.8 | 26.6 | 10.2 |

The above Tables 3 and 4 and FIG. 1 show that the compounds according to the present invention effectively arrest the cell cycle of a cancer cell in G2/M phase. In particular, while the compound at low concentration of 75 nM arrested the cell cycle of the colon carcinoma cell line HCT116 in G2/M phase, the normal cell line MRC5 showed the cell cycle similar to the control group even at 150 nM of the compound. Therefore, it is expected that the compounds according to the present invention may kill a cancer cell by arresting the cell cycle of the cancer cells in G2/M phase, but may not affect the cell cycle of a normal cell and thus be safe.

Experimental Example 4: Analysis for Tumor Growth Inhibition in an Animal Model

The following experiment was conducted to confirm whether the compounds according to the present invention inhibit a tumor growth in an animal model injected with cancer cells.

Human colon carcinoma HCT116 cell line of $5 \times 10^6$ cells/0.1 ml (Matrigel:PBS=6:4) was injected subcutaneously into the right flank of a Balb/c nude mouse. When a tumor grew to 220 mm$^3$, 5 mice were assigned for each group so that tumor sizes of all groups are consistent and a test compound was orally administered daily for 12 days. Tumor size was measured twice a week using Caliper. The test compound was the one obtained in Example 61 at 1 mg/kg, 3 mg/kg, 10 mg/kg, and 30 mg/kg. A vehicle control was 20% propylene glycol (PG) and a positive control was Xeloda at 100 mg/kg. Tumor size (volume) was calculated from the tumor length measured in each animal using the following Equation 1.

Tumor volume=(length of major axis×length of minor axis$^2$)/2  [Equation 1]

Table 5 below and FIG. 2 show the actual tumor sizes measured over time and the tumor growth inhibition, TGI (%) based on the tumor size for each group compared to the vehicle control group.

TABLE 5

| Experimental group | | Tumor size (mm³) | tumor growth inhibition (%) |
|---|---|---|---|
| 1 | Vehicle control | 1842.6 ± 302.4 | 0 |
| 2 | Xeloda - 100 mpk | 994.7 ± 405.5 | 46.0 |
| 3 | Example 61 - 1 mpk | 1082.4 ± 994.6 | 41.3 |
| 4 | Example 61 - 3 mpk | 773.7 ± 253.9 | 58.0 |
| 5 | Example 61 - 10 mpk | 647.4 ± 462.1 | 64.9 |
| 6 | Example 61 - 30 mpk | 403.4 ± 224.1 | 78.1 |

As shown in the above Table 5 and FIG. 2, after the end of administration, Xeloda at 100 mg/kg used as a positive control exhibited 46% tumor growth inhibition compared to the tumor size of the vehicle control. However, the compound of Example 61 at 1 mg/kg, 3 mg/kg, 10 mg/kg, and 30 mg/k exhibited 41.3%, 58.0%, 64.9%, and 78.1% tumor growth inhibition, respectively, and therefore showed a superior tumor growth inhibition effect compared to Xeloda used as a positive control.

Accordingly, it is expected that the compounds according to the present invention may exhibit a superior anticancer effect against various cancers including colon cancer.

Experimental Example 5: Analysis for Tumor Growth Inhibition by Combined Administration in an Animal Model The following experiment was conducted to confirm whether the compounds according to the present invention exhibit synergistic anticancer effect by combined administration in an animal model injected with a tumor cell.

Human glioblastoma U-87MG cell line of $5 \times 10^6$ cells/0.1 ml PBS was injected subcutaneously into the right flank of a Balb/c nude mouse. When a tumor grew to 150 mm$^3$, 5 mice were assigned for each group so that tumor sizes of all groups are consistent and a test compound was orally administered daily. Tumor size was measured three times a week using Caliper. The test compound was the one obtained in Example 61 at 15 mg/kg and 30 mg/kg. Temozolomide (TMZ) at 2.5 mg/kg as a positive control was orally administered daily for the first 5 days. Further, in order to analyze the effect of combined administration of TMZ and the compound of Example 61, a tumor growth inhibition test was conducted with the group of TMZ at 2.5 mg/kg combined with the compound of Example 61 at 15 mg/kg and the group of TMZ at 2.5 mg/kg combined with the compound of Example 61 at 30 mg/kg. For the combined administration, TMZ was orally administered daily for the first 5 days. For the single administration, the compound of Example 61 was orally administered daily for 30 days. For the combined administration, the compound of Example 61 was administered orally daily for 34 days. 20% propylene glycol (PG) was used as a vehicle control. Tumor size (volume) was calculated from the tumor length measured in each animal using the following Equation 1.

Tumor volume=(length of major axis×length of minor axis)/2  [Equation 1]

Table 6 below and FIG. 3 show the actual tumor sizes measured over time and the tumor growth inhibition, TGI (%) based on the tumor size for each group compared to the vehicle control group.

TABLE 6

| Experimental group | | Tumor size (mm³) | Tumor growth inhibition (%) |
|---|---|---|---|
| 1 | Vehicle control | 4211.7 ± 813.8 | 0.0 |
| 2 | Temozolomide - 2.5 mpk | 926.7 ± 604.4 | 78.0 |
| 3 | Example 61 - 15 mpk | 3503.3 ± 674.9 | 16.8 |
| 4 | Example 61 - 30 mpk | 2015.0 ± 1023 | 52.2 |
| 5 | TMZ 2.5 mpk + Example 61 - 10 mpk | 62.3 ± 74.6 | 98.5 |
| 6 | TMZ 2.5 mpk + Example 61 - 30 mpk | 5.0 ± 5.0 | 99.9 |

As shown in the above Table 6 and FIG. 3, the compound of Example 61 administered alone at 15 mg/kg and 30 mg/kg exhibited 16.8% and 52.2% tumor growth inhibition, respectively, compared to the tumor size of the vehicle control administered for 30 days. Further, TMZ administered alone at 2.5 mg/kg appeared to diminish the tumor, but the tumor started to grow again after 23 days. The compound of Example 61 administered at 15 mg/kg in combination with TMZ diminished a tumor, but the tumor started to grow again after 32 days. However, the compound of Example 61 administered at 30 mg/kg in combination with TMZ diminished the tumor and there was no tumor growth until 34 days. Thus, it is confirmed that the compound of Example 61 has an anticancer effect to inhibit tumor growth of glioblastoma. Further, while temozolomide (TMZ) is used as a medication for treating glioblastoma, it is administered for 5 days only in 28 day cycle administration since its efficacy is weak and it exhibits severe side effects due to cytotoxicity. It is confirmed that the compound of Example 61 combined with TMZ has a synergistic tumor growth inhibitory effect and delays recurrence of cancer cells.

Accordingly, the compounds according to the present invention may be used in combination with various anticancer agents including a molecular targeted agent, a cytotoxic agent or a hormonal agent as well as in a single therapy. Also, it is expected that the compound will exhibit a superior anticancer effect in brain tumor treatment.

Experimental Example 6: Analysis for Blood Brain Barrier Permeation

The following experiment was conducted to confirm whether the compounds according to the present invention penetrate the blood brain barrier and migrate into a brain.

Using 9-week-old male ICR mice, the compounds obtained in the above Examples were orally administered once at a dose of 10 mg/kg or 30 mg/kg, and after 1 hr and 4 hrs, the concentrations of the compounds in the blood and brain of the mice were determined. 3 ICR mice were assigned in each group. Plasma was separated from the blood obtained after sacrificing the mice at each time, the brain of the mice was extracted, and the blood was washed with PBS, followed by pulverizing the brain tissue. The blood was placed in a test tube containing heparin to prevent coagulation and then was centrifuged at 12,000 rpm at 4° C. for 3 min to give a supernatant from which plasma was collected. Brain tissue was weighed, and the brain was pulverized using Dounce's homogenizer after adding 3 times as much volume of PBS as the brain weight. Each of the obtained analytical samples was quantitatively analyzed using a tandem liquid chromatography-mass spectrometer (Tandem LC/MS/MS, API3000 & Agilent 1100 series). Brain permeability of a compound is expressed as a value obtained by dividing the concentration of the compound in the brain by the concentration of the compound in the plasma (B/P ratio), and when the B/P ratio is greater than 1, it means that the concentration in the brain is higher than the one in the blood.

Table 7 below shows B/P ratios for the representative compounds obtained in Examples.

present invention may penetrate into a brain through the blood-brain barrier (BBB) after orally administrated. Further, in consideration of that the concentrations of the compound in the brain decreases after 4 hrs, it is confirmed that the compounds in a brain do not accumulate but have clearance similar to that in blood.

Accordingly, it is expected that the compounds according to the present invention may penetrate into a brain through the BBB and thus exhibit superior effect in the treatment of brain tumor and degenerative brain diseases such as Alzheimer's disease.

Experimental Example 7: Analysis for Inhibition of Tau Phosphorylation

Western blot experiments were carried out as follows to confirm whether the compounds according to the present invention can inhibit phosphorylation of tau protein.

SH-SY5Y cells expressing Tau protein were cultured in DMEM containing 10% FBS. $2.5 \times 10^6$ cells were placed in a 6-well plate and incubated at 5% $CO_2$ and 37° C. for 16 hrs. The compounds obtained in the above Examples serially diluted ⅓ from 3 uM to 0.5 nM or the compounds in a concentration of 0.3, 0.1, 0.03, 0.01, 0.003 uM were treated for 4 hrs in DMEM containing 5% FBS. After 4 hrs, the culture solution was removed, washed with PBS, and cells were lysed by adding 100 ul of lysis buffer. The lysis buffer consisted of 50 mM Tris-HCl (pH 7.5), 150 mM NaCl, 5 mM EDT, 1 mM EGTA, 50 mM NaF, 1 mM PMSF, 1 mM $Na_3VO_4$, 2.5 mM DTT, 1% Triton X-100, and Protease inhibitor (Pierce). The lysed cells were centrifuged at 10,000 rpm and 4° C. for 10 min and the proteins in the supernatant were quantified. 25 ug of the proteins were electrophoresed on a SDS-PAGE gel and transferred to PVDF (Amersharm) membrane. The PVDF membrane was immersed in T-PBS containing 10% skim milk and shaken for 1 hr at room temperature. The primary antibody, Phosph-Tau[pSer202] (Abcam), diluted 1:1500 in T-PBS solution containing 5% skim milk was reacted with the membrane at room tempera-

TABLE 7

|  | 1 hr | | | 4 hrs | | |
| --- | --- | --- | --- | --- | --- | --- |
|  | Concentration in the brain (ng/g) | Concentraion in the plasma (ng/ml) | B/P ratio | Concentration in the brain (ng/g) | Concentraion in the plasma (ng/ml) | B/P ratio |
| Example 8—30 mg/kg | 144.4 | 94.3 | 1.53 | 70.9 | 29.4 | 2.41 |
| Example 12—10 mg/kg | 71.1 | 17.3 | 4.10 | 9.1 | 2.6 | 3.54 |
| Example 10—30 mg/kg | 128.7 | 82.6 | 1.56 | 23.2 | 8.3 | 2.78 |
| Example 61—10 mg/kg | 296.4 | 283.0 | 1.05 | 90.3 | 86.5 | 1.04 |
| Example 67—10 mg/kg | 55.1 | 24.9 | 2.21 | 15.5 | 3.9 | 3.97 |
| Example 61—30 mg/kg | 768.0 | 278.1 | 2.76 | 577.2 | 128.6 | 4.49 |
| Example 66—10 mg/kg | 80.5 | 32.9 | 2.44 | 58.9 | 20.1 | 2.93 |
| Example 71—10 mg/kg | 3124.0 | 1380.0 | 2.26 | 165.3 | 52.1 | 3.18 |

As shown in Table 7, the compounds according to the present invention exhibit B/P ratio greater than 1. Accordingly, it is confirmed that the compounds according to the ture for 2 hrs. The membrane was washed with T-PBS. The secondary antibody, Anti-rabbit IgG HRP, diluted 1:5000 was added to the membrane, reacted at room temperature for 1 hr, and washed. The results obtained by exposing the membrane to ECL (Amersharm) solution are shown in Table 8 below and FIG. 4.

TABLE 8

| | Phosphorylation (%) | | | | | |
|---|---|---|---|---|---|---|
| | Concentration | | | | | |
| | 0.012 uM | 0.037 uM | 0.11 uM | 0.33 uM | 1 uM | 3 uM |
| Example 1 | 88 | 92 | 51 | 28 | 30 | 25 |
| Example 10 | 101 | 84 | 60 | 39 | 11 | 13 |
| | Concentration | | | | | |
| | 0.0005 uM | 0.0014 uM | 0.0041 uM | 0.012 uM | 0.037 uM | 0.11 uM |
| Example 8 | 40 | 43 | 23 | 0 | 0 | 0 |
| | Concentration | | | | | |
| | 0.003 uM | 0.01 uM | 0.03 uM | 0.1 uM | 0.3 uM | |
| Example 34 | 103 | 27 | 13 | 21 | 21 | |
| Example 71 | 110 | 101 | 35 | 26 | ND | |

As shown in Table 8 and FIG. 4, the compounds according to the present invention exhibited a superior inhibitory effect on the phosphorylation of tau protein.

Accordingly, it is expected that the compounds according to the present invention may inhibit the generation of NFT due to hyperphosphorylation of tau protein and thus will be effective in the prevention and treatment of Alzheimer's disease caused by NFT.

Experimental Example 8: Analysis for Inhibition of APP Phosphorylation and AD Generation The following experiment was conducted to confirm whether the compounds according to the present invention inhibit the phosphorylation of APP (amyloid precursor protein) to prevent Aβ (amyloid β protein) generation.

The APP gene was inserted into B103 cells so that APP could be stably expressed and the resulting B103/APP cells were used to confirm inhibition of APP phosphorylation and AP generation.

To confirm the effect of APP phosphorylation inhibition by the compounds obtained in the above Examples, 8×10⁵ B103/APP cells were cultured in a 6-well plate for 16 hrs in DMEM containing 500 ug/ml of G418 and 5% FBS. The compounds serially diluted ⅓ from 3 uM to 0.5 nM or the compounds in a concentration of 0.1, 0.03, 0.01, 0.003, 0.001 uM were treated for 4 hrs in DMEM containing 5% FBS. After 4 hrs, the culture solution was removed, washed with PBS, and cells were lysed by adding 100 ul of lysis buffer. 25 ug of proteins were electrophoresed on SDS-Page gel and transferred to PVDF membrane and western blotting experiment was conducted in the same manner as Experimental Example 7. A primary antibody was Phospho-APP [pThr668] (cell signaling technology) diluted 1:1000, and a secondary antibody was Anti-rabbit IgG HRP diluted 1:5000. The results obtained by exposing the membrane to ECL solution are shown in FIG. 5.

Further, to confirm whether Aβ generation is reduced due to APP phosphorylation inhibition, 5×10⁵ B103/APP cells were cultured in a 6-well plate for 16 hrs. Afterwards, the compounds obtained in the above Examples were added at 100 nM, 75 nM, 50 nM, 25 nM, 12.5 nM to a medium containing 500 ug/ml of G418 and 0.5% FBS and incubated for 72 hrs. After 72 hrs, the amount of Aβ was quantified using the medium by Human Aβ42 ELISA kit (Invitrogen). The results are shown in Table 9 below and FIG. 6.

TABLE 9

| | Inhibition of Aβ generation (%) | | | | | |
|---|---|---|---|---|---|---|
| | Concentration | | | | | |
| | 0 | 12.5 nM | 25 nM | 50 nM | 75 nM | 100 nM |
| Example 66 | 0 | 36.6 | 46.6 | 75.9 | 100.0 | 100.0 |
| Example 71 | 0.0 | 37.6 | 36.2 | 46.7 | 76.8 | 100.0 |

As shown in Table 9 and FIGS. 5 and 6, it was confirmed that the phosphorylation of Threonine 668 residue of APP was effectively inhibited by the compounds according to the present invention and accordingly the generation of Aβ was inhibited. The compound according to the present invention will prevent the formation of amyloid plaques by inhibiting the phosphorylation of Threonine 668 residue of APP and accordingly inhibiting the generation of Aβ.

Therefore, the compounds according to the present invention are expected to have superior efficacy in the prevention and treatment of Alzheimer's disease by simultaneously inhibiting the formation of amyloid plaques and the generation of NFT which are the causes of Alzheimer's disease.

The invention claimed is:

1. A method for treating a pancreatic cancer in a subject in need thereof, comprising administering a composition comprising a compound of the following formula (I) or pharmaceutically acceptable salt thereof:

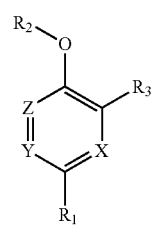

(I)

wherein,

X is nitrogen, Y and Z are carbon;

$R_1$ is phenyl, pyridine, or pyrimidine substituted or unsubstituted with one or more substituents selected from the group consisting of hydroxy, amino, and halogen;

$R_2$ is hydrogen; and $R_3$ is pyrimidine substituted or unsubstituted with one or more substituents selected from the group consisting of $C_1$-$C_6$ alkyl, tetrahydropyranyl, piperidinyl substituted or unsubstituted with $C_1$-$C_6$ alkyl, morpholino, piperazinyl substituted or unsubstituted with $C_1$-$C_6$ alkyl, amino, $C_1$-$C_6$ alkylamino, and halogen, to the subject.

2. The method according to claim 1, wherein the compound of formula (I) or a pharmaceutically acceptable salt thereof is selected from the group consisting of the following compounds:

2,6-bis(2-aminopyrimidin-4-yl)pyridin-3-ol;

2'-amino-6-(2-aminopyrimidin-4-yl)-3'-fluoro-[2,4'-bipyridin]-5-ol;

2-(2-aminopyrimidin-4-yl)-6-(4-hydroxyphenyl)pyridin-3-ol;
2'-amino-6-(2-aminopyrimidin-4-yl)-[2,4'-bipyridin]-5-ol;
6-(2-aminopyrimidin-4-yl)-[2,3'-bipyridin]-5-ol;
6-(2-aminopyrimidin-4-yl)-[2,4'-bipyridin]-5-ol;
2-(2-aminopyrimidin-4-yl)-6-(3-hydroxyphenyl)pyridin-3-ol;
6-(2-aminopyrimidin-4-yl)-3'-fluoro-[2,4'-bipyridin]-5-ol;
6-(4-amino-2-fluorophenyl)-2-(2-aminopyrimidin-4-yl)pyridin-3-ol;
6-(3-aminophenyl)-2-(2-aminopyrimidin-4-yl)pyridin-3-ol;
2-(2-aminopyrimidin-4-yl)-6-(2-fluoro-4-hydroxyphenyl)pyridin-3-ol;
6-(3-amino-2-fluorophenyl)-2-(2-aminopyrimidin-4-yl)pyridin-3-ol;
2-(2-aminopyrimidin-4-yl)-6-(3-fluoro-4-hydroxyphenyl)pyridin-3-ol;
2-(2-aminopyrimidin-4-yl)-6-(2,3-difluoro-4-hydroxyphenyl)pyridin-3-ol;
2'-amino-6-(2-aminopyrimidin-4-yl)-[2,4'-bipyridin]-3',5-diol;
2'-amino-6-(2-amino-6-methylpyrimidin-4-yl)-3'-fluoro-[2,4'-bipyridin]-5-ol;
6-(2-amino-6-methylpyrimidin-4-yl)-[2,4'-bipyridin]-5-ol;
6-(2-amino-6-methylpyrimidin-4-yl)-3'-fluoro-[2,4'-bipyridin]-5-ol;
2-(2-amino-6-methylpyrimidin-4-yl)-6-(4-hydroxyphenyl)pyridin-3-ol;
2-(2-amino-6-methylpyrimidin-4-yl)-6-(2,3-difluoro-4-hydroxyphenyl)pyridin-3-ol;
2-(2-amino-6-methylpyrimidin-4-yl)-6-(2-fluoro-4-hydroxyphenyl)pyridin-3-ol;
2-(2-amino-6-methylpyrimidin-4-yl)-6-(3-aminophenyl)pyridin-3-ol;
2'-amino-6-(2-amino-6-isopropylpyrimidin-4-yl)-3'-fluoro-[2,4'-bipyridin]-5-ol;
2'-amino-6-(2-amino-6-(tetrahydro-2H-pyran-4-yl)pyrimidin-4-yl)-3'-fluoro-[2,4'-bipyridin]-5-ol;
2'-amino-6-(2-amino-6-(piperidin-4-yl)pyrimidin-4-yl)-3'-fluoro-[2,4'-bipyridin]-5-ol;
2'-amino-6-(2-amino-6-(1-methylpiperidin-4-yl)pyrimidin-4-yl)-3'-fluoro-[2,4'-bipyridin]-5-ol;
2'-amino-6-(2-amino-6-(1-ethylpiperidin-4-yl)pyrimidin-4-yl)-3'-fluoro-[2,4'-bipyridin]-5-ol;
2'-amino-6-(2-amino-6-(1-propylpiperidin-4-yl)pyrimidin-4-yl)-3'-fluoro-[2,4'-bipyridin]-5-ol;
2'-amino-6-(2-amino-6-(1-isopropylpiperidin-4-yl)pyrimidin-4-yl)-3'-fluoro-[2,4'-bipyridin]-5-ol;
2'-amino-6-(2-amino-6-(1-methylpiperidin-3-yl)pyrimidin-4-yl)-3'-fluoro-[2,4'-bipyridin]-5-ol;
2'-amino-6-(2-amino-6-(1-ethylpiperidin-3-yl)pyrimidin-4-yl)-3'-fluoro-[2,4'-bipyridin]-5-ol;
2'-amino-6-(2-amino-6-(1-propylpiperidin-3-yl)pyrimidin-4-yl)-3'-fluoro-[2,4'-bipyridin]-5-ol;
2'-amino-6-(2-amino-6-(1-isopropylpiperidin-3-yl)pyrimidin-4-yl)-3'-fluoro-[2,4'-bipyridin]-5-ol;
2'-amino-6-(2-amino-5-methyl-6-(1-methylpiperidin-4-yl)pyrimidin-4-yl)-3'-fluoro-[2,4'-bipyridin]-5-ol;
2'-amino-6-(2-amino-6-(1-ethylpiperidin-4-yl)-5-methylpyrimidin-4-yl)-3'-fluoro-[2,4'-bipyridin]-5-ol;
2'-amino-6-(2-amino-5-methyl-6-(1-propylpiperidin-4-yl)pyrimidin-4-yl)-3'-fluoro-[2,4'-bipyridin]-5-ol;
2'-amino-6-(2-amino-6-(1-isopropylpiperidin-4-yl)-5-methylpyrimidin-4-yl)-3'-fluoro-[2,4'-bipyridin]-5-ol;
2'-amino-6-(2-amino-5-methyl-6-(1-methylpiperidin-3-yl)pyrimidin-3-yl)-3'-fluoro-[2,4'-bipyridin]-5-ol;
2'-amino-6-(2-amino-5-methyl-6-(1-propylpiperidin-3-yl)pyrimidin-4-yl)-3'-fluoro-[2,4'-bipyridin]-5-ol;
2'-amino-6-(2-amino-6-(1-isopropylpiperidin-3-yl)-5-methylpyrimidin-4-yl)-3'-fluoro-[2,4'-bipyridin]-5-ol;
2'-amino-6-(2-amino-5-ethyl-6-(1-isopropylpiperidin-4-yl)pyrimidin-4-yl)-3'-fluoro-[2,4'-bipyridin]-5-ol;
2'-amino-6-(2-amino-6-(1-isopropylpiperidin-4-yl)-5-propylpyrimidin-4-yl)-3'-fluoro-[2,4'-bipyridin]-5-ol;
2'-amino-6-(2-amino-6-morpholinopyrimidin-4-yl)-3'-fluoro-[2,4'-bipyridin]-5-ol;
2'-amino-6-(2-amino-6-(dimethylamino)pyrimidin-4-yl)-3'-fluoro-[2,4'-bipyridin]-5-ol;
2'-amino-6-(2-amino-6-(4-methylpiperazin-1-yl)pyrimidin-4-yl)-3'-fluoro-[2,4'-bipyridin]-5-ol;
6-(2-amino-6-chloropyrimidin-4-yl)-[2,4'-bipyridin]-5-ol;
2'-amino-6-(2-amino-5-methylpyrimidin-4-yl)-3'-fluoro-[2,4'-bipyridin]-5-ol;
2'-amino-6-(2-amino-5-ethylpyrimidin-4-yl)-3'-fluoro-[2,4'-bipyridin]-5-ol;
2'-amino-6-(2-amino-5-propylpyrimidin-4-yl)-3'-fluoro-[2,4'-bipyridin]-5-ol;
2'-amino-6-(2-amino-5-isopropylpyrimidin-5-yl)-3'-fluoro-[2,4'-bipyridin]-5-ol;
2'-amino-3'-fluoro-6-(2-(methylamino)-6-(1-methylpiperidin-4-yl)pyrimidin-4-yl)-[2,4'-bipyridin]-5-ol;
2'-amino-6-(2-amino-5,6-dimethylpyrimidin-4-yl)-3'-fluoro-[2,4'-bipyridin]-5-ol;
2,6-bis(2-aminopyrimidin-4-yl)pyridin-3-ol 3hydrochloride;
2,6-bis(2-aminopyrimidin-4-yl)pyridin-3-ol oxalate;
2,6-bis(2-aminopyrimidin-4-yl)pyridin-3-ol malonate;
2,6-bis(2-aminopyrimidin-4-yl)pyridin-3-ol sulfate;
2'-amino-4-(2-aminopyrimidin-4-yl)-[2,4'-bipyridin]-5-ol oxalate;
2'-amino-6-(2-aminopyrimidin-4-yl)-3'-fluoro-[2,4'-bipyridin]-5-ol 3hydrochloride;
2'-amino-6-(2-aminopyrimidin-4-yl)-3'-fluoro-[2,4'-bipyridin]-5-ol acetate;
2'-amino-6-(2-aminopyrimidin-4-yl)-3'-fluoro-[2,4'-bipyridin]-5-ol oxalate;
2'-amino-6-(2-aminopyrimidin-4-yl)-3'-fluoro-[2,4'-bipyridin]-5-ol 2malonate;
2-(2-aminopyrimidin-4-yl)-6-(2-fluoro-4-hydroxyphenyl)pyridin-3-ol 2hydrochloride;
2'-amino-6-(2-amino-6-methylpyrimidin-4-yl)-3'-fluoro-[2,4'-bipyridin]-5-ol 3hydrochloride;
2'-amino-6-(2-amino-6-morpholinopyrimidin-4-yl)-3'-fluoro-[2,4'-bipyridin]-5-ol 4hydrochloride;
2'-amino-6-(2-amino-6-morpholinopyrimidin-4-yl)-3'-fluoro-[2,4'-bipyridin]-5-ol acetate;
2'-amino-6-(2-amino-6-(dimethylamino)pyrimidin-4-yl)-3'-fluoro-[2,4'-bipyridin]-5-ol 4hydrochloride;
2'-amino-6-(2-amino-6-(4-methylpiperazin-1-yl)pyrimidin-4-yl)-3'-fluoro-[2,4'-bipyridin]-5-ol 5hydrochloride;
2'-amino-6-(2-amino-6-(4-methylpiperazin-1-yl)pyrimidin-4-yl)-3'-fluoro-[2,4'-bipyridin]-5-ol acetate;
2'-amino-6-(2-amino-(6-(1-methylpiperidin-4-yl)pyrimidin-4-yl)-3'-fluoro-[2,4'-bipyridin]-5-ol 4hydrochloride;
2'-amino-6-(2-amino-6-(1-methylpiperidin-4-yl)pyrimidin-4-yl)-3'-fluoro-[2,4'-bipyridin]-5-ol 2acetate;

2'-amino-6-(2-amino-6-(1-methylpiperidin-4-yl)pyrimidin-4-yl)-3'-fluoro-[2,4'-bipyridin]-5-ol oxalate;
2'-amino-6-(2-amino-6-(1-methylpiperidin-4-yl)pyrimidin-4-yl)-3'-fluoro-[2,4'-bipyridin]-5-ol malonate;
2'-amino-6-(2-amino-6-isopropylpyrimidin-4-yl)-3'-fluoro-[2,4'-bipyridin]-5-ol 3hydrochloride;
2'-amino-6-(2-amino-6-isopropylpyrimidin-4-yl)-3'-fluoro-[2,4'-bipyridin]-5-ol 2acetate;
2'-amino-6-(2-amino-6-(piperidin-4-yl)pyrimidin-4-yl)-3'-fluoro-[2,4'-bipyridin]-5-ol 4hydrochloride;
2'-amino-6-(2-amino-6-(piperidin-4-yl)pyrimidin-4-yl)-3'-fluoro-[2,4'-bipyridin]-5-ol acetate;
2'-amino-6-(2-amino-6-(tetrahydro-2H-pyran-4-yl)pyrimidin-4-yl)-3'-fluoro-[2,4'-bipyridin]-5-ol 3hydrochloride;
2'-amino-6-(2-amino-6-(1-ethylpiperidin-4-yl)pyrimidin-4-yl)-3'-fluoro-[2,4'-bipyridin]-5-ol 4hydrochloride;
2'-amino-6-(2-amino-6-(1-propylpiperidin-4-yl)pyrimidin-4-yl)-3'-fluoro-[2,4'-bipyridin]-5-ol 4hydrochloride;
2'-amino-6-(2-amino-6-(1-isopropylpiperidin-4-yl)pyrimidin-4-yl)-3'-fluoro-[2,4'-bipyridin]-5-ol 4hydrochloride;
2'-amino-6-(2-amino-6-(1-methylpiperidin-3-yl)pyrimidin-4-yl)-3'-fluoro-[2,4'-bipyridin]-5-ol 4hydrochloride;
2'-amino-6-(2-amino-6-(1-ethylpiperidin-3-yl)pyrimidin-4-yl)-3'-fluoro-[2,4'-bipyridin]-5-ol 4hydrochloride;
2'-amino-6-(2-amino-6-(1-propylpiperidin-3-yl)pyrimidin-4-yl)-3'-fluoro-[2,4'-bipyridin]-5-ol 4hydrochloride;
2'-amino-6-(2-amino-6-(1-isopropylpiperidin-3-yl)pyrimidin-4-yl)-3'-fluoro[2,4'-bipyridin]-5-ol 4hydrochloride;
2'-amino-6-(2-amino-5-methyl-6-(1-methylpiperidin-4-yl)pyrimidin-4-yl)-3'-fluoro-[2,4'-bipyridin]-5-ol 4hydrochloride;
2'-amino-6-(2-amino-6-(1-ethylpiperidin-4-yl)-5-methylpyrimidin-4-yl)-3'-fluoro-[2,4'-bipyridin]-5-ol 4hydrochloride;
2'-amino-6-(2-amino-5-methyl-6-(1-propylpiperidin-4-yl)pyrimidin-4-yl)-3'-fluoro-[2,4'-bipyridin]-5-ol 4hydrochloride;
2'-amino-6-(2-amino-6-(1-isopropylpiperidin-4-yl)-5-methylpyrimidin-4-yl)-3'-fluoro-[2,4'-bipyridin]-5-ol 4hydrochloride;
2'-amino-6-(2-amino-5-methyl-6-(1-methylpiperidin-3-yl)pyrimidin-3-yl)-3'-fluoro-[2,4'-bipyridin]-5-ol 4hydrochloride;
2'-amino-6-(2-amino-5-methyl-6-(1-propylpiperidin-3-yl)pyrimidin-4-yl)-3'-fluoro-[2,4'-bipyridin]-5-ol 4hydrochloride;
2'-amino-6-(2-amino-6-(1-isopropylpiperidin-3-yl)-5-methylpyrimidin-4-yl)-3'-fluoro-[2,4'-bipyridin]-5-ol 4hydrochloride;
2'-amino-6-(2-amino-5-methylpyrimidin-4-yl)-3'-fluoro-[2,4'-bipyridin]-5-ol 3hydrochloride;
2'-amino-6-(2-amino-5,6-dimethylpyrimidin-4-yl)-3'-fluoro-[2,4'-bipyridin]-5-ol 3hydrochloride;
2'-amino-6-(2-amino-5-ethylpyrimidin-4-yl)-3'-fluoro-[2,4'-bipyridin]-5-ol 3hydrochloride;
2'-amino-6-(2-amino-5-propylpyrimidin-4-yl)-3'-fluoro-[2,4'-bipyridin]-5-ol 3hydrochloride;
2'-amino-6-(2-amino-5-isopropylpyrimidin-5-yl)-3'-fluoro-[2,4'-bipyridin]-5-ol 3hydrochloride;
2'-amino-6-(2-amino-5-ethyl-6-(1-isopropylpiperidin-4-yl)pyrimidin-4-yl)-3'-fluoro-[2,4'-bipyridin]-5-ol 4hydrochloride; and
2'-amino-6-(2-amino-6-(1-isopropylpiperidin-4-yl)-5-propylpyrimidin-4-yl)-3'-fluoro-[2,4'-bipyridin]-5-ol 4hydrochloride.

3. The method of claim 1, which further comprises administering one or more anticancer agents selected from the group consisting of capecitabine, 5-fluorouracil, thioguanine, chlorambucil, oxaliplatin, cisplatin, carboplatin, paclitaxel, docetaxel, irinotecan, doxorubicin, vinorelbin, gemcitabine, pemetrexed, etoposide, vincristine, citarabine, cyclophosphamide, iphosphamide, tamoxifen, anastrozole, retrozole, exemestane, fulvestrant, temozolomide, camustine, lomustine, epirubicine, eribulin, toremifene, goserelin, megestrol, vinblastine, bendamustine, thiotepa, bleomycin, topotecan, leucovorin, trifluridine, tipiracil, mitomycin C, aldesleukin, temsirolimus, everolimus, mitoxantrone, mecloretamine, methotrexate, trastuzumab, bevacizumab, cetuximab, aflibercept, pertuzumab, ramucirumab, panitumumab, nivolumab, necitumumab, pembrolizumab, obinutuzumab, ofatumumab, erlotinib, gefitinib, sorafenib, lapatinib, palbociclib, regorafenib, imatinib, sunitinib, axitinib, pazopanib, apatinib, ceritinib, crizotinib, osimertinib, bosutinib, dasatinib, nilotinib, ponatinib, hydroxyurea, and procarbazine.

4. A method for treating a cancer in a subject in need thereof, comprising administering a composition comprising a compound of the following formula (I) or pharmaceutically acceptable salt thereof:

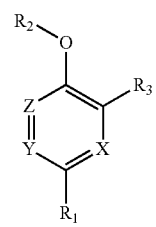

(I)

wherein,
X is nitrogen, Y and Z are carbon;
$R_1$ is phenyl, pyridine, or pyrimidine substituted or unsubstituted with one or more substituents selected from the group consisting of hydroxy, amino, and halogen;
$R_2$ is hydrogen; and
$R_3$ is pyrimidine substituted or unsubstituted with one or more substituents selected from the group consisting of $C_1$-$C_6$ alkyl, tetrahydropyranyl, piperidinyl substituted or unsubstituted with $C_1$-$C_6$ alkyl, morpholino, piperazinyl substituted or unsubstituted with $C_1$-$C_6$ alkyl, amino, $C_1$-$C_6$ alkylamino, and halogen,
to the subject, wherein the cancer is acute lymphoblastic leukemia (ALL), chronic lymphoblastic leukemia (CLL), acute myeloid leukemia (AML), chronic myeloid leukemia (CML), multiple myeloma (MM), Hodgkin's lymphoma, non-Hodgkin's lymphoma, pancreatic cancer, gastric cancer, breast cancer, head and neck squamous cell cancer, liver cancer, melanoma, uterine cancer, prostate cancer, ovarian cancer, thyroid cancer, biliary tract cancer, gallbladder cancer, bladder cancer, kidney cancer, or esophageal cancer.

5. The method according to claim 4, wherein the compound of formula (I) or a pharmaceutically acceptable salt thereof is selected from the group consisting of the following compounds:

2,6-bis(2-aminopyrimidin-4-yl)pyridin-3-ol;
2'-amino-6-(2-aminopyrimidin-4-yl)-3'-fluoro-[2,4'-bipyridin]-5-ol;
2-(2-aminopyrimidin-4-yl)-6-(4-hydroxyphenyl)pyridin-3-ol;
2'-amino-6-(2-aminopyrimidin-4-yl)-[2,4'-bipyridin]-5-ol;
6-(2-aminopyrimidin-4-yl)-[2,3'-bipyridin]-5-ol;
6-(2-aminopyrimidin-4-yl)-[2,4'-bipyridin]-5-ol;
2-(2-aminopyrimidin-4-yl)-6-(3-hydroxyphenyl)pyridin-3-ol;
6-(2-aminopyrimidin-4-yl)-3'-fluoro-[2,4'-bipyridin]-5-ol;
6-(4-amino-2-fluorophenyl)-2-(2-aminopyrimidin-4-yl)pyridin-3-ol;
6-(3-aminophenyl)-2-(2-aminopyrimidin-4-yl)pyridin-3-ol;
2-(2-aminopyrimidin-4-yl)-6-(2-fluoro-4-hydroxyphenyl)pyridin-3-ol;
6-(3-amino-2-fluorophenyl)-2-(2-aminopyrimidin-4-yl)pyridin-3-ol;
2-(2-aminopyrimidin-4-yl)-6-(3-fluoro-4-hydroxyphenyl)pyridin-3-ol;
2-(2-aminopyrimidin-4-yl)-6-(2,3-difluoro-4-hydroxyphenyl)pyridin-3-ol;
2'-amino-6-(2-aminopyrimidin-4-yl)-[2,4'-bipyridin]-3',5-diol;
2'-amino-6-(2-amino-6-methylpyrimidin-4-yl)-3'-fluoro-[2,4'-bipyridin]-5-ol;
6-(2-amino-6-methylpyrimidin-4-yl)-[2,4'-bipyridin]-5-ol;
6-(2-amino-6-methylpyrimidin-4-yl)-3'-fluoro-[2,4'-bipyridin]-5-ol;
2-(2-amino-6-methylpyrimidin-4-yl)-6-(4-hydroxyphenyl)pyridin-3-ol;
2-(2-amino-6-methylpyrimidin-4-yl)-6-(2,3-difluoro-4-hydroxyphenyl)pyridin-3-ol;
2-(2-amino-6-methylpyrimidin-4-yl)-6-(2-fluoro-4-hydroxyphenyl)pyridin-3-ol;
2-(2-amino-6-methylpyrimidin-4-yl)-6-(3-aminophenyl)pyridin-3-ol;
2'-amino-6-(2-amino-6-isopropylpyrimidin-4-yl)-3'-fluoro-[2,4'-bipyridin]-5-ol;
2'-amino-6-(2-amino-6-(tetrahydro-2H-pyran-4-yl)pyrimidin-4-yl)-3'-fluoro-[2,4'-bipyridin]-5-ol;
2'-amino-6-(2-amino-6-(piperidin-4-yl)pyrimidin-4-yl)-3'-fluoro-[2,4'-bipyridin]-5-ol;
2'-amino-6-(2-amino-6-(1-methylpiperidin-4-yl)pyrimidin-4-yl)-3'-fluoro-[2,4'-bipyridin]-5-ol;
2'-amino-6-(2-amino-6-(1-ethylpiperidin-4-yl)pyrimidin-4-yl)-3'-fluoro-[2,4'-bipyridin]-5-ol;
2'-amino-6-(2-amino-6-(1-propylpiperidin-4-yl)pyrimidin-4-yl)-3'-fluoro-[2,4'-bipyridin]-5-ol;
2'-amino-6-(2-amino-6-(1-isopropylpiperidin-4-yl)pyrimidin-4-yl)-3'-fluoro-[2,4'-bipyridin]-5-ol;
2'-amino-6-(2-amino-6-(1-methylpiperidin-3-yl)pyrimidin-4-yl)-3'-fluoro-[2,4'-bipyridin]-5-ol;
2'-amino-6-(2-amino-6-(1-ethylpiperidin-3-yl)pyrimidin-4-yl)-3'-fluoro-[2,4'-bipyridin]-5-ol;
2'-amino-6-(2-amino-6-(1-propylpiperidin-3-yl)pyrimidin-4-yl)-3'-fluoro-[2,4'-bipyridin]-5-ol;
2'-amino-6-(2-amino-6-(1-isopropylpiperidin-3-yl)pyrimidin-4-yl)-3'-fluoro-[2,4'-bipyridin]-5-ol;
2'-amino-6-(2-amino-5-methyl-6-(1-methylpiperidin-4-yl)pyrimidin-4-yl)-3'-fluoro-[2,4'-bipyridin]-5-ol;
2'-amino-6-(2-amino-6-(1-ethylpiperidin-4-yl)-5-methylpyrimidin-4-yl)-3'-fluoro-[2,4'-bipyridin]-5-ol;
2'-amino-6-(2-amino-5-methyl-6-(1-propylpiperidin-4-yl)pyrimidin-4-yl)-3'-fluoro-[2,4'-bipyridin]-5-ol;
2'-amino-6-(2-amino-6-(1-isopropylpiperidin-4-yl)-5-methylpyrimidin-4-yl)-3'-fluoro-[2,4'-bipyridin]-5-ol;
2'-amino-6-(2-amino-5-methyl-6-(1-methylpiperidin-3-yl)pyrimidin-3-yl)-3'-fluoro-[2,4'-bipyridin]-5-ol;
2'-amino-6-(2-amino-5-methyl-6-(1-propylpiperidin-3-yl)pyrimidin-4-yl)-3'-fluoro-[2,4'-bipyridin]-5-ol;
2'-amino-6-(2-amino-6-(1-isopropylpiperidin-3-yl)-5-methylpyrimidin-4-yl)-3'-fluoro-[2,4'-bipyridin]-5-ol;
2'-amino-6-(2-amino-5-ethyl-6-(1-isopropylpiperidin-4-yl)pyrimidin-4-yl)-3'-fluoro-[2,4'-bipyridin]-5-ol;
2'-amino-6-(2-amino-6-(1-isopropylpiperidin-4-yl)-5-propylpyrimidin-4-yl)-3'-fluoro-[2,4'-bipyridin]-5-ol;
2'-amino-6-(2-amino-6-morpholinopyrimidin-4-yl)-3'-fluoro-[2,4'-bipyridin]-5-ol;
2'-amino-6-(2-amino-6-(dimethylamino)pyrimidin-4-yl)-3'-fluoro-[2,4'-bipyridin]-5-ol;
2'-amino-6-(2-amino-6-(4-methylpiperazin-1-yl)pyrimidin-4-yl)-3'-fluoro-[2,4'-bipyridin]-5-ol;
6-(2-amino-6-chloropyrimidin-4-yl)-[2,4'-bipyridin]-5-ol;
2'-amino-6-(2-amino-5-methylpyrimidin-4-yl)-3'-fluoro-[2,4'-bipyridin]-5-ol;
2'-amino-6-(2-amino-5-ethylpyrimidin-4-yl)-3'-fluoro-[2,4'-bipyridin]-5-ol;
2'-amino-6-(2-amino-5-propylpyrimidin-4-yl)-3'-fluoro-[2,4'-bipyridin]-5-ol;
2'-amino-6-(2-amino-5-isopropylpyrimidin-5-yl)-3'-fluoro-[2,4'-bipyridin]-5-ol;
2'-amino-3'-fluoro-6-(2-(methylamino)-6-(1-methylpiperidin-4-yl)pyrimidin-4-yl)-[2,4'-bipyridin]-5-ol;
2'-amino-6-(2-amino-5,6-dimethylpyrimidin-4-yl)-3'-fluoro-[2,4'-bipyridin]-5-ol;
2,6-bis(2-aminopyrimidin-4-yl)pyridin-3-ol 3hydrochloride;
2,6-bis(2-aminopyrimidin-4-yl)pyridin-3-ol oxalate;
2,6-bis(2-aminopyrimidin-4-yl)pyridin-3-ol malonate;
2,6-bis(2-aminopyrimidin-4-yl)pyridin-3-ol sulfate;
2'-amino-4-(2-aminopyrimidin-4-yl)-[2,4'-bipyridin]-5-ol oxalate;
2'-amino-6-(2-aminopyrimidin-4-yl)-3'-fluoro-[2,4'-bipyridin]-5-ol 3hydrochloride;
2'-amino-6-(2-aminopyrimidin-4-yl)-3'-fluoro-[2,4'-bipyridin]-5-ol acetate;
2'-amino-6-(2-aminopyrimidin-4-yl)-3'-fluoro-[2,4'-bipyridin]-5-ol oxalate;
2'-amino-6-(2-aminopyrimidin-4-yl)-3'-fluoro-[2,4'-bipyridin]-5-ol 2malonate;
2-(2-aminopyrimidin-4-yl)-6-(2-fluoro-4-hydroxyphenyl)pyridin-3-ol 2hydrochloride;
2'-amino-6-(2-amino-6-methylpyrimidin-4-yl)-3'-fluoro-[2,4'-bipyridin]-5-ol 3hydrochloride;
2'-amino-6-(2-amino-6-morpholinopyrimidin-4-yl)-3'-fluoro-[2,4'-bipyridin]-5-ol 4hydrochloride;
2'-amino-6-(2-amino-6-morpholinopyrimidin-4-yl)-3'-fluoro-[2,4'-bipyridin]-5-ol acetate;
2'-amino-6-(2-amino-6-(dimethylamino)pyrimidin-4-yl)-3'-fluoro-[2,4'-bipyridin]-5-ol 4hydrochloride;
2'-amino-6-(2-amino-6-(4-methylpiperazin-1-yl)pyrimidin-4-yl)-3'-fluoro-[2,4'-bipyridin]-5-ol 5hydrochloride;
2'-amino-6-(2-amino-6-(4-methylpiperazin-1-yl)pyrimidin-4-yl)-3'-fluoro-[2,4'-bipyridin]-5-ol acetate;
2'-amino-6-(2-amino-6-(6-(1-methylpiperidin-4-yl)pyrimidin-4-yl)-3'-fluoro-[2,4'-bipyridin]-5-ol 4hydrochloride;

2'-amino-6-(2-amino-6-(1-methylpiperidin-4-yl)pyrimidin-4-yl)-3'-fluoro-[2,4'-bipyridin]-5-ol 2acetate;
2'-amino-6-(2-amino-6-(1-methylpiperidin-4-yl)pyrimidin-4-yl)-3'-fluoro-[2,4'-bipyridin]-5-ol oxalate;
2'-amino-6-(2-amino-6-(1-methylpiperidin-4-yl)pyrimidin-4-yl)-3'-fluoro-[2,4'-bipyridin]-5-ol malonate;
2'-amino-6-(2-amino-6-isopropylpyrimidin-4-yl)-3'-fluoro-[2,4'-bipyridin]-5-ol 3hydrochloride;
2'-amino-6-(2-amino-6-isopropylpyrimidin-4-yl)-3'-fluoro-[2,4'-bipyridin]-5-ol 2acetate;
2'-amino-6-(2-amino-6-(piperidin-4-yl)pyrimidin-4-yl)-3'-fluoro-[2,4'-bipyridin]-5-ol 4hydrochloride;
2'-amino-6-(2-amino-6-(piperidin-4-yl)pyrimidin-4-yl)-3'-fluoro-[2,4'-bipyridin]-5-ol acetate;
2'-amino-6-(2-amino-6-(tetrahydro-2H-pyran-4-yl)pyrimidin-4-yl)-3'-fluoro-[2,4'-bipyridin]-5-ol 3hydrochloride;
2'-amino-6-(2-amino-6-(1-ethylpiperidin-4-yl)pyrimidin-4-yl)-3'-fluoro-[2,4'-bipyridin]-5-ol 4hydrochloride;
2'-amino-6-(2-amino-6-(1-propylpiperidin-4-yl)pyrimidin-4-yl)-3'-fluoro-[2,4'-bipyridin]-5-ol 4hydrochloride;
2'-amino-6-(2-amino-6-(1-isopropylpiperidin-4-yl)pyrimidin-4-yl)-3'-fluoro-[2,4'-bipyridin]-5-ol 4hydrochloride;
2'-amino-6-(2-amino-6-(1-methylpiperidin-3-yl)pyrimidin-4-yl)-3'-fluoro-[2,4'-bipyridin]-5-ol 4hydrochloride;
2'-amino-6-(2-amino-6-(1-ethylpiperidin-3-yl)pyrimidin-4-yl)-3'-fluoro-[2,4'-bipyridin]-5-ol 4hydrochloride;
2'-amino-6-(2-amino-6-(1-propylpiperidin-3-yl)pyrimidin-4-yl)-3'-fluoro-[2,4'-bipyridin]-5-ol 4hydrochloride;
2'-amino-6-(2-amino-6-(1-isopropylpiperidin-3-yl)pyrimidin-4-yl)-3'-fluoro[2,4'-bipyridin]-5-ol 4hydrochloride;
2'-amino-6-(2-amino-5-methyl-6-(1-methylpiperidin-4-yl)pyrimidin-4-yl)-3'-fluoro-[2,4'-bipyridin]-5-ol 4hydrochloride;
2'-amino-6-(2-amino-6-(1-ethylpiperidin-4-yl)-5-methylpyrimidin-4-yl)-3'-fluoro-[2,4'-bipyridin]-5-ol 4hydrochloride;
2'-amino-6-(2-amino-5-methyl-6-(1-propylpiperidin-4-yl)pyrimidin-4-yl)-3'-fluoro-[2,4'-bipyridin]-5-ol 4hydrochloride;
2'-amino-6-(2-amino-6-(1-isopropylpiperidin-4-yl)-5-methylpyrimidin-4-yl)-3'-fluoro-[2,4'-bipyridin]-5-ol 4hydrochloride;
2'-amino-6-(2-amino-5-methyl-6-(1-methylpiperidin-3-yl)pyrimidin-3-yl)-3'-fluoro-[2,4'-bipyridin]-5-ol 4hydrochloride;
2'-amino-6-(2-amino-5-methyl-6-(1-propylpiperidin-3-yl)pyrimidin-4-yl)-3'-fluoro-[2,4'-bipyridin]-5-ol 4hydrochloride;
2'-amino-6-(2-amino-6-(1-isopropylpiperidin-3-yl)-5-methylpyrimidin-4-yl)-3'-fluoro-[2,4'-bipyridin]-5-ol 4hydrochloride;
2'-amino-6-(2-amino-5-methylpyrimidin-4-yl)-3'-fluoro-[2,4'-bipyridin]-5-ol 3hydrochloride;
2'-amino-6-(2-amino-5,6-dimethylpyrimidin-4-yl)-3'-fluoro-[2,4'-bipyridin]-5-ol 3hydrochloride;
2'-amino-6-(2-amino-5-ethylpyrimidin-4-yl)-3'-fluoro-[2,4'-bipyridin]-5-ol 3hydrochloride;
2'-amino-6-(2-amino-5-propylpyrimidin-4-yl)-3'-fluoro-[2,4'-bipyridin]-5-ol 3hydrochloride;
2'-amino-6-(2-amino-5-isopropylpyrimidin-5-yl)-3'-fluoro-[2,4'-bipyridin]-5-ol 3hydrochloride;
2'-amino-6-(2-amino-5-ethyl-6-(1-isopropylpiperidin-4-yl)pyrimidin-4-yl)-3'-fluoro-[2,4'-bipyridin]-5-ol 4hydrochloride; and
2'-amino-6-(2-amino-6-(1-isopropylpiperidin-4-yl)-5-propylpyrimidin-4-yl)-3'-fluoro-[2,4'-bipyridin]-5-ol 4hydrochloride.

6. The method of claim 4, which further comprises administering one or more anticancer agents selected from the group consisting of capecitabine, 5-fluorouracil, thioguanine, chlorambucil, oxaliplatin, cisplatin, carboplatin, paclitaxel, docetaxel, irinotecan, doxorubicin, vinorelbin, gemcitabine, pemetrexed, etoposide, vincristine, citarabine, cyclophosphamide, iphosphamide, tamoxifen, anastrozole, retrozole, exemestane, fulvestrant, temozolomide, camustine, lomustine, epirubicine, eribulin, toremifene, goserelin, megestrol, vinblastine, bendamustine, thiotepa, bleomycin, topotecan, leucovorin, trifluridine, tipiracil, mitomycin C, aldesleukin, temsirolimus, everolimus, mitoxantrone, mecloretamine, methotrexate, trastuzumab, bevacizumab, cetuximab, aflibercept, pertuzumab, ramucirumab, panitumumab, nivolumab, necitumumab, pembrolizumab, obinutuzumab, ofatumumab, erlotinib, gefitinib, sorafenib, lapatinib, palbociclib, regorafenib, imatinib, sunitinib, axitinib, pazopanib, apatinib, ceritinib, crizotinib, osimertinib, bosutinib, dasatinib, nilotinib, ponatinib, hydroxyurea, and procarbazine.

7. A method for treating a degenerative brain disease in a subject in need thereof, comprising administering a composition comprising a compound of the following formula (I) or pharmaceutically acceptable salt thereof:

wherein,
X is nitrogen, Y and Z are carbon;
$R_1$ is phenyl, pyridine, or pyrimidine substituted or unsubstituted with one or more substituents selected from the group consisting of hydroxy, amino, and halogen;
$R_2$ is hydrogen; and
$R_3$ is pyrimidine substituted or unsubstituted with one or more substituents selected from the group consisting of $C_1$-$C_6$ alkyl, tetrahydropyranyl, piperidinyl substituted or unsubstituted with $C_1$-$C_6$ alkyl, morpholino, piperazinyl substituted or unsubstituted with $C_1$-$C_6$ alkyl, amino, $C_1$-$C_6$ alkylamino, and halogen,
to the subject, wherein the degenerative brain disease is Huntington's chorea or Parkinson's disease.

8. The method according to claim 7, wherein the compound of formula (I) or a pharmaceutically acceptable salt thereof is selected from the group consisting of the following compounds:
2,6-bis(2-aminopyrimidin-4-yl)pyridin-3-ol;
2'-amino-6-(2-aminopyrimidin-4-yl)-3'-fluoro-[2,4'-bipyridin]-5-ol;
2-(2-aminopyrimidin-4-yl)-6-(4-hydroxyphenyl)pyridin-3-ol;

2'-amino-6-(2-aminopyrimidin-4-yl)-[2,4'-bipyridin]-5-ol;
6-(2-aminopyrimidin-4-yl)-[2,3'-bipyridin]-5-ol;
6-(2-aminopyrimidin-4-yl)-[2,4'-bipyridin]-5-ol;
2-(2-aminopyrimidin-4-yl)-6-(3-hydroxyphenyl)pyridin-3-ol;
6-(2-aminopyrimidin-4-yl)-3'-fluoro-[2,4'-bipyridin]-5-ol;
6-(4-amino-2-fluorophenyl)-2-(2-aminopyrimidin-4-yl)pyridin-3-ol;
6-(3-aminophenyl)-2-(2-aminopyrimidin-4-yl)pyridin-3-ol;
2-(2-aminopyrimidin-4-yl)-6-(2-fluoro-4-hydroxyphenyl)pyridin-3-ol;
6-(3-amino-2-fluorophenyl)-2-(2-aminopyrimidin-4-yl)pyridin-3-ol;
2-(2-aminopyrimidin-4-yl)-6-(3-fluoro-4-hydroxyphenyl)pyridin-3-ol;
2-(2-aminopyrimidin-4-yl)-6-(2,3-difluoro-4-hydroxyphenyl)pyridin-3-ol;
2'-amino-6-(2-aminopyrimidin-4-yl)-[2,4'-bipyridin]-3',5-diol;
2'-amino-6-(2-amino-6-methylpyrimidin-4-yl)-3'-fluoro-[2,4'-bipyridin]-5-ol;
6-(2-amino-6-methylpyrimidin-4-yl)-[2,4'-bipyridin]-5-ol;
6-(2-amino-6-methylpyrimidin-4-yl)-3'-fluoro-[2,4'-bipyridin]-5-ol;
2-(2-amino-6-methylpyrimidin-4-yl)-6-(4-hydroxyphenyl)pyridin-3-ol;
2-(2-amino-6-methylpyrimidin-4-yl)-6-(2,3-difluoro-4-hydroxyphenyl)pyridin-3-ol;
2-(2-amino-6-methylpyrimidin-4-yl)-6-(2-fluoro-4-hydroxyphenyl)pyridin-3-ol;
2-(2-amino-6-methylpyrimidin-4-yl)-6-(3-aminophenyl)pyridin-3-ol;
2'-amino-6-(2-amino-6-isopropylpyrimidin-4-yl)-3'-fluoro-[2,4'-bipyridin]-5-ol;
2'-amino-6-(2-amino-6-(tetrahydro-2H-pyran-4-yl)pyrimidin-4-yl)-3'-fluoro-[2,4'-bipyridin]-5-ol;
2'-amino-6-(2-amino-6-(piperidin-4-yl)pyrimidin-4-yl)-3'-fluoro-[2,4'-bipyridin]-5-ol;
2'-amino-6-(2-amino-6-(1-methylpiperidin-4-yl)pyrimidin-4-yl)-3'-fluoro-[2,4'-bipyridin]-5-ol;
2'-amino-6-(2-amino-6-(1-ethylpiperidin-4-yl)pyrimidin-4-yl)-3'-fluoro-[2,4'-bipyridin]-5-ol;
2'-amino-6-(2-amino-6-(1-propylpiperidin-4-yl)pyrimidin-4-yl)-3'-fluoro-[2,4'-bipyridin]-5-ol;
2'-amino-6-(2-amino-6-(1-isopropylpiperidin-4-yl)pyrimidin-4-yl)-3'-fluoro-[2,4'-bipyridin]-5-ol;
2'-amino-6-(2-amino-6-(1-methylpiperidin-3-yl)pyrimidin-4-yl)-3'-fluoro-[2,4'-bipyridin]-5-ol;
2'-amino-6-(2-amino-6-(1-ethylpiperidin-3-yl)pyrimidin-4-yl)-3'-fluoro-[2,4'-bipyridin]-5-ol;
2'-amino-6-(2-amino-6-(1-propylpiperidin-3-yl)pyrimidin-4-yl)-3'-fluoro-[2,4'-bipyridin]-5-ol;
2'-amino-6-(2-amino-6-(1-isopropylpiperidin-3-yl)pyrimidin-4-yl)-3'-fluoro-[2,4'-bipyridin]-5-ol;
2'-amino-6-(2-amino-5-methyl-6-(1-methylpiperidin-4-yl)pyrimidin-4-yl)-3'-fluoro-[2,4'-bipyridin]-5-ol;
2'-amino-6-(2-amino-6-(1-ethylpiperidin-4-yl)-5-methylpyrimidin-4-yl)-3'-fluoro-[2,4'-bipyridin]-5-ol;
2'-amino-6-(2-amino-5-methyl-6-(1-propylpiperidin-4-yl)pyrimidin-4-yl)-3'-fluoro-[2,4'-bipyridin]-5-ol;
2'-amino-6-(2-amino-6-(1-isopropylpiperidin-4-yl)-5-methylpyrimidin-4-yl)-3'-fluoro-[2,4'-bipyridin]-5-ol;
2'-amino-6-(2-amino-5-methyl-6-(1-methylpiperidin-3-yl)pyrimidin-3-yl)-3'-fluoro-[2,4'-bipyridin]-5-ol;
2'-amino-6-(2-amino-5-methyl-6-(1-propylpiperidin-3-yl)pyrimidin-4-yl)-3'-fluoro-[2,4'-bipyridin]-5-ol;
2'-amino-6-(2-amino-6-(1-isopropylpiperidin-3-yl)-5-methylpyrimidin-4-yl)-3'-fluoro-[2,4'-bipyridin]-5-ol;
2'-amino-6-(2-amino-5-ethyl-6-(1-isopropylpiperidin-4-yl)pyrimidin-4-yl)-3'-fluoro-[2,4'-bipyridin]-5-ol;
2'-amino-6-(2-amino-6-(1-isopropylpiperidin-4-yl)-5-propylpyrimidin-4-yl)-3'-fluoro-[2,4'-bipyridin]-5-ol;
2'-amino-6-(2-amino-6-morpholinopyrimidin-4-yl)-3'-fluoro-[2,4'-bipyridin]-5-ol;
2'-amino-6-(2-amino-6-(dimethylamino)pyrimidin-4-yl)-3'-fluoro-[2,4'-bipyridin]-5-ol;
2'-amino-6-(2-amino-6-(4-methylpiperazin-1-yl)pyrimidin-4-yl)-3'-fluoro-[2,4'-bipyridin]-5-ol;
6-(2-amino-6-chloropyrimidin-4-yl)-[2,4'-bipyridin]-5-ol;
2'-amino-6-(2-amino-5-methylpyrimidin-4-yl)-3'-fluoro-[2,4'-bipyridin]-5-ol;
2'-amino-6-(2-amino-5-ethylpyrimidin-4-yl)-3'-fluoro-[2,4'-bipyridin]-5-ol;
2'-amino-6-(2-amino-5-propylpyrimidin-4-yl)-3'-fluoro-[2,4'-bipyridin]-5-ol;
2'-amino-6-(2-amino-5-isopropylpyrimidin-5-yl)-3'-fluoro-[2,4'-bipyridin]-5-ol;
2'-amino-3'-fluoro-6-(2-(methylamino)-6-(1-methylpiperidin-4-yl)pyrimidin-4-yl)-[2,4'-bipyridin]-5-ol;
2'-amino-6-(2-amino-5,6-dimethylpyrimidin-4-yl)-3'-fluoro-[2,4'-bipyridin]-5-ol;
2,6-bis(2-aminopyrimidin-4-yl)pyridin-3-ol 3hydrochloride;
2,6-bis(2-aminopyrimidin-4-yl)pyridin-3-ol oxalate;
2,6-bis(2-aminopyrimidin-4-yl)pyridin-3-ol malonate;
2,6-bis(2-aminopyrimidin-4-yl)pyridin-3-ol sulfate;
2'-amino-4-(2-aminopyrimidin-4-yl)-[2,4'-bipyridin]-5-ol oxalate;
2'-amino-6-(2-aminopyrimidin-4-yl)-3'-fluoro-[2,4'-bipyridin]-5-ol 3hydrochloride;
2'-amino-6-(2-aminopyrimidin-4-yl)-3'-fluoro-[2,4'-bipyridin]-5-ol acetate;
2'-amino-6-(2-aminopyrimidin-4-yl)-3'-fluoro-[2,4'-bipyridin]-5-ol oxalate;
2'-amino-6-(2-aminopyrimidin-4-yl)-3'-fluoro-[2,4'-bipyridin]-5-ol 2malonate;
2-(2-aminopyrimidin-4-yl)-6-(2-fluoro-4-hydroxyphenyl)pyridin-3-ol 2hydrochloride;
2'-amino-6-(2-amino-6-methylpyrimidin-4-yl)-3'-fluoro-[2,4'-bipyridin]-5-ol 3hydrochloride;
2'-amino-6-(2-amino-6-morpholinopyrimidin-4-yl)-3'-fluoro-[2,4'-bipyridin]-5-ol 4hydrochloride;
2'-amino-6-(2-amino-6-morpholinopyrimidin-4-yl)-3'-fluoro-[2,4'-bipyridin]-5-ol acetate;
2'-amino-6-(2-amino-6-(dimethylamino)pyrimidin-4-yl)-3'-fluoro-[2,4'-bipyridin]-5-ol 4hydrochloride;
2'-amino-6-(2-amino-6-(4-methylpiperazin-1-yl)pyrimidin-4-yl)-3'-fluoro-[2,4'-bipyridin]-5-ol 5hydrochloride;
2'-amino-6-(2-amino-6-(4-methylpiperazin-1-yl)pyrimidin-4-yl)-3'-fluoro-[2,4'-bipyridin]-5-ol acetate;
2'-amino-6-(2-amino-(6-(1-methylpiperidin-4-yl)pyrimidin-4-yl)-3'-fluoro-[2,4'-bipyridin]-5-ol 4hydrochloride;
2'-amino-6-(2-amino-6-(1-methylpiperidin-4-yl)pyrimidin-4-yl)-3'-fluoro-[2,4'-bipyridin]-5-ol 2acetate;
2'-amino-6-(2-amino-6-(1-methylpiperidin-4-yl)pyrimidin-4-yl)-3'-fluoro-[2,4'-bipyridin]-5-ol oxalate;

2'-amino-6-(2-amino-6-(1-methylpiperidin-4-yl)pyrimidin-4-yl)-3'-fluoro-[2,4'-bipyridin]-5-ol malonate;

2'-amino-6-(2-amino-6-isopropylpyrimidin-4-yl)-3'-fluoro-[2,4'-bipyridin]-5-ol 3hydrochloride;

2'-amino-6-(2-amino-6-isopropylpyrimidin-4-yl)-3'-fluoro-[2,4'-bipyridin]-5-ol 2acetate;

2'-amino-6-(2-amino-6-(piperidin-4-yl)pyrimidin-4-yl)-3'-fluoro-[2,4'-bipyridin]-5-ol 4hydrochloride;

2'-amino-6-(2-amino-6-(piperidin-4-yl)pyrimidin-4-yl)-3'-fluoro-[2,4'-bipyridin]-5-ol acetate;

2'-amino-6-(2-amino-6-(tetrahydro-2H-pyran-4-yl)pyrimidin-4-yl)-3'-fluoro-[2,4'-bipyridin]-5-ol 3hydrochloride;

2'-amino-6-(2-amino-6-(1-ethylpiperidin-4-yl)pyrimidin-4-yl)-3'-fluoro-[2,4'-bipyridin]-5-ol 4hydrochloride;

2'-amino-6-(2-amino-6-(1-propylpiperidin-4-yl)pyrimidin-4-yl)-3'-fluoro-[2,4'-bipyridin]-5-ol 4hydrochloride;

2'-amino-6-(2-amino-6-(1-isopropylpiperidin-4-yl)pyrimidin-4-yl)-3'-fluoro-[2,4'-bipyridin]-5-ol 4hydrochloride;

2'-amino-6-(2-amino-6-(1-methylpiperidin-3-yl)pyrimidin-4-yl)-3'-fluoro-[2,4'-bipyridin]-5-ol 4hydrochloride;

2'-amino-6-(2-amino-6-(1-ethylpiperidin-3-yl)pyrimidin-4-yl)-3'-fluoro-[2,4'-bipyridin]-5-ol 4hydrochloride;

2'-amino-6-(2-amino-6-(1-propylpiperidin-3-yl)pyrimidin-4-yl)-3'-fluoro-[2,4'-bipyridin]-5-ol 4hydrochloride;

2'-amino-6-(2-amino-6-(1-isopropylpiperidin-3-yl)pyrimidin-4-yl)-3'-fluoro[2,4'-bipyridin]-5-ol 4hydrochloride;

2'-amino-6-(2-amino-5-methyl-6-(1-methylpiperidin-4-yl)pyrimidin-4-yl)-3'-fluoro-[2,4'-bipyridin]-5-ol 4hydrochloride;

2'-amino-6-(2-amino-6-(1-ethylpiperidin-4-yl)-5-methylpyrimidin-4-yl)-3'-fluoro-[2,4'-bipyridin]-5-ol 4hydrochloride;

2'-amino-6-(2-amino-5-methyl-6-(1-propylpiperidin-4-yl)pyrimidin-4-yl)-3'-fluoro-[2,4'-bipyridin]-5-ol 4hydrochloride;

2'-amino-6-(2-amino-6-(1-isopropylpiperidin-4-yl)-5-methylpyrimidin-4-yl)-3'-fluoro-[2,4'-bipyridin]-5-ol 4hydrochloride;

2'-amino-6-(2-amino-5-methyl-6-(1-methylpiperidin-3-yl)pyrimidin-3-yl)-3'-fluoro-[2,4'-bipyridin]-5-ol 4hydrochloride;

2'-amino-6-(2-amino-5-methyl-6-(1-propylpiperidin-3-yl)pyrimidin-4-yl)-3'-fluoro-[2,4'-bipyridin]-5-ol 4hydrochloride;

2'-amino-6-(2-amino-6-(1-isopropylpiperidin-3-yl)-5-methylpyrimidin-4-yl)-3'-fluoro-[2,4'-bipyridin]-5-ol 4hydrochloride;

2'-amino-6-(2-amino-5-methylpyrimidin-4-yl)-3'-fluoro-[2,4'-bipyridin]-5-ol 3hydrochloride;

2'-amino-6-(2-amino-5,6-dimethylpyrimidin-4-yl)-3'-fluoro-[2,4'-bipyridin]-5-ol 3hydrochloride;

2'-amino-6-(2-amino-5-ethylpyrimidin-4-yl)-3'-fluoro-[2,4'-bipyridin]-5-ol 3hydrochloride;

2'-amino-6-(2-amino-5-propylpyrimidin-4-yl)-3'-fluoro-[2,4'-bipyridin]-5-ol 3hydrochloride;

2'-amino-6-(2-amino-5-isopropylpyrimidin-5-yl)-3'-fluoro-[2,4'-bipyridin]-5-ol 3hydrochloride;

2'-amino-6-(2-amino-5-ethyl-6-(1-isopropylpiperidin-4-yl)pyrimidin-4-yl)-3'-fluoro-[2,4'-bipyridin]-5-ol 4hydrochloride; and 2'-amino-6-(2-amino-6-(1-isopropylpiperidin-4-yl)-5-propylpyrimidin-4-yl)-3'-fluoro-[2,4'-bipyridin]-5-ol 4hydrochloride.

9. The method of claim 7, which further comprises administering one or more drugs selected from the group consisting of levodopa, bromocriptine, ropinirole, pramipexole, rotigotine, trihexyphenidyl, benztropine, procyclidine, entacapone, selegiline, rasagiline, amantadine, tetrabenazine, donepezil, rivastigmine, galantamine and memantine.

* * * * *